US009504675B2

(12) United States Patent
Boger

(10) Patent No.: US 9,504,675 B2
(45) Date of Patent: Nov. 29, 2016

(54) ALPHA-KETOHETEROCYCLES AND METHODS OF MAKING AND USING

(75) Inventor: Dale L. Boger, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 281 days.

(21) Appl. No.: 13/983,369

(22) PCT Filed: Feb. 3, 2012

(86) PCT No.: PCT/US2012/023718
§ 371 (c)(1),
(2), (4) Date: Aug. 30, 2013

(87) PCT Pub. No.: WO2012/106569
PCT Pub. Date: Aug. 9, 2012

(65) Prior Publication Data
US 2013/0338196 A1 Dec. 19, 2013

Related U.S. Application Data

(60) Provisional application No. 61/439,415, filed on Feb. 4, 2011.

(51) Int. Cl.
| | |
|---|---|
| C07D 413/04 | (2006.01) |
| A61K 31/421 | (2006.01) |
| A61K 45/06 | (2006.01) |
| C07D 271/10 | (2006.01) |
| A61K 31/4439 | (2006.01) |
| A61K 31/4245 | (2006.01) |
| C07D 263/32 | (2006.01) |
| C07D 263/34 | (2006.01) |

(52) U.S. Cl.
CPC ......... *A61K 31/421* (2013.01); *A61K 31/4245* (2013.01); *A61K 31/4439* (2013.01); *A61K 45/06* (2013.01); *C07D 263/32* (2013.01); *C07D 263/34* (2013.01); *C07D 271/10* (2013.01); *C07D 413/04* (2013.01)

(58) Field of Classification Search
CPC ........... A61K 31/421; A61K 31/4439; A61K 31/4245; A61K 45/06; C07D 271/10; C07D 413/04; C07D 263/32; C07D 263/34
See application file for complete search history.

(56) References Cited

FOREIGN PATENT DOCUMENTS

| | | |
|---|---|---|
| EP | 2670245 B1 | 9/2015 |
| JP | 2006-516095 A | 6/2006 |
| JP | 2010-517934 A | 5/2010 |
| JP | 2014504648 A | 2/2014 |
| WO | WO-2004044169 A2 | 5/2004 |
| WO | WO-2007/140005 A2 | 12/2007 |
| WO | WO-2010005572 A2 | 1/2010 |
| WO | WO-2010039186 A2 | 4/2010 |

OTHER PUBLICATIONS

"International Application Serial No. PCT/US2012/023718, International Preliminary Report on Patentability mailed Aug. 15, 2013", 7 pgs.
"International Application Serial No. PCT/US/2012/023718, Search Report mailed May 29, 2012", 2 pgs.
"International Application Serial No. PCT/US2012/023718, Written Opinion mailed May 29, 2012", 5 pgs.
Ezzili, et al., abstract of "Reversible Competitive alpha-Ketoheterocycle Inhibitors of Fatty Acid Amide Hydrolase Containing Additional Conformational Constraints in the Acle Side Chain: Orally Active, Long-Acting Analgesics", Journal of Medicinal Chemistry, 2011, 54(8), pp. 2805-2822, (2011), 2 pgs.
"European Application Serial No. 12741464.7, Response filed Dec. 8, 2014 to Office Action mailed Jun. 2, 2014", 14 pgs.
"European Application Searial No. 12741464.7, Supplementary European Search Report mailed Jun. 2, 2014", 5 pgs.
Ezzili, Cyrine, et al., "Reversible Competitive α-Ketoheterocycle Inhibitors of Fatty Acid Amide Hydrolase Containing Additional Conformational Constraints in the Acyl Side Chain: Orally Active, Long-Acting Analgesics", *Journal of Medicinal Chemistry*, 54(8), (w/ supporting information), (2011), 2805-2822 (71 pgs.).
"Japanese Application Serial No. 2013-552663, Amendment filed Jan. 20, 2015", 30 pgs.
"Japanese Application Serial No. 2013-552663, Office Action mailed Dec. 16, 2015", 3 pgs.
"Japanese Application Serial No. 2013-552663, Response filed Nov. 20, 2015 to Office Action mailed Aug. 24, 2015", 22 pgs.
"Australian Application Serial No. 2012212088, Examination Report mailed Jul. 8, 2015", 2 pgs.
"Japanese Application Serial No. 2013-552663, Office Action mailed Aug. 24, 2015", (w/English Translation), 4 pgs.

*Primary Examiner* — Sarah Pihonak
*Assistant Examiner* — Jason A Deck
(74) *Attorney, Agent, or Firm* — Schwegman Lundberg & Woessner, P.A.

(57) ABSTRACT

Compounds are disclosed that are effective in inhibition of fatty acid amide hydrolase, an enzyme responsible for catabolism of endogenous cannabinoids such as anandamide. The compounds are useful as analgesic compounds and as sleep-inducing compounds, that can be orally administered, and that can have a relatively long duration of effect. Methods of preparation of the compounds are also provided. The compounds are conformationally constrained analogs of heterocyclylketones such as oxazolylketones.

23 Claims, 11 Drawing Sheets

ALPHA-KETOHETEROCYCLES AND METHODS OF MAKING AND USING

CROSS-REFERENCE TO RELATED APPLICATION

This application is a national stage application under 35 U.S.C. §371 of PCT/US2012/023718, filed Feb. 3, 2012, and published as WO 2012/106569 A1 on Aug. 9, 2012, which claims the benefit of priority of U.S. patent application Ser. No. 61/439,415, entitled "ALPHA-KETOHETEROCYCLES HAVING ANALGESIC ACTIVITY," filed on Feb. 4, 2011, which applications and publication are incorporated by reference as if reproduced herein and made a part hereof in their entirety, and the benefit of priority of each of which is claimed herein.

STATEMENT OF GOVERNMENT SUPPORT

This invention was made with government support under grant number DA015648, awarded by the National Institutes of Health. The U.S. government has certain rights in the invention.

BACKGROUND

Fatty acid amide hydrolase (FAAH) serves as the catabolic regulator of several endogenous lipid amides including anandamide (1a) and oleamide (1b), below. Its distribution is consistent with its role in hydrolyzing and regulating such signaling fatty acid amides at their sites of action. Although it is a member of the amidase signature family of serine hydrolases for which there are a number of prokaryotic enzymes, it is the only well characterized mammalian enzyme bearing the family's unusual Ser-Ser-Lys catalytic triad.

Substrates of Fatty Acid Amide Hydrolase (FAAH):

of selective inhibitors of the enzyme. Early studies following the initial characterization of the enzyme led to the discovery that the endogenous sleep-inducing molecule 2-octyl α-bromoacetoacetate is an effective FAAH inhibitor, and the disclosure of a series of nonselective reversible inhibitors bearing an electrophilic ketone. Subsequent studies have defined two major classes of inhibitors that provide opportunities for the development of inhibitors with greater therapeutic potential. One class is the reactive aryl carbamates and ureas that irreversibly acylate a FAAH active site serine and that have been shown to exhibit anxiolytic activity and produce antinociceptive effects. A second class is the α-ketoheterocycle-based inhibitors that bind to FAAH by reversible hemiketal formation with an active site serine.

Compound 2 (OL-135), which is disclosed and claimed in U.S. Pat. No. 7,662,971 by certain of the inventors herein,

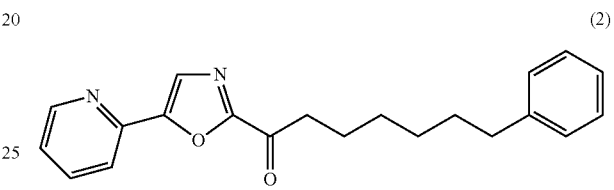

(2)

is a FAAH inhibitor that induces analgesia and increases endogenous anandamide levels. It exhibits antinociceptive and anti-inflammatory activity in a range of preclinical animal models that include the tail flick assay, hot plate assay, formalin test of noxious chemical pain ($1^{st}$ and $2^{nd}$ phase), the mild thermal injury (MTI) model of peripheral pain, the spinal nerve ligation (SNL) and chronic constriction injury (CCI) models of neuropathic pain, and an inflammatory model of pruritus with good efficacy.

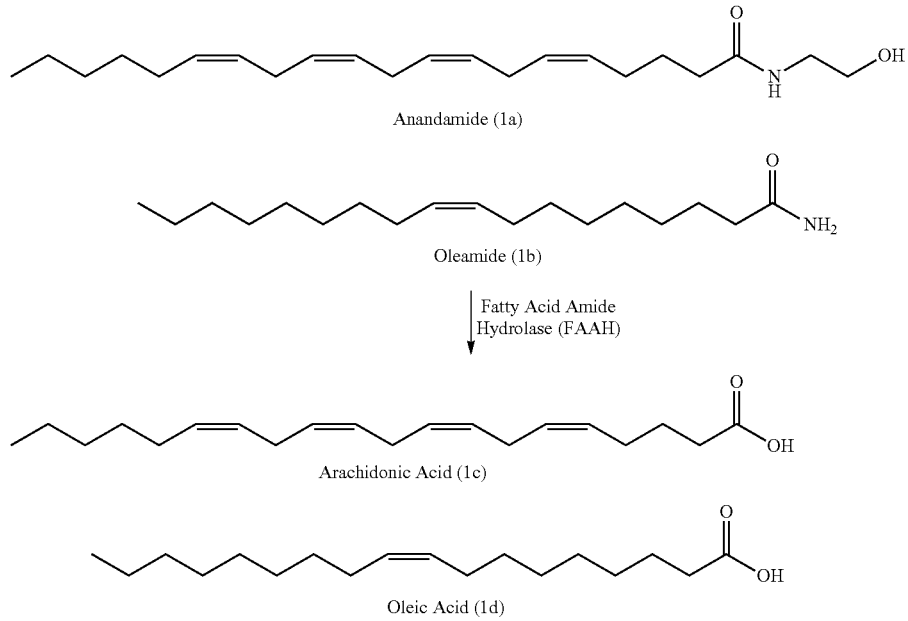

Due to the therapeutic potential of inhibiting FAAH for the treatment of pain inflammation, or sleep disorders, for example, there has been growing interest in the development There is a need, however, for improved antinociceptive compounds that is believed can be filled by FAAH inhibitors having appropriate characteristics.

SUMMARY

The present invention is directed in various embodiments to compounds that inhibit the enzymatic activity of fatty acid amide hydrolase (FAAH), to methods of preparing the compounds, and to methods of using the compounds for medicinal purposes, such as in the amelioration of pain as experienced by patients suffering therefrom, or in the treatment of sleep disorders by patients. In various embodiments, compounds of the invention are found to be, at effective doses, potent analgesic compounds, orally active, and therefore useful for the management of pain resulting from injury or disease. Compounds of the invention can also be used to induce sleep or for treatment of sleep disorders.

In various embodiments, the invention provides compounds of the general formula (I),

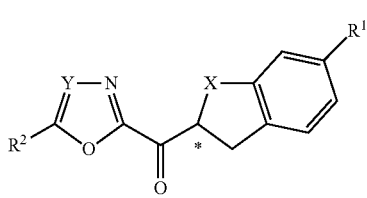

wherein the variables are as described herein, and methods of synthesis thereof.

In various embodiments, methods of treatment are provided comprising administration of effective amounts of the compounds to patients, wherein the compounds can inhibit the enzymatic activity of FAAH, which is believed to boost tissue levels of pain-ameliorating naturally occurring fatty acid amides such as anandamide.

DETAILED DESCRIPTION

Definitions

Figure 1:
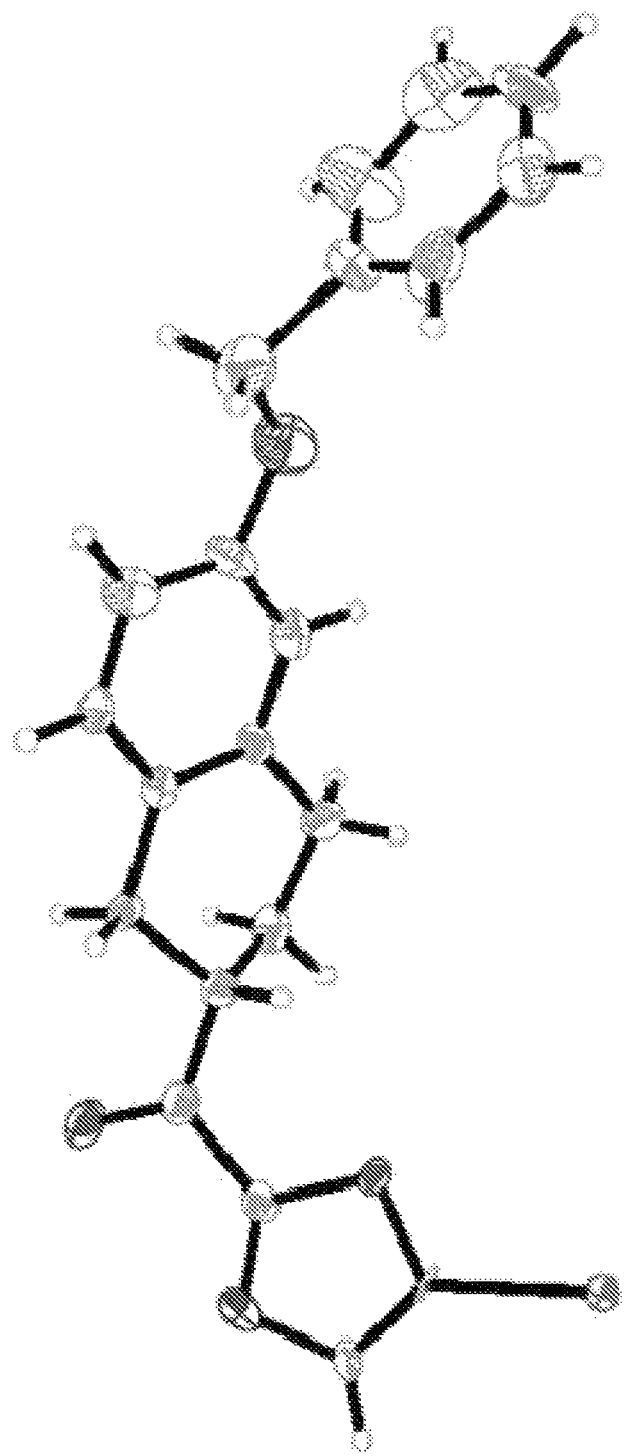
FIG. 1 shows an X-ray crystal structure of compound 21. This enantiomer was shown to be a more potent inhibitor of FAAH.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) or "patient" means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein a fatty acid amide hydrolase enzyme (FAAH) plays a role in the biochemical mechanisms involved in the disease or malcondition or symptom(s) thereof, such that a therapeutically beneficial effect can be achieved by acting on FAAH. "Acting on" FAAH, or "modulating" FAAH, can include binding to FAAH and/or inhibiting the bioactivity of FAAH and/or allosterically regulating the bioactivity of FAAH in vivo. For example, a malcondition can include pain, i.e., the perception of a painful stimulus, by a patient, regardless of the cause of the pain, be it injury, disease, neurological pathology, or the like.

Compounds of the present invention possess nociceptive, i.e., analgesic medicinal properties, interfering with the perception of pain by the patient. Compounds having such bioactivities are referred to herein as "analgesics", i.e., pain-killing compounds. Compounds of the invention can possess analgesic bioactivity when administered alone. They need not be administered in combination with a second analgesic compound such as an opiate or a cannabinoid, but can themselves exert an analgesic effect on the patient directly. Likewise, compounds of the invention can be used alone for inducing sleep or for treatment of sleep disorders without a need for administering any other compound to the patient.

An analgesic or sleep-inducing compound is said to possess "long-lasting" properties if the duration of the bioactivity following administration of an effective amount of a compound of the invention is longer than that of a standard analgesic or sleep-inducing compound, e.g., morphine, which is in the order of a few hours for most patients at most dosages. Certain compounds of the invention can have long-lasting bioactivity when administered to a patient, e.g, orally administered. Other compounds of the invention can exhibit analgesic bioactivity of normal or typical duration, a few hours, when administered to a patient.

The expression "effective amount", when used to describe therapy to an individual suffering from a disorder such as pain and the perception thereof refers to an amount or concentration of a compound of the invention that is effective to inhibit, block, or interfere with the perception of pain by the patient, wherein such inhibition or other action occurs to an extent sufficient to produce a beneficial therapeutic effect such as analgesia.

A "therapeutically achievable concentration" as the term is used herein refers to a concentration of a compound of the invention in the tissue of a living patient that can be obtained by administration, orally or parenterally, single-dose or in repeated doses, of less than about 1 gram of the compound, i.e., using oral dosage forms or injectable dosage forms of an amount such as is typical in medicinal chemistry.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of pain symptoms associated with a disorder or disease or injury or neurological disorder in a patient, human or non-human. A cessation or decrease in the perception of pain is a beneficial therapeutic effect even when an underlying cause of the pain, e.g., a wound, is still present.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, N$_3$ (azido), CF$_3$, OCF$_3$, R', O (oxo), S (thiono), C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

C(O) and S(O)$_2$ groups can also be bound to one or two heteroatoms, such as nitrogen or oxygen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a "urea." When a C(O) is bonded to one oxygen and one nitrogen atom, the resulting group is termed a "carbamate" or "urethane." When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself or of another substituent that itself recites the first substituent. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, —CH$_2$CH$_2$—S(=O)—CH$_3$, and —CH$_2$CH$_2$—O—CH$_2$CH$_2$—O—CH$_3$. Up to two heteroatoms may be consecutive, such as, for example, —CH$_2$—NH—OCH$_3$, or —CH$_2$—CH$_2$—S—S—CH$_3$.

A "cycloheteroalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, —CH$_2$—CH=CH—CH$_2$—SH, and —CH=CH—O—CH$_2$CH$_2$—O—CH$_3$.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a C$_2$-heteroaryl can be a 5-ring with two carbon atoms and three heteroatoms, a 6-ring with two carbon atoms and four heteroatoms and so forth. Likewise a C$_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "$(C_x\text{-}C_y)$perfluoroalkyl," wherein x<y, means an alkyl group with a minimum of x carbon atoms and a maximum of y carbon atoms, wherein all hydrogen atoms are replaced by fluorine atoms. Preferred is —$(C_1\text{-}C_6)$perfluoroalkyl, more preferred is —$(C_1\text{-}C_3)$perfluoroalkyl, most preferred is —$CF_3$.

The term "$(C_x\text{-}C_y)$perfluoroalkylene," wherein x<y, means an alkyl group with a minimum of x carbon atoms and a maximum of y carbon atoms, wherein all hydrogen atoms are replaced by fluorine atoms. Preferred is —$(C_1\text{-}C_6)$perfluoroalkylene, more preferred is —$(C_1\text{-}C_3)$perfluoroalkylene, most preferred is —$CF_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

An "amino" group is a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion NH$_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR$_2$, and —NRC(O)R groups, respectively. Amide groups therefore include but are not limited to primary carboxamide groups (—C(O)NH$_2$) and formamide groups (—NHC(O)H). A "carboxamido" group is a group of the formula C(O)NR$_2$, wherein R can be H, alkyl, aryl, etc.

The term "azido" refers to an N$_3$ group. An "azide" can be an organic azide or can be a salt of the azide (N$_3^-$) anion. The term "nitro" refers to an NO$_2$ group bonded to an organic moiety. The term "nitroso" refers to an NO group bonded to an organic moiety. The term nitrate refers to an ONO$_2$ group bonded to an organic moiety or to a salt of the nitrate (NO$_3^-$) anion.

The term "urethane" ("carbamoyl" or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), Int J. Pharm., 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present invention further embraces isolated compounds according to formula (I). The expression "isolated compound" refers to a preparation of a compound of formula (I), or a mixture of compounds according to formula (I), wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically.

Preferably an "isolated compound" refers to a preparation of a compound of formula (I) or a mixture of compounds according to formula (I), which contains the named compound or mixture of compounds according to formula (I) in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds of the Invention
Tautomerism

Within the present invention it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

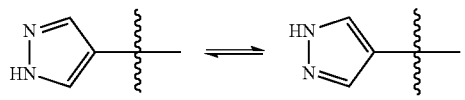

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

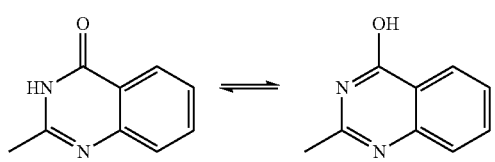

is an example of tautomerism. Accordingly, a structure depicted herein as one tautomer is intended to also include the other tautomer.

Optical Isomerism

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

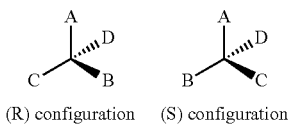

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

DETAILED DESCRIPTION

Herein, we report results of studies examining candidate inhibitors containing further conformational constraints in the C2 acyl side chain of compound 2 and related inhibitors. We describe the X-ray crystal structure characterization of a prototypical inhibitor in the series bound to the enzyme. Certain details of an in vivo characterization of two exemplary inhibitors of this series are also provided. These studies have resulted in the discovery of a new structural class of FAAH inhibitors, many of which having $IC_{50}$ values in the low nanomolar range, that can be orally administered to patients, and which can reduce the perception of pain. The inventors herein believe that the pain reduction is a result, at least in part, of the higher resulting concentrations of endogenous antinociceptive compounds such as anandamide and related fatty acid amides that arise when FAAH, their principal catabolic enzyme, is subjected to inhibition by the inventive compounds. Also, due to the role of fatty acid amides such as oleoylethanolamide and arachindonoylethanolamide in sleep, compounds of the invention believed to be capable of inducing sleep and therefore be useful in the treatment of sleep disorders.

In various embodiments, the invention provides a compound of formula (I)

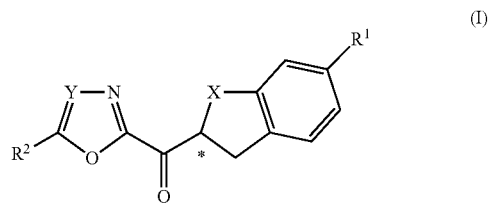

wherein:

$R^2$ is hydrogen, halo, haloalkyl, nitrile, C(O)OR', C(O)N(R')$_2$, aryl, or heteroaryl, wherein the aryl or heteroaryl is optionally mono- or independently multisubstituted with J;

X is (C1-C2) alkylene, wherein one of the carbon atoms of the alkylene can be replaced by O, NR', or S;

Y is CH or N;

$R^1$ is selected from the group consisting of H, aryl, —Z-aryl, heteroaryl, and —Z-heteroaryl, wherein Z is selected from $C_{1-6}$alkylene, oxy, —O—$C_{1-6}$alkylene, —S(O)$_w$, —S(O)$_w$—$C_{1-6}$alkylene, wherein w is 0, 1 or 2, NR', and alkyleneNR', wherein aryl or heteroaryl can be mono- or independently multi-substituted with J, or can be fused with a 5-7 membered cycloalkyl, heterocyclyl, aryl, or heteroaryl optionally further mono- or independently multi-substituted with J, or both;

* indicates a chiral carbon atom which can be of the S absolute configuration, the R absolute configuration, or any mixture thereof, including a racemic mixture;

J is selected from the group consisting of F, Cl, Br, I, OR', OC(O)N(R')$_2$, CN, NO, NO$_2$, ONO$_2$, N$_3$, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', and C(=NOR')R'; R' is independently at each occurrence selected from the group consisting of hydrogen, alkyl, acyl, cycloalkyl, aryl, aralkyl, heterocyclyl, heteroaryl, and heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J, wherein cycloalkyl, aryl, aralkyl, heterocyclyl, or heteroaryl can be fused or spiro with an independently selected cycloalkyl, aryl, aralkyl, heterocyclyl, or heteroaryl, any of which can be independently mono- or multi-substituted with J;

or a pharmaceutically acceptable salt thereof.

In various embodiments, the invention provides A compound of formula (I)

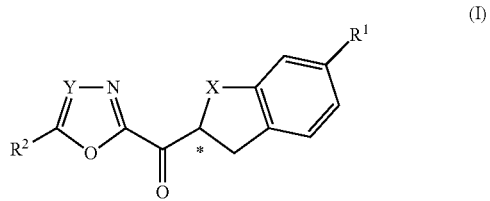

wherein:

R² is hydrogen, halo, haloalkyl, nitrile, C(O)OR', C(O)N (R')₂, aryl, or heteroaryl, wherein the aryl or heteroaryl is optionally mono- or independently multisubstituted with J;

X is (C1-C2) alkylene, wherein one of the carbon atoms of the alkylene can be replaced by O, NR', or S;

Y is CH or N;

R¹ is selected from the group consisting of H, aryl, —Z-aryl, heteroaryl, and —Z-heteroaryl, wherein Z is selected from $C_{1-6}$alkylene, oxy, —O—$C_{1-6}$alkylene, —S(O)$_w$, —S(O)$_w$—$C_{1-6}$alkylene, wherein w is 0, 1 or 2, NR', and alkyleneNR', wherein aryl or heteroaryl can be mono- or independently multi-substituted with J, or can be fused with a 5-7 membered cycloalkyl, heterocyclyl, aryl, or heteroaryl optionally further mono- or independently multi-substituted with J, or both;

* indicates a chiral carbon atom which can be of the S absolute configuration, the R absolute configuration, or any mixture thereof, including a racemic mixture;

J is selected from the group consisting of F, Cl, Br, I, OR', OC(O)N(R')₂, CN, NO, NO₂, ONO₂, N₃, CF₃. OCF₃, R', O, S, C(O), S(O), methylenedioxy, ethylenedioxy, N(R')₂, SR', SOR', SO₂R', SO₂N(R')₂, SO₃R', C(O)R', C(O)C(O)R', C(O)CH₂C(O)R', C(S)R', C(O)OR', OC(O)R', C(O)N(R')₂, OC(O)N(R')₂, C(S)N(R')₂, (CH₂)₀₋₂N(R')C(O)R', (CH₂)₀₋₂N(R')N(R')₂, N(R')N(R')C(O)R', N(R')N(R')C(O) OR', N(R')N(R')CON(R')₂, N(R')SO₂R', N(R')SO₂N(R')₂, N(R')C(O)OR', N(R')C(O)R', N(R')C(S)R', N(R')C(O) N(R')₂, N(R')C(S)N(R')₂, N(COR')COR', N(OR')R', C(=NH)N(R')₂, C(O)N(OR')R', and C(=NOR')R'; R' is selected, independently for each occurrence, from the group consisting of hydrogen, $C_{1-6}$alkyl, acyl, $C_{3-6}$cycloalkyl, $C_{2-6}$alkenyl, phenyl, heterocyclyl, heteroaryl, and heteroarylalkyl, wherein alkyl, acyl, cycloalkyl, phenyl, heterocyclyl, heteroaryl, or heteroarylalkyl is optionally substituted with one, two or three substituents selected from the group consisting of halogen, cyano, hydroxyl, phenyl, and heterocyclyl, or wherein two R' groups, when bonded to a nitrogen atom or to two adjacent nitrogen atoms can together with the nitrogen atom or atoms form a heterocyclyl, which is optionally mono- or independently multi-substituted with one, two or three substitutents selected from the group consisting of halogen, hydroxyl, cyano, $C_{1-6}$alkyl, acyl, $C_{3-6}$cycloalkyl, $C_{2-6}$alkenyl, phenyl, and heterocyclyl;

or a pharmaceutically acceptable salt thereof.

More specifically, in various embodiments the invention provides a compound of formula (I) wherein R² is heteroaryl; more exactly, R² can be pyridyl, such as a 2-, 3-, or 4-pyridyl, wherein any pyridyl can be mono- or independently multi-substituted with J, and any pyridyl can be fused with a 5-7 membered cycloalkyl, heterocyclyl, aryl, or heteroaryl, any of which cycloalkyl, heterocyclyl, aryl, or heteroaryl can be further mono- or independently multi-substituted with J.

For example, in some embodiments, R' is selected, independently for each occurrence, from the group consisting of hydrogen, $C_{1-6}$-alkyl, acyl, $C_{3-6}$cycloalkyl, $C_{2-6}$alkenyl, phenyl, heterocyclyl, heteroaryl, or heteroarylalkyl, wherein alkyl, acyl, cycloalkyl, phenyl, heterocyclyl, heteroaryl, or heteroarylalkyl may be optionally substituted with; one, two or three substituents selected from the group consisting of halogen, cyano, hydroxyl, phenyl, heterocyclyl, or wherein two R' groups, when bonded to a nitrogen atom or to adjacent nitrogen atoms can together with the nitrogen atom or atoms form a heterocyclyl, which can be mono- or independently multi-substituted with one, two or three substitutents selected from the group consisting of halogen, hydroxyl, cyano, $C_{1-6}$alkyl, acyl, $C_{3-6}$cycloalkyl, $C_{2-6}$alkenyl, phenyl, or heterocyclyl.

In various embodiments, R² is 2-pyridyl, optionally mono- or independently multi-substituted with J. More specifically, the 2-pyridyl can be unsubstituted or is substituted with a carboxylic acid, alkoxycarbonyl or carboxamido group.

For example, R² is

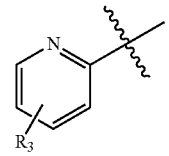

wherein R³ is selected from the group consisting of hydrogen, halo, hydroxyl, cyano, $C_{1-6}$alkyl, $C_{2-6}$alkenyl, and —C(O)O—R⁴, wherein R⁴ is H or $C_{1-4}$alkyl, and wherein a wavy line indicates a point of bonding.

For example, R² can selected from the set consisting of

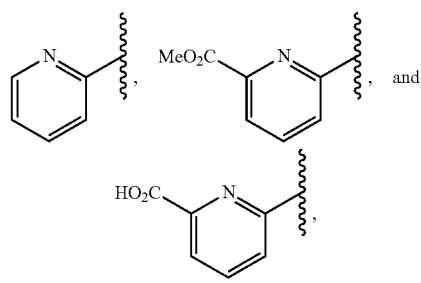

wherein a wavy line indicates a point of attachment.

In various embodiments, the bridging group X can be a (C1-C2)alkyl group. For instance, X can be CH₂ or CH₂CH₂, providing an indane or a tetrahydronaphthalene respectively. The bridge group, bonded to the ketone α-carbon, forms a chiral carbon center, which can be of either absolute configuration, or a mixture thereof. In various embodiments, the chiral center is of the S absolute configuration. In many examples, the S-isomer possesses an FAAH-inhibitory bioactivity orders of magnitude greater than that of the comparable R-isomer. As it is possible, due to the rules for assigning S and R designations, that disposition of a substituent on the X bridge would result in a change in the designation of the absolute configuration at that chiral carbon center, for clarity what is meant for such analogs is that the chiral center has the same configuration in space as is defined by the S isomer of the unsubstituted molecule. Accordingly, if a carbon atom of the bridge is replaced by a heteroatom such as O, it is believed that the FAAH-inhibitory bioactivity would be greater for the molecule having the S configuration as defined for the all-carbon bridge, even though the formal designation might change.

In various embodiments, $R^1$ is aryl, aryl-Z, heteroaryl, or heteroaryl-Z, wherein Z is alkylene, oxy, alkyleneoxy, thio, alkylenethio, NR', or alkyleneNR', wherein any of which aryl, or heteroaryl, can be mono- or independently multi-substituted with J, or can be fused with a 5-7 membered cycloalkyl, heterocyclyl, aryl, or heteroaryl optionally further mono- or independently multi-substituted with J, or both; More specifically, $R^1$ can be phenyl, phenoxy, or benzyloxy, any of which optionally mono- or independently multi-substituted with J.

In various embodiments, the compound is any of the following compounds can be any of the compounds shown below in the list of Exemplary Compounds of the Invention 3-40.

Synthetic Methods and Bioactivity Evaluations

A general method for the synthesis of the oxazole-based inhibitors bearing a C5 substituent, such as an aryl or heteroaryl substituent, and containing a ring resulting in a conformational restriction of the C2 acyl side chain, is shown in Scheme 1, below. By C2 is meant that the acyl group is bonded to C2 of the heterocyclyl, i.e., oxazole or oxadiazole ring nucleus, analogous to the configuration of compound 2, above. The inhibitors can contain a tetrahydronaphthalene or indane ring system bonded to the C2 acyl chain, which as a result includes a chiral center adjacent to the electrophilic carbonyl, and which can bear pendant aryl or heteroaryl groups as substituents of the aryl ring of the tetrahydronaphthalene or indane ring system. In the below Scheme 1, the pendant substituent is shown meta to the X bridge, but can be in any position.

Scheme 1: Synthetic approaches to indane and tetrahydronaphthalene 5-aryloxazoles

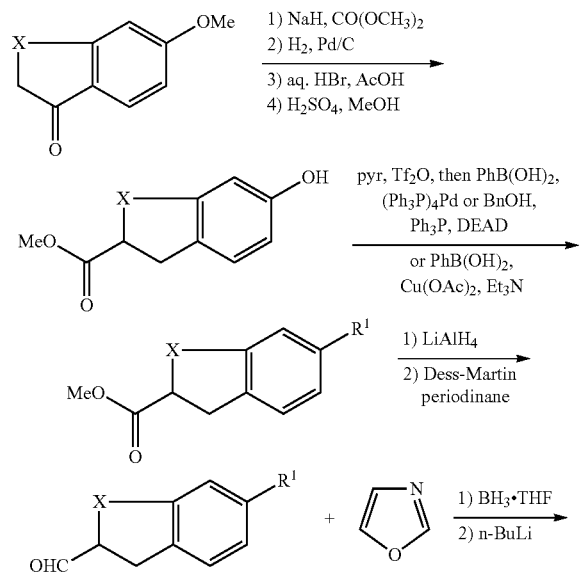

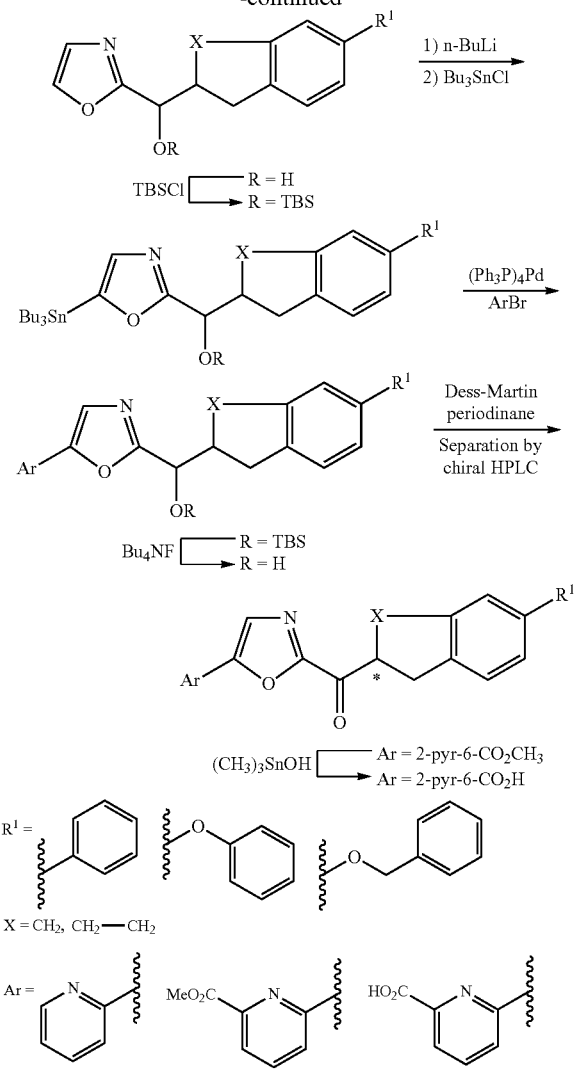

The synthesis of this class of compounds can be carried out as follows. Preparation of analogs can be carried out using alternative reagents and procedures, including the use of appropriate protecting groups, such as are apparent to a person of ordinary skill in the art of organic synthesis. Introduction of a methyl ester α to the ketone of the commercially available 6-methoxytetralone or 6-methoxyindanone proceeded as reported using dimethylcarbonate and NaH, and was followed by reduction of the cyclic ketone using $H_2$ and Pd/C. Simultaneous deprotection of the aryl methyl ether and the methyl ester with aqueous HBr in HOAc yielded the phenolic carboxylic acid. Esterification of the carboxylic acid using $H_2SO_4$ and MeOH afforded the advanced phenol intermediates on which the varied aryl substituent was added. A Suzuki coupling with phenylboronic acid via the corresponding triflate intermediate, a Mitsunobu alkylation of the phenol with benzyl alcohol and $Ph_3P$-DEAD, and a modified Ullmann reaction of the phenol with phenylboronic acid yielded the corresponding 6-phenyl, 6-benzyloxy, and 6-phenoxy-1,2,3,4-tetrahydronapthalenes and indanes, respectively. Reduction of the methyl ester to the primary alcohol using $LiAlH_4$ followed by oxidation with Dess-Martin periodinane gave the corresponding aldehyde. Vedejs oxazole metalation and condensation with the various C2 side chain aldehydes was followed by TBS protection of the resulting alcohols. Selective C5-oxazole lithiation of these intermediates followed by treatment with $Bu_3SnCl$ afforded the corresponding C5 tributylstannanes. Stille coupling of the stannane intermediates with pyridine halides produced the C5-substituted oxazoles, which could be readily converted to the corresponding ketones by TBS ether deprotection ($Bu_4NF$) and oxidation of the liberated alcohol with Dess-Martin periodinane.

These candidate inhibitors were separated into their two enantiomers by resolution on a semipreparative Chiracel OD or AD column. The candidate inhibitors containing a methyl ester were then converted to their corresponding carboxylic acid using $(CH_3)_3SnOH$. This reagent and the conditions employed resulted in minimal racemization of the chiral center whereas the conventional use of LiOH (1 equiv, $THF/H_2O$ 3:2, 25° C.) resulted in more extensive racemization.

The synthesis of candidate inhibitors that bear a non-aromatic oxazole C5-substituent is summarized in Scheme 2, below. The synthetic scheme is illustrated for oxazoles bearing a 5-substituent including a hydrogen, a carboxy ester, and a nitrile. However, compounds bearing other substituents, such as alkyls, carboxamides, and other groups, can be prepared by the person of ordinary skill using appropriate reagents and procedures such as are known and reported in the literature. Following oxazole C5-lithiation, treatment with Mander's reagent ($NCCO_2Me$) provided the corresponding C5-substituted oxazoles bearing a methoxycarbonyl group in good conversions. In each case, deprotection of the TBS ether followed by Dess-Martin periodinane oxidation of the liberated alcohol yielded the corresponding α-ketooxazole. The methyl esters were also converted to the corresponding carboxamides by treatment with $NH_3$—$CH_3OH$ and the carboxamides were dehydrated with TFAA and pyridine to provide the C5 nitriles that were converted to the α-ketooxazoles as well. These derivatives were separated into their two enantiomers by resolution on a semipreparative Chiracel OD or AD column.

Scheme 2: Synthetic approaches to indane and tetrahydronaphthalene oxazoles lacking 5-aryls

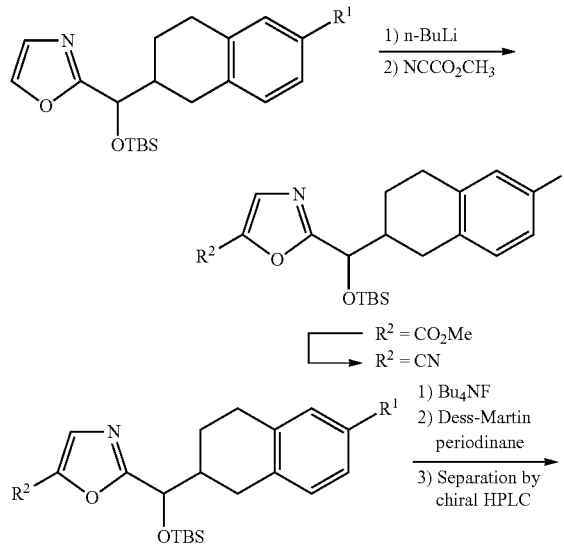

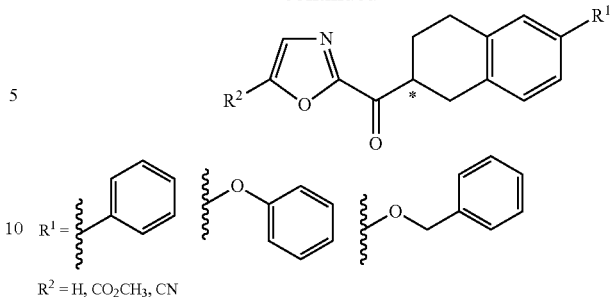

$R^2$ = H, $CO_2CH_3$, CN

Enzyme assays, determining $IC_{50}$ values for inhibition of FAAH, were carried out on representative compounds of these series as described in the Examples, below. Certain of the inventors herein had previously discovered that some of the most potent inhibitors previously discovered contained conformational constraints in the flexible C2 acyl side chain of compounds analogous to compound 2. This domain of the inhibitor molecule is believed to bind in a hydrophobic channel of the FAAH active site evolved to bind the unsaturated lipid chain of the natural fatty acid amide substrates. Three improved C2 side chains previously identified (Table 1) were now incorporated into the candidate inhibitors that contain a 1,2,3,4-tetrahydronaphthalene or indane core and were combined with representative or optimized C5 oxazole substituents that were found to impact inhibitor potency, selectivity, and physical properties.

TABLE 1

Prior constraints in the C2 acyl side chain and impact of the terminal aryl substituent.

| X | $K_i$, μM | X | $K_i$, μM |
|---|---|---|---|
| $CH_2O$ | 0.0010 | $CH_2$ | 0.0032 |
| O | 0.0034 | S | 0.0022 |
| NH | 0.002 | $OCH_2$ | 0.0013 |
| biphenyl derivative → | — | | 0.00075 |

$K_i$ = 0.20 μM[53]

Compounds of the Tetrahydronaphthalene Series.

The series examined include the 6-phenyl, 6-phenoxy, and 6-benzyloxy-1,2,3,4-tetrahydronaphthalene C2 acyl side chains combined with a set of representative oxazole C5-substituents. For each derivative, the racemic mixture as well as the pure enantiomers were prepared and examined, but only the results of the examination of the individual enantiomers are reported in Table 2. In each instance, it was the slower eluting, second enantiomer obtained from chromatographic resolution (Chiralcel OD or AD) that was found to be more potent and, as detailed later, it was established to be the (S)-enantiomer. Thus, the inhibitors displayed a consistently more potent activity for the assigned (S)-enantiomer that was of a magnitude and range (10-400 fold, avg=70-fold) that suggests the observed activity for the less active (R)-enantiomer is not distinguishable from that potentially derived from contaminant (S)-enantiomer in the assayed samples. For each oxazole C5-substituent, the potency of the (S)-enantiomers of the C2 acyl side chain aryl substituents consistently followed the order phenoxy>benzyloxy>phenyl indicating that the added conformational constraints in the C2 acyl linking chain has subtly reordered this aryl substituent preference (Table 2). Here the distinctions between a phenoxy and benzyloxy substituent are small (typically 1.4-4 fold), whereas the differences with the less active and more rigid phenyl substituent are larger and more easily distinguished. Interestingly, and unlike observations made with respect to compound 2, the impact of the oxazole C5-substituent on the activity in each series is much more modest, although it is most significant in the less active biaryl series. However, the trends for the oxazole C5-substituent, but not their magnitude, are maintained in these series and most significant is the enhanced potency observed with inhibitors that lack the C5 substituent. This suggests that beneficial enhancements in binding affinity in this series are gained by the C2 acyl side conformational restriction and the added hydrophobic interactions of the tetrahydronaphthalene.

In order to establish the absolute stereochemical assignment for the active enantiomer, an inhibitor in 6-benzyloxy-1,2,3,4-tetrahydronaphthalene series was prepared with an iodo substituent at the oxazole C5 position following the general procedure described earlier, Scheme 1. The racemic mixture and the pure enantiomers were tested for FAAH inhibition and one enantiomer was found to be ca. 200-fold more active. Its structure and absolute stereochemistry were established with an X-ray crystal structure determination indicating that the most potent enantiomer is the (S)-enantiomer, Scheme 3. The X-ray structure is shown in FIG. 1. A star identifies the chiral carbon center. With 21, the activity of the less potent (R)-enantiomer as isolated cannot be distinguished from potential contaminate (S)-enantiomer (0.5%) in the assay sample, and this comparison indicates that the active (S)-enantiomers may be ≥200-fold more active than the corresponding (R)-enantiomers.

Scheme 3: Synthesis and Bioactivity of Compound 21 Enantiomers

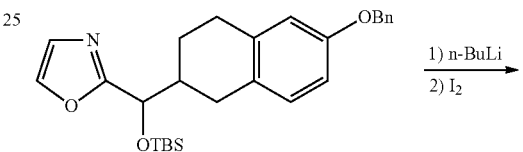

TABLE 2

FAAH inhibitors with 1,2,3,4-tetrahydronaphthalene C2 acyl side chain, $K_i$ (nM).

| $R^1$ | $R^2$ = phenyl | | $R^2$ = phenoxy | | $R^2$ = benzyloxy | |
|---|---|---|---|---|---|---|
| | (S) | (R) | (S) | (R) | (S) | (R) |
| —H | 57 | 460 (3) | 2.2 | 410 (9) | 6.1 | 87 (15) |
| —CO$_2$Me | 55 | 1400 (4) | 5.4 | 59 (10) | 2.9 | 53 (16) |
| —CN | 3.4 | 62 (5) | 1.3 | 54 (11) | 3.2 | 120 (17) |
| pyridin-2-yl | 7.2 | 240 (6) | 4.4 | 290 (12) | 3.2 | 300 (18) |
| MeO$_2$C-pyridinyl | 27 | 700 (7) | 2.2 | 870 (13) | 18 | 4500 (19) |
| HO$_2$C-pyridinyl | 39 | 500 (8) | 25 | 220 (14) | 34 | 740 (20) |

* indicates a chiral carbon center

-continued

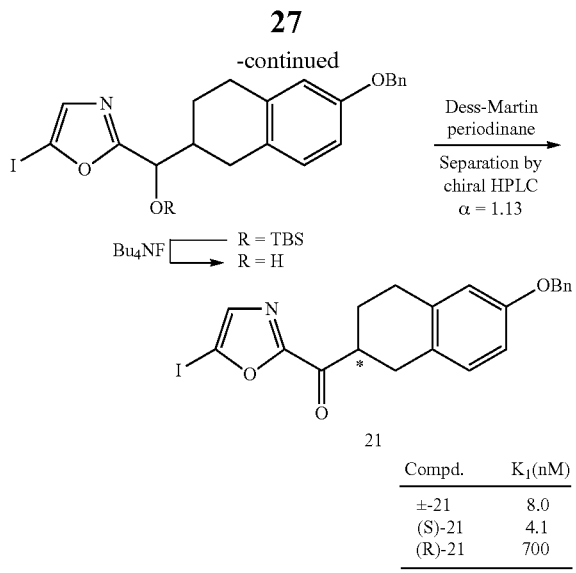

| Compd. | $K_i$(nM) |
| --- | --- |
| ±-21 | 8.0 |
| (S)-21 | 4.1 |
| (R)-21 | 700 |

Compounds of the Indane Series.

An analogous series of related inhibitors containing the 5-phenyl, 5-phenoxy, and 5-benzyloxyindane acyl chains was examined, Table 3.

In several instances, the diastereomeric mixture of racemic alcohols used as the penultimate precursors to the α-ketoheterocycles 15, 19, 30, and 32 were also assessed for FAAH inhibition and all were found to be inactive ($K_i$>10 μM) confirming the importance of the electrophilic carbonyl.

A set of additional derivatives in the 6-phenoxy-1,2,3,4-tetrahydronaphthalene series were examined that incorporate a 1,3,4-oxadiazole as the central activating heterocycle. In earlier studies, comprehensive systematic changes in the central activating heterocycle of 2 were examined and found to significantly influence the inhibitor activity with the 1,3,4-oxadiazole derivatives providing extraordinarily potent inhibitors. Accordingly, the preparation of a representative small series of 1,3,4-oxadiazoles containing the 6-phenoxy-1,2,3,4-tetrahydronaphthalene side chain was conducted and is illustrated in Scheme 4. Reaction of the C2 side chain aldehyde with KCN afforded the corresponding cyanohydrin and was followed by conversion of the nitrile to the methyl ester. TBS protection of the alcohol followed by saponification of the methyl ester yielded the carboxylic acid that was condensed with a series of hydrazides in a reaction promoted by EDCI to provide the diacyl hydrazide intermediates. These intermediates were cyclized to the corresponding 1,3,4-oxadiazoles upon treatment with

TABLE 3

FAAH inhibitors with indane C2 acyl side chain, $K_i$ (nM).

| $R^1$ | $R^2 = $ phenyl | | $R^2 = $ phenoxy | | $R^2 = $ benzyloxy | |
| --- | --- | --- | --- | --- | --- | --- |
| | (S) | (R) | (S) | (R) | (S) | (R) |
| —H | 27 | 140 (22) | 10 | 200 (26) | 24[a] | (30) |
| 2-pyridyl | 1.9 | 600 (23) | 2.1 | 42 (27) | 1.4 | 110 (31) |
| MeO$_2$C-pyridyl | 6.2[a] | (24) | 98 | 790 (28) | 5.8 | 130 (32) |
| HO$_2$C-pyridyl | 57[a] | (25) | 71 | 550 (29) | 51 | 660 (33) |

[a]Racemate. Enantiomers not separable.

This series exhibited an analogous enantiomeric selectivity with the tentatively assigned (S)-enantiomers being on average 60-fold (10-320 fold, avg=60-fold) more potent than the corresponding (R)-enantiomers, and they approached or matched the potency of the corresponding inhibitors bearing the 1,2,3,4-tetrahydronaphthalene C2 acyl chain core.

p-toluenesulfonyl chloride (TsCl) and Et$_3$N. The desired α-keto-1,3,4-oxadiazoles were obtained after TBS ether deprotection (Bu$_4$NF or TASF) and oxidation of the liberated alcohol with Dess-Martin periodinane. These derivatives were separated into their two enantiomers by resolution on a semipreparative Chiracel OD column.

Scheme 4: Synthesis of 1,3,4-oxadiazoles

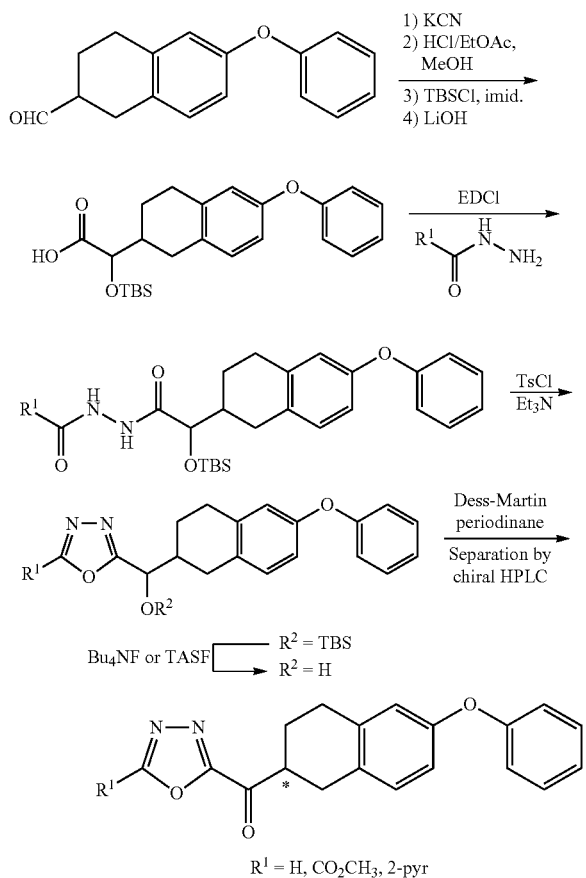

$R^1$ = H, $CO_2CH_3$, 2-pyr

For comparison purposes, a series of derivatives were prepared and examined that lack an aryl substituent on the acyl side chain 1,2,3,4-tetrahydronaphthalene or indane core. Their synthesis entailed Vedejs C2-lithiation of oxazole followed by condensation of the corresponding aldehyde and TBS protection of the resulting alcohol. Selective oxazole C5-lithiation (n-BuLi) followed by treatment with $Bu_3SnCl$ afforded the corresponding tributylstannane intermediates. Subsequent Stille coupling with 2-bromopyridine produced the C5 substituted oxazoles, which were converted to the corresponding ketones by TBS ether deprotection ($Bu_4NF$) and oxidation of the liberated alcohols using Dess-Martin periodinane, Scheme 5. The 1,2,3,4-tetrahydronaphthalene derivatives were separated into their two enantiomers by resolution on a semipreparative Chiracel OD column. The indane derivatives are meso compounds and no resolution is required.

Scheme 5: Synthesis of compounds lacking indane/tetrahydronaphthalene aryl substituent

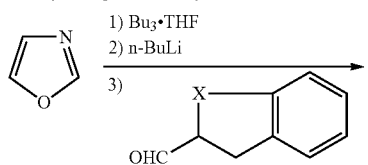

$R^1$ = H, 2-pyr
X = $CH_2$, $CH_2$—$CH_2$

The results of the examination of these derivatives are summarized in Table 4. The incorporation of the activating 1,3,4-oxadiazole heterocycle in the 6-phenoxy-1,2,3,4-tetrahydronaphthalene series further enhanced the activity of the candidate inhibitors providing extraordinarily potent inhibitors. This was most evident with 37, lacking a 1,3,4-oxadiazole C5-substituent, that exhibited a $K_i$ of 500 μM (0.5 nM) for the more potent (S)-enantiomer, representing a 4-5 fold improvement in potency relative to the corresponding oxazole 9. In this series, the measured differences between the (S)- and (R)-enantiomers proved modest, indicating that a well-precedented enhanced racemization of the 1,3,4-oxadiazole most likely occurs under the conditions (pH 9) and time course of the assay because of the stronger electron-withdrawing properties of the activating heterocycle.

Figure 3B:
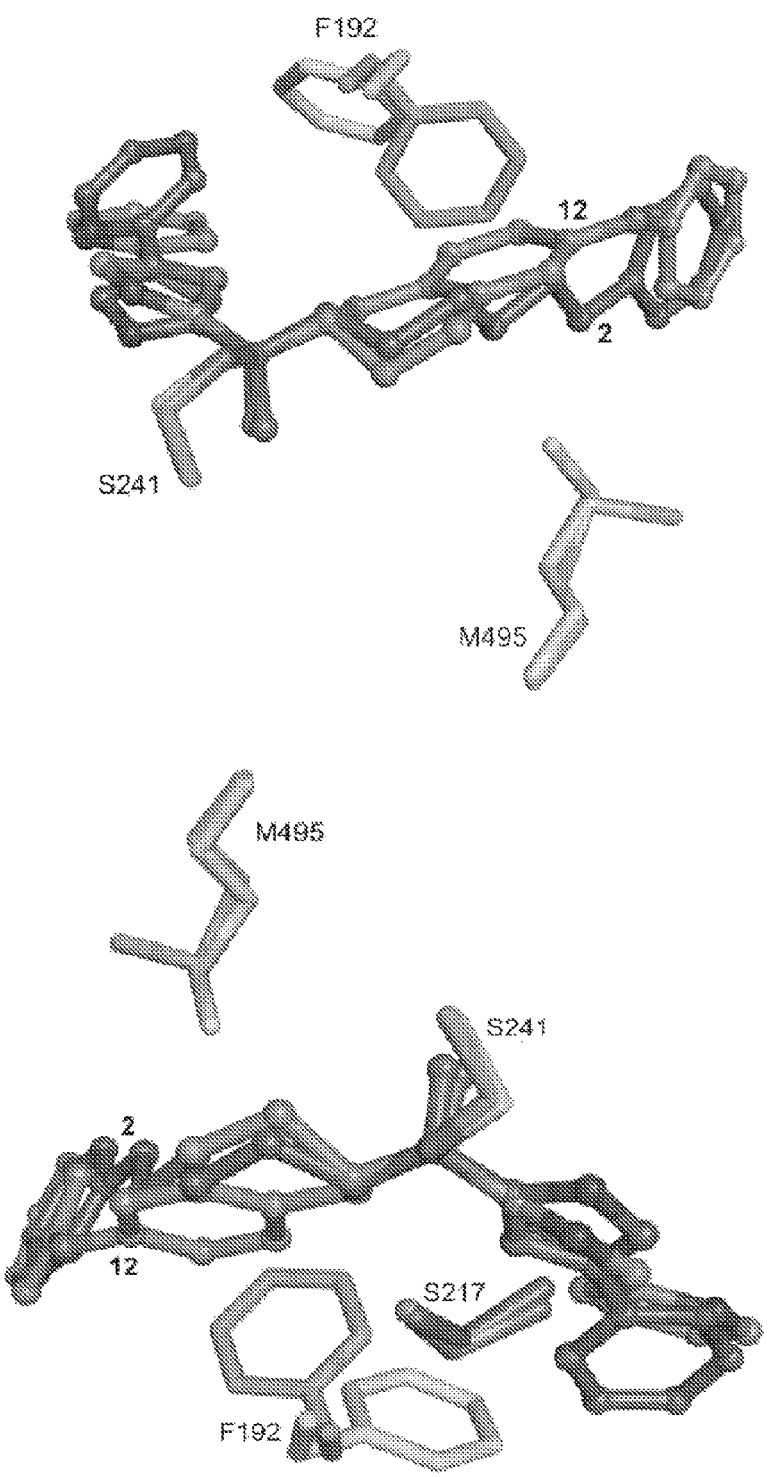
FIG. 3 shows two views of the superposition of the FAAH-12 complex with FAAH-2 complex[76]. The rearrangement of Phe192 and Met495 residues are shown.

For the candidate inhibitors without an acyl side chain aryl substituent, a substantial loss in potency (from nM to μM range) is observed highlighting the importance of its anchoring interaction within the enzyme active site, see Table 4, below. Notably, 38 (2-fold, $K_i$=430 nM) and 40 (5-fold, $K_i$=1.1 μM) approach the activity of the FAAH inhibitor lacking the conformational constraints ($K_i$=200 nM, FIG. 3) indicating that their introduction may subtly, but not seriously, affect their active site affinity. More interestingly, the enantiomer distinctions with 37 were modest (5.1 vs 12 μM, ca. 2-fold). As revealed in the X-ray structure of 12 bound to FAAH, it is the spatial relationship of the dominant anchoring C6-phenoxy substituent of 12 with the chiral center that imposes the enantiomeric selectivity observed in the tetrahydronaphthalene or indane series. Additionally, the introduction of the oxazole C5 pyridyl substituent increased the potency 7-12 fold compared to their unsubstituted counterparts in this series (38 vs 37 and 40 vs 39), analogous to prior observations, suggesting the hydrogen-bond capability of the weakly basic pyridyl substitutent is responsible for their enhanced affinities.

and open membrane access channel with truncation of the acyl chain-binding pocket. The α, β, and γ carbons of the

TABLE 4

Additional FAAH inhibitors, $K_i$ (nM)

| R | (S) | (R) | | (S) | (R) | | meso | |
|---|---|---|---|---|---|---|---|---|
| —H | 0.5 | 1.4 | (34) | 5100 | 12000 | (37) | 7100 | (39) |
| —CO$_2$Me | 1.5 | 1.6 | (35) | — | | | — | |
| 2-pyridyl | 1.0 | 6.3 | (36) | 430 | 3200 | (38) | 1100 | (40) |

Inhibition of Recombinant Human FAAH

Rat and human FAAH are very homologous (82% sequence identity), exhibit near identical substrate selectivity and inhibitor sensitivity in our studies with the α-ketoheterocycles disclosed to date, and embody an identical amidase signature sequence, suggesting the observations made with rat FAAH (rFAAH) would be analogous to those made with human FAAH (hFAAH). Consequently, the active (S)-enantiomers of two representative inhibitors, 12 and 14, were examined with hFAAH and the results are summarized in Table 5. As observed with 2, no significant distinction was observed for 12, whereas 14 exhibited a modest 4-fold reduction in activity against the human enzyme.

TABLE 5

Inhibition of human versus rat fatty acid amide hydrolase (hFAAH vs rFAAH), $K_i$ (nM)

| Compound | rFAAH | hFAAH |
|---|---|---|
| 12 | 4.4 | 5.8 |
| 14 | 25 | 110 |

X-Ray Structure of the Active Enantiomer of Inhibitor 12 Bound to FAAH.

Figure 2A:
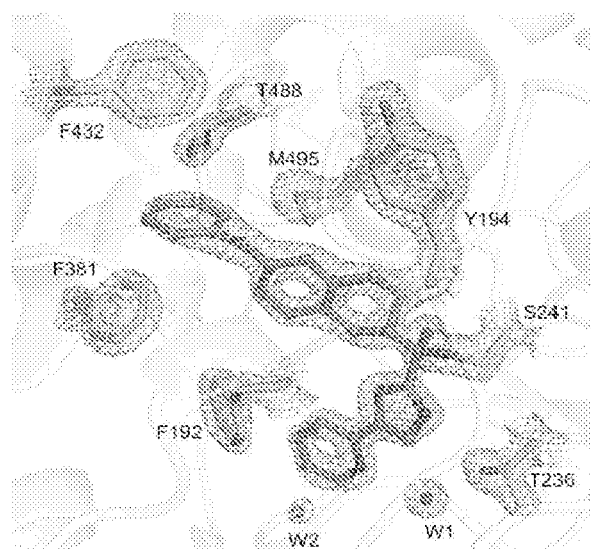
FIG. 2 shows: A: View of compound 12 in the binding pocket of FAAH and its interactions. B: An enlarged view of the chiral center within the tetrahydronaphthalene is shown. Electron density at 1.5σ contour is shown with white meshes.
Figure 2B:
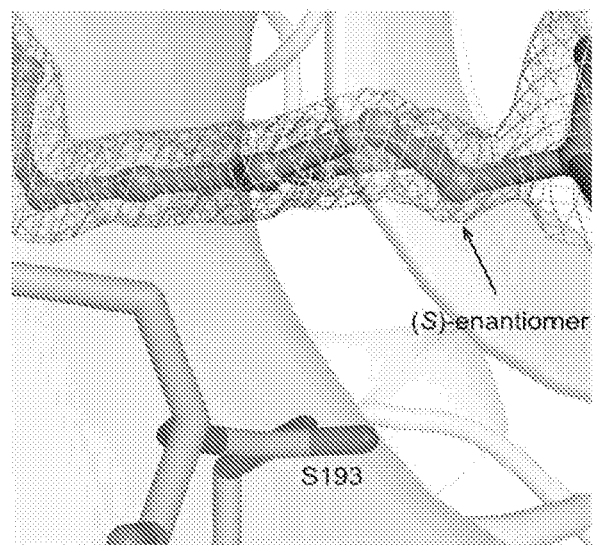

The X-ray structure of the active enantiomer of the α-ketooxazole 12 bound to h/rFAAH was solved at 1.9 Å resolution and the data processing and refinement statistics are summarized in below in the Examples. Compound 12 was found covalently attached to the catalytic Ser241 residue through its electrophilic carbonyl bound as a deprotonated hemiketal mimicking the enzymatic tetrahedral intermediate, a hallmark of the α-ketoheterocycle class of FAAH inhibitors. The electron density of the bound inhibitor and its excellent resolution provide an unambiguous depiction of the chiral center of 12 confirming that it is the (S)-enantiomer, see FIGS. 2A and 2B. A structural overlay of the X-ray crystal structure of 2 and 12 is provided in FIG. 3. The terminal phenyl ring of the acyl side chain of 12 is positioned in the same plane and only slightly shifted (0.6 Å) from the analogous group of 2, FIG. 3. This phenyl group serves as a key anchoring interaction with FAAH, which adopts an active site conformation that leads to a broadened and open membrane access channel with truncation of the acyl chain-binding pocket. The α, β, and γ carbons of the intervening flexible hydrophobic linker in the acyl side chain of 2, which adopt a gauche conformation, nearly superimpose with C2-C4 of the tetrahydronaphthalene core of 12, FIG. 3.

The backbone of the enzyme bound to 12 did not exhibit any major conformational changes relative to previously published structures, although two residues lining the active site undergo rearrangement. The most significant change is the relocation of the side chain of the Phe192 residue that rotates and shifts away from the compound acyl chain due to the size of the tetrahydronaphthalene core of 12, FIG. 3. This reorganization of the lining of the hydrophobic binding pocket, also observed in other structures, confirms that this residue is highly flexible and is likely a major adapter residue when binding different substrates and inhibitors. As a consequence of this rearrangement, the inhibitor oxazole C5-pyridyl substituent is pushed towards Ile238 and Leu278. In spite of this, the pyridyl nitrogen remains hydrogen-bonded to an ordered cytosolic port water molecule that in turn is hydrogen-bonded to Thr236, a feature that is conserved in all related structures analyzed to date. Interestingly, the space generated by the shift of the pyridine is compensated by the appearance of a new water molecule in the cytosolic port that had not appeared in earlier structures. It sits above the aromatic ring of the pyridine at a distance of 3.6 Å, and is coordinated, perhaps polarized, by the backbone amide of Cys269, previously identified as a key residue forming part of an anion binding site, FIG. 2. The activating oxazole and its attached pyridine substituent are bound in the cytosolic port, adopting bound orientations and a biaxial twist (18°) analogous to those found with 2 (15°) and related inhibitors. However, the unusual Ser217 OH hydrogen bond to the π-system of activating oxazole observed with 2 is now replaced with a hydrogen bond directly from Ser217 OH to the oxazole nitrogen in a fashion observed for histidine in serine proteases, FIG. 3. This change is not derived from a significant relocation of the Ser217 residue, but rather is a result of the reorientation of activating heterocycle (oxazole) and the displacement of its attached C5-pyridyl substituent. These offsetting changes, which still provide inhibitors more potent than 2, may account for the reason that the introduction of the pyridine substituent did not improve affinity in this series (12 vs 9 and 18 vs 15) although it still enhances their selectivity for FAAH. An additional change unique to this structure is the rearrangement of the distal rotamer of Met495, which now points towards the inhibitor and sits over the acyl chain linker aromatic ring at a distance of 4.4 Å, FIG. 3.

In order to establish the origin of the inhibitor enantiomer selectivity extrapolated from the crystal structure, molecular modeling studies were performed and used to calculate the relative energies involved in the binding of the two enantiomers. Covalent docking (ICM, Molsoft Inc.) of 12 with Ser241 and Monte Carlo simulations for sampling bound conformations were used to compare the two enantiomers of 12. As empirically predicted from the crystal structure analysis and established in the enzymatic assays, the (R)-enantiomer binding is destabilized relative to the (S)-enantiomer suffering from a large penalty in the van der Waals term (steric clash). Analysis of the contributions of single amino acids to the total binding energy established that this coincides predominately with a van der Waals repulsion with Ser193. When bound with the same orientation as (S)-12 and in order to maintain phenoxy binding at the terminus of the truncated acyl chain binding pocket, (R)-12 suffers a destabilizing steric clash with Ser193 proximal to the chiral center (FIG. 2: bottom). If (R)-12 is flipped 180° to avoid this steric interaction and arrange the tetrahydronaphthalene core in a disposition similar to (S)-12 (chiral C2-H down as found in FIG. 2: bottom), the terminal phenoxy group is no longer positioned to bind in this key region of the acyl chain binding pocket. Thus, it is not surprising that while the two enantiomers of 37 and 38 that lack the phenoxy group bind FAAH with comparable, albeit weak affinities, the two enantiomers of 12 and related inhibitors exhibit much more pronounced differences.

In Vivo Characterization

In initial efforts to evaluate in vivo inhibition of FAAH and the potential pharmacological effects, a select set of the conformationally restricted inhibitors (12, 14, 27, and 29) were examined alongside 2 for their ability to increase the endogenous levels of a series of lipid amide signaling molecules in both the brain (CNS effect) and liver (peripheral effect). This includes monitoring the effects of the inhibitors on the endogenous levels of the FAAH substrates anandamide (AEA, N-arachidonoyl ethanolamine), N-oleoyl ethanolamine (OEA), and N-palmitoyl ethanolamine (PEA), as well as the key lipids 2-arachidonoylglycerol (2-AG) and arachidonic acid (AA) that are not endogenous substrates for FAAH. Notably, it is the increase in endogenous levels of anandamide (AEA) and its subsequent action at cannabinoid ($CB_1$ and $CB_2$) receptors that are thought to be responsible for the antinociceptive and anti-inflammatory effects of FAAH inhibitors although both N-palmitoyl ethanolamine and 2-AG are also known to exhibit anti-inflammatory and cannabinoid receptor-mediated antinociceptive effects, respectively. Pharmacological effects were initially established 1 h after intraperitoneal (i.p.) administration of 30 mg/kg inhibitor in a single mouse for the initial screen and the results are summarized in Table 6 and FIG. 5, below. The inhibitors 12 and 27 increased the endogenous levels of key lipid amides thought to be responsible for antinociceptive effects (AEA, PEA) without impacting the endogenous levels of 2-AG, and had a minimal impact on reducing the endogenous levels of arachidonic acid (AA), the hydrolysis product of anandamide and a key proinflammatory fatty acid. The effects of 12 and 27 were observed both in the brain (CNS) and liver (peripheral) matching or exceeding the effects of 2, whereas the impact of the more polar inhibitors 14 and 29 was principally seen peripherally (liver) with more muted effects in the CNS (brain).

TABLE 6

Initial screen for the effects of FAAH inhibitors on brain and liver lipid levels following in vivo inhibitor treatment; n = 1 per group.

| | Brain, pmol/g (fold increase) | | | | Liver, pmol/g (fold increase) | | | |
|---|---|---|---|---|---|---|---|---|
| Compd. | AEA | PEA | 2-AG | AA | Compd. | AEA | PEA | 2-AG |
| 12 | 42 (5.2) | 785 (7.2) | 13 (0.9) | 170 (0.8) | 12 | 12 (6) | 472 (3.6) | 0.25 (0.8) |
| 27 | 24 (3.0) | 800 (7.4) | 11 (0.8) | 190 (0.9) | 27 | nd | nd | nd |
| 14 | 12 (1.5) | 224 (2.0) | 14 (1.0) | 154 (0.7) | 14 | 10 (5) | 284 (2.1) | 0.35 (1.1) |
| 29 | 8 (1.0) | 131 (1.2) | 12 (0.9) | 172 (0.8) | 29 | nd | nd | nd |
| 2 | 38 (4.8) | 540 (5.0) | nd | nd | 2 | 14 (7) | 208 (1.6) | 0.28 (0.9) |
| Vehicle | 8 (1.0) | 108 (1.0) | 14 (1.0) | 215 (1.0) | Vehicle | 2 (1.0) | 130 (1.0) | 0.33 (1.0) | nd = not determined

Figure 6A:
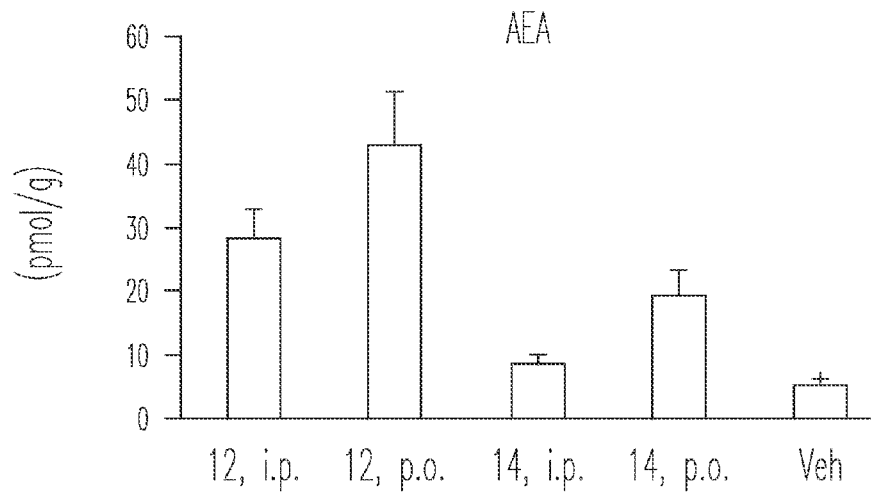
FIG. 6 shows brain lipid amide levels following oral versus intraperitoneal dosing.
Figure 6B:
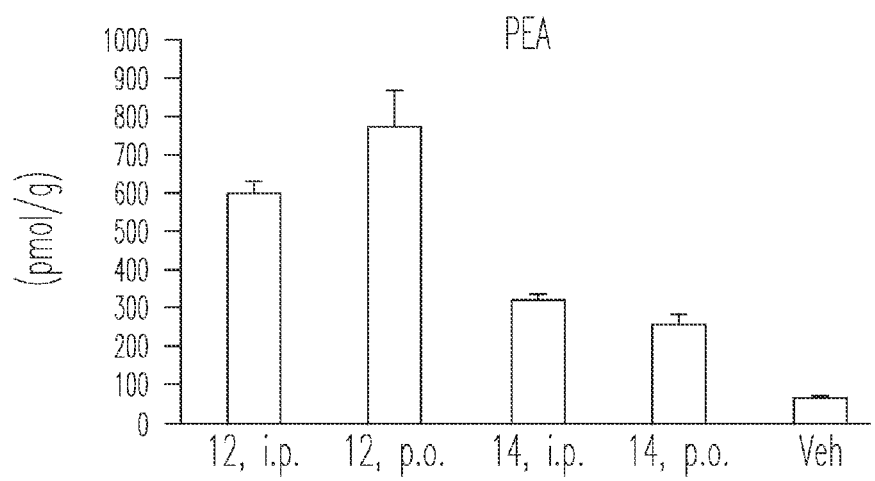

Given the results of this initial screen, both 12 and 14 were examined side-by-side not only with i.p. (30 mg/kg), but also oral (50 mg/kg) dosing with 3 mice per group to provide the results presented in Table 7 and FIG. 6, below. Significantly, the oral dosing matched and even improved on the results observed with i.p. administration.

TABLE 7

Brain lipid amide levels following oral versus intraperitoneal dosing.
Brain, pmol/g (fold increase)

| Compd. | AEA | PEA | 2-AG |
|---|---|---|---|
| 12, i.p. | 28.6 (5.1) | 599 (8.5) | 7.0 |
| 12, oral | 43.2 (7.7) | 772 (11.0) | 11.5 |
| 14, i.p. | 9.0 (1.6) | 321 (4.5) | 8.5 |
| 14, oral | 19.8 (3.5) | 260 (3.7) | 11.2 |
| Vehicle | 5.6 (1.0) | 70 (1.0) | 8.1 |

Figure 7A:
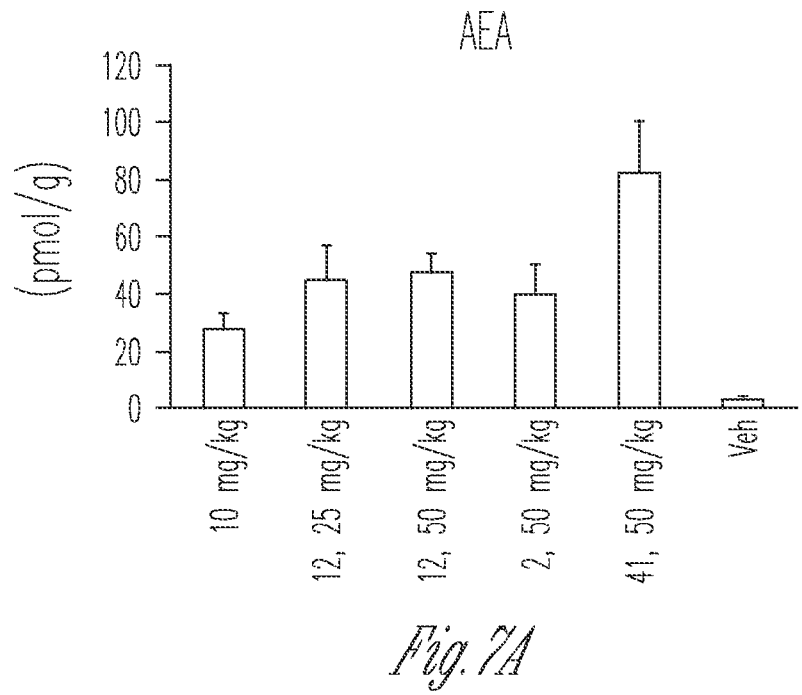
FIG. 7 shows dose (panels A and B, analysis performed 1 h post-treatment) and time (panels C and D at 50 mg/kg 12) dependent impact on brain lipid amide levels following oral dosing of 12; (E) structures of compounds 2, 41, and 12.
Figure 7B:
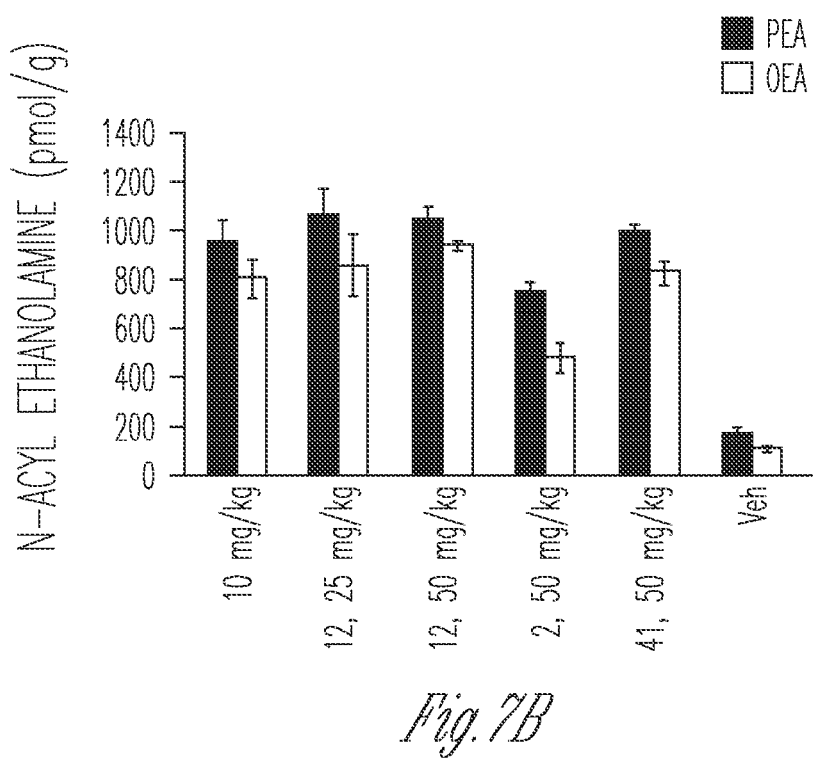
Figure 7C:
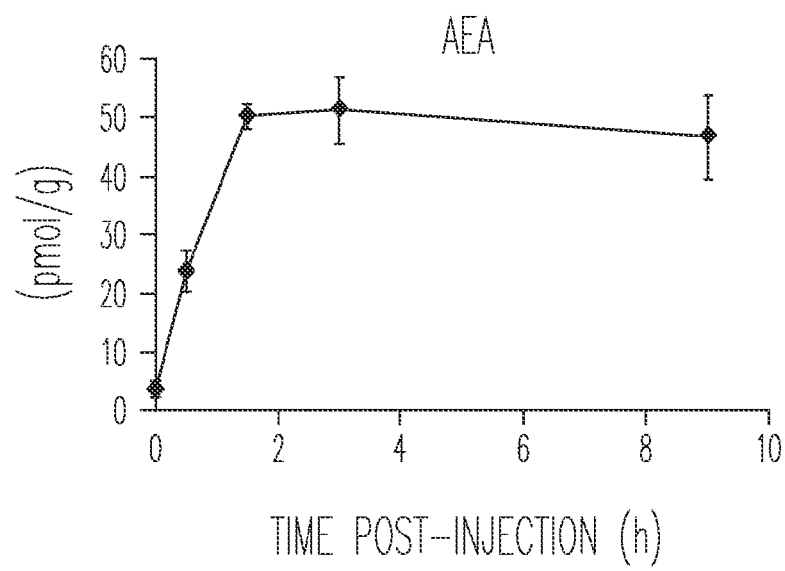
Figure 7D:
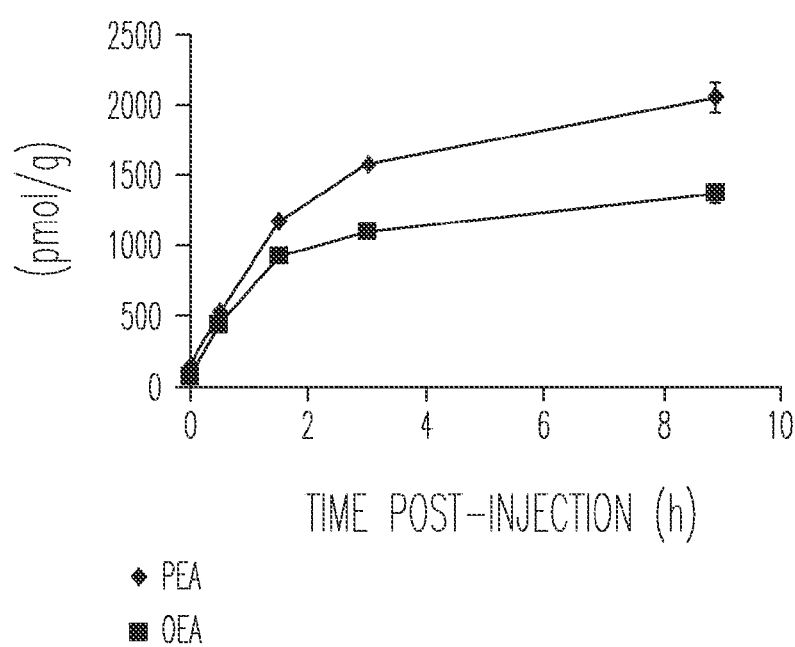
Figure 7H:
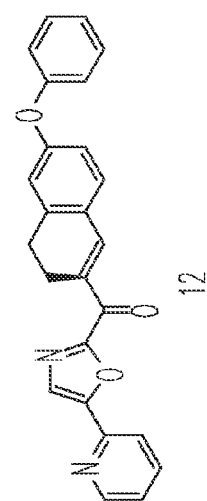
Figure 7H:
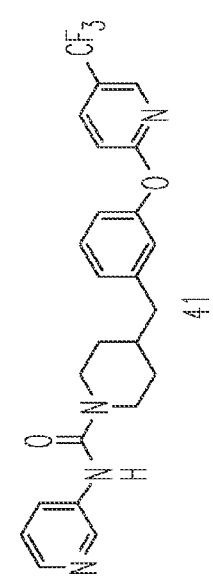
Figure 7H:
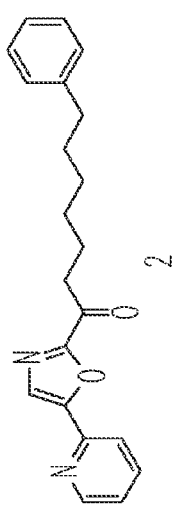

Given the oral activity established in the PD model with 12, a follow up dose- and time-dependent study of its effects on the endogenous brain levels of anandamide (AEA), N-palmitoyl ethanolamine (PEA) and N-oleoyl ethanolamine (OEA) was conducted alongside 2 and the irreversible FAAH inhibitor 41 (PF-3845) (see FIG. 7E for structures). In the first of these studies, each of the comparison standards (2 and 41) was administered orally (p.o.) at 50 mg/kg, 12 was administered orally at 10, 25, and 50 mg/kg, and the resulting impact on the endogenous brain levels of fatty acid amides was measured at a single time point (1 h). Compound 12 increased the levels of anandamide (12-13 fold at 25-50 mg/kg) in a dose dependent manner more efficaciously and more potently than 2 (11-fold at 50 mg/kg), but not as effectively as the irreversible FAAH inhibitor 41, FIG. 7A. In contrast, the increases in the brain levels of N-palmitoyl ethanolamine and N-oleoyl ethanolamine observed with 12 at 1 h were substantial (5.5-7.8 fold) and essentially the same at all three administered doses examined, all of which exceeded the effects observed with 2 at 50 mg/kg and that matched the effects of the irreversible inhibitor 41 administered at 50 mg/kg, FIG. 7B. These data are consistent with reports showing that partial blockade of FAAH can cause elevations in PEA and OEA, but that >90% FAAH blockade is required to elevate anandamide levels. In the second of the studies, 12 was administered to mice (50 mg/kg, p.o.) and the animals were sacrificed at various time points up to 9 h post-administration. Brains from these mice were analyzed for levels of anandamide and the additional FAAH substrates PEA and OEA. Administration of 12 caused dramatic accumulations of all three N-acylethanolamines (NAEs) in brain, with peak levels of anandamide achieved between 1.5-3 h (FIGS. 7C and 7D). Remarkably, the elevations in these lipids were maintained over the 9 h time course, similar to the time course reported for the irreversible FAAH inhibitor 41 and significantly longer than that reported for the carbamate inhibitor URB597. These time course data suggest that the reversible inhibitor 12 remains in the brain after its initial dosing at sufficiently high concentrations to completely inhibit FAAH (>90%) for a prolonged period.

An additional feature of the α-ketoheterocycle FAAH inhibitors that we have not disclosed previously is that they rapidly establish an equilibrium mixture of active ketone and reduced alcohol in vivo. Although this is likely a general feature of the entire class of α-ketoheterocycles that have been examined as enzyme inhibitors, we are not aware of its prior disclosure elsewhere. Consequently, triaging screens for compound development using rat or human liver microsomes (rlm and hlm) may often misleadingly suggest rapid metabolic reduction that is not representative of the true metabolic fate of such candidate inhibitors (e.g., rlm and hlm $t_{1/2}$ for 2 and 18 are 2-4 min and 12-15 min, respectively). Rather, we have found that they are subject to competitive reduction/reoxidation metabolism that sets up a steady-state equilibrium between the two states (ketone/alcohol) with the true in vivo fate of the candidate inhibitors being determined by other features of the molecule. For 2, this steady state equilibrium is established within 15 min and was found to be 1/3(ketone/alcohol) independent of the means of in vivo administration (i.v., i.p., or p.o.). For 12, we also measured the compound levels in the brain following its oral administration (50 mg/kg) and could detect both the parent ketone and the reduced alcohol in inhibitor-treated, but not vehicle-treated, mice. The relative ratio of ketone/alcohol was 3-3.5/1 at early stages following compound administration (0.5-1 h) and slowly equilibrated to 1-1.5/1 at the longer times following administration (1.5-9 h) where both the ratio and brain levels persisted. Although preliminary, the results seem to indicate that the added conformational constraints in the C2 acyl chain and the increased steric hindrance surrounding the electrophilic ketone both slow the rate of equilibration and improve the ketone/alcohol ratio in vivo.

Figure 8A:
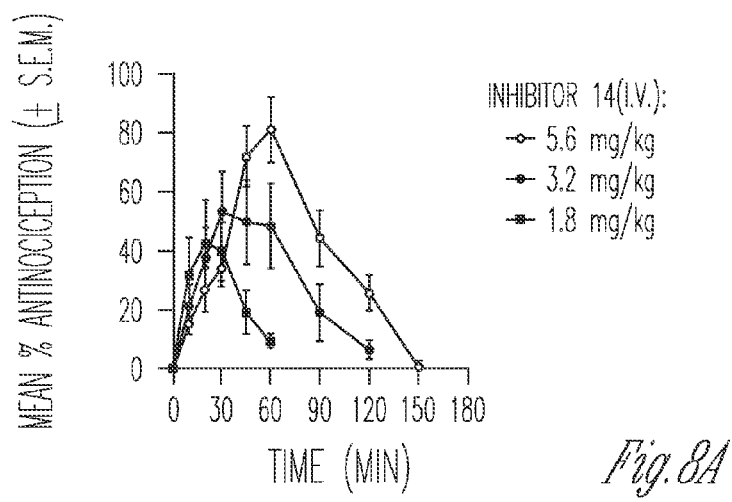
FIG. 8 shows antinociception in the tail flick assay (52° C.) following i.v. administration of 14, 2 and morphine.
Figure 8B:
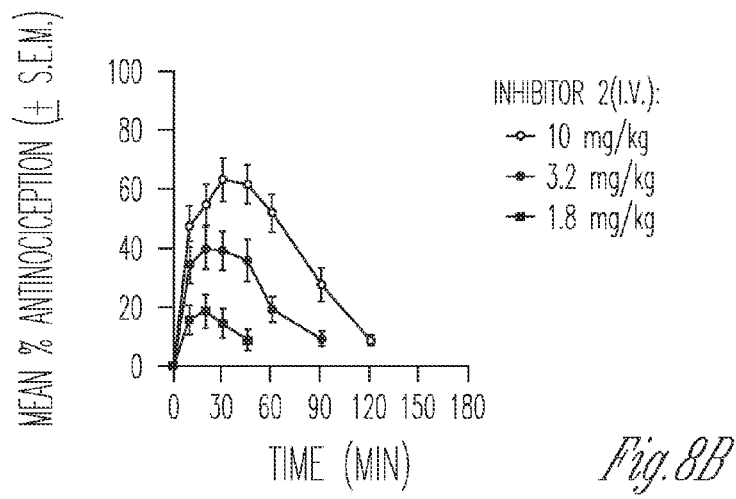
Figure 8C:
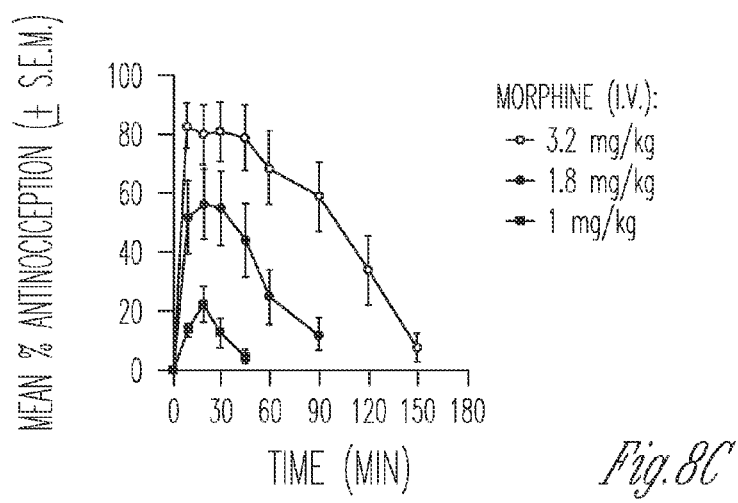

Concurrent with these studies, two prototypical inhibitors 12 and 14 were examined for antinociceptive activity in a preclinical model of acute thermal pain (tail flick at 52° C.) in mice alongside 2 and morphine (i.v. administration). The results of the dose-response studies for 14, the more soluble of the two inhibitors, are summarized in FIG. 8 alongside those of morphine where it produced the same maximal effect (efficacy) observed with morphine requiring only a 2-fold higher dose, reaching its maximal effect at 30-60 min and exhibiting a duration of effect matching that of morphine (150 min).

Figure 9A:
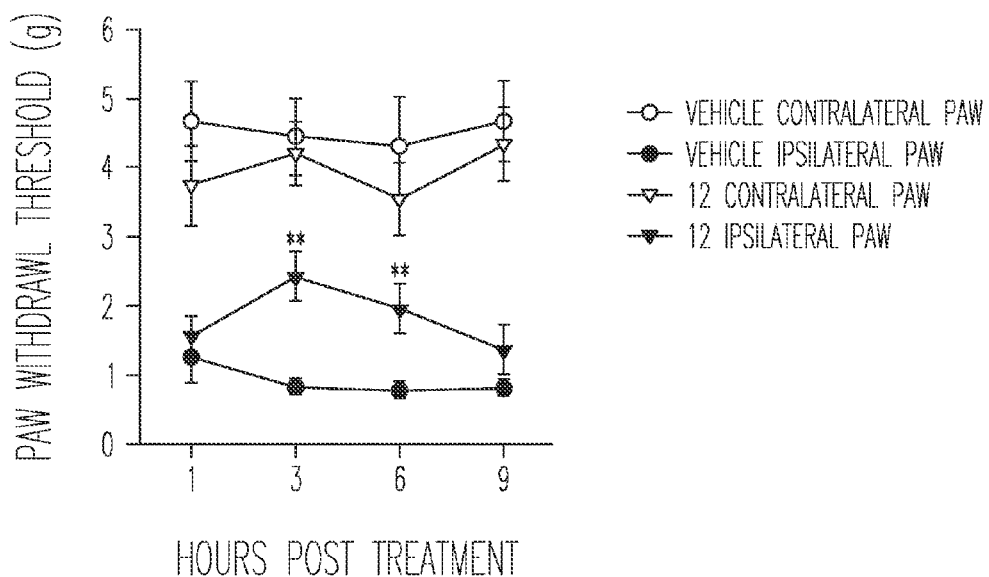
FIG. 9 shows FAAH inhibition by 12 significantly attenuated neuropathic pain for up to 9 hours. (A) Male C57BL/6 mice were subjected to chronic constriction injury (CCI) of the sciatic nerve and tested 10 days later for mechanical allodynia, as measured with von Frey filaments, and (B) acetone-induced cold allodynia. Inhibitor 12 (50 mg/kg, p.o.) significantly attenuated CCI-induced mechanical allodynia, as well as cold allodynia, in paws ipsilateral to CCI surgery, but had no effect in paws contralateral to CCI surgery. Circles, vehicle treatment; triangles, 12 treatment; Open shapes, control paws; filled shapes, CCI paws. Data expressed as mean±SEM. (n=9–10). * $p<0.05$, ** $p<0.01$, vs vehicle.
Figure 9B:
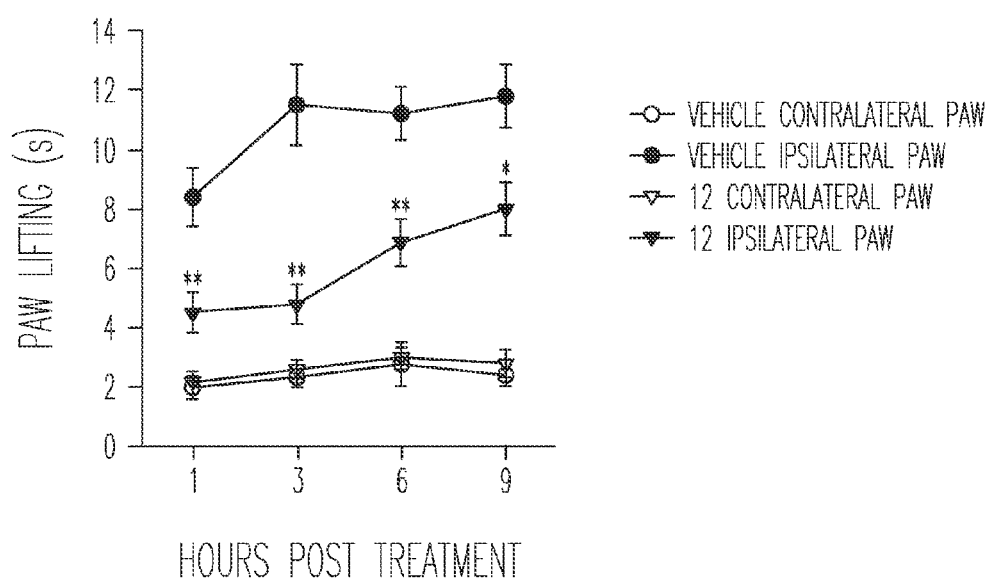

In an important extension of the studies and following the observation of the long acting in vivo effects of 12 on endogenous anandamide levels following oral administration, mice were subjected to chronic constriction injury (CCI) and tested 10 days later for signs of neuropathic pain. Inhibitor 12 administered orally (50 mg/kg) significantly attenuated mechanical allodynia [$F(1,51)=17.1$; $p<0.001$; FIG. 9A] and cold allodynia [$F(1-51)=26.4$; $p<0.0001$; FIG. 9B], in paws ipsilateral to CCI surgery. In the control paws of the same mice, 12 had no effect on mechanical ($p=0.16$) or cold allodynia ($p=0.48$), indicating a lack of sedative effects. Significantly, the effects of 12 following its oral dosing were sustained, lasting >6 h in the mechanical allodynia and >9 h in the cold allodynia consistent with its long acting effects in raising the endogenous concentration of anandamide.

Finally and significantly, inhibitor 12 was examined for cannabimimetic side effects following oral administration at a dose that provided its analgesic effects (50 mg/kg). Like 2 and earlier FAAH inhibitors in this class, 12 did not produce catalepsy, hypothermia, or hypomotility indicating that it does not produce THC-like effects characteristic of a classical CB receptor agonist.

In summary, a series of α-ketooxazoles containing conformational constraints in the C2 acyl side chain of 2 were prepared and examined as inhibitors of FAAH. Members of this new series exhibited comparable or improved enzyme inhibition potency relative to 2, indicating that the additional conformational restriction in the C2 acyl side chain is achievable and beneficial. A cocrystal X-ray structure of the prototypical α-ketoheterocycle 12 bound to a humanized variant of rat FAAH confirmed that the (S)-enantiomer is the bound active inhibitor, shed light on the structural origin of enantiomeric selectivity, and confirmed that the active site catalytic Ser241 is covalently bound to the electrophilic carbonyl mimicking the enzymatic tetrahedral intermediate. Preliminary in vivo characterization of the prototypical inhibitors 12 and 14 in mice was reported demonstrating that they raise endogenous anandamide levels with either intraperitoneal (i.p.) or oral (p.o.) administration, that the oral administration of 12 caused sustained accumulation of three major N-acylethanolamines (anandamide, N-oleoyl ethanolamine, and N-palmitoyl ethanolamine) in the brain with peak levels of anandamide achieved between 1.5-3 h with elevations that were maintained over the 9 h time course of the examination, and that two representative members of the series (12 and 14) exhibit robust analgesic activity in mouse models of thermal hyperalgesia and neuropathic pain including the demonstration that oral administration of 12 (50 mg/kg) significantly attenuated both mechanical (>6 h) and cold (>9 h) allodynia for sustained periods consistent with its long acting effects in raising the endogenous concentration of anandamide.

Pharmaceutical Compositions

In various embodiments, the invention provides a pharmaceutical composition comprising a compound of the invention and a pharmaceutically acceptable excipient. For example, the composition can be adapted for oral administration.

Compositions of the compounds of the invention, alone or in combination with another medicament, are provided herein. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: *The Science and Practice of Pharmacy*, 19th Ed., 1995, or later versions thereof, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tabletting techniques can contain:

| Core: | |
|---|---|
| Active compound (as free compound or salt thereof) | 250 mg |
| Colloidal silicon dioxide (AEROSIL ®) | 1.5 mg |
| Cellulose, microcryst. (AVICEL ®) | 70 mg |
| Modified cellulose gum (AC-DI-SOL ®) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The compounds of the invention can be administered to a mammal, especially a human in need of such elimination or amelioration of pain. Such mammals include also animals, both domestic animals, e.g. household pets, farm animals, and non-domestic animals such as wildlife.

Compounds of the invention can be used as stand-alone analgesics, i.e., need not be administered in combination with any other drug to produce an analgesic effect. Compounds of the invention can be administered orally as well as parenterally.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

Combinations with second medicaments can include combinations wherein the second medicament comprises an opiate analgesic, a non-opiate analgesic, a cannabinoid, an anti-inflammatory, a COX-2 inhibitor, or a febricide. An example of an opiate analgesic is morphine; an example of a non-opiate analgesic or a febricide is a salicylate; an example of a cannabinoid is THC; an example of an anti-inflammatory is indacin; an example of a COX-2 inhibitor is ibuprofen. In various embodiment, for example wherein the second medicament is degraded by the action of an FAAH, coadministration of an FAAH-inhibitory compound of the present invention and such a second medicament can serve to potentiate the effect of the second medicament.

In various embodiments, the invention provides the use of a compound or of a composition of the invention for treatment of pain, or the use of a compound of the invention for manufacture of a medicament for treatment of pain.

In various embodiments, the invention provides a method of inhibiting FAAH, comprising contacting the FAAH with an effective amount or concentration of a compound of the invention. For example, the contacting can take place in vitro such as in a bioassay for determination of the IC50 for inhibition of FAAH such as human FAAH; or the contacting can take place in vivo, such as in administration of the compound to a patient for treatment of pain.

In various embodiments, the invention provides a method of treating pain (e.g., post-operative pain or nociceptive pain) in a patient afflicted therewith, comprising administering to the patient an effective amount of a compound or a composition of the invention at a frequency and for a duration of time sufficient to provide a beneficial effect to the patient. For example, the compound of the invention can be administered orally. Oral administration can be repeated at a sufficient frequency and for a sufficient duration of time to eliminate or ameliorate the pain experienced by a patient suffering therefrom.

In various embodiments, the duration of effect of a single effective dose of a compound of the invention is greater than the usual or average duration of the effect of analgesics presently in use in the medical profession. For example, effect of a single dose of the compound or composition can result in an amelioration of pain for a period of time greater than the period of time that would result from administration of a dose of morphine having comparable analgesic effect.

The method can further comprise administration of a second medicament, as can be determined by the knowledge and skill of an attending physician. For example, the second medicament can be an opiate analgesic, a non-opiate analgesic, a cannabinoid, an anti-inflammatory, a COX-2 inhibitor, or a febricide, or any drug suitable for treatment of a medical condition that is accompanied by the perception of pain by the patient.

Also contemplated herein is a method of treating anxiety, post-traumatic stress disorder, addiction (such as nicotine addiction) or insomnia in a patient in need thereof, comprising administering a pharmaceutically effective amount of a compound disclosed herein. For example, compounds contemplated herein may be used to treat certain central nervous system disorders, for example, depression.

Evaluations

It is within ordinary skill to evaluate any compound disclosed and claimed herein for effectiveness the inhibition of the enzymic activity of FAAH, in decreasing the perception of pain using the various bioassays described above or found in the scientific literature. Accordingly, the person of ordinary skill can prepare and evaluate any of the claimed compounds as a long-lasting analgesic compound without undue experimentation.

Any compound found to be an effective inhibitor of FAAH enzymic activity can likewise be tested in animal models and in human clinical studies using the skill and experience of the investigator to guide the selection of dosages and treatment regimens.

EXAMPLES

The following examples are provided to illustrate the practice of the invention but the invention is not to be interpreted as limited by the examples.

The following abbreviations are used throughout:

AA, arachidonic acid; AEA, arachidonyl ethanolamide; 2-AG, 2-arachidonylglycerol; CB, cannabinoid; DEAD, diethyl azodicarboxylate; FAAH, fatty acid amide hydrolase; OEA, oleoyl ethanolamide; PEA, palmitoyl ethanolamide; TBS, tert-butyldimethylsilyl; TGH, triacylglycerol hydrolase;

Bu Butyl
DMF N,N-Dimethylformamide
eq Equivalents
ESI Electrospray ionization
$Et_2O$ Diethyl ether
EtOH Ethanol
EtOAc Ethyl acetate
h Hours
HRMS High resolution mass spectroscopy M Molar
mg Milligrams
min Minutes
mL Milliliters
μL Microliters
mmole Millimoles
MS Mass spectroscopy
MeOH Methanol
nM Nanomolar
pM Picomolar
RT Room temperature
sat. Saturated
TBS tert-butyl dimethylsilyl
THF Tetrahydrofuran
TOF Time of flight (6-Phenoxy-1,2,3,4-tetrahydronaphthalen-2-yl)(5-(pyridin-2-yl)oxazol-2-yl)methanone (12)

A solution of oxazole (0.226 mL, 3.44 mmol) in anhydrous THF (20 mL) was treated with $BH_3 \cdot THF$ (1 M, 3.74 mL, 3.74 mmol) and the solution was stirred at room temperature for 1 h before being cooled to −78° C. and treated with 2.16 M n-BuLi (2 mL, 4.47 mmol) dropwise. The reaction mixture was stirred at −78° C. for 40 min before a solution of 6-phenoxy-1,2,3,4-tetrahydronaphthalene-2-carboxaldehyde (870 mg, 3.44 mmol) in THF (20 mL) was added. The reaction mixture was stirred at −78° C. for 2 h before being warmed to room temperature. A 5% HOAc-EtOH solution (50 mL) was added and this mixture was stirred at room temperature for 12 h. The solvent was removed under reduced pressure and the residue was dissolved in EtOAc, washed with $H_2O$, saturated aqueous $NaHCO_3$ and saturated aqueous NaCl before the organic layer was dried over $MgSO_4$ and the solvent was removed under reduced pressure. Flash chromatography ($SiO_2$, 40% EtOAc-hexanes) afforded oxazol-2-yl(6-phenoxy-1,2,3,4-tetrahydronaphthalen-2-yl)methanol (740 mg, 67%) as colorless oil: $^1H$ NMR ($CDCl_3$, 600 MHz) δ 7.65 (s, 1H), 7.32-7.31 (m, 2H), 7.10-6.98 (m, 6H), 6.78-6.75 (m, 2H), 4.78-4.74 (m, 1H), 2.88-2.78 (m, 4H), 2.61-2.59 (m, 0.5H), 2.34 (m, 0.5H), 2.14-2.12 (m, 0.5H), 1.80-1.77 (m, 0.5H), 1.62-1.51 (m, 1H); $^{13}C$ NMR ($CDCl_3$, 150 MHz) δ 165.3, 157.5, 154.8, 138.9, 137.9, 137.7, 130.5, 130.3, 130.2, 130.1, 129.5 (2C), 126.5, 122.8, 122.7, 118.86 (2C), 118.82, 118.49, 118.42, 116.78, 116.73, 71.2, 71.0, 39.8, 39.7, 30.8, 30.2, 29.6, 28.9, 28.8, 25.1, 24.4.

A solution of oxazol-2-yl(6-phenoxy-1,2,3,4-tetrahydronaphthalen-2-yl)methanol (400 mg, 1.24 mmol), TBSCl (450 mg, 2.98 mmol) and imidazole (421 mg, 6.2 mmol) in DMF (20 mL) was stirred at room temperature for 16 h before it was diluted with EtOAc, washed with $H_2O$, and saturated aqueous NaCl. The organic layer was dried over $MgSO_4$ and the solvent was removed under reduced pressure. Flash chromatography ($SiO_2$, 10% EtOAc-hexanes) yielded 2-((tert-butyldimethylsilyloxy)(6-phenoxy-1,2,3,4-tetrahydronaphthalen-2-yl)methyl)oxazole (459 mg, 85%) as a thick colorless oil: $^1H$ NMR ($CDCl_3$, 500 MHz) δ 7.65 (s, 1H), 7.31 (t, 2H, J=8.5 Hz), 7.12 (d, 1H, J=8.0 Hz), 7.01-6.97 (m, 4H), 6.81-6.75 (m, 2H), 4.80 (d, 0.5H, J=7.0 Hz), 4.74 (d, 0.5H, J=7.0 Hz), 2.99-2.73 (m, 3H), 2.55-2.51 (m, 1H), 2.39-2.25 (m, 1H), 1.74-1.71 (m, 0.5H), 1.53-1.49 (m, 1H), 0.96 (s, 4.5H), 0.93 (s, 4.5H), −0.03 (s, 1.5H), −0.04 (s, 1.5H), −0.05 (s, 1.5H), −0.06 (s, 1.5H); $^{13}C$ NMR ($CDCl_3$, 125 MHz) δ 164.4, 164.3, 157.6, 157.5, 154.7, 154.6, 138.47, 138.41, 138.0, 137.7, 130.7, 130.4, 130.3, 130.1 (2C), 129.4, 126.7, 122.6, 122.5, 118.8, 118.3, 118.2, 116.7, 116.6, 72.2, 72.1, 40.3, 30.67, 30.62, 28.8, 28.7, 25.6 (3C), 25.1, 24.8, 18.0, −5.3, −5.41, −5.44, −5.6.

A solution of 2-((tert-butyldimethylsilyloxy)(6-phenoxy-1,2,3,4-tetrahydronaphthalen-2-yl)methyl)-oxazole (459 mg, 1.05 mmol) in THF (15 mL) was cooled to −78° C. before it was treated with 2.16 M n-BuLi (0.6 mL, 1.15 mmol) dropwise. The reaction mixture was stirred at −78° C. for 2 h, and treated with a solution of $Bu_3SnCl$ (0.6 mL, 2.1 mmol) and stirred for 5 min. The solution was warmed to room temperature, diluted with EtOAc, and washed with saturated aqueous NaCl. The organic layer was dried over $MgSO_4$ and the solvent was removed under reduced pressure. Flash chromatography ($SiO_2$, 10% EtOAc-hexanes) yielded 2-((tert-butyldimethylsilyloxy)(6-phenoxy-1,2,3,4-tetrahydronaphthalen-2-yl)methyl)-5-(tributylstannyl)oxazole (500 mg, 78%) as a thick colorless oil: $^1H$ NMR ($CDCl_3$, 500 MHz) δ 7.30 (t, 2H, J=7.5 Hz), 7.12 (d, 1H, J=6.0 Hz), 7.06 (t, 1H, J=7.0 Hz), 6.97 (m, 2H), 6.77 (dd, 1H, J=2.5, 8.5 Hz), 4.80 (d, 0.5H, J=7.0 Hz), 4.75 (d, 0.5H, J=7.0 Hz), 2.82-2.70 (m, 2H), 2.52-2.22 (m, 2H), 1.58-1.46 (m, 8H), 1.36-1.30 (m, 7H), 1.15-1.11 (m, 5H), 0.94-0.90 (s, 18H), 0.08 (s, 1.5H), 0.06 (s, 1.5H), −0.11 (s, 1.5H), −0.12 (s, 1.5H); $^{13}C$ NMR ($CDCl_3$, 125 MHz) δ 168.5, 168.4, 157.8, 154.9, 154.8, 154.7, 154.6, 138.2, 138.0, 137.1, 131.2, 130.8, 130.4, 130.2, 129.5 (2C), 122.67, 122.64, 118.9, 118.4, 118.3, 116.8, 116.6, 72.5, 72.3, 40.69, 40.64, 30.85, 30.81, 29.3, 29.2 (3C), 29.1, 29.0, 28.98, 28.90, 28.8, 28.5, 27.6, 27.4, 27.3, 27.2 (3C), 27.1, 27.0, 26.8, 25.7, 25.2, 25.0, 18.1, 13.69, 13.60 (3C), 11.6, 10.7, 10.2 (3C), 9.98, −5.3, −5.4, −5.61, −5.62.

2-((tert-Butyldimethylsilyloxy)(6-phenoxy-1,2,3,4-tetrahydronaphthalen-2-yl)methyl)-5-(tributylstannyl)oxazole (5.0 g, 6.89 mmol), $Pd(PPh_3)_4$ (800 mg, 0.689 mmol) and 2-bromopyridine (0.9 mL, 8.96 mmol) were dissolved in anhydrous 1,4-dioxane (30 mL) and the mixture was warmed at reflux for 16 h under Ar. The mixture was diluted with EtOAc, washed with saturated aqueous NaCl, and dried over $Na_2SO_4$. Flash chromatography ($SiO_2$, 20% EtOAc-hexanes) yielded 2-((tert-butyldimethylsilyloxy)(6-phenoxy-1,2,3,4-tetrahydronaphthalen-2-yl)methyl)-5-(pyridin-2-yl)oxazole (1.49 g, 42%; typically 42-61%) as a colorless oil: $^1H$ NMR ($CDCl_3$, 500 MHz) δ 8.64 (d, 1H, J=4.5 Hz), 7.78-7.76 (m, 1H), 7.71-7.67 (m, 2H), 7.30 (t, 2H, J=7.5 Hz), 7.24-7.22 (m, 1.5H), 7.07-7.04 (m, 1.5H), 6.98-6.95 (m, 2H), 6.78-7.72 (m, 2H), 4.81 (d, 0.5H, J=7.0 Hz), 4.75 (d, 0.5H, J=7.0 Hz), 2.96-2.73 (m, 2H), 2.58-2.55 (m, 0.5H), 2.39-2.34 (m, 1H), 2.26-2.20 (m, 1H), 1.81-1.77 (m, 1H), 1.58-1.53 (m, 1H), 0.90 (s, 9H), 0.11 (s, 1.5H), 0.09 (s, 1.5H), −0.05 (s, 1.5H), −0.04 (s, 1.5H): $^{13}C$ NMR ($CDCl_3$, 125 MHz) δ 157.7, 157.6, 154.8, 154.7, 149.6, 138.1, 137.9, 137.18, 137.14, 132.1, 130.8, 130.5, 130.4 (2C), 130.3, 129.5, 128.5 (2C), 125.5, 125.4, 122.8, 122.78, 122.73, 119.1, 118.9, 118.4, 118.3, 116.8, 116.7, 72.5, 72.4, 40.5, 30.9, 30.5, 29.0, 28.9, 25.7 (3C), 25.3, 24.9, 18.2, −5.0, −5.23, −5.26.

2-((tert-Butyldimethylsilyloxy)(6-phenoxy-1,2,3,4-tetrahydronaphthalen-2-yl)methyl)-5-(pyridin-2-yl)oxazole (1.49 g, 2.90 mmol) was dissolved in THF (30 mL), treated with $Bu_4NF$ (1 M in THF, 4 mL, 3.48 mmol) and the solution was stirred at room temperature for 2 h under Ar. The reaction mixture was diluted with EtOAc, washed with saturated aqueous NaCl, and dried over $Na_2SO_4$ and the solvent was removed under reduced pressure. Flash chromatography ($SiO_2$, 50-100% EtOAc-hexanes) yielded (6-phenoxy-1,2,3,4-tetrahydronaphthalen-2-yl)(5-(pyridin-2-yl)oxazol-2-yl)methanol (740 mg, 64%) as a yellow oil: $^1H$ NMR ($CDCl_3$, 600 MHz) δ 8.63 (d, 1H, J=4.2 Hz), 7.78

(t, 1H, J=7.8 Hz), 7.71-7.65 (m, 2H), 7.30 (t, 2H, J=7.2 Hz), 7.27-7.25 (m, 2H), 7.07-6.96 (m, 3H), 6.77-6.73 (m, 2H), 4.87 (d, 0.5H, J=7.0 Hz), 4.82 (d, 0.5H, J=7.0 Hz), 2.86-2.68 (m, 4H), 2.45-2.42 (m, 1H), 2.17-2.15 (m, 1H), 1.92-1.89 (m, 1H), 1.66-1.61 (m, 1H); $^{13}$C NMR (CDCl$_3$, 150 MHz) δ 157.6, 154.8, 149.5, 146.7, 137.9, 137.7, 137.3, 130.5, 130.4, 130.3, 130.2, 129.6 (2C), 125.37, 125.34, 123.1, 122.8, 119.4, 118.9, 118.8, 118.4 (2C), 116.85, 116.81, 71.5, 71.3, 39.9, 39.8, 30.9, 30.0, 29.6, 28.98, 28.94, 25.3, 24.3.

(6-Phenoxy-1,2,3,4-tetrahydronaphthalen-2-yl)(5-(pyridin-2-yl)oxazol-2-yl)methanol (740 mg, 1.85 mmol) was dissolved in CH$_2$Cl$_2$ (40 mL) and Dess-Martin periodinane (1.0 g, 2.22 mmol) was added. The mixture was stirred at room temperature for 2 h and the reaction mixture was evaporated in vacuo. Flash chromatography (SiO$_2$, 20% EtOAc-hexanes) yielded (6-phenoxy-1,2,3,4-tetrahydronaphthalen-2-yl)(5-(pyridin-2-yl)oxazol-2-yl)methanone (12, 650 mg, 88%) as a yellow oil: $^1$H NMR (CDCl$_3$, 600 MHz) δ 8.68 (d, 1H, J=4.2 Hz), 7.93 (s, 1H), 7.90-7.83 (m, 2H), 7.34-7.31 (m, 3H), 7.19-7.14 (m, 4H), 6.88-6.78 (m, 2H), 3.92-3.90 (m, 1H), 3.10-2.90 (m, 4H), 2.32-2.30 (m, 1H), 1.95-1.93 (m, 1H); $^{13}$C NMR (CDCl$_3$, 150 MHz) δ 190.5, 157.5, 156.8, 155.1, 153.3, 150.0, 146.1, 137.2, 137.0, 130.2, 129.7, 129.6 (2C), 127.0, 124.2, 122.9, 120.4, 118.9, 118.5 (2C), 116.9, 43.5, 30.6, 28.8, 25.7; HRMS-ESI-TOF m/z 397.1551 ([M+H]$^+$, C$_{25}$H$_{20}$N$_2$O$_3$ requires 397.1547). The enantiomers were separated using a semipreparative chiral phase HPLC column (Daicel ChiraCel OD, 10 μm, 2×25 cm, 10% EtOH-hexanes, 7 mL/min, α=1.35).

(S)-12: [α]$^{23}_D$ −2.0 (c 0.1, THF).
(R)-12: [α]$^{23}_D$ +1.8 (c 0.1, THF).

Methyl 6-(2-(6-Phenoxy-1,2,3,4-tetrahydronaphthalene-2-carbonyl)oxazol-5-yl)picolinate (13)

2-((tert-Butyldimethylsilyloxy)(6-phenoxy-1,2,3,4-tetrahydronaphthalen-2-yl)methyl)-5-(tributylstannyl)oxazole (5.0 g, 6.89 mmol), Pd(PPh$_3$)$_4$ (800 mg, 0.68 mmol), and methyl 6-bromopicolinate (2.0 g, 8.96 mmol) were dissolved in anhydrous 1,4-dioxane (30 mL) and the mixture was warmed at reflux for 16 h under Ar. The mixture was diluted with EtOAc, washed with saturated aqueous NaCl, and dried over Na$_2$SO$_4$. The reaction mixture was diluted with EtOAc, washed with saturated aqueous NaCl, dried over Na$_2$SO$_4$ and the solvent was removed under reduced pressure. Flash chromatography (SiO$_2$, 30% EtOAc-hexanes) yielded methyl 6-(2-((tert-butyldimethylsilyloxy)(6-phenoxy-1,2,3,4-tetrahydronaphthalen-2-yl)methyl)oxazol-5-yl)picolinate (2.88 g, 73%) as a colorless oil: $^1$H NMR (CDCl$_3$, 500 MHz) δ 8.01 (dd, 1H, J=4.5, 7.0 Hz), 7.99-7.97 (m, 1H), 7.89-7.85 (m, 1H), 7.80-7.78 (m, 1H), 7.65-7.59 (m, 1H), 7.25-7.22 (m, 2H), 7.01-6.97 (m, 1H), 6.92-6.90 (m, 1H), 6.73-6.66 (m, 1H), 4.80 (d, 0.5H, J=7.0 Hz), 4.77 (d, 0.5H, J=7.0 Hz), 3.96 (s, 1.5H), 3.93 (s, 1.5H), 2.91-2.87 (m, 1H), 2.78-2.76 (m, 3H), 2.73-2.71 (m, 1H), 2.55-2.52 (m, 1H), 2.38-2.33 (m, 1H), 2.23-2.20 (m, 1H), 1.62-1.52 (m, 1H), 0.90 (s, 9H), 0.11 (s, 1.5H), 0.09 (s, 1.5H), −0.05 (s, 1.5H), −0.04 (s, 1.5H); $^{13}$C NMR (CDCl$_3$, 125 MHz) δ 165.0, 164.9, 164.8, 164.0, 157.47, 157.40, 154.6, 154.5, 149.9, 149.8, 148.4, 148.0, 147.38, 147.35, 141.8, 138.9, 137.8, 137.6, 131.8, 131.7, 131.5, 130.5, 130.2, 130.1, 130.0, 129.3 (2C), 128.3, 128.23, 126.20, 126.1, 123.8, 123.7, 122.56, 122.52, 121.8 (2C), 118.7, 118.2, 118.1, 72.5, 72.1, 52.8, 52.6, 40.2, 30.7, 30.3, 28.7, 28.6, 27.7, 26.5, 25.5 (3C), 25.1, 24.6, 17.9, 17.3, 13.3, −5.2, −5.40, −5.44.

Methyl 6-(2-((tert-butyldimethylsilyloxy)(6-phenoxy-1,2,3,4-tetrahydronaphthalen-2-yl)methyl)oxazol-5-yl)picolinate (2.88 g, 5.04 mmol) was dissolved in THF (50 mL), treated with Bu$_4$NF (1 M in THF, 6 mL, 6.05 mmol) and the solution was stirred at room temperature for 2 h under Ar. The reaction mixture was diluted with EtOAc, washed with saturated aqueous NaCl, dried over Na$_2$SO$_4$ and the solvent was removed under reduced pressure. Flash chromatography (SiO$_2$, 50-100% EtOAc-hexanes) yielded methyl 6-(2-(hydroxy(6-phenoxy-1,2,3,4-tetrahydronaphthalen-2-yl)methyl)oxazol-5-yl)picolinate (2.0 g, 86%) as a yellow oil: $^1$H NMR (CDCl$_3$, 400 MHz) δ 8.20 (dd, 1H, J=1.2, 7.6 Hz), 8.05 (t, 1H, J=8.0 Hz), 7.98-7.96 (m, 2H), 7.48 (t, 2H, J=7.2 Hz), 7.25-7.12 (m, 4H), 6.95-6.90 (m, 2H), 5.06 (d, 0.5H, J=6.8 Hz), 5.01 (d, 0.5H, J=6.8 Hz), 4.18 (s, 3H), 3.08-2.95 (m, 3H), 2.84-2.81 (m, 1H), 2.65-2.61 (m, 1H), 2.38-2.03 (m, 1H), 1.81-1.45 (m, 2H); $^{13}$C NMR (CDCl$_3$, 100 MHz) δ 165.8, 165.7, 165.1, 157.4, 154.77, 154.74, 150.1, 148.0, 147.1, 137.8, 137.6, 130.4, 130.3, 130.2, 130.1, 129.49 (2C), 129.47, 125.9, 123.9, 122.6, 122.2, 118.79, 117.74, 118.33, 118.30, 116.7, 116.6, 71.2, 71.0, 64.2, 52.8, 39.69, 39.65, 30.9, 30.1, 28.8, 25.2, 24.4, 18.9, 17.4, 13.4.

Methyl 6-(2-(hydroxy(6-phenoxy-1,2,3,4-tetrahydronaphthalen-2-yl)methyl)oxazol-5-yl)picolinate (2.0 g, 4.38 mmol) was dissolved in CH$_2$Cl$_2$ (60 mL) and Dess-Martin periodinane (2.7 g, 6.25 mmol) was added. The mixture was stirred at room temperature for 2 h before the reaction mixture was evaporated in vacuo. Flash chromatography (SiO$_2$, 30% EtOAc-hexanes) yielded methyl 6-(2-(6-phenoxy-1,2,3,4-tetrahydronaphthalene-2-carbonyl)oxazol-5-yl)picolinate (13, 1.67 g, 70%) as a white solid: $^1$H NMR (CDCl$_3$, 500 MHz) δ 8.09 (dd, 1H, J=1.0, 8.0 Hz), 8.03 (s, 1H), 8.01 (dd, 1H, J=1.5, 8.0 Hz), 7.95 (t, 1H, J=7.5 Hz), 7.29 (t, 2H, J=7.5 Hz), 7.06 (t, 2H, J=7.5 Hz), 6.98-6.96 (m, 2H), 6.79-6.77 (m, 2H), 4.01 (s, 3H), 3.91-3.86 (m, 1H), 3.08 (d, 2H, J=8.0 Hz), 2.93-2.87 (m, 2H), 2.31-2.27 (m, 1H), 1.94-1.89 (m, 1H); $^{13}$C NMR (CDCl$_3$, 125 MHz) δ 190.3, 164.9, 157.4, 156.8, 154.9, 152.3, 148.4, 146.3, 138.1, 137.1, 130.0, 129.6 (2C), 129.5, 127.8, 125.0, 123.1, 122.7, 118.8, 118.4 (2C), 116.8, 52.9, 43.4, 30.4, 28.6, 25.6; HRMS-ESI-TOF m/z 455.1617 ([M+H]$^+$, C$_{27}$H$_{22}$N$_2$O$_5$ requires 455.1601). The enantiomers were separated using a semipreparative chiral phase HPLC column (Daicel ChiraCel OD, 10 μm, 2×25 cm, 40% EtOH-hexanes, 7 mL/min, α=1.19).

(S)-13: [α]$^{23}_D$ −0.7 (c 0.8, THF).
(R)-13: [α]$^{23}_D$ +0.5 (c 0.8, THF).

6-(2-(6-Phenoxy-1,2,3,4-tetrahydronaphthalene-2-carbonyl)oxazol-5-yl)picolinic acid (14)

Each pure enantiomer (S)-13 and (R)-13 (0.010 mmol) were dissolved in 1,2-dichloroethane and after addition of trimethyltin hydroxide (3 equiv), the mixture was warmed at 70° C. for 16 h. The mixture was concentrated in vacuo and diluted with EtOAc and the organic layer was washed with aqueous 0.01 N KHSO$_4$, saturated aqueous NaCl, and dried over Na$_2$SO$_4$. Evaporation in vacuo yielded the crude acid that was purified by flash chromatography (SiO$_2$). Flash chromatography (SiO$_2$, 5% HOAc-EtOAc) yielded 6-(2-(6-phenoxy-1,2,3,4-tetrahydronaphthalene-2-carbonyl)oxazol-5-yl)picolinic acid (14, 70%) as a yellow solid: $^1$H NMR (CDCl$_3$+0.1% TFA, 600 MHz) δ 8.34 (d, 1H, J=6.0 Hz), 8.22-8.19 (m, 2H), 7.36 (t, 2H, J=8.0 Hz), 7.13-7.10 (m, 2H), 7.03 (d, 2H, J=7.8 Hz), 6.85-6.78 (m, 2H), 3.85-3.84 (m, 1H), 3.13-3.09 (m, 2H), 2.96-2.90 (m, 2H), 2.34-2.31 (m, 1H), 1.97-1.94 (m, 1H); $^{13}$C NMR (CDCl$_3$+0.1% TFA, 150 MHz) δ 191.0, 157.2, 156.8, 155.3, 151.2, 145.0, 140.5, 136.8, 130.2, 129.7 (2C), 128.9, 127.9, 125.8, 125.2, 123.2, 118.9 (2C), 118.6, 117.1, 43.9, 30.2, 28.5, 25.7; HRMS-ESI-TOF m/z 441.1451 ([M+H]$^+$, $C_{26}H_{20}N_2O_5$ requires 441.1445).

(S)-14: $[\alpha]^{23}_D$ −4.5 (c 0.7, THF).

(R)-14: $[\alpha]^{23}_D$ +5.4 (c 0.6, THF).

Enzyme Assay

Enzyme assays were performed at 20-23° C. with purified recombinant rat FAAH expressed in *Escherichia coli* or with solubilized COS-7 membrane extracts from cells transiently transfected with human FAAH cDNA (where specifically indicated) in a buffer of 125 mM Tris/1 mM EDTA/0.2% glycerol/0.02% Triton X-100/0.4 mM Hepes, pH 9.0. The initial rates of hydrolysis (≤10-20% reaction) were monitored using enzyme concentrations (typically 1 nM) at least three times below the measured K; by following the breakdown of $^{14}$C-oleamide, and $K_i$ values (standard deviations are provided in the Supporting Information tables) were established as described (Dixon plot). Lineweaver-Burk analysis of 12 established that it behaves as reversible, competitive inhibitor analogous to 2 and related inhibitors (see experimental).

$^{14}$C-labeled oleamide was prepared from $^{14}$C-labeled oleic acid. The truncated rat FAAH (rFAAH) was expressed in *E. coli* and purified. The purified recombinant rFAAH was used in the inhibition assays unless otherwise indicated. The full-length human FAAH (hFAAH) was expressed in COS-7 cells as described, and the lysate of hFAAH-transfected COS-7 cells was used in the inhibition assays where explicitly indicated.

Figure 4:
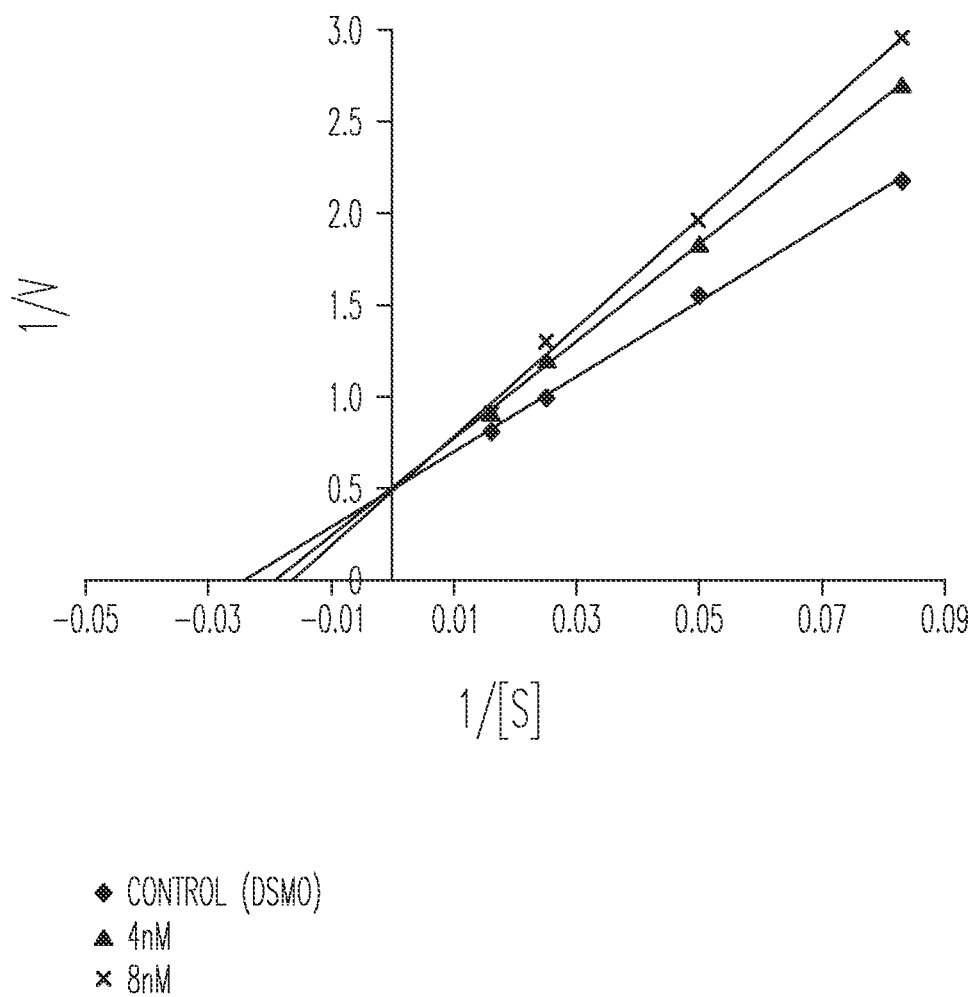
FIG. 4 is a Lineweaver-Burk analysis of compound 12 illustrating reversible, competitive inhibition of FAAH.
Figure 5A:
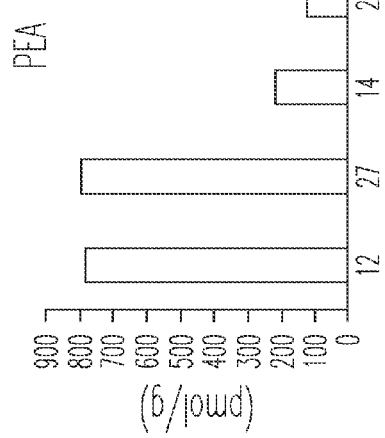
FIG. 5 shows an initial screen for the effects of FAAH inhibitors on brain and liver lipid levels following in vivo inhibitor treatment; n=1 per group.
Figure 5B:
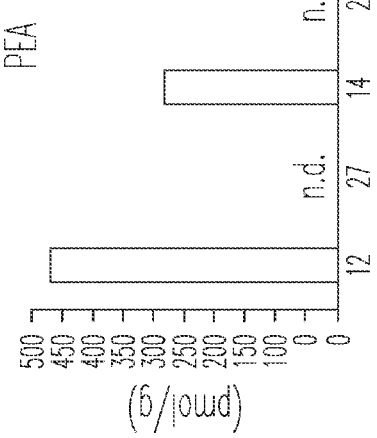
Figure 5C:
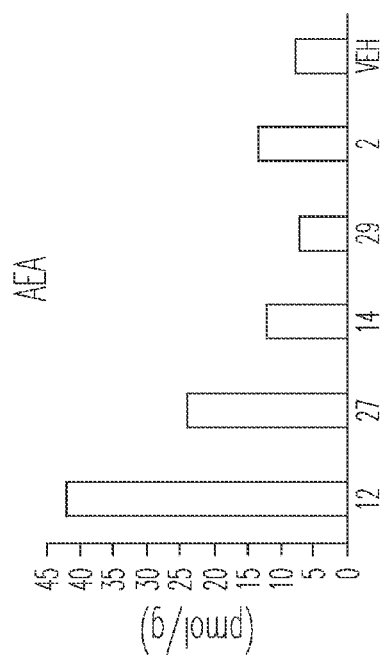
Figure 5D:
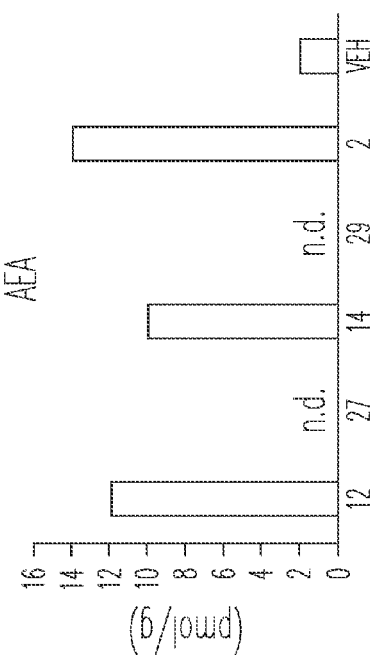

The inhibition assays were performed as follows. In brief, the enzyme reaction was initiated by mixing 1 nM of rFAAH (800, 500, or 200 pM rFAAH for inhibitors with $K_i$≤1-2 nM) with 20 μM of $^{14}$C-labeled oleamide in 500 μL of reaction buffer (125 mM TrisCl, 1 mM EDTA, 0.2% glycerol, 0.02% Triton X-100, 0.4 mM Hepes, pH 9.0) at room temperature in the presence of three different concentrations of inhibitor. The enzyme reaction was terminated by transferring 20 μL of the reaction mixture to 500 μL of 0.1 N HCl at three different time points. The $^{14}$C-labeled oleamide (substrate) and oleic acid (product) were extracted with EtOAc and analyzed by TLC as detailed. The $K_i$ of the inhibitor was calculated using a Dixon plot as described (standard deviations are provided in the Supporting Information tables). Lineweaver-Burk analysis was performed as described confirming competitive, reversible inhibition for 12, FIG. 4.

In Vivo Pharmacodynamic Studies with Inhibitors

Inhibitors were prepared as a saline-emulphor emulsion for intraperitoneal (i.p.) administration by vortexing, sonicating, and gently heating neat compound directly into an 18:1:1 v/v/v solution of saline:ethanol:emulphor, or as a homogeneous PEG solution for oral administration (p.o.) by vortexing, sonicating, and gently heating neat compound directly into PEG300 (Fluka). Male C57BL/6J mice (<6 months old, 20-28 g) were administered inhibitors in saline-emulphor emulsion or an 18:1:1 v/v/v saline:emulphor:ethanol vehicle i.p. at a volume of 10 μL/g weight, or alternatively inhibitors in PEG300 or a PEG300 vehicle p.o. at a volume of 4 μL/g weight. After the indicated amount of time, mice were anesthetized with isofluorane and killed by decapitation. Total brains (~400 mg) and a portion of the liver (~100 mg) were removed and flash frozen in liquid $N_2$. Animal experiments were conducted in accordance with the guidelines of the Institutional Animal Care and Use Committee of The Scripps Research Institute.

Measurement of Brain Lipids.

Tissue was weighed and subsequently Dounce homogenized in 2:1:1 v/v/v $CHCl_3$:MeOH:Tris pH 8.0 (8 mL) containing standards for lipids (50 pmol $d_4$-PEA, 2 pmol $d_4$-AEA, 0.5 nmol $d_5$-2-AG, and 10 nmol pentadecanoic acid). The mixture was vortexed and then centrifuged (1,400×g, 10 min). The organic layer was removed, dried under a stream of $N_2$, resolubilized in 2:1 v/v $CHCl_3$:MeOH (120 μL), and 10 μL of this resolubilized lipid was injected onto an Agilent G6410B QQQ instrument. LC separation was achieved with a Gemini reverse-phase C18 column (5 rpm, 4.6 mm×50 mm, Phenomonex) together with a pre-column (C18, 3.5 μm, 2 mm×20 mm). Mobile phase A was composed of a 95:5 v/v $H_2O$:MeOH, and mobile phase B was composed of a 65:35:5 v/v/v i-PrOH:MeOH:$H_2O$. 0.1% Formic acid or 0.1% ammonium hydroxide was included to assist in ion formation in positive and negative ionization mode, respectively. The flow rate for each run started at 0.1 mL/min with 0% B. At 5 min, the solvent was immediately changed to 60% B with a flow rate of 0.4 mL/min and increased linearly to 100% B over 10 min. This was followed by an isocratic gradient of 100% B for 5 min at 0.5 mL/min before equilibrating for 3 min at 0% B at 0.5 mL/min (23 min total per sample). MS analysis was performed with an electrospray ionization (ESI) source. The following MS parameters were used to measure the indicated metabolites in positive mode (precursor ion, product ion, collision energy in V): AEA (348, 62, 11), OEA (326, 62, 11), PEA (300, 62, 11), $d_4$-AEA (352, 66, 11), $d_4$-PEA (304, 62, 11), 2-AG (379, 287, 8), $d_5$-2-AG (384, 287, 8). For negative polarity, the analysis was performed in MS2 scan mode from 100-1000 m/z. The capillary was set to 4 kV, the fragmentor was set to 100 V, and the delta EMV was set to 0. Lipids were quantified by measuring the area under the peak in comparison to the standards.

Mouse Tail Flick Assay.

Male CD-1 (25-35 g, Charles River) mice were housed in groups of five in Plexiglas chambers with food and water available ad libitum. All animals were maintained on a 12 h light/dark cycle (lights on at 7:00 AM) in a temperature- and humidity-controlled animal colony. All tail-flick experiments were performed under an approved University of New England animal protocol in accordance with institutional guidelines and in accordance with the Guide for the Care and Use of Laboratory Animals as adopted and promulgated by the National Institutes of Health. Efficacy of the test compound was assessed using the 52° C. warm water tail-flick test. The latency to the first sign of a rapid tail-flick was taken as the behavioral endpoint. Each mouse was first tested for baseline latency by immersing its tail in the water and recording the time to response. Mice not responding within 5 sec were excluded from further testing. Mice were then administered the test compound and tested for antinociception at various time points afterwards. Antinociception was calculated by the following formula: % Antinociception=100×(test latency−control latency)/(10−control latency). A maximum score was assigned (100%) to animals not responding within 10 sec to avoid tissue damage.

Chronic Constriction Injury (CCI).

Surgery was performed as follows. Briefly, the right hind leg of male C57BL/6 mice was shaved and swabbed with betadine solution and ethanol. Posterior to the femur, an incision was made and the sciatic nerve was visualized and isolated, following muscle separation. The nerve was ligated twice with 5-0 (1.0 metric) black silk braided suture (Surgical Specialties Corporation, Reading, Pa.). The surrounding muscle and skin were then sutured with 6-0 nylon. Mice were recovered in a heated cage and observed for approximately 2 h before being returned to the vivarium. Anesthesia was maintained by constant inhalation of 1.5% isoflurane. In addition, mice were administered acetaminophen (2.4 mg/mL in drinking water) from 24 h before surgery through 48 h post surgery.

Allodynia Assays.

Allodynia was initially tested 10 days after surgery. Male C57BL/6 mice were habituated to the test apparatus for 2 h on the 2 days prior to testing. On the test day, the mice were brought into the test room, weighed, and allowed to acclimate for at least 1 h before the start of the experiment. Mice were administered inhibitor 12 (50 mg/kg) in PEG300 (4 µL/g body weight) or vehicle (p.o.), then placed in ventilated polycarbonate cylinders on a mesh table. Mechanical (von Frey) and cold (acetone-induced) allodynia were tested at 1, 3, 6, and 9 h post drug administration. Testing was carried out by a separate observer who was blinded to treatment conditions. Mechanical allodynia was assessed with von Frey filaments (North Coast Medical, Morgan Hill, Calif.), using the "up-down" method. Each hind paw was stimulated 5 times per filament (0.16-6.0 g), starting with the 0.6 g filament and increasing weight. Paw clutching or lifting, in response to three or more stimulations, was coded as a positive response. Once a positive response was detected, sequentially lighter-weight filaments were used to assess paw withdrawal threshold. Approximately 30 min after completing the von Frey test, cold allodynia was tested by propelling 10 µL of acetone (Fisher Bioscience) via air burst, from a 200 µL pipette (Rainin Instruments, Oakland, Calif.) onto the plantar surface of each hind paw. Total time lifting or clutching each paw was recorded, with a maximum time of 20 s.

Data Analyses: Behavioral data were analyzed using a two-way mixed factorial analysis of variance (ANOVA) for each paw, with drug treatment as the between subjects measure, and time as the within subjects measure. Follow-up comparisons were made using the Bonferroni test. All animals were included in the analyses. Differences between groups were considered statistically significant at $p<0.05$.

FAAH Production, Crystallization, and Crystal Structure Determination.

The N-terminal transmembrane-deleted humanized version of FAAH (amino acids 32-579) was expressed in E. coli and purified using 0.08% n-undecyl-β-D-maltoside in the ion exchange and size exclusion chromatography steps of the purification. Samples of pure protein were concentrated up to 35 mg/mL and supplemented with 13% xylitol and 2% benzyldimethyl(2-dodecyloxyethyl)ammonium chloride (Aldrich). Large crystals of h/rFAAH were obtained using a reservoir buffer (ratio 1:1) containing 100 mM MES pH 5.5, 100 mM KCl, 100 mM NaF, 30% PEG400, and 8% polypropylene glycol-P400 by sitting drop vapor diffusion at 14° C. in 96-well plates (Innovaplate SD-2, Innovadyne Technologies, Inc.). The crystals were frozen directly in liquid nitrogen and complete datasets were collected from a single crystal at the Stanford Synchrotron Radiation Laboratory (SSRL, Menlo Park, Calif.) on beamline 11-1 at a temperature of 100K. The cocrystal structure of FAAH bound to 12 was solved at 1.90 Å resolution (Table 11, Examples). Data processing was performed using the XDS software package and the structure solved by molecular replacement (Phaser, CCP4 package[85]) using the coordinates from a previous h/rFAAH structure (PDB code 2WJ1) as a search model and refined using programs Phenix suite, coot, Refmac5, and BUSTER. Chemical parameters for the inhibitors were calculated by the Dundee PRODRG Web server. For the last step of refinement, TLS (Translation/Libration/Screw) parameterization has been applied by dividing each monomer in 8 partitions (16 partitions in the crystallographic asymmetric unit).

Molecular Modeling and Binding Energy Evaluation.

The program ICM-Pro (Molsoft, L.L.C.), employing a Monte Carlo minimization algorithm for energy stochastic optimization of ligands, has been previously adopted for covalent docking simulation and binding energy calculation of FAAH inhibitors. Here, the coordinates of h/rFAAH crystal structure with bound 12 (PDB 3OJ8) were used for the simulation of both the (R)- and (S)-enantiomers (X and Y) and binding energies were calculated. The energy functions included the following ICM terms: van der Waals ('vw') and 1-4 van der Waals, hydrogen bonding ('hb'), electrostatics ('el'), entropic free energy, and constant surface tension ('sf'). Estimation of the electrostatic energy was accurately calculated with analytical molecular surface as dielectric boundary. After adding hydrogens, applying global energy-minimization, and assigning partial charges, the inhibitor was removed from the model and each enantiomer was created in silico and manually conjugated to the γ-oxygen of the catalytic Ser241. The docking of(S)-12 was, as expected, fully superimposable to the experimentally (X-ray) determined structure. The dockings were performed with free torsion variables in the ligand and the side chains and backbone of amino acids 192-195 given the flexibility observed in that region of the binding pocket.

Exemplary Compounds of the Invention

| Compound # | Structure |
|---|---|
| 2 (ref.) | 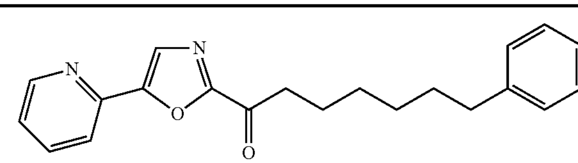 |
| 3 | 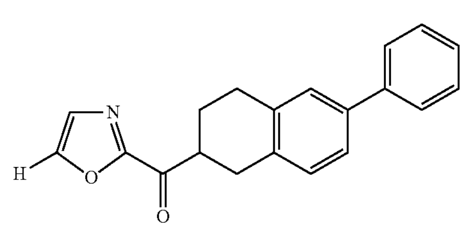 [SMILES: O=C(c1ncco1)C1CCc2cc(-c3ccccc3)ccc2C1] |

| Compound # | Structure |
|---|---|
| 4 | (oxazole with H₃CO₂C at 5-position, C(=O)-linked to 6-phenyl-tetrahydronaphthalen-2-yl) |
| 5 | (oxazole with NC at 5-position, C(=O)-linked to 6-phenyl-tetrahydronaphthalen-2-yl) |
| 6 | (5-(pyridin-2-yl)oxazol-2-yl C(=O)-linked to 6-phenyl-tetrahydronaphthalen-2-yl) |
| 7 | (5-(6-(MeO₂C)pyridin-2-yl)oxazol-2-yl C(=O)-linked to 6-phenyl-tetrahydronaphthalen-2-yl) |
| 8 | (5-(6-(HO₂C)pyridin-2-yl)oxazol-2-yl C(=O)-linked to 6-phenyl-tetrahydronaphthalen-2-yl) |
| 9 | (oxazol-2-yl C(=O)-linked to 6-phenoxy-tetrahydronaphthalen-2-yl) |

-continued
| Compound # | Structure |
|---|---|
| 10 | 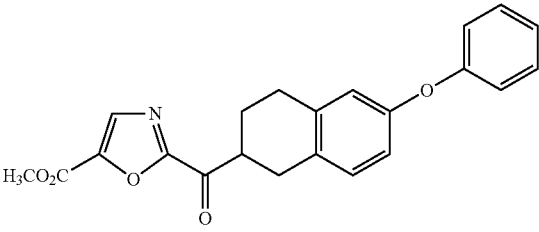 [SMILES: COC(=O)c1cnc(C(=O)C2CCc3cc(Oc4ccccc4)ccc3C2)o1] |
| 11 | 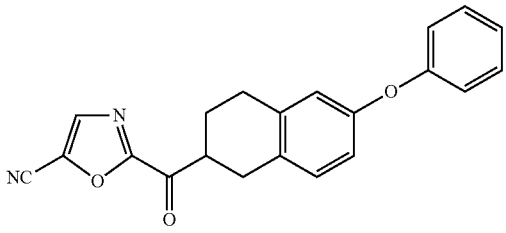 [SMILES: N#Cc1cnc(C(=O)C2CCc3cc(Oc4ccccc4)ccc3C2)o1] |
| 12 | 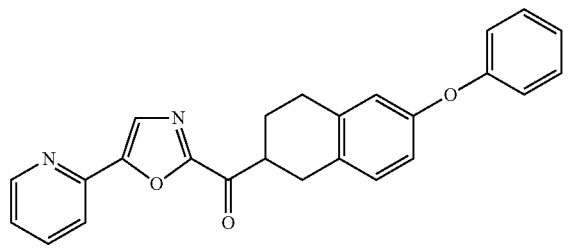 [SMILES: O=C(c1ncc(-c2ccccn2)o1)C1CCc2cc(Oc3ccccc3)ccc2C1] |
| 13 | 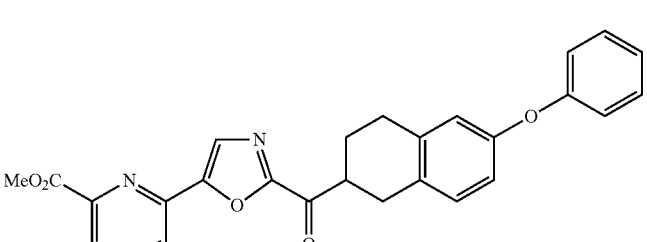 |
| 14 | 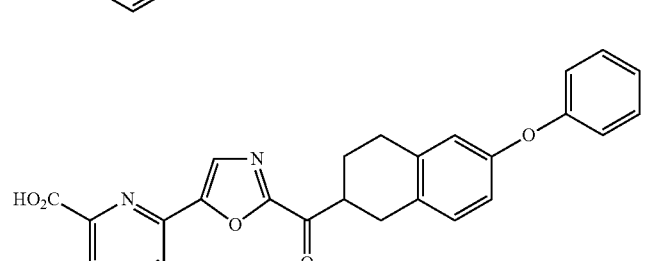 |
| 15 | 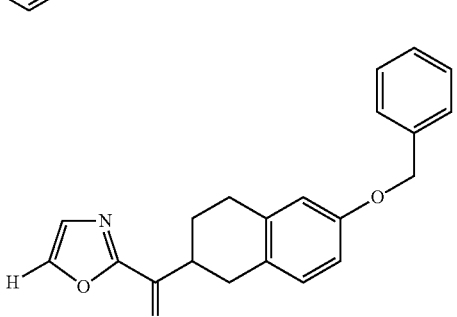 |

-continued

| Compound # | Structure |
|---|---|
| 16 | Methyl 2-(6-(benzyloxy)-1,2,3,4-tetrahydronaphthalene-2-carbonyl)oxazole-5-carboxylate |
| 17 | 2-(6-(benzyloxy)-1,2,3,4-tetrahydronaphthalene-2-carbonyl)oxazole-5-carbonitrile |
| 18 | (6-(benzyloxy)-1,2,3,4-tetrahydronaphthalen-2-yl)(5-(pyridin-2-yl)oxazol-2-yl)methanone |
| 19 | Methyl 6-(2-(6-(benzyloxy)-1,2,3,4-tetrahydronaphthalene-2-carbonyl)oxazol-5-yl)picolinate |
| 20 | 6-(2-(6-(benzyloxy)-1,2,3,4-tetrahydronaphthalene-2-carbonyl)oxazol-5-yl)picolinic acid |

-continued

| Compound # | Structure |
|---|---|
| 21 | 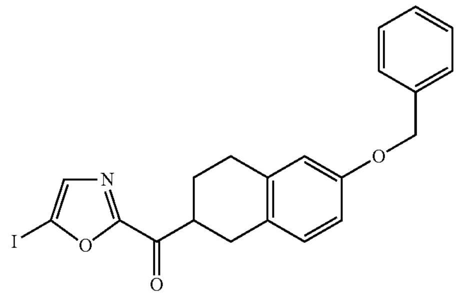 [SMILES: O=C(c1ncc(I)o1)C1CCc2cc(OCc3ccccc3)ccc2C1] |
| 22 | 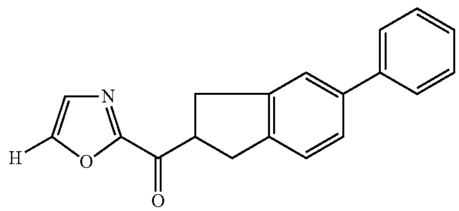 [SMILES: O=C(c1ncco1)C1Cc2ccc(-c3ccccc3)cc2C1] |
| 23 | 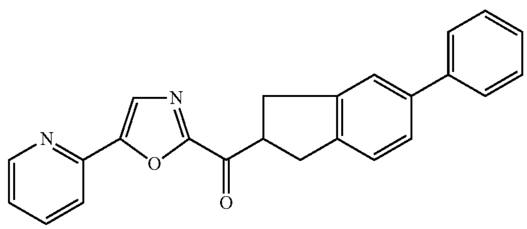 [SMILES: O=C(c1ncc(-c2ccccn2)o1)C1Cc2ccc(-c3ccccc3)cc2C1] |
| 24 | 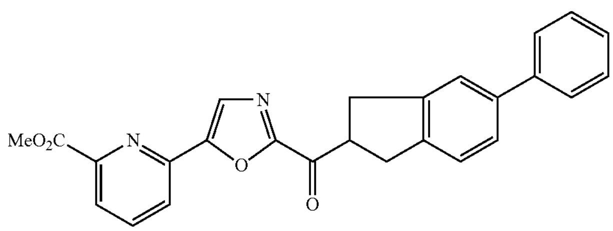 [SMILES: COC(=O)c1cccc(-c2cnc(C(=O)C3Cc4ccc(-c5ccccc5)cc4C3)o2)n1] |
| 25 | 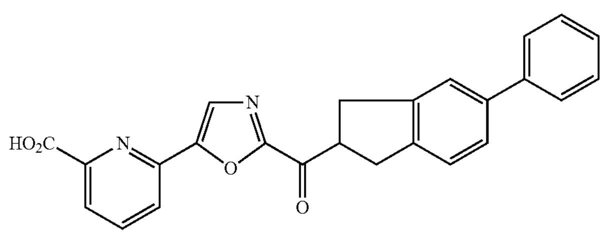 [SMILES: O=C(O)c1cccc(-c2cnc(C(=O)C3Cc4ccc(-c5ccccc5)cc4C3)o2)n1] |
| 26 | 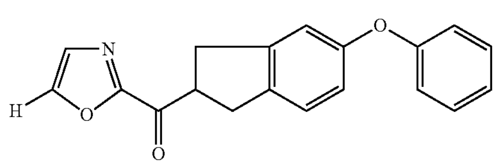 [SMILES: O=C(c1ncco1)C1Cc2ccc(Oc3ccccc3)cc2C1] |
| 27 | 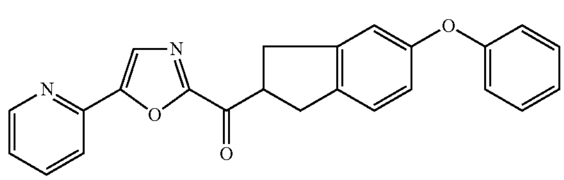 [SMILES: O=C(c1ncc(-c2ccccn2)o1)C1Cc2ccc(Oc3ccccc3)cc2C1] |

| Compound # | Structure |
|---|---|
| 28 | (structure: methyl pyridine-2-carboxylate linked to oxazole, carbonyl, indane, phenoxy-phenyl) |
| 29 | (structure: pyridine-2-carboxylic acid linked to oxazole, carbonyl, indane, phenoxy-phenyl) |
| 30 | (structure: oxazole-CH, carbonyl, indane, O-benzyl) |
| 31 | (structure: pyridine linked to oxazole, carbonyl, indane, O-benzyl) |
| 32 | (structure: methyl pyridine-2-carboxylate linked to oxazole, carbonyl, indane, O-benzyl) |
| 33 | (structure: pyridine-2-carboxylic acid linked to oxazole, carbonyl, indane, O-benzyl) |
| 34 | (structure: 1,3,4-oxadiazole, carbonyl, tetrahydronaphthalene, phenoxy) |
| 35 | (structure: methyl 1,3,4-oxadiazole-2-carboxylate, carbonyl, tetrahydronaphthalene, phenoxy) |

-continued

| Compound # | Structure |
|---|---|
| 36 | 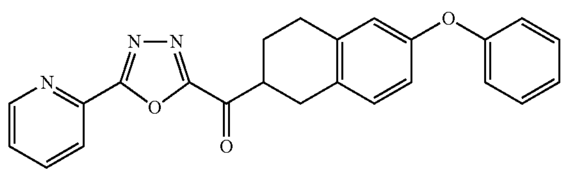 [SMILES: O=C(c1nnc(-c2ccccn2)o1)C1CCc2cc(Oc3ccccc3)ccc2C1] |
| 37 | 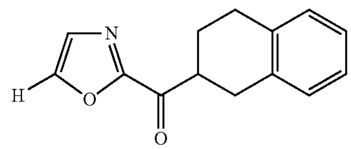 [SMILES: O=C(c1ncco1)C1CCc2ccccc2C1] |
| 38 | 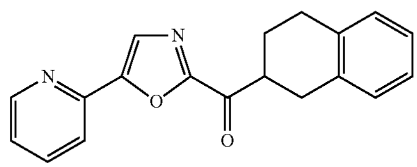 [SMILES: O=C(c1ncc(-c2ccccn2)o1)C1CCc2ccccc2C1] |
| 39 | 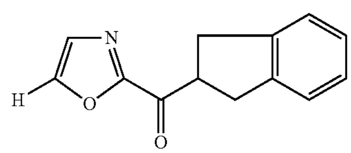 [SMILES: O=C(c1ncco1)C1Cc2ccccc2C1] |
| 40 | 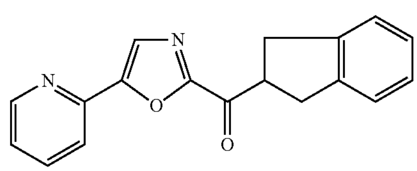 [SMILES: O=C(c1ncc(-c2ccccn2)o1)C1Cc2ccccc2C1] |

Ref. = -reference compound

Exemplary Synthetic Procedures

General Procedure A. The methyl ester (1 equiv) was dissolved in THF and cooled to 0° C. LiAlH$_4$ (2 equiv) was added portionwise to the cooled solution due to the evolution of H$_2$ gas. The mixture was allowed to slowly warm to room temperature and after 2 h the reaction was quenched with the addition of 5% HOAc in EtOH (1 mL). The solution was diluted with EtOAc, washed with H$_2$O, saturated aqueous NaCl, and dried over Na$_2$SO$_4$. Evaporation yielded the crude alcohol that was purified by flash chromatography (SiO$_2$).

General Procedure B. The alcohol (1 equiv) was dissolved in CH$_2$Cl$_2$ (0.03 M) and Dess-Martin periodinane (1.5 equiv) was added. The mixture was stirred at room temperature for 2 h before the reaction mixture was reduced to half volume and then was directly loaded onto silica gel and purified by flash chromatography (SiO$_2$) yielding the desired aldehyde.

General Procedure C. The stannane intermediate (1 equiv), (Ph$_3$P)$_4$Pd (0.1 equiv), and aryl halide (2 equiv) were dissolved in anhydrous 1,4-dioxane (8 mL/0.150 mmol of stannane) and the mixture was warmed to reflux for 16 h under Ar. The mixture was diluted with EtOAc, washed with saturated aqueous NaCl, and dried over Na$_2$SO$_4$. Evaporation in vacuo yielded the crude coupling product that was purified by flash chromatography (SiO$_2$).

General Procedure D. The TBS ether (1 equiv) was dissolved in THF (3 mL/0.163 mmol of TBS ether), treated with Bu$_4$NF (1 M in THF, 1.2 equiv) and stirred at room temperature for 2 h under Ar. The reaction mixture was diluted with EtOAc, washed with saturated aqueous NaCl, and dried over Na$_2$SO$_4$. Evaporation in vacuo yielded the crude alcohol that was filtered through a short silica gel pad.

General Procedure E. The alcohol (1 equiv) was dissolved in CH$_2$Cl$_2$ (3 mL/0.068 mmol of alcohol) and Dess-Martin periodinane (1.2 equiv) was added. The mixture was stirred at room temperature for 2 h before silica gel was added and the reaction mixture was evaporated in vacuo to afford the crude ketone absorbed on silica gel. This mixture was subsequently purified by flash chromatography (SiO$_2$) yielding the pure α-ketoheterocycle.

General Procedure F. The ester (1 equiv) was dissolved in a mixture of 3:2 THF/H$_2$O and LiOH (1 equiv) was added. The reaction mixture was stirred for 2 h at room temperature before the mixture was made acidic with the addition of aqueous 1 N HCl. The solution was diluted with EtOAc and the organic layer was separated from the aqueous layer. The aqueous layer was extracted with EtOAc. The combined organic extracts were washed with saturated aqueous NaCl, and dried over Na$_2$SO$_4$. Evaporation in vacuo yielded the crude acid that was purified by chromatography (SiO$_2$).

General Procedure G. The ester (0.01 mmol) was dissolved in 1,2-dichloroethane and after addition of trimethyltin hydroxide (3 equiv), the mixture was warmed to 70° C. for 16 h. The mixture was concentrated in vacuo and diluted with EtOAc and the organic layer was washed with aqueous 0.01 N KHSO$_4$, saturated aqueous NaCl, and dried over Na$_2$SO$_4$. Evaporation in vacuo yielded the crude acid that was purified by flash chromatography (SiO$_2$).

Methyl 1,2,3,4-Tetrahydro-6-methoxy-1-oxonaphthalene-2-carboxylate (S1)

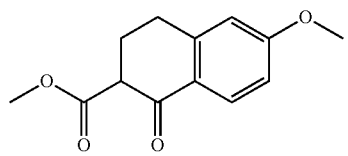

A solution of NaH (4.70 g, 323.5 mmol) in anhydrous THF (50 mL) was treated with dimethylcarbonate (19 mL, 215.6 mmol). The reaction mixture was cooled to 0° C. under Ar and a solution of 6-methoxy-3,4-dihydronaphthalen-1(2H)-one (10 g, 56.75 mmol) in THF (10 mL) was added dropwise. The reaction mixture was warmed at reflux for 12 h then quenched with the addition of HOAc (until pH=7) and diluted with EtOAc. The organic layer was washed with H$_2$O, saturated aqueous NaCl, and dried over Na$_2$SO$_4$. Evaporation in vacuo yielded the crude product that was purified by flash chromatography (SiO$_2$, 30% EtOAc-hexanes) to provide the title compound (11.70 g, 88%) as a white solid: $^1$H NMR (CDCl$_3$, 500 MHz) δ 7.98 (d, 1H, J=9.0 Hz), 6.81 (dd, 1H, J=2.5, 9.0 Hz), 6.66 (d, 1H, J=2.5 Hz), 3.83 (s, 3H), 3.74 (s, 3H), 3.56-3.53 (m, 1H), 3.03-2.89 (m, 2H), 2.47-2.43 (m, 1H), 2.33-2.30 (m, 1H); $^{13}$C NMR (CDCl$_3$, 125 MHz) δ 191.6, 170.7, 163.8, 146.1, 130.1, 125.1, 113.4, 112.4, 55.3, 54.0, 52.1, 27.9, 26.3.

Methyl 1,2,3,4-Tetrahydro-6-methoxynaphthalene-2-carboxylate (S2)

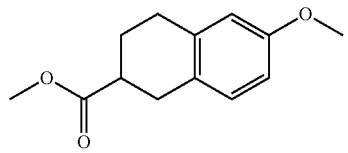

A sample of methyl 1,2,3,4-tetrahydro-6-methoxy-1-oxonaphthalene-2-carboxylate (S1, 11.70 g, 49.9 mmol) was dissolved in HOAc (60 mL), containing perchloric acid (0.5 mL) and 10% Pd/C (2 g, 4.99 mmol). The mixture was flushed with H$_2$ and kept under an atmosphere of H$_2$ for 16 h. Upon completion, the reaction mixture was filtered through a pad of Celite and washed with EtOAc. The organic layer was washed with H$_2$O then saturated aqueous NaCl, and dried over Na$_2$SO$_4$. Evaporation in vacuo yielded the crude product that was purified by flash chromatography (SiO$_2$, 10% EtOAc-hexanes) to provide the title compound (6.41 g, 58%) as a colorless oil: $^1$H NMR (CDCl$_3$, 600 MHz) δ 7.01 (d, 1H, J=8.4 Hz), 6.69 (dd, 1H, J=2.4, 8.4 Hz), 6.62 (d, 1H, J=2.4 Hz), 3.77 (s, 3H), 3.72 (s, 3H), 2.97-2.92 (m, 2H), 2.89-2.82 (m, 2H), 2.73-2.70 (m, 1H), 2.20-2.17 (m, 1H), 1.87-1.82 (m, 1H); $^{13}$C NMR (CDCl$_3$, 150 MHz) δ 175.9, 157.7, 136.7, 129.8, 126.9, 113.3, 112.1, 55.2, 51.7, 40.1, 30.8, 28.8, 25.8.

1,2,3,4-Tetrahydro-6-hydroxynaphthalene-2-carboxylic Acid (S3)

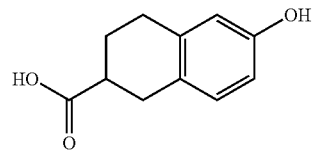 [SMILES: O=C(O)C1CCc2cc(O)ccc2C1]

A sample of methyl 1,2,3,4-tetrahydro-6-methoxynaphthalene-2-carboxylate (S2, 6.41 g, 29.1 mmol) was dissolved in HOAc (50 mL) and 10% aqueous HBr (50 mL). The mixture was warmed to reflux under Ar for 2 h then cooled to room temperature and diluted with EtOAc. The organic layer was washed with H$_2$O then saturated aqueous NaCl, and dried over Na$_2$SO$_4$. Evaporation in vacuo yielded the crude product that was purified by flash chromatography (SiO$_2$, 50% EtOAc-hexanes) to provide the title compound (6.6 g, 98%) as a white solid: $^1$H NMR (CDCl$_3$+0.1% DMSO-d$_6$, 400 MHz) δ 7.99 (brs, 1H), 6.89 (d, 1H, J=8.4 Hz), 6.61 (dd, 1H, J=2.4, 8.4 Hz), 6.55 (d, 1H, J=2.4 Hz), 2.95-2.62 (m, 5H), 2.18-2.14 (m, 1H), 1.84-1.78 (m, 1H); $^{13}$C NMR (CDCl$_3$+0.1% DMSO-d$_6$, 100 MHz) δ 179.0, 154.5, 136.7, 129.8, 125.9, 114.9, 113.3, 39.9, 30.7, 28.5, 25.6.

Methyl 1,2,3,4-Tetrahydro-6-hydroxynaphthalene-2-carboxylate (S4)

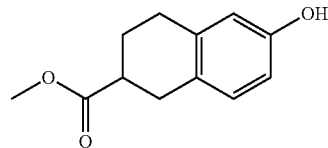

A sample of 1,2,3,4-tetrahydro-6-hydroxynaphthalene-2-carboxylic acid (S3, 6.6 g, 34.3 mmol) was dissolved in MeOH (30 mL) and concentrated H$_2$SO$_4$ (3 mL). The mixture was warmed to reflux under Ar for 1 h then cooled to room temperature and diluted with EtOAc. The organic layer was washed with H$_2$O then saturated aqueous NaCl, and dried over Na$_2$SO$_4$. Evaporation in vacuo yielded the crude product that was purified by flash chromatography (SiO$_2$, 50% EtOAc-hexanes) to provide the title compound (4.75 g, 67%) as a white solid: $^1$H NMR (CDCl$_3$, 600 MHz) δ 6.93 (d, 1H, J=8.4 Hz), 6.64 (dd, 1H, J=2.4, 8.4 Hz), 6.58 (d, 1H, J=2.4 Hz), 6.22 (s, 1H), 3.75 (s, 3H), 2.97-2.87 (m, 2H), 2.79-2.70 (m, 3H), 2.19-2.16 (m, 1H), 1.86-1.80 (m, 1H); $^{13}$C NMR (CDCl$_3$, 150 MHz) δ 176.6, 153.7, 136.7, 129.9, 126.4, 114.9, 113.2, 51.9, 40.1, 30.8, 28.4, 25.6.

Methyl 6-(Trifluoromethanesulfonyloxy)-1,2,3,4-tetrahydronaphthalene-2-carboxylate (S5)

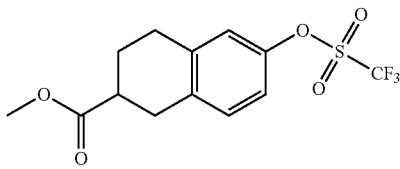 [SMILES: COC(=O)C1CCc2cc(OS(=O)(=O)C(F)(F)F)ccc2C1]

A sample of methyl 1,2,3,4-tetrahydro-6-hydroxynaphthalene-2-carboxylate (S4, 1 g, 4.84 mmol) was dissolved in anhydrous pyridine (20 mL), cooled to 0° C. and triflic anydride (1.2 mL, 7.27 mmol) was added. The reaction mixture was warmed to room temperature and stirred under Ar for 2 h. The mixture was diluted with $CH_2Cl_2$, washed with $H_2O$, saturated aqueous NaCl, and dried over $Na_2SO_4$. Evaporation in vacuo yielded the crude product that was not further purified to provide the title compound (1.74 g, 98%) as a white solid: $^1$H NMR (CDCl$_3$, 500 MHz) δ 7.11 (d, 1H, J=8.5 Hz), 6.99-6.96 (m, 2H), 3.68 (s, 3H), 2.98-2.94 (m, 2H), 2.85-2.79 (m, 2H), 2.74-2.68 (m, 1H), 2.19-2.15 (m, 1H), 1.86-1.80 (m, 1H); $^{13}$C NMR (CDCl$_3$, 125 MHz) δ 174.9, 147.4, 138.1, 135.3, 130.5, 120.9, 118.5 (q, CF$_3$, J=320 Hz), 118.4, 51.5, 39.3, 39.1, 30.8, 28.2, 25.0.

Methyl 6-Phenyl-1,2,3,4-tetrahydronaphthalene-2-carboxylate (S6)

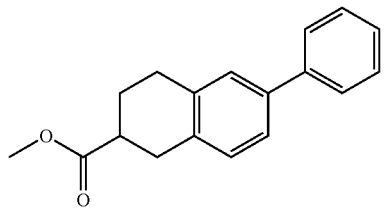 [SMILES: COC(=O)C1CCc2cc(-c3ccccc3)ccc2C1]

A mixture of methyl 6-(trifluoromethanesulfonyloxy)-1,2,3,4-tetrahydronaphthalene-2-carboxylate (S5, 1.74 g, 5.14 mmol), (PPh$_3$)$_4$Pd (178 mg, 0.15 mmol), and phenylboronic acid (760 mg, 6.17 mmol) and 2 M aqueous $Na_2CO_3$ (5 mL) were dissolved in anhydrous THF (30 mL) and the mixture was warmed at reflux for 16 h under Ar. The mixture was diluted with EtOAc, washed with saturated aqueous NaCl, and dried over $Na_2SO_4$. Evaporation in vacuo yielded crude product that was purified by column chromatography (SiO$_2$, 10% EtOAc-hexanes) to give the title compound (1.09 g, 79%) as a white solid: $^1$H NMR (CDCl$_3$, 600 MHz) δ 7.66 (d, 2H, J=8.5 Hz), 7.50 (t, 2H, J=7.8 Hz), 7.45-7.39 (m, 3H), 7.25 (d, 1H, J=7.8 Hz), 3.82 (s, 3H), 3.16-3.13 (m, 2H), 3.04-2.93 (m, 2H), 2.87-2.82 (m, 1H), 2.34-2.30 (m, 1H), 2.02-1.97 (m, 1H); $^{13}$C NMR (CDCl$_3$, 150 MHz) δ 175.8, 141.0, 138.9, 136.0, 134.0, 129.4, 128.6 (2C), 127.4, 127.0, 126.9 (2C), 124.6, 51.8, 39.9, 31.3, 28.6, 25.9.

(6-Phenyl-1,2,3,4-tetrahydronaphthalen-2-yl)methanol (S7)

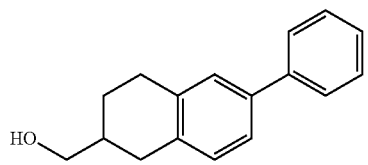 [SMILES: OCC1CCc2cc(-c3ccccc3)ccc2C1]

The title compound was prepared from methyl 6-phenyl-1,2,3,4-tetrahydronaphthalene-2-carboxylate (S6, 1.09 g, 4.09 mmol) following general procedure A. Flash chromatography (SiO$_2$, 50% EtOAc-hexanes) afforded the title compound (910 mg, 93%) as a colorless oil: $^1$H NMR (CDCl$_3$, 500 MHz) δ 7.69 (d, 2H, J=8.5 Hz), 7.52 (t, 2H, J=7.8 Hz), 7.46-7.41 (m, 3H), 7.25 (d, 1H, J=7.8 Hz), 3.72 (d, 2H, J=6.5 Hz), 3.05-2.96 (m, 3H), 2.73 (s, 1H), 2.66-2.61 (m, 1H), 2.15-2.07 (m, 2H), 1.59-1.55 (m, 1H); $^{13}$C NMR (CDCl$_3$, 125 MHz) δ 141.0, 138.4, 136.9, 135.0, 129.5 (2C), 128.5, 127.3, 126.7 (3C), 124.3, 67.3, 36.9, 32.0, 28.7, 25.8.

6-Phenyl-1,2,3,4-tetrahydronaphthalene-2-carboxaldehyde (S8)

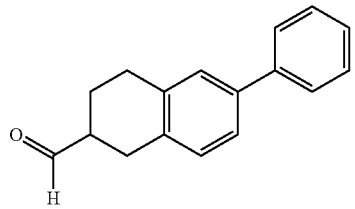 [SMILES: O=CC1CCc2cc(-c3ccccc3)ccc2C1]

The title compound was prepared from (6-phenyl-1,2,3,4-tetrahydronaphthalen-2-yl)methanol (S7, 910 mg, 3.81 mmol) following general procedure B. Flash chromatography (SiO$_2$, 20% EtOAc-hexanes) afforded the title compound (720 mg, 79%) as a white solid: $^1$H NMR (CDCl$_3$, 500 MHz) δ 9.79 (s, 1H), 7.63 (d, 2H, J=8.5 Hz), 7.48 (t, 2H, J=7.8 Hz), 7.42-7.36 (m, 3H), 7.23 (d, 1H, J=7.8 Hz), 3.02 (d, 2H, J=6.5 Hz), 2.98-2.88 (m, 2H), 2.72-2.66 (m, 1H), 2.26-2.21 (m, 1H), 1.86-1.78 (m, 1H); $^{13}$C NMR (CDCl$_3$, 125 MHz) δ 203.2, 140.6, 138.7, 136.0, 133.2, 129.4, 128.5, 128.4 (2C), 127.1, 126.8, 126.7, 126.6 (2C), 124.4, 46.5, 27.9, 27.8, 22.6, 13.9.

Oxazol-2-yl(6-phenyl-1,2,3,4-tetrahydronaphthalen-2-yl)methanol (S9)

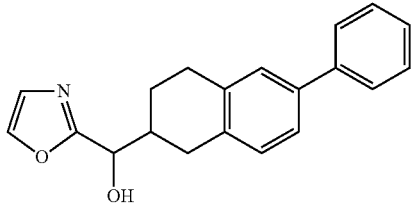 [SMILES: OC(c1ncco1)C1CCc2cc(-c3ccccc3)ccc2C1]

Oxazole (0.2 mL, 3.04 mmol) in anhydrous THF (30 mL) was treated with BH$_3$.THF (1 M, 3.32 mL, 3.32 mmol) and the solution was stirred at room temperature for 1 h before being cooled to −78° C. and treated with 2.16 M n-BuLi (1.8 mL, 3.95 mmol) dropwise. The reaction mixture was stirred at −78° C. for 40 min before a solution of 6-phenyl-1,2,3,4-tetrahydronaphthalene-2-carboxaldehyde (S8, 720 mg, 3.04 mmol) in THF (20 mL) was added. The reaction mixture was stirred at −78° C. for 2 h before being warmed to room temperature. A 5% HOAc-EtOH solution (50 mL) was added and this mixture was stirred at room temperature for 12 h. The solvent was removed under reduced pressure and the residue was dissolved in EtOAc, and washed with $H_2O$, saturated aqueous NaHCO$_3$ and saturated aqueous NaCl before the organic layer was dried over MgSO$_4$ and the solvent was removed under reduced pressure. Flash chromatography (SiO$_2$, 40% EtOAc-hexanes) afforded the title compound (510 mg, 55%) as a colorless oil: $^1$H NMR (CDCl$_3$, 500 MHz) δ 7.65 (d, 1H, J=2.0 Hz), 7.58 (d, 2H, J=8.5 Hz), 7.43 (t, 2H, J=7.8 Hz), 7.37-7.33 (m, 2H), 7.18

(d, 1H, J=7.8 Hz), 7.11-7.10 (m, 1H), 4.80 (q, 1H, J=6.5 Hz), 4.42 (s, 1H, OH), 3.00-2.83 (m, 2H), 2.69-2.68 (m, 2H), 2.45-2.40 (m, 1H), 2.23-2.19 (m, 1H), 1.86-1.83 (m, 1H), 1.68-1.56 (m, 1H); $^{13}$C NMR (CDCl$_3$, 125 MHz) δ 165.4, 165.3, 141.0, 138.8, 138.6, 136.7, 136.5, 134.7, 134.5, 129.6, 129.5, 128.5 (2C), 127.35, 127.31, 126.8 (2C), 126.5, 124.47, 124.43, 71.2, 71.0, 39.7, 39.6, 31.1, 30.7, 28.9, 28.8, 25.3, 24.6.

Oxazol-2-yl(6-phenyl-1,2,3,4-tetrahydronaphthalen-2-yl)methanone (3)

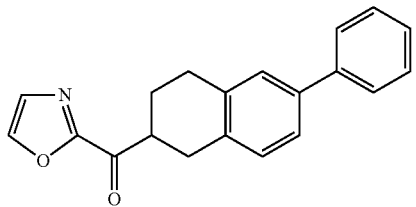 [SMILES: O=C(c1ncco1)C1CCc2cc(-c3ccccc3)ccc2C1]

The title compound was prepared from oxazol-2-yl(6-phenyl-1,2,3,4-tetrahydronapthalen-2-yl)methanol (S9, 50 mg, 0.163 mmol) following general procedure E. Flash chromatography (SiO$_2$, 20% EtOAc-hexanes) yielded the title compound (44.8 mg, 90%) as a white solid: $^1$H NMR (CDCl$_3$, 600 MHz) δ 7.86 (s, 1H), 7.58 (d, 2H, J=8.5 Hz), 7.43 (t, 2H, J=7.8 Hz), 7.38-7.33 (m, 4H), 7.20 (d, 1H, J=7.8 Hz), 3.92-3.87 (m, 1H), 3.19-3.01 (m, 4H), 2.36-2.33 (m, 1H), 1.99-1.93 (m, 1H); $^{13}$C NMR (CDCl$_3$, 150 MHz) δ 190.4, 157.5, 141.6, 141.0, 139.0, 135.9, 133.9, 129.4, 129.0, 128.6 (2C), 127.4, 127.0, 126.9 (2C), 124.7, 43.5, 30.7, 28.8, 25.9; HRMS-ESI-TOF m/z 304.1322 ([M+H]$^+$, C$_{20}$H$_{17}$NO$_2$ requires 304.1332). The enantiomers were separated using a semipreparative chiral phase HPLC column (ChiralPAK AD, 10 μm, 2×25 cm, 1% i-PrOH-hexanes, 7 mL/min, α=1.18).
(S)-3: [α]$^{23}_D$ −16 (c 0.1, THF).
(R)-3: [α]$^{23}_D$ +15 (c 0.1, THF).

2-((tert-Butyldimethylsilyloxy)(6-phenyl-1,2,3,4-tetrahydronaphthalen-2-yl)methyl)oxazole (S10)

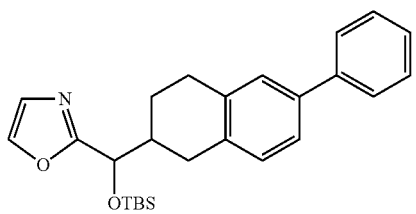 [SMILES: CC(C)(C)[Si](C)(C)OC(c1ncco1)C1CCc2cc(-c3ccccc3)ccc2C1]

A solution of oxazol-2-yl(6-phenyl-1,2,3,4-tetrahydronaphthalen-2-yl)methanol (S9, 400 mg, 1.3 mmol), TBSCl (470 mg, 3.12 mmol) and imidazole (445 mg, 6.54 mmol) in DMF (20 mL) was stirred at room temperature for 16 h before it was diluted with EtOAc, washed with H$_2$O, and saturated aqueous NaCl. The organic layer was dried over MgSO$_4$ and the solvent was removed under reduced pressure. Flash chromatography (SiO$_2$, 10% EtOAc-hexanes) yielded the title compound (420 mg, 77%) as a thick colorless oil: $^1$H NMR (CDCl$_3$, 500 MHz) δ 7.68 (s, 1H), 7.62-7.60 (d, 2H, J=8.5 Hz), 7.45 (t, 2H, J=7.8 Hz), 7.40-7.34 (m, 2H), 7.22 (d, 1H, J=7.8 Hz), 7.16-7.12 (m, 1H), 3.99-3.87 (m, 1H), 4.85 (d, 0.5H, J=7.0 Hz), 4.80 (d, 0.5H, J=7.0 Hz), 3.08-2.82 (m, 2H), 2.69-2.57 (m, 2H), 2.46-2.24 (m, 2H), 1.82-1.79 (m, 1H), 1.63-1.55 (m, 1H), 0.98 (s, 9H), 0.16 (s, 1.5H), 0.15 (s, 1.5H), −0.01 (s, 1.5H), −0.02 (s, 1.5H); $^{13}$C NMR (CDCl$_3$, 125 MHz) δ 164.5, 164.4, 141.1, 138.6, 138.56, 138.50, 138.4, 136.8, 136.6, 135.0, 134.6, 129.7, 129.5, 128.5 (2C), 127.3, 127.2, 126.87, 126.83 (2C), 126.7, 124.4, 72.35, 72.31, 40.4, 40.3, 31.0, 30.9, 28.98, 28.91, 25.6 (3C), 25.4, 25.1, 18.1, −5.31, −5.39.

2-((tert-Butyldimethylsilyloxy)(6-phenyl-1,2,3,4-tetrahydronaphthalen-2-yl)methyl)-5-(tributylstannyl)oxazole (S11)

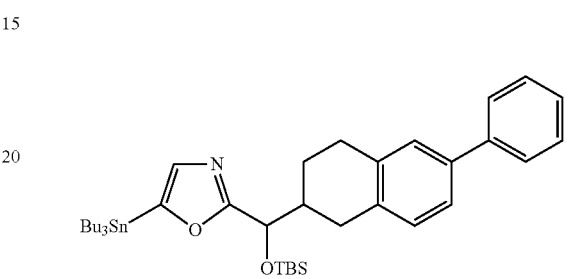

A solution of 2-((tert-butyldimethylsilyloxy)(6-phenyl-1,2,3,4-tetrahydronaphthalen-2-yl)methyl)oxazole (S10, 219 mg, 0.52 mmol) in THF (10 mL) was cooled to −78° C. before it was treated with 2.16 M n-BuLi (0.26 mL, 0.57 mmol) dropwise. The reaction mixture was stirred at −78° C. for 2 h, and treated with a solution of Bu$_3$SnCl (0.28 mL, 1.04 mmol) and stirred for 5 min. The solution was warmed to room temperature and diluted with EtOAc, and washed with saturated aqueous NaCl. The organic layer was dried over MgSO$_4$ and the solvent was removed under reduced pressure. Flash chromatography (SiO$_2$, 0-5% EtOAc-hexanes) yielded the title compound (350 mg, 65%) as a thick colorless oil: $^1$H NMR (CDCl$_3$, 600 MHz) δ 7.58-7.56 (d, 2H, J=8.5 Hz), 7.41 (t, 2H, J=7.8 Hz), 7.35-7.30 (m, 3H), 7.18-7.13 (m, 3H), 4.83 (d, 0.5H, J=7.0 Hz), 4.77 (d, 0.5H, J=7.0 Hz), 3.00-2.81 (m, 4H), 2.39-2.20 (m, 4H), 1.59-1.12 (m, 25H), 0.94 (s, 9H), 0.05 (s, 1.5H), 0.04 (s, 1.5H), −0.12 (s, 1.5H), −0.13 (s, 1.5H); $^{13}$C NMR (CDCl$_3$, 150 MHz) δ 168.6, 168.4, 154.9, 154.8, 141.28, 141.27, 138.66, 138.60, 137.3, 137.2, 137.05, 137.02, 136.8, 135.3, 135.0, 129.7, 129.63, 128.60 (2C), 127.4, 127.3, 126.96, 126.91 (2C), 126.8, 124.44, 124.41, 72.5, 40.7, 31.2, 29.36, 29.30, 29.23 (3C), 29.1, 28.9, 27.8, 27.6, 27.4 (3C), 27.2, 27.1, 26.8, 25.7, 18.2, 17.4, 13.7 (3C), 13.6, 13.5, 10.2, 9.78, 9.73, 8.7 (3C), 7.75, 7.71, −5.29, −5.30, −5.34, −5.36.

Methyl 2-((tert-Butyldimethylsilyloxy)(6-phenyl-1,2,3,4-tetrahydronaphthalen-2-yl)methyl)oxazole-5-carboxylate (S12)

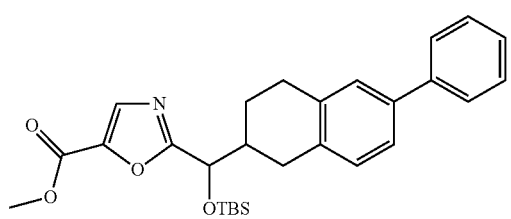 [SMILES: COC(=O)c1cnc(C(O[Si](C)(C)C(C)(C)C)C2CCc3cc(-c4ccccc4)ccc3C2)o1]

A solution of 2-((tert-butyldimethylsilyloxy)(6-phenyl-1,2,3,4-tetrahydronaphthalen-2-yl)methyl)oxazole (S11, 28.7 mg, 0.068 mmol) in THF (0.5 mL) was cooled to −78° C. before it was treated with 2.16 M n-BuLi (0.034 mL, 0.075 mmol) dropwise. The reaction mixture was stirred at −78° C. for 2 h, treated with a solution of Mander's reagent (MeO$_2$CCN, 0.027 mL, 0.34 mmol) in THF (0.5 mL), and stirred for 5 min. The solution was warmed to room temperature and diluted with EtOAc, and washed with saturated aqueous NaCl. The organic layer was dried over MgSO$_4$ and the solvent was removed under reduced pressure. Flash chromatography (SiO$_2$, 10% EtOAc-hexanes) yielded the title compound (28.5 mg, 87%) as a colorless oil: $^1$H NMR (CDCl$_3$, 600 MHz) δ 7.75 (d, 1H, J=4.8 Hz), 7.57-7.55 (m, 2H), 7.41 (t, 2H J=7.8 Hz), 7.34-7.30 (m, 2H), 7.16 (d, 1H, J=8.4 Hz), 7.08 (d, 1H, J=8.4 Hz), 4.83 (d, 0.5H, J=6.0 Hz), 4.76 (d, 0.5H, J=6.0 Hz), 3.93 (s, 3H), 2.94-2.80 (m, 3H), 2.64-2.60 (m, 2H), 2.43-2.40 (m, 1H), 2.23-2.20 (m, 0.5H), 1.84-1.79 (m, 0.5H), 0.92 (s, 9H), 0.10 (s, 1.5H), 0.08 (s, 1.5H), −0.05 (s, 1.5H), −0.04 (s, 1.5H); $^{13}$C NMR (CDCl$_3$, 150 MHz) δ 167.8, 167.6, 158.08, 158.06, 142.26, 142.20, 141.14, 141.11, 138.8, 138.7, 136.8, 136.5, 134.8, 134.4, 134.06, 134.03, 129.7, 129.5, 128.6 (2C), 127.4, 127.3, 126.9 (2C), 126.8, 124.54, 124.51, 72.4, 72.3, 52.2, 40.4, 40.3, 31.1, 30.4, 28.97, 28.95, 25.6 (3C), 24.8, 18.2, −5.14, −5.27, −5.29.

Methyl 2-(Hydroxy(6-phenyl-1,2,3,4-tetrahydronaphthalen-2-yl)methyl)oxazole-5-carboxylate (S13)

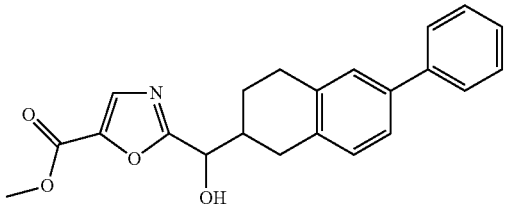 [SMILES: COC(=O)c1cnc(C(O)C2CCc3cc(-c4ccccc4)ccc3C2)o1]

The title compound was prepared from methyl 2-((tert-butyldimethylsilyloxy)(6-phenyl-1,2,3,4-tetrahydronaphthalen-2-yl)methyl)oxazole-5-carboxylate (S12, 9.4 mg, 0.019 mmol) following general procedure D. Flash chromatography (SiO$_2$, 50-100% EtOAc-hexanes) yielded the title compound (7.8 mg, 98%) as a white solid: $^1$H NMR (CDCl$_3$, 600 MHz) δ 7.76 (s, 1H), 7.56 (d, 2H, J=4.8 Hz), 7.41 (t, 2H, J=7.8 Hz), 7.34-7.31 (m, 3H), 7.15 (d, 0.5H, J=7.8 Hz), 7.10 (d, 0.5H, J=7.8 Hz), 4.86 (s, 0.5H), 4.83 (s, 0.5H), 3.93 (s, 3H), 2.96-2.74 (m, 3H), 2.45-2.41 (m, 1H), 2.11-2.09 (m, 0.5H), 1.93-1.90 (m, 0.5H), 1.68-1.58 (m, 3H); $^{13}$C NMR (CDCl$_3$, 150 MHz) δ 167.76, 167.71, 157.96, 157.95, 142.75, 142.73, 141.0, 138.8, 136.5, 136.4, 134.4, 134.3, 133.79, 133.77, 129.7, 129.5, 128.6 (2C), 127.4, 126.99 (2C), 126.96, 124.63, 124.61, 124.5, 71.6, 71.4, 52.3, 39.9, 39.8, 31.1, 30.8, 28.95, 28.91, 25.4, 24.2.

Methyl 2-(6-Phenyl-1,2,3,4-tetrahydronaphthalene-2-carbonyl)oxazole-5-carboxylate (4)

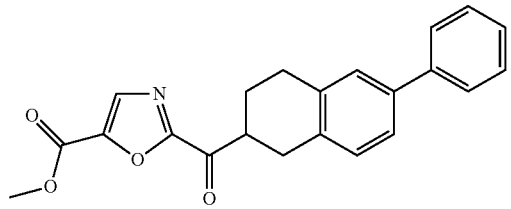 [SMILES: COC(=O)c1cnc(C(=O)C2CCc3cc(-c4ccccc4)ccc3C2)o1]

The title compound was prepared from methyl 2-(hydroxy(6-phenyl-1,2,3,4-tetrahydronaphthalen-2-yl)methyl)oxazole-5-carboxylate (S13, 7.8 mg, 0.021 mmol) following general procedure E. Flash chromatography (SiO$_2$, 20% EtOAc-hexanes) yielded the title compound (5 mg, 65%) as a white solid: $^1$H NMR (CDCl$_3$, 600 MHz) δ 7.92 (s, 1H), 7.58 (d, 2H, J=4.8 Hz), 7.42 (t, 2H, J=7.8 Hz), 7.37-7.33 (m, 2H), 7.19 (d, 1H, J=7.8 Hz), 3.98 (s, 3H), 3.90-3.87 (m, 1H), 3.15-3.02 (m, 2H), 2.35-2.32 (m, 2H), 1.96-1.94 (m, 2H); $^{13}$C NMR (CDCl$_3$, 150 MHz) δ 190.2, 157.8, 157.4, 143.9, 141.0, 139.1, 135.8, 134.6, 133.6, 129.5, 128.8, 128.7, 127.4, 127.08, 127.04, 124.8, 52.7, 43.8, 30.68, 30.60, 28.7, 25.7; HRMS-ESI-TOF m/z 362.1385 ([M+H]$^+$, C$_{22}$H$_{19}$NO$_4$ requires 362.1387). The enantiomers were separated using a semipreparative chiral phase HPLC column (Daicel ChiraCel OD, 10 μm, 2×25 cm, 1% EtOH-hexanes, 7 mL/min, α=1.55).

(S)-4: $[α]^{23}_D$ −20 (c 0.1, THF).
(R)-4: $[α]^{23}_D$ +22 (c 0.1, THF).

2-((tert-Butyldimethylsilyloxy)(6-phenyl-1,2,3,4-tetrahydronaphthalen-2-yl)methyl)oxazole-5-carboxamide (S14)

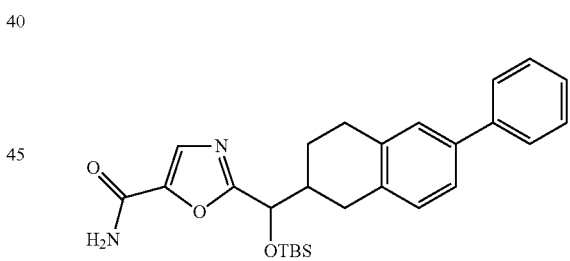

A solution of methyl 2-((tert-butyldimethylsilyloxy)(6-phenyl-1,2,3,4-tetrahydronaphthalen-2-yl)methyl)oxazole-5-carboxylate (S12, 16.4 mg, 0.034 mmol) was dissolved in a saturated solution of NH$_3$—CH$_3$OH (3 mL) and the mixture was stirred for 2 h at room temperature. Evaporation in vacuo yielded the crude carboxamide that was purified by flash chromatography (SiO$_2$, 50% EtOAc-hexanes) to provide the title compound (17 mg, 98%) as a white solid: $^1$H NMR (CDCl$_3$, 600 MHz) δ 7.74 (d, 1H, J=4.8 Hz), 7.57-7.55 (m, 4H), 7.41 (t, 2H, J=7.8 Hz), 7.35-7.31 (m, 2H), 7.16 (d, 0.5H, J=7.8 Hz), 7.09 (d, 0.5H, J=7.8 Hz), 6.18 (brs, 1H, NH), 5.99 (brs, 1H, NH), 4.80 (d, 0.5H, J=6.0 Hz), 4.75 (d, 0.5H, J=6.0 Hz), 2.93-2.80 (m, 2H), 2.62-2.60 (m, 1H), 2.38-2.34 (m, 1H), 1.81-1.79 (m, 1H), 1.62-1.55 (m, 1H), 0.87 (s, 9H), 0.12 (s, 1.5H), 0.11 (s, 1.5H), −0.05 (s, 1.5H), −0.04 (s, 1.5H); $^{13}$C NMR (CDCl$_3$, 150 MHz) δ 165.9, 165.8, 158.5, 158.4, 144.6, 144.5, 141.07, 141.03, 138.9, 138.8, 136.6, 136.4, 134.6, 134.2, 131.66, 131.64, 129.7, 129.6, 128.6 (3C), 127.4, 127.3, 127.1, 127.0 (2C), 126.98, 126.95, 72.5, 72.4, 40.55, 40.53, 31.1, 30.7, 28.9, 28.8, 25.6 (3C), 25.5, 25.0, 18.1, −5.15, −5.20, −5.22.

2-(Hydroxy(6-phenyl-1,2,3,4-tetrahydronaphthalen-2-yl)methyl)oxazole-5-carboxamide (S15)

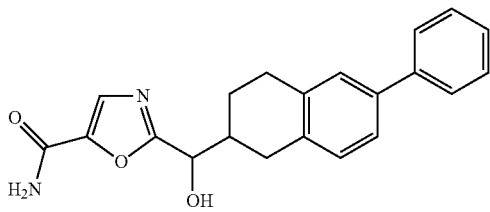 [SMILES: NC(=O)c1cnc(C(O)C2CCc3cc(-c4ccccc4)ccc3C2)o1]

The title compound was prepared from 2-((tert-butyldimethylsilyloxy)(6-phenyl-1,2,3,4-tetrahydronaphthalen-2-yl)methyl)oxazole-5-carboxamide (S14, 13.9 mg, 0.03 mmol) following general procedure D. Flash chromatography (SiO$_2$, 5% MeOH—CH$_2$C2) yielded the title compound (10.4 mg, 98%) as a white solid: $^1$H NMR (CDCl$_3$+0.1% TFA, 600 MHz) δ 7.96 (s, 1H), 7.55 (d, 2H, J=7.8 Hz), 7.42 (t, 2H, J=7.8 Hz), 7.38-7.32 (m, 3H), 7.17 (d, 0.5H, J=7.8 Hz), 7.10 (d, 0.5H, J=7.8 Hz), 5.03 (t, 1H, J=6.0 Hz), 3.02-2.85 (m, 3H), 2.66-2.64 (m, 1H), 2.47-2.45 (m, 1H), 2.21-2.17 (m, 1H), 1.83-1.80 (m, 1H), 1.63-1.60 (m, 1H), 1.31-1.27 (m, 2H); $^{13}$C NMR (CDCl$_3$+0.1% TFA, 150 MHz) δ 165.9, 165.8, 144.33, 144.30, 140.8, 140.7, 139.47, 139.41, 136.1, 135.8, 133.2, 132.8, 130.5, 129.7, 129.4, 128.7 (3C), 127.5, 127.4, 127.23, 127.21, 126.96, 129.90 (2C), 124.99, 124.91, 71.6, 71.2, 39.7, 31.0, 30.5, 29.7, 28.4, 28.3, 25.3, 24.5.

2-(6-Phenyl-1,2,3,4-tetrahydronaphthalene-2-carbonyl)oxazole-5-carboxamide (S16)

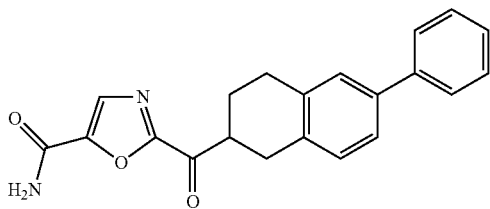 [SMILES: NC(=O)c1cnc(C(=O)C2CCc3cc(-c4ccccc4)ccc3C2)o1]

The title compound was prepared from 2-(hydroxy(6-phenyl-1,2,3,4-tetrahydronaphthalen-2-yl)methyl)oxazole-5-carboxamide (S15, 10.4 mg, 0.029 mmol) following general procedure E. Flash chromatography (SiO$_2$, 50% EtOAc-hexanes) yielded the title compound (5.9 mg, 58%) as a white solid: $^1$H NMR (CDCl$_3$+0.1% TFA, 600 MHz) δ 8.06 (s, 1H), 7.57 (d, 2H, J=7.8 Hz), 7.43 (t, 2H, J=7.8 Hz), 7.40-7.34 (m, 3H), 3.92-3.90 (m, 1H), 3.17-3.14 (m, 2H), 3.06-3.03 (m, 2H), 2.37-2.33 (m, 1H), 1.99-1.96 (m, 1H); $^{13}$C NMR (CDCl$_3$+0.1% TFA, 150 MHz) δ 191.8, 169.7, 150.6, 140.8, 139.4, 135.5, 133.9, 133.0, 129.4, 128.7 (2C), 127.5, 127.2, 126.9 (2C), 125.0, 44.0, 30.5, 29.7, 28.5, 25.9.

2-(6-Phenyl-1,2,3,4-tetrahydronaphthalene-2-carbonyl)oxazole-5-carbonitrile (5)

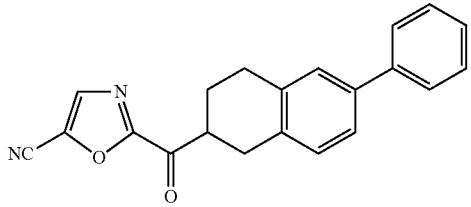 [SMILES: N#Cc1cnc(C(=O)C2CCc3cc(-c4ccccc4)ccc3C2)o1]

A solution of 2-(6-phenyl-1,2,3,4-tetrahydronaphthalene-2-carbonyl)oxazole-5-carboxamide (S16, 5.9 mg, 0.017 mmol) was dissolved in 1,4-dioxane (1 mL) and pyridine (0.0034 mL, 0.042 mmol) and trifluoroacetic anhydride (0.003 mL, 0.022 mmol) were added. The reaction mixture stirred for 2 h at room temperature. The mixture was diluted with CH$_2$Cl$_2$ and the combined organic layers were washed with saturated aqueous NaCl, and dried over Na$_2$SO$_4$. Evaporation in vacuo yielded the crude nitrile that was purified by flash chromatography (SiO$_2$, 10% EtOAc-hexanes) to afford the title compound (4 mg, 71%) as a white solid: $^1$H NMR (CDCl$_3$, 600 MHz) δ 7.89 (s, 1H), 7.58 (d, 2H, J=7.8 Hz), 7.43 (t, 2H, J=7.8 Hz), 7.39-7.32 (m, 3H), 7.20 (d, 1H, J=7.8 Hz), 3.87-3.82 (m, 1H), 3.15-3.12 (m, 2H), 3.03-3.02 (m, 2H), 2.35-2.33 (m, 1H), 1.99-1.93 (m, 1H); $^{13}$C NMR (CDCl$_3$, 150 MHz) δ 189.3, 158.2, 140.9, 139.3, 138.1, 135.6, 133.3, 129.4, 128.7 (2C), 127.5, 127.1, 126.9, 126.6, 124.9, 108.1, 44.2, 30.5, 29.6, 28.6, 25.7, HRMS-ESI-TOF m/z 329.1288 ([M+H]$^+$, C$_{21}$H$_{16}$N$_2$O$_2$ requires 329.1284). The enantiomers were separated using a semipreparative chiral phase HPLC column (Daicel ChiraCel OD, 10 µm, 2×25 cm, 1% EtOH-hexanes, 7 mL/min, α=1.16).
(S)-5: [α]$^{23}_D$ −14 (c 0.1, THF).
(R)-5: [α]$^{23}_D$ +15 (c 0.1, THF).

2-((tert-Butyldimethylsilyloxy)(6-phenyl-1,2,3,4-tetrahydronaphthalen-2-yl)methyl)-5-(pyridin-2-yl)oxazole (S17)

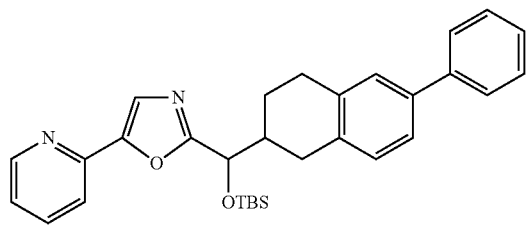 [SMILES: CC(C)(C)[Si](C)(C)OC(c1ncc(-c2ccccn2)o1)C1CCc2cc(-c3ccccc3)ccc2C1]

The title compound was prepared from 2-((tert-butyldimethylsilyloxy)(6-phenyl-1,2,3,4-tetrahydronaphthalen-2-yl)methyl)-5-(tributylstannyl)oxazole (Sit, 64.9 mg, 0.15 mmol) and 2-bromopyridine following general procedure C. Flash chromatography (SiO$_2$, 10% EtOAc-hexanes) yielded the title compound (28 mg, 36%) as a white solid: $^1$H NMR (CDCl$_3$, 600 MHz) δ 8.64 (d, 1H, J=4.8 Hz), 7.77 (qd, 1H, J=1.8, 7.8 Hz), 7.70-7.66 (m, 2H), 7.55 (d, 2H, J=7.8 Hz), 7.42 (t, 2H, J=7.8 Hz), 7.34-7.31 (m, 3H), 7.24-7.21 (m, 1H), 7.18 (d, 0.5H, J=8.4 Hz), 7.08 (d, 0.5H, J=7.0 Hz), 4.83 (d, 0.5H, J=7.0 Hz), 4.77 (d, 0.5H, J=7.0 Hz), 3.02-2.81 (m, 2H), 2.66-2.63 (m, 1H), 2.45-2.42 (m, 1H), 2.39-2.34 (m, 1H), 1.86-1.83 (m, 1H), 1.67-1.57 (m, 1H), 0.94 (s, 4.5H), 0.98 (s, 4.5H), 0.13 (s, 1.5H), 0.11 (s, 1.5H), −0.04 (s, 3H); $^{13}$C NMR (CDCl$_3$, 150 MHz) δ 164.9, 164.7, 150.89, 150.80, 149.9, 147.4, 147.3, 141.18, 141.15, 138.7, 138.6, 136.9, 136.6, 135.0, 134.7, 129.7 (3C), 129.6, 128.6, 127.4, 127.3, 126.95, 126.92, 126.91 (2C), 125.19, 125.14, 124.4, 122.87, 122.84, 119.1, 119.0, 72.57, 72.53, 40.55, 40.50, 31.2, 30.9, 29.6, 29.06, 29.01, 25.7 (3C), 25.6, 25.1, 18.2, 13.5, −5.07, −5.22, −5.24.

(6-Phenyl-1,2,3,4-tetrahydronaphthalen-2-yl)(5-(pyridin-2-yl)oxazol-2-yl)methanol (S18)

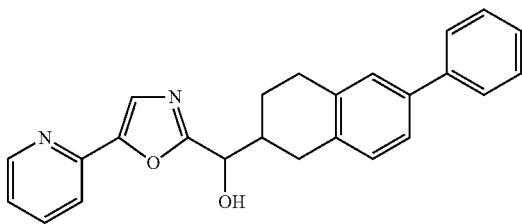 [SMILES: OC(c1ncc(-c2ccccn2)o1)C1CCc2cc(-c3ccccc3)ccc2C1]

The title compound was prepared from 2-((tert-butyldimethylsilyloxy)(6-phenyl-1,2,3,4-tetrahydronaphthalen-2-yl)methyl)-5-(pyridin-2-yl)oxazole (S17, 28 mg, 0.05 mmol) following general procedure D. Flash chromatography (SiO$_2$, 50-100% EtOAc-hexanes) yielded the title compound (19.3 mg, 90%) as a white solid: $^1$H NMR (CDCl$_3$, 600 MHz) δ 8.64 (d, 1H, J=4.8 Hz), 7.78 (td, 2H, J=1.2, 7.2 Hz), 7.70 (s, 1H), 7.55 (d, 2H, J=7.8 Hz), 7.40 (t, 2H, J=7.2 Hz), 7.33-7.23 (m, 4H), 7.16 (d, 0.5H, J=8.4 Hz), 7.09 (d, 0.5H, J=7.0 Hz), 4.88 (d, 0.5H, J=7.0 Hz), 4.85 (d, 0.5H, J=7.0 Hz), 2.98-2.87 (m, 2H), 2.77 (d, 1H, J=7.8 Hz), 2.49-2.47 (m, 1H), 2.23-2.20 (m, 1H), 1.97-1.94 (m, 2H), 1.72-1.66 (m, 1H); $^{13}$C NMR (CDCl$_3$, 150 MHz) δ 149.6, 146.8, 141.11, 141.10, 138.79, 138.77, 137.1, 136.7, 136.5, 134.7, 134.5, 129.7, 129.6, 128.6 (2C), 127.43, 127.40, 126.9 (3C), 125.1, 124.56, 124.53, 123.0, 119.4, 71.5, 71.3, 39.88, 39.85, 31.3, 30.4, 29.0, 28.7, 25.5, 24.5.

(6-Phenyl-1,2,4-tetrahydronaphthalen-2-yl)(5-(pyridin-2-yl)oxazol-2-yl)methanone (6)

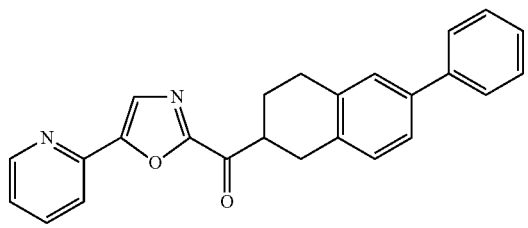 [SMILES: O=C(c1ncc(-c2ccccn2)o1)C1CCc2cc(-c3ccccc3)ccc2C1]

The title compound was prepared from (6-phenyl-1,2,3,4-tetrahydronaphthalen-2-yl)(5-(pyridin-2-yl)oxazol-2-yl)methanol (S18, 19.3 mg, 0.05 mmol) following general procedure E. Flash chromatography (SiO$_2$, 20% EtOAc-hexanes) yielded the title compound (16.3 mg, 85%) as a yellow oil: $^1$H NMR (CDCl$_3$, 600 MHz) δ 8.68 (d, 1H, J=4.8 Hz), 7.94 (s, 1H), 7.90 (d, 1H, J=7.2 Hz), 7.83 (td, 1H, J=1.2, 7.2 Hz), 7.59 (d, 2H, J=7.8 Hz), 7.44-7.31 (m, 6H), 7.22 (d, 1H, J=7.8 Hz), 3.97-3.94 (m, 1H), 3.19-3.15 (m, 2H), 3.07-3.02 (m, 2H), 2.39-2.36 (m, 1H), 2.00-1.96 (m, 1H); $^{13}$C NMR (CDCl$_3$, 150 MHz) δ 190.5, 156.8, 153.3, 150.0, 146.1, 141.0, 139.0, 137.2, 136.0, 134.0, 129.5, 128.6 (2C), 127.4, 127.08, 127.03, 126.9 (2C), 124.7, 124.1, 120.4, 43.3, 30.8, 28.8, 26.0; HRMS-ESI-TOF m/z 381.1600 ([M+H]$^+$, C$_{25}$H$_{20}$N$_2$O$_2$ requires 381.1597). The enantiomers were separated using a semipreparative chiral phase HPLC column (ChiralPAK AD, 10 μm, 2×25 cm, 10% i-PrOH-hexanes, 7 mL/min, α=1.13).

(S)-6: [α]$^{23}_D$ −18 (c 0.1, THF).
(R)-6: [α]$^{23}_D$ +20 (c 0.1, THF).

Methyl 6-(2-((tert-Butyldimethylsilyloxy)(6-phenyl-1,2,3,4-tetrahydronaphthalen-2-yl)methyl)oxazol-5-yl)picolinate (S19)

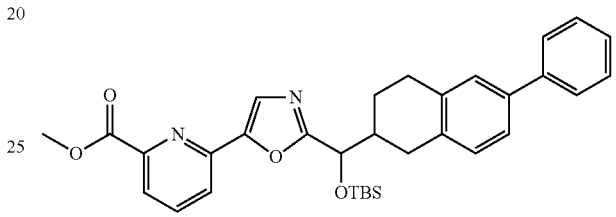

The title compound was prepared from 2-((tert-butyldimethylsilyloxy)(6-phenyl-1,2,3,4-tetrahydronaphthalen-2-yl)methyl)-5-(tributylstannyl)oxazole (S11, 220 mg, 0.52 mmol) and methyl 6-bromopicolinate following general procedure C. Flash chromatography (SiO$_2$, 20% EtOAc-hexanes) yielded the title compound (232 mg, 80%) as a colorless oil: $^1$H NMR (CDCl$_3$, 500 MHz) δ 8.34 (d, 1H, J=4.8 Hz), 8.24 (d, 1H, J=4.8 Hz), 8.02-8.00 (m, 1H), 7.91-7.87 (m, 1H), 7.84-7.81 (m, 1H), 7.64-7.61 (m, 1H), 7.55-7.52 (m, 2H), 7.39-7.31 (m, 2H), 7.36-7.31 (m, 1H), 7.18 (d, 0.5H, J=8.4 Hz), 7.08 (d, 0.5H, J=7.0 Hz), 4.85 (d, 0.5H, J=7.0 Hz), 4.78 (d, 0.5H, J=7.0 Hz), 3.99 (s, 1.5H), 3.96 (s, 1.5H), 2.97-2.84 (m, 1H), 2.63-2.60 (m, 1H), 2.44-2.42 (m, 1H), 1.63-1.59 (m, 1H), 1.35-1.30 (m, 3H), 0.92 (s, 9H), 0.12 (s, 1.5H), 0.11 (s, 1.5H), −0.03 (s, 1.5H), −0.04 (s, 1.5H); $^{13}$C NMR (CDCl$_3$, 125 MHz) δ 165.1, 165.0, 164.9, 164.1, 149.99, 149.90, 148.5, 148.1, 147.46, 147.43, 141.8, 140.9, 139.0, 138.5, 138.4, 137.8, 136.6, 136.4, 134.8, 134.4, 131.6, 129.6 (3C), 129.4, 128.4, 127.2, 127.1 (2C), 126.7, 126.28, 126.23, 124.3, 123.8, 123.7, 72.4, 72.3, 52.9, 52.7, 40.3, 31.1, 30.7, 28.86, 28.81, 27.9, 26.5, 25.57 (3C), 25.50, 24.9, 18.0, 17.2, 13.4, −5.23, −5.37.

Methyl 6-(2-(Hydroxy(6-phenyl-1,2,3,4-tetrahydronaphthalen-2-yl)methyl)oxazol-5-yl)picolinate (S20)

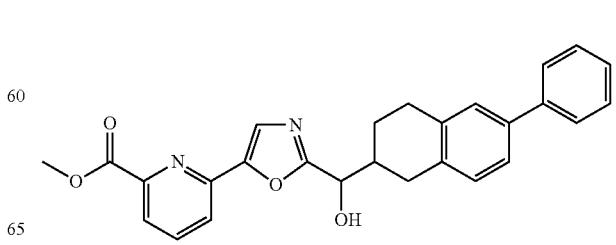

The title compound was prepared from methyl 6-(2-((tert-butyldimethylsilyloxy)(6-phenyl-1,2,3,4-tetrahydronaphthalen-2-yl)methyl)oxazol-5-yl)picolinate (S19, 232 mg, 0.41 mmol) following general procedure D. Flash chromatography (SiO$_2$, 50-100% EtOAc-hexanes) yielded the title compound (175 mg, 94%) as a yellow oil: $^1$H NMR (CDCl$_3$, 500 MHz) δ 7.98 (d, 1H, J=4.8 Hz), 7.84-7.75 (m, 3H), 7.53 (d, 2H, J=4.8 Hz), 7.38 (t, 2H, J=7.5 Hz), 7.30-7.27 (m, 2H), 7.11 (d, 0.5H, J=8.4 Hz), 7.04 (d, 0.5H, J=7.0 Hz), 4.88 (d, 0.5H, J=7.0 Hz), 4.84 (d, 0.5H, J=7.0 Hz), 3.98 (s, 3H), 3.01-2.84 (m, 3H), 2.73-2.68 (m, 2H), 2.50-2.47 (m, 1H), 2.28-2.25 (m, 0.5H), 1.91-1.88 (m, 0.5H), 1.70-1.58 (m, 1H), 1.39-1.32 (m, 1H); $^{13}$C NMR (CDCl$_3$, 125 MHz) δ 165.8, 165.7, 165.0, 150.1, 147.9, 147.1, 140.9, 138.5, 138.4, 137.8, 136.6, 136.4, 134.6, 134.4, 129.5, 129.4, 128.4 (2C), 127.2, 127.1, 126.76 (2C), 126.72, 125.9, 124.34, 124.30, 123.8, 122.1, 71.2, 71.0, 64.1, 60.2, 52.7, 51.8, 39.6, 39.5, 31.2, 30.5, 30.4, 28.7, 25.4, 24.6, 20.8, 20.0, 18.9, 14.0, 13.5, 13.4.

Methyl 6-(2-(6-Phenyl-1,2,3,4-tetrahydronaphthalene-2-carbonyl)oxazol-5-yl)picolinate (7)

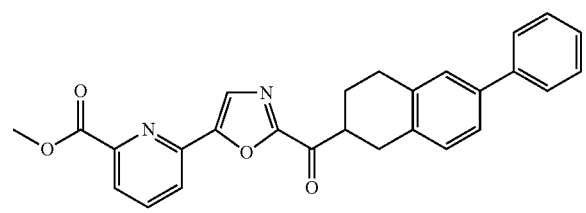 [SMILES: COC(=O)c1cccc(-c2cnc(C(=O)C3CCc4cc(-c5ccccc5)ccc4C3)o2)n1]

The title compound was prepared from methyl 6-(2-(hydroxy(6-phenyl-1,2,3,4-tetrahydronaphthalen-2-yl)methyl)oxazol-5-yl)picolinate (S20, 170 mg, 0.38 mmol) following general procedure E. Flash chromatography (SiO$_{2,30}$% EtOAc-hexanes) yielded the title compound (130 mg, 77%) as a white solid: $^1$H NMR (CDCl$_3$, 500 MHz) δ 8.10 (dd, 1H, J=1.0, 8.0 Hz), 8.05 (s, 1H), 8.01 (dd, 1H, J=1.0, 8.0 Hz), 7.94 (t, 1H, J=7.5 Hz), 7.58 (d, 2H, J=8.5 Hz), 7.41 (t, 2H, J=8.4 Hz), 7.36-7.29 (m, 3H), 7.18 (d, 1H, J=8.0 Hz), 4.02 (s, 3H), 3.97-3.91 (m, 1H), 3.17-3.00 (m, 4H), 2.37-2.34 (m, 1H), 1.98-1.93 (m, 1H); $^{13}$C NMR (CDCl$_3$, 125 MHz) δ 190.3, 164.9, 156.8, 152.3, 148.3, 146.3, 140.8, 138.8, 138.1, 135.8, 133.8, 129.3, 128.5 (2C), 127.8, 127.2, 126.9, 126.8 (2C), 125.0, 124.5, 123.1, 52.8, 43.3, 30.6, 28.7, 25.9; HRMS-ESI-TOF m/z 439.1658 ([M+H]$^+$, C$_{27}$H$_{22}$N$_2$O$_4$ requires 439.1652). The enantiomers were separated using a semipreparative chiral phase HPLC column (Daicel ChiraCel OD, 10 μm, 2×25 cm, 40% EtOH-hexanes, 7 mL/min, α=1.12).

(S)-7: [α]$^{23}_D$ +7 (c 0.1, THF).
(R)-7: [α]$^{23}_D$ −7 (c 0.1, THF).

6-(2-(6-Phenyl-1,2,3,4-tetrahydronaphthalene-2-carbonyl)oxazol-5-yl)picolinic acid (8)

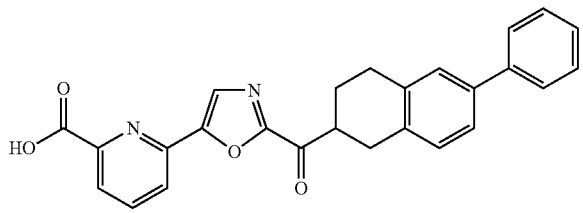 [SMILES: O=C(O)c1cccc(-c2cnc(C(=O)C3CCc4cc(-c5ccccc5)ccc4C3)o2)n1]

The title compound was prepared from methyl 6-(2-(6-phenyl-1,2,3,4-tetrahydronaphthalene-2-carbonyl)oxazol-5-yl)picolinate (7, 6.6 mg, 0.015 mmol) following general procedure F. Each pure enantiomer of the methyl ester were converted to their corresponding carboxylic acid using general procedure G. Flash chromatography (SiO$_2$, 0-5% HOAc-EtOAc) yielded the title compound (5 mg, 90%) as a white solid: $^1$H NMR (CDCl$_3$+0.1% TFA, 600 MHz) δ 8.32 (d, 1H, J=6.0 Hz), 8.20-8.15 (m, 2H), 8.12 (s, 1H), 7.60 (d, 2H, J=8.0 Hz), 7.44 (t, 2H, J=8.0 Hz), 7.41-7.35 (m, 3H), 7.22 (d, 1H, J=7.8 Hz), 3.90-3.89 (m, 1H), 3.20-3.06 (m, 4H), 2.40-2.37 (m, 1H), 2.01-1.99 (m, 1H); $^{13}$C NMR (CDCl$_3$+0.1% TFA, 150 MHz) δ 190.7, 166.2, 156.8, 151.5, 145.9, 145.1, 140.9, 140.2, 139.3, 135.6, 133.1, 129.4, 128.7 (2C), 127.7, 127.5, 127.1, 127.0 (2C), 125.3, 125.0, 124.9, 43.8, 30.5, 28.6, 26.1; HRMS-ESI-TOF m/z 425.1492 ([M+H]$^+$, C$_{26}$H$_{20}$N$_2$O$_4$ requires 425.1496).
(S)-8: [α]$^{23}_D$ +4.2 (c 0.1, THF).
(R)-8: [α]$^{23}_D$ −3.5 (c 0.4, THF).

Methyl 6-Phenoxy-1,2,3,4-tetrahydronaphthalene-2-carboxylate (S21)

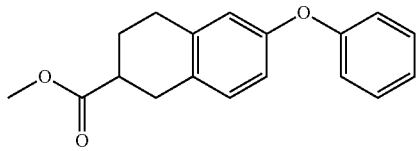 [SMILES: COC(=O)C1CCc2cc(Oc3ccccc3)ccc2C1]

A sample of methyl 1,2,3,4-tetrahydro-6-hydroxynaphthalene-2-carboxylate (S4, 1 g, 4.84 mmol), phenylboronic acid (1.20 g, 9.69 mmol), Cu(OAc)$_2$ (879 mg, 4.84 mmol), and 4 Å MS (1 g) were placed in anhydrous CH$_2$Cl$_2$ (60 mL). The reaction mixture was stirred at room temperature for 15 min before Et$_3$N (1.4 mL, 9.69 mmol) was added dropwise. The reaction mixture was stirred at room temperature for 17 h under Ar. The mixture was diluted with EtOAc, washed with saturated aqueous NH$_4$Cl, saturated aqueous NaCl, and dried over Na$_2$SO$_4$. Evaporation in vacuo yielded the crude product that was purified by flash chromatography (SiO$_2$, 10% EtOAc-hexanes) to provide the title compound (800 mg, 59%) as a colorless oil: $^1$H NMR (CDCl$_3$, 600 MHz) δ 7.32 (t, 2H, J=7.2 Hz), 7.09-7.05 (m, 2H), 6.99 (d, 2H, J=8.4 Hz), 6.80 (dd, 1H, J=2.4, 8.4 Hz), 6.74-6.70 (m, 1H), 3.73 (s, 3H), 3.02-2.94 (m, 2H), 2.83-2.80 (m, 2H), 2.77-2.72 (m, 1H), 2.21-2.18 (m, 1H), 1.89-1.83 (m, 1H); $^{13}$C NMR (CDCl$_3$, 150 MHz) δ 175.7, 157.5, 155.0, 137.2, 130.1, 129.7, 129.6 (2C), 122.8, 118.8, 118.5 (2C), 116.8, 51.7, 39.9, 31.0, 28.6, 25.6.

(6-Phenoxy-1,2,3,4-tetrahydronaphthalen-2-yl)methanol (S22)

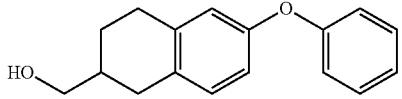 [SMILES: OCC1CCc2cc(Oc3ccccc3)ccc2C1]

The title compound was prepared from methyl 6-phenoxy-1,2,3,4-tetrahydronaphthalene-2-carboxylate (S21, 800 mg, 2.83 mmol) following general procedure A. Flash chromatography (SiO$_2$, 50% EtOAc-hexanes) afforded the title compound (743 mg, 98%) as a colorless oil: $^1$H NMR (CDCl$_3$, 400 MHz) δ 7.33 (t, 2H, J=7.2 Hz), 7.11-7.01 (m, 4H), 6.82-6.79 (m, 2H), 3.65 (d, 2H, J=6.4 Hz), 2.92-2.80 (m, 2H), 2.52-2.45 (m, 2H), 2.30 (s, 1H), 2.08-1.99 (m, 2H); $^{13}$C NMR (CDCl$_3$, 100 MHz) δ 157.5, 154.6, 138.1, 130.8, 130.2, 129.5 (2C), 122.6, 118.8, 118.3 (2C), 116.6, 67.3, 37.0, 31.6, 28.7, 25.6.

6-Phenoxy-1,2,3,4-tetrahydronaphthalene-2-carboxaldehyde (S23)

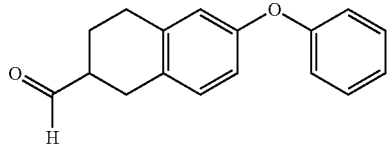 [SMILES: O=CC1CCc2cc(Oc3ccccc3)ccc2C1]

The title compound was prepared from (6-phenoxy-1,2,3,4-tetrahydronaphthalen-2-yl)methanol (S22, 200 mg, 0.78 mmol) following general procedure B. Flash chromatography (SiO$_2$, 20% EtOAc-hexanes) afforded the title compound (196 mg, 98%) as a colorless oil: $^1$H NMR (CDCl$_3$, 400 MHz) δ 9.79 (s, 1H), 7.36 (t, 2H, J=7.2 Hz), 7.13-7.09 (m, 2H), 7.03 (d, 2H, J=8.0 Hz), 6.85-6.74 (m, 2H), 2.99-2.95 (m, 2H), 2.87-2.78 (m, 2H), 2.73-2.66 (m, 1H), 2.24-2.17 (m, 1H), 1.85-1.78 (m, 1H); $^{13}$C NMR (CDCl$_3$, 100 MHz) δ203.4, 157.2, 154.9, 137.3, 130.2, 129.5 (2C), 129.0, 122.7, 118.7, 118.3 (2C), 116.8, 46.6, 28.0, 27.6, 22.5.

Oxazol-2-yl(6-phenoxy-1,2,3,4-tetrahydronaphthalen-2-yl)methanol (S24)

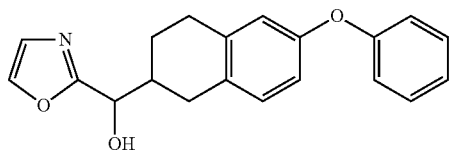

Oxazole (0.226 mL, 3.44 mmol) in anhydrous THF (20 mL) was treated with BH$_3$.THF (1 M, 3.74 mL, 3.74 mmol) and the solution was stirred at room temperature for 1 h before being cooled to −78° C. and treated with 2.16 M n-BuLi (2 mL, 4.47 mmol) dropwise. The reaction mixture was stirred at −78° C. for 40 min before a solution of 6-phenoxy-1,2,3,4-tetrahydronaphthalene-2-carboxaldehyde (S23, 870 mg, 3.44 mmol) in THF (20 mL) was added. The reaction mixture was stirred at −78° C. for 2 h before being warmed to room temperature. A 5% HOAc-EtOH solution (50 mL) was added and this mixture was stirred at room temperature for 12 h. The solvent was removed under reduced pressure and the residue was dissolved in EtOAc, washed with H$_2$O, saturated aqueous NaHCO$_3$ and saturated aqueous NaCl before the organic layer was dried over MgSO$_4$ and the solvent was removed under reduced pressure. Flash chromatography (SiO$_2$, 40% EtOAc-hexanes) afforded the title compound (740 mg, 67%) as colorless oil: $^1$H NMR (CDCl$_3$, 600 MHz) δ 7.65 (s, 1H), 7.32-7.31 (m, 2H), 7.10-6.98 (m, 6H), 6.78-6.75 (m, 2H), 4.78-4.74 (m, 1H), 2.88-2.78 (m, 4H), 2.61-2.59 (m, 0.5H), 2.34 (m, 0.5H), 2.14-2.12 (m, 0.5H), 1.80-1.77 (m, 0.5H), 1.62-1.51 (m, 1H); $^{13}$C NMR (CDCl$_3$, 150 MHz) δ 165.3, 157.5, 154.8, 138.9, 137.9, 137.7, 130.5, 130.3, 130.2, 130.1, 129.5 (2C), 126.5, 122.8, 122.7, 118.86 (2C), 118.82, 118.49, 118.42, 116.78, 116.73, 71.2, 71.0, 39.8, 39.7, 30.8, 30.2, 29.6, 28.9, 28.8, 25.1, 24.4.

Oxazol-2-yl(6-phenoxy-1,2,3,4-tetrahydronaphthalen-2-yl)methanone (9)

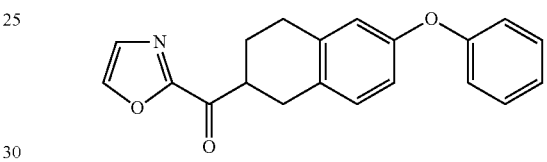

The title compound was prepared from oxazol-2-yl(6-phenoxy-1,2,3,4-tetrahydronaphthalen-2-yl)methanol (S24, 58.5 mg, 0.182 mmol) following general procedure E. Flash chromatography (SiO$_2$, 20% EtOAc-hexanes) yielded the title compound (21.4 mg, 37%) as a colorless oil: $^1$H NMR (CDCl$_3$, 600 MHz) δ 7.85 (s, 1H), 7.36 (s, 1H), 7.32 (t, 2H, J=7.8 Hz), 7.09-7.06 (m, 2H), 7.00 (d, 2H, J=9.0 Hz), 6.81-6.78 (m, 2H), 3.87-3.84 (m, 1H), 3.05 (d, 2H, J=8.4 Hz), 2.94-2.88 (m, 2H), 2.30-2.26 (m, 1H), 1.93-1.86 (m, 1H); $^{13}$C NMR (CDCl$_3$, 150 MHz) δ 190.4, 157.5, 157.4, 155.0, 141.6, 137.2, 130.1, 129.7, 129.6 (2C), 129.0, 122.8, 118.8, 118.5 (2C), 116.9, 43.5, 30.4, 28.7, 25.6; HRMS-ESI-TOF m/z 320.1281 ([M+H]$^+$, C$_{20}$H$_{17}$NO$_3$ requires 320.1281). The enantiomers were separated using a semipreparative chiral phase HPLC column (ChiralPAK AD, 10 μm, 2×25 cm, 1% i-PrOH-hexanes gradient, 7 mL/min, α=1.19).

(S)-9: [α]$^{23}_D$ −38 (c 0.1, THF).
(R)-9: [α]$^{23}_D$ +42 (c 0.1, THF).

2-((tert-Butyldimethylsilyloxy)(6-phenoxy-1,2,3,4-tetrahydronaphthalen-2-yl)methyl)oxazole (S25)

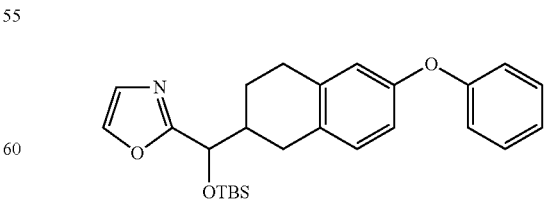

A solution of oxazol-2-yl(6-phenoxy-1,2,3,4-tetrahydronaphthalen-2-yl)methanol (S24, 400 mg, 1.24 mmol), TBSCl (450 mg, 2.98 mmol) and imidazole (421 mg, 6.2 mmol) in DMF (20 mL) was stirred at room temperature for 16 h before it was diluted with EtOAc, washed with H₂O, and saturated aqueous NaCl. The organic layer was dried over MgSO₄ and the solvent was removed under reduced pressure. Flash chromatography (SiO₂, 10% EtOAc-hexanes) yielded the title compound (459 mg, 85%) as a thick colorless oil: ¹H NMR (CDCl₃, 500 MHz) δ 7.65 (s, 1H), 7.31 (t, 2H, J=8.5 Hz), 7.12 (d, 1H, J=8.0 Hz), 7.01-6.97 (m, 4H), 6.81-6.75 (m, 2H), 4.80 (d, 0.5H, J=7.0 Hz), 4.74 (d, 0.5H, J=7.0 Hz), 2.99-2.73 (m, 3H), 2.55-2.51 (m, 1H), 2.39-2.25 (m, 1H), 1.74-1.71 (m, 1H), 1.53-1.49 (m, 1H), 0.96 (s, 4.5H), 0.93 (s, 4.5H), −0.03 (s, 1.5H), −0.04 (s, 1.5H), −0.05 (s, 1.5H), −0.06 (s, 1.5H); ¹³C NMR (CDCl₃, 125 MHz) δ 164.4, 164.3, 157.6, 157.5, 154.7, 154.6, 138.47, 138.41, 138.0, 137.7, 130.7, 130.4, 130.3, 130.1 (2C), 129.4, 126.7, 122.6, 122.5, 118.8, 118.3, 118.2, 116.7, 116.6, 72.2, 72.1, 40.3, 30.67, 30.62, 28.8, 28.7, 25.6 (3C), 25.1, 24.8, 18.0, −5.3, −5.41, −5.44, −5.6.

2-((tert-Butyldimethylsilyloxy)(6-phenoxy-1,2,3,4-tetrahydronaphthalen-2-yl)methyl)-5-(tributylstannyl)oxazole (S26)

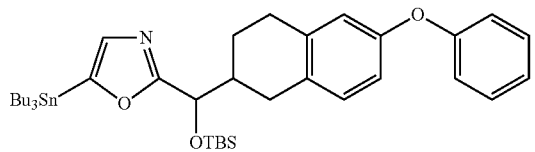

A solution of 2-((tert-butyldimethylsilyloxy)(6-phenoxy-1,2,3,4-tetrahydronaphthalen-2-yl)methyl)oxazole (S25, 459.3 mg, 1.05 mmol) in THF (15 mL) was cooled to −78° C. before it was treated with 2.16 M n-BuLi (0.6 mL, 1.15 mmol) dropwise. The reaction mixture was stirred at −78° C. for 2 h, and treated with a solution of Bu₃SnCl (0.6 mL, 2.1 mmol) and stirred for 5 min. The solution was warmed to room temperature, diluted with EtOAc, and washed with saturated aqueous NaCl. The organic layer was dried over MgSO₄ and the solvent was removed under reduced pressure. Flash chromatography (SiO₂, 10% EtOAc-hexanes) yielded the title compound (500 mg, 78%) as a thick colorless oil: ¹H NMR (CDCl₃, 500 MHz) δ 7.30 (t, 2H, J=7.5 Hz), 7.12 (d, 1H, J=6.0 Hz), 7.06 (t, 2H, J=7.0 Hz), 6.97 (m, 2H), 6.77 (dd, 1H, J=2.5, 8.5 Hz), 4.80 (d, 0.5H, J=7.0 Hz), 4.75 (d, 0.5H, J=7.0 Hz), 2.82-2.70 (m, 2H), 2.52-2.22 (m, 2H), 1.58-1.46 (m, 8H), 1.36-1.30 (m, 7H), 1.15-1.11 (m, 5H), 0.94-0.90 (m, 18H), 0.08 (s, 1.5H), 0.06 (s, 1.5H), −0.11 (s, 1.5H), −0.12 (s, 1.5H); ¹³C NMR (CDCl₃, 125 MHz) δ 168.5, 168.4, 157.8, 154.9, 154.8, 154.7, 154.6, 138.2, 138.0, 137.1, 131.2, 130.8, 130.4, 130.2, 129.5 (2C), 122.67, 122.64, 118.9, 118.4, 118.3, 116.8, 116.6, 72.5, 72.3, 40.69, 40.64, 30.85, 30.81, 29.3, 29.2 (3C), 29.1, 29.0, 28.98, 28.90, 28.8, 28.5, 27.6, 27.4, 27.3, 27.2 (3C), 27.1, 27.0, 26.8, 25.7, 25.2, 25.0, 18.1, 13.69, 13.60 (3C), 11.6, 10.7, 10.2 (3C), 9.98, −5.3, −5.4, −5.61, −5.62.

Methyl 2-((tert-Butyldimethylsilyloxy)(6-phenoxy-1,2,3,4-tetrahydronaphthalen-2-yl)methyl)oxazole-5-carboxylate (S27)

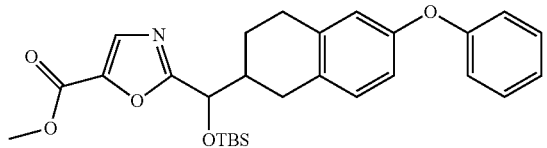 [SMILES: COC(=O)c1cnc(C(O[Si](C)(C)C(C)(C)C)C2CCc3cc(Oc4ccccc4)ccc3C2)o1]

A solution of 2-((tert-butyldimethylsilyloxy)(6-phenoxy-1,2,3,4-tetrahydronaphthalen-2-yl)methyl)oxazole (S25, 148 mg, 0.33 mmol) in THF (2 mL) was cooled to −78° C. before it was treated with 2.16 M n-BuLi (0.18 mL, 0.37 mmol) dropwise. The reaction mixture was stirred at −78° C. for 2 h, and treated with a solution of Mander's reagent (MeO₂CCN, 0.165 mL, 1.65 mmol) in THF (2 mL) and stirred for 5 min. The solution was warmed to room temperature and diluted with EtOAc and washed with saturated aqueous NaCl. The organic layer was dried over MgSO₄ and the solvent was removed under reduced pressure. Flash chromatography (SiO₂, 10% EtOAc-hexanes) yielded the title compound (174 mg, 98%) as a yellow oil: ¹H NMR (CDCl₃, 500 MHz) δ 7.74 (d, 1H, J=4.0 Hz), 7.30 (t, 2H, J=8.5 Hz), 7.07-7.04 (m, 2H), 6.98-6.96 (m, 2H), 6.79-6.73 (m, 2H), 4.81 (d, 0.5H, J=7.0 Hz), 4.75 (d, 0.5H, J=7.0 Hz), 3.92 (s, 3H), 2.87-2.73 (m, 3H), 2.57-2.54 (m, 1H), 2.39-2.16 (m, 1H), 1.77-1.74 (m, 1H), 1.57-1.50 (m, 1H), 0.97 (s, 9H), −0.03 (s, 1.5H), −0.04 (s, 1.5H), −0.05 (s, 1.5H), −0.06 (s, 1.5H); ¹³C NMR (CDCl₃, 125 MHz) δ 167.7, 167.5, 157.9, 157.6, 157.5, 154.7, 142.2, 142.1, 137.9, 137.6, 133.9, 130.6, 130.4, 130.2, 129.5 (2C), 122.74, 122.70, 118.8, 118.4, 118.3 (2C), 116.8, 116.7, 99.5, 72.3, 72.2, 52.1, 40.3, 30.7, 30.1, 28.88, 28.80, 25.6 (3C), 25.3, 24.5, 18.1, −5.1, −5.31, −5.34.

Methyl 2-(Hydroxy(6-phenoxy-1,2,3,4-tetrahydronaphthalen-2-yl)methyl)oxazole-5-carboxylate (S28)

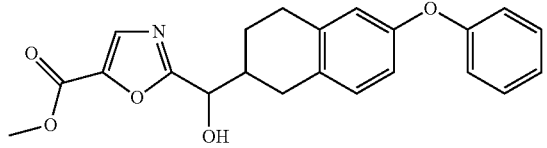 [SMILES: COC(=O)c1cnc(C(O)C2CCc3cc(Oc4ccccc4)ccc3C2)o1]

The title compound was prepared from methyl 2-((tert-butyldimethylsilyloxy)(6-phenoxy-1,2,3,4-tetrahydronaphthalen-2-yl)methyl)oxazole-5-carboxylate (S27, 75 mg, 0.15 mmol) following general procedure D. Flash chromatography (SiO₂, 50% EtOAc-hexanes) yielded the title compound (41.8 mg, 73%) as a colorless oil: ¹H NMR (CDCl₃, 600 MHz) δ 7.74 (s, 1H), 7.31 (t, 2H, J=8.5 Hz), 7.08-7.01 (m, 2H), 6.98-6.96 (m, 2H), 6.78-6.73 (m, 2H), 4.84 (t, 0.5H, J=7.0 Hz), 4.80 (t, 0.5H, J=7.0 Hz), 3.92 (s, 3H), 3.18-3.15 (m, 1H), 2.82-2.77 (m, 3H), 2.66-2.65 (m, 1H), 2.41-2.37 (m, 1H), 2.08-2.04 (m, 0.5H), 1.86-1.83 (m, 0.5H), 1.80-1.72 (m, 1H); ¹³C NMR (CDCl₃, 150 MHz) δ 157.9, 157.5, 154.9, 137.7, 137.6, 133.7, 133.6, 130.3, 130.2, 130.1, 130.0, 129.6 (2C), 122.8, 118.86, 118.85, 118.4 (2C), 116.87, 116.83, 71.4, 71.3, 52.3, 39.9, 39.8, 30.8, 29.7, 28.87, 28.84, 25.2, 24.0.

Methyl 2-(6-Phenoxy-1,2,3,4-tetrahydronaphthalene-2-carbonyl)oxazole-5-carboxylate (10)

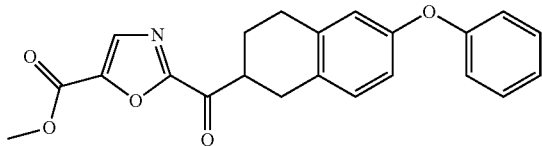 [SMILES: COC(=O)c1cnc(C(=O)C2CCc3cc(Oc4ccccc4)ccc3C2)o1]

The title compound was prepared from methyl 2-(hydroxy(6-phenoxy-1,2,3,4-tetrahydronaphthalen-2-yl)methyl)oxazole-5-carboxylate (S28, 41.8 mg, 0.11 mmol) following general procedure E. Flash chromatography (SiO$_2$, 20% EtOAc-hexanes) yielded the title compound (27.5 mg, 66%) as a yellow oil: $^1$H NMR (CDCl$_3$, 600 MHz) δ 7.91 (s, 1H), 7.32 (t, 2H, J=7.2 Hz), 7.08 (t, 2H, J=7.2 Hz), 7.00 (d, 2H, J=7.5 Hz), 6.81-6.77 (m, 2H), 3.97 (s, 3H), 3.85-3.82 (m, 1H), 3.07 (d, 2H, J=8.0 Hz), 2.93-2.89 (m, 2H), 2.29-2.26 (m, 1H), 1.91-1.88 (m, 1H); $^{13}$C NMR (CDCl$_3$, 150 MHz) δ 190.2, 157.8, 157.49, 157.45, 155.2, 143.9, 137.0, 134.6, 130.1, 129.6 (2C), 129.3, 122.9, 118.8, 118.5 (2C), 117.0, 52.7, 43.8, 30.3, 28.7, 25.4; HRMS-ESI-TOF m/z 378.1335 ([M+H]$^+$, C$_{22}$H$_{19}$NO$_5$ requires 378.1336). The enantiomers were separated using a semipreparative chiral phase HPLC column (Daicel ChiraCel OD, 10 μm, 2×25 cm, 1% EtOH-hexanes, 7 mL/min, α=1.14).
(S)-10: [α]$^{23}_D$ −14 (c 0.1, THF).
(R)-10: [α]$^{23}_D$ +16 (c 0.1, THF).

2-((tert-Butyldimethylsilyloxy)(6-phenoxy-1,2,3,4-tetrahydronaphthalen-2-yl)methyl)oxazole-5-carboxamide (S29)

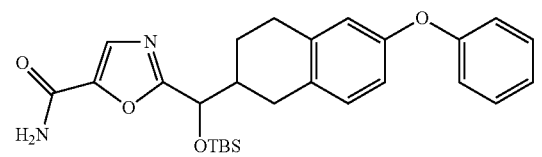 [SMILES: CC(C)(C)[Si](C)(C)OC(c1ncc(C(N)=O)o1)C1CCc2cc(Oc3ccccc3)ccc2C1]

A solution of methyl 2-((tert-butyldimethylsilyloxy)(6-phenoxy-1,2,3,4-tetrahydronaphthalen-2-yl)methyl)oxazole-5-carboxylate (S27, 100 mg, 0.20 mmol) was dissolved in a saturated solution of NH$_3$—CH$_3$OH (5 mL) and the mixture was stirred for 2 h at room temperature. Evaporation in vacuo yielded the crude carboxamide that was purified by flash chromatography (SiO$_2$, 50% EtOAc-hexanes) to provide the title compound (98.2 mg, 98%) as a colorless oil: $^1$H NMR (CDCl$_3$, 600 MHz) δ 7.74 (d, 1H, J=6.6 Hz), 7.30 (t, 2H, J=8.5 Hz), 7.07-7.03 (m, 2H), 6.98-6.96 (m, 2H), 6.79-6.73 (m, 2H), 6.45 (brs, 1H, NH), 6.24 (brs, 1H, NH), 4.79 (d, 0.5H, J=7.0 Hz), 4.72 (d, 0.5H, J=7.0 Hz), 2.87-2.70 (m, 3H), 2.54-2.50 (m, 1H), 2.34-2.04 (m, 1H), 1.75-1.72 (m, 1H), 1.54-1.49 (m, 1H), 0.97 (s, 9H), −0.03 (s, 1.5H), −0.04 (s, 1.5H), −0.05 (s, 1.5H), −0.06 (s, 1.5H); $^{13}$C NMR (CDCl$_3$, 150 MHz) δ 166.5, 165.7, 158.78, 158.74, 157.58, 157.51, 154.9, 154.8, 144.6, 144.5, 137.8, 137.6, 131.53, 131.51, 130.4, 130.3, 130.2, 130.0, 129.5 (2C), 122.8, 122.7, 118.8, 118.4, 118.3 (2C), 116.8, 116.7, 72.4, 72.3, 40.53, 40.50, 30.8, 30.3, 28.8, 28.7, 25.6 (3C), 25.2, 24.7, 18.1, −5.2, −5.24, −5.27.

2-((tert-Butyldimethylsilyloxy)(6-phenoxy-1,2,3,4-tetrahydronaphthalen-2-yl)methyl)oxazole-5-carbonitrile (S30)

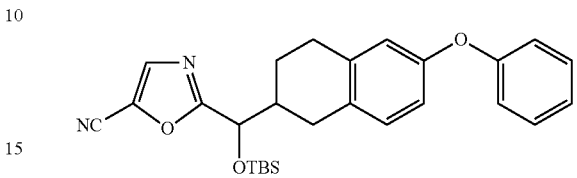

A solution of 2-((tert-butyldimethylsilyloxy)(6-phenoxy-1,2,3,4-tetrahydronaphthalen-2-yl)methyl)oxazole-5-carboxamide (S29, 98.2 mg, 0.20 mmol) was dissolved in 1,4-dioxane (6 mL) and pyridine (0.042 mL, 0.51 mmol) and trifluoroacetic anhydride (0.036 mL, 0.26 mmol) were added. The reaction mixture stirred for 2 h at room temperature. The mixture was diluted with CH$_2$Cl$_2$ and the organic layer was washed with saturated aqueous NaCl, and dried over Na$_2$SO$_4$. Evaporation in vacuo yielded the crude nitrile that was purified by flash chromatography (SiO$_2$, 10% EtOAc-hexanes) to afford the title compound (81.2 mg, 88%) as a colorless oil: $^1$H NMR (CDCl$_3$, 600 MHz) δ 7.71 (d, 1H, J=6.6 Hz), 7.32 (t, 2H, J=8.5 Hz), 7.09-7.05 (m, 2H), 6.99-6.97 (d, 2H, J=7.8 Hz), 6.80-6.75 (m, 2H), 4.84 (d, 0.5H, J=7.0 Hz), 4.77 (d, 0.5H, J=7.0 Hz), 2.85-2.72 (m, 3H), 2.56-2.53 (m, 1H), 2.35-2.31 (m, 1H), 2.14-2.12 (m, 0.5H), 1.77-1.74 (m, 0.5H), 1.55-1.48 (m, 1H), 0.91 (s, 9H), 0.11 (s, 1.5H), 0.09 (s, 1.5H), −0.04 (s, 1.5H), −0.05 (s, 1.5H); $^{13}$C NMR (CDCl$_3$, 150 MHz) δ 168.6, 157.57, 157.52, 154.99, 154.91, 137.8, 137.5, 130.4, 130.2, 129.8, 129.5 (2C), 124.5, 124.4, 122.9, 122.8, 118.6, 118.47, 118.41 (2C), 116.9, 116.8, 109.04, 109.00, 72.2, 72.1, 40.4, 30.6, 30.0, 28.8, 28.7, 25.5 (3C), 25.2, 24.5, 18.1, −5.23, −5.29, −5.31.

2-(Hydroxy(6-phenoxy-1,2,3,4-tetrahydronaphthalen-2-yl)methyl)oxazole-5-carbonitrile (S31)

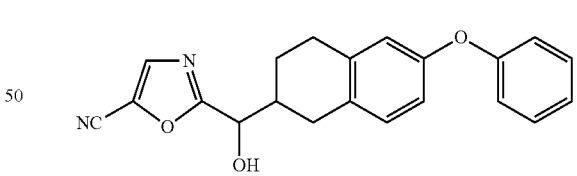

The title compound was prepared from 2-((tert-butyldimethylsilyloxy)(6-phenoxy-1,2,3,4-tetrahydronaphthalen-2-yl)methyl)oxazole-5-carbonitrile (S30, 81.2 mg, 0.17 mmol) following general procedure D. Flash chromatography (SiO$_2$, 20% EtOAc-hexanes) yielded the title compound (29.3 mg, 48%) as a white solid: $^1$H NMR (CDCl$_3$, 600 MHz) δ 7.72 (s, 1H), 7.31 (t, 2H, J=8.5 Hz), 7.08 (t, 1H, J=8.5 Hz), 7.04 (d, 1H, J=8.5 Hz), 7.00-6.97 (m, 2H), 6.79-6.75 (m, 2H), 4.84 (d, 0.5H, J=7.0 Hz), 4.80 (d, 0.5H, J=7.0 Hz), 2.84-2.76 (m, 3H), 2.66-2.63 (m, 1H), 2.38-2.36 (m, 1H), 2.07-2.04 (m, 1H), 1.85-1.82 (m, 1H), 1.63-1.55 (m, 1H); $^{13}$C NMR (CDCl$_3$, 150 MHz) δ 168.5, 157.4, 155.0, 137.6, 137.44, 137.41, 137.40, 130.3, 130.2, 129.7, 129.6 (2C), 124.9, 122.9, 118.85, 118.83, 118.5, 116.94, 116.90, 108.7, 71.4, 71.3, 39.87, 39.80, 30.7, 29.8, 28.7, 25.1, 24.0.

2-(6-Phenoxy-1,2,3,4-tetrahydronaphthalene-2-carbonyl)oxazole-5-carbonitrile (11)

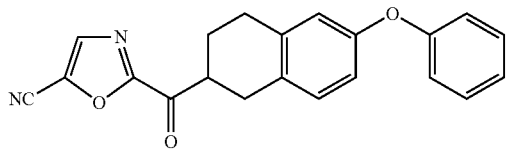 [SMILES: N#Cc1cnc(C(=O)C2CCc3cc(Oc4ccccc4)ccc3C2)o1]

The title compound was prepared from 2-(hydroxy(6-phenoxy-1,2,3,4-tetrahydronaphthalen-2-yl)methyl)oxazole-5-carbonitrile (S31, 29.3 mg, 0.08 mmol) following general procedure E. Flash chromatography (SiO$_2$, 20% EtOAc-hexanes) yielded the title compound (28.4 mg, 98%) as a yellow solid: $^1$H NMR (CDCl$_3$, 600 MHz) δ 7.88 (s, 1H), 7.33 (t, 2H, J=7.2 Hz), 7.10 (t, 2H, J=7.2 Hz), 7.00 (d, 2H, J=7.5 Hz), 6.82-6.78 (m, 2H), 3.82-3.80 (m, 1H), 3.07 (d, 2H, J=8.0 Hz), 2.93-2.90 (m, 2H), 2.30-2.27 (m, 1H), 1.93-1.89 (m, 1H); $^{13}$C NMR (CDCl$_3$, 150 MHz) δ 189.2, 158.1, 157.3, 155.3, 138.0, 136.9, 130.1, 129.6 (2C), 129.0, 126.5, 123.0, 118.8, 118.5 (2C), 117.0, 108.1, 44.1, 30.2, 28.6, 25.4; HRMS-ESI-TOF m/z 345.1240 ([M+H]$^+$, C$_{21}$H$_{16}$N$_2$O$_3$ requires 345.1234). The enantiomers were separated using a semipreparative chiral phase HPLC column (Daicel ChiraCel OD, 10 μm, 2×25 cm, 1% EtOH-hexanes, 7 mL/min, α=1.12).

(S)-11: [α]$^{23}_D$ −19 (c 0.1, THF).
(R)-11: [α]$^{23}_D$ +20 (c 0.1, THF).

2-((tert-Butyldimethylsilyloxy)(6-phenoxy-1,2,3,4-tetrahydronaphthalen-2-yl)methyl)-5-(pyridin-2-yl)oxazole (S32)

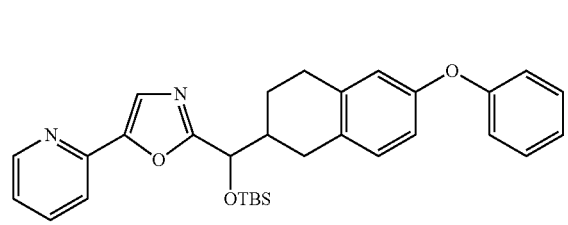 [SMILES: CC(C)(C)[Si](C)(C)OC(c1ncc(-c2ccccn2)o1)C1CCc2cc(Oc3ccccc3)ccc2C1]

The title compound was prepared from 2-((tert-butyldimethylsilyloxy)(6-phenoxy-1,2,3,4-tetrahydronaphthalen-2-yl)methyl)-5-(tributylstannyl)oxazole (S26, 5 g, 6.89 mmol) and 2-bromopyridine following general procedure C. Flash chromatography (SiO$_2$, 20% EtOAc-hexanes) yielded the title compound (1.49 g, 42%) as a colorless oil: $^1$H NMR (CDCl$_3$, 500 MHz) δ 8.64 (d, 1H, J=4.5 Hz), 7.78-7.76 (m, 1H), 7.71-7.67 (m, 2H), 7.30 (t, 2H, J=7.5 Hz), 7.24-7.22 (m, 1.5H), 7.07-7.04 (m, 1.5H), 6.98-6.95 (m, 2H), 6.78-7.72 (m, 2H), 4.81 (d, 0.5H, J=7.0 Hz), 4.75 (d, 0.5H, J=7.0 Hz), 2.96-2.73 (m, 2H), 2.58-2.55 (m, 1H), 2.39-2.34 (m, 1H), 2.26-2.20 (m, 1H), 1.81-1.77 (m, 1H), 1.58-1.53 (m, 1H), 0.90 (s, 9H), 0.11 (s, 1.5H), 0.09 (s, 1.5H), −0.05 (s, 1.5H), −0.04 (s, 1.5H); $^{13}$C NMR (CDCl$_3$, 125 MHz) δ 157.7, 157.6, 154.8, 154.7, 149.6, 138.1, 137.9, 137.18, 137.14, 132.1, 130.8, 130.5, 130.4 (2C), 130.3, 129.5, 128.5 (2C), 125.5, 125.4, 122.8, 122.78, 122.73, 119.1, 118.9, 118.4, 118.3, 116.8, 116.7, 72.5, 72.4, 40.5, 30.9, 30.5, 29.0, 28.9, 25.7 (3C), 25.3, 24.9, 18.2, −5.0, −5.23, −5.26.

(6-Phenoxy-1,2,3,4-tetrahydronaphthalen-2-yl)(5-(pyridin-2-yl)oxazol-2-yl)methanol (S33)

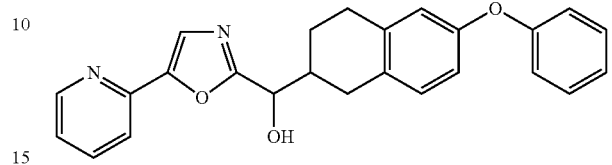

The title compound was prepared from 2-((tert-butyldimethylsilyloxy)(6-phenoxy-1,2,3,4-tetrahydronaphthalen-2-yl)methyl)-5-(pyridin-2-yl)oxazole (S32, 1.49 g, 2.90 mmol) following general procedure D. Flash chromatography (SiO$_2$, 50-100% EtOAc-hexanes) yielded the title compound (740 mg, 64%) as a yellow oil: $^1$H NMR (CDCl$_3$, 600 MHz) δ 8.63 (d, 1H, J=4.2 Hz), 7.78 (t, 1H, J=7.8 Hz), 7.71-7.65 (m, 2H), 7.30 (t, 2H, J=7.2 Hz), 7.27-7.25 (m, 2H), 7.07-6.96 (m, 3H), 6.77-6.73 (m, 2H), 4.87 (d, 0.5H, J=7.0 Hz), 4.82 (d, 0.5H, J=7.0 Hz), 2.86-2.68 (m, 4H), 2.45-2.42 (m, 1H), 2.17-2.15 (m, 1H), 1.92-1.89 (m, 1H), 1.66-1.61 (m, 1H); $^{13}$C NMR (CDCl$_3$, 150 MHz) δ 157.6, 154.8, 149.5, 146.7, 137.9, 137.7, 137.3, 130.5, 130.4, 130.3, 130.2, 129.6 (2C), 125.37, 125.34, 123.1, 122.8, 119.4, 118.9, 118.8, 118.4 (2C), 116.85, 116.81, 71.5, 71.3, 39.9, 39.8, 30.9, 30.0, 29.6, 28.98, 28.94, 25.3, 24.3.

(6-Phenoxy-1,2,3,4-tetrahydronaphthalen-2-yl)(5-(pyridin-2-yl)oxazol-2-yl)methanone (12)

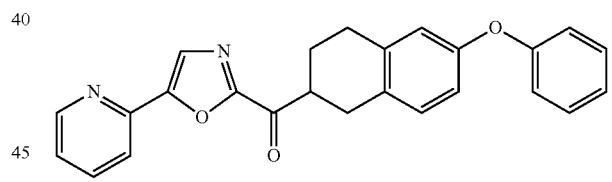

The title compound was prepared from (6-phenoxy-1,2,3,4-tetrahydronaphthalen-2-yl)(5-(pyridin-2-yl)oxazol-2-yl)methanol (S33, 740 mg, 1.85 mmol) following general procedure E. Flash chromatography (SiO$_2$, 20% EtOAc-hexanes) yielded the title compound (650 mg, 88%) as a yellow oil: $^1$H NMR (CDCl$_3$, 600 MHz) δ 8.68 (d, 1H, J=4.2 Hz), 7.93 (s, 1H), 7.90-7.83 (m, 2H), 7.34-7.31 (m, 3H), 7.19-7.14 (m, 4H), 6.88-6.78 (m, 2H), 3.92-3.90 (m, 1H), 3.10-2.90 (m, 4H), 2.32-2.30 (m, 1H), 1.95-1.93 (m, 1H); $^{13}$C NMR (CDCl$_3$, 150 MHz) δ 190.5, 157.5, 156.8, 155.1, 153.3, 150.0, 146.1, 137.2, 137.0, 130.2, 129.7, 129.6 (2C), 127.0, 124.2, 122.9, 120.4, 118.9, 118.5 (2C), 116.9, 43.5, 30.6, 28.8, 25.7; HRMS-ESI-TOF m/z 397.1551 ([M+H]$^+$, C$_{25}$H$_{20}$N$_2$O$_3$ requires 397.1547). The enantiomers were separated using a semipreparative chiral phase HPLC column (Daicel ChiraCel OD, 10 μm, 2×25 cm, 10% EtOH-hexanes, 7 mL/min, α=1.35).

(S)-12: [α]$^{23}_D$ −2.0 (c 0.1, THF).
(R)-12: [α]$^{23}_D$ +1.8 (c 0.1, THF).

Methyl 6-(2-((tert-Butyldimethylsilyloxy)(6-phenoxy-1,2,3,4-tetrahydronaphthalen-2-yl)methyl)oxazol-5-yl)picolinate (S34)

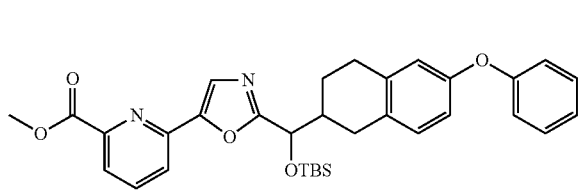 [SMILES: COC(=O)c1cccc(-c2cnc(C(O[Si](C)(C)C(C)(C)C)C3CCc4cc(Oc5ccccc5)ccc4C3)o2)n1]

The title compound was prepared from 2-((tert-butyldimethylsilyloxy)(6-phenoxy-1,2,3,4-tetrahydronaphthalen-2-yl)methyl)-5-(tributylstannyl)oxazole (S26, 5 g, 6.89 mmol) and methyl 6-bromopicolinate following general procedure C. Flash chromatography (SiO$_2$, 30% EtOAc-hexanes) yielded the title compound (2.88 g, 73%) as a colorless oil: $^1$H NMR (CDCl$_3$, 500 MHz) δ 8.01 (dd, 1H, J=4.5, 7.0 Hz), 7.99-7.97 (m, 1H), 7.89-7.85 (m, 1H), 7.80-7.78 (m, 1H), 7.65-7.59 (m, 1H), 7.25-7.22 (m, 2H), 7.01-6.97 (m, 1H), 6.92-6.90 (m, 1H), 6.73-6.66 (m, 1H), 4.80 (d, 0.5H, J=7.0 Hz), 4.77 (d, 0.5H, J=7.0 Hz), 3.96 (s, 1.5H), 3.93 (s, 1.5H), 2.91-2.87 (m, 1H), 2.78-2.76 (m, 3H), 2.73-2.71 (m, 1H), 2.55-2.52 (m, 1H), 2.38-2.33 (m, 1H), 2.23-2.20 (m, 1H), 1.62-1.52 (m, 1H), 0.90 (s, 9H), 0.11 (s, 1.5H), 0.09 (s, 1.5H), −0.05 (s, 1.5H), −0.04 (s, 1.5H); $^{13}$C NMR (CDCl$_3$, 125 MHz) δ 165.0, 164.9, 164.8, 164.0, 157.47, 157.40, 154.6, 154.5, 149.9, 149.8, 148.4, 148.0, 147.38, 147.35, 141.8, 138.9, 137.8, 137.6, 131.8, 131.7, 131.5, 130.5, 130.2, 130.1, 130.0, 129.3 (2C), 128.3, 128.23, 126.20, 126.1, 123.8, 123.7, 122.56, 122.52, 121.8 (2C), 118.7, 118.2, 118.1, 72.3, 72.1, 52.8, 52.6, 40.2, 30.7, 30.3, 28.7, 28.6, 27.6, 26.5, 25.5 (3C), 25.1, 24.6, 17.9, 17.3, 13.3, −5.2, −5.40, −5.44.

Methyl 6-(2-(Hydroxy(6-phenoxy-1,2,3,4-tetrahydronaphthalen-2-yl)methyl)oxazol-5-yl)picolinate (S35)

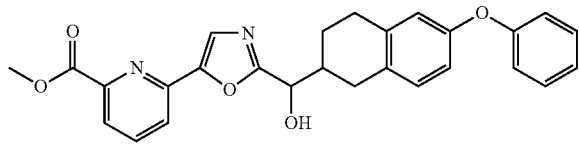 [SMILES: COC(=O)c1cccc(-c2cnc(C(O)C3CCc4cc(Oc5ccccc5)ccc4C3)o2)n1]

The title compound was prepared from methyl 6-(2-((tert-butyldimethylsilyloxy)(6-phenoxy-1,2,3,4-tetrahydronaphthalen-2-yl)methyl)oxazol-5-yl)picolinate (S34, 2.88 g, 5.04 mmol) following general procedure D. Flash chromatography (SiO$_2$, 50-100% EtOAc-hexanes) yielded the title compound (2 g, 86%) as a colorless oil: $^1$H NMR (CDCl$_3$, 400 MHz) δ 8.20 (dd, 1H, J=1.2, 7.6 Hz), 8.05 (t, 1H, J=8.0 Hz), 7.98-7.96 (m, 2H), 7.48 (t, 2H, J=7.2 Hz), 7.25-7.12 (m, 4H), 6.95-6.90 (m, 2H), 5.06 (d, 0.5H, J=6.8 Hz), 5.01 (d, 0.5H, J=6.8 Hz), 4.18 (s, 3H), 3.08-2.95 (m, 3H), 2.84-2.81 (m, 1H), 2.65-2.61 (m, 1H), 2.38-2.03 (m, 1H), 1.81-1.45 (m, 2H); $^{13}$C NMR (CDCl$_3$, 100 MHz) δ 165.8, 165.7, 165.1, 157.4, 154.77, 154.74, 150.1, 148.0, 147.1, 137.8, 137.6, 130.4, 130.3, 130.2, 130.1, 129.49 (2C), 129.47, 125.9, 123.9, 122.6, 122.2, 118.79, 117.74, 118.33, 118.30, 116.7, 116.6, 71.2, 71.0, 64.2, 52.8, 39.69, 39.65, 30.9, 30.1, 28.8, 25.2, 24.4, 18.9, 17.4, 13.4.

Methyl 6-(2-(6-Phenoxy-1,2,3,4-tetrahydronaphthalene-2-carbonyl)oxazol-5-yl)picolinate (13)

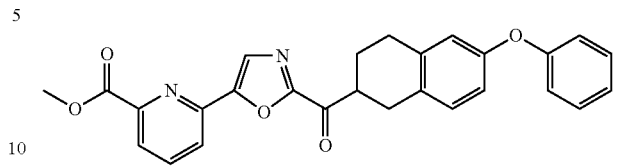

The title compound was prepared from methyl 6-(2-(hydroxy(6-phenoxy-1,2,3,4-tetrahydronaphthalen-2-yl)methyl)oxazol-5-yl)picolinate (S35, 2 g, 4.38 mmol) following general procedure E. Flash chromatography (SiO$_2$, 30% EtOAc-hexanes) yielded the title compound (1.67 g, 70%) as a white solid: $^1$H NMR (CDCl$_3$, 500 MHz) δ 8.09 (dd, 1H, J=1.0, 8.0 Hz), 8.03 (s, 1H), 8.01 (dd, 1H, J=1.5, 8.0 Hz), 7.95 (t, 1H, J=7.5 Hz), 7.29 (t, 2H, J=7.5 Hz), 7.06 (t, 2H, J=7.5 Hz), 6.98-6.96 (m, 2H), 6.79-6.77 (m, 2H), 4.01 (s, 3H), 3.91-3.86 (m, 1H), 3.08 (d, 2H, J=8.0 Hz), 2.93-2.87 (m, 2H), 2.31-2.27 (m, 1H), 1.94-1.89 (m, 1H); $^{13}$C NMR (CDCl$_3$, 125 MHz) δ 190.3, 164.9, 157.4, 156.8, 154.9, 152.3, 148.4, 146.3, 138.1, 137.1, 130.0, 129.6 (2C), 129.5, 127.8, 125.0, 123.1, 122.7, 118.8, 118.4 (2C), 116.8, 52.9, 43.4, 30.4, 28.6, 25.6; HRMS-ESI-TOF m/z 455.1617 ([M+H]$^+$, C$_{27}$H$_{22}$N$_2$O$_5$ requires 455.1601). The enantiomers were separated using a semipreparative chiral phase HPLC column (Daicel ChiraCel OD, 10 μm, 2×25 cm, 40% EtOH-hexanes, 7 mL/min, α=1.19).

(S)-13: [α]$^{23}_D$ −0.7 (c 0.8, THF).

(R)-13: [α]$^{23}_D$ +0.5 (c 0.8, THF).

6-(2-(6-Phenoxy-1,2,3,4-tetrahydronaphthalene-2-carbonyl)oxazol-5-yl)picolinic acid (14)

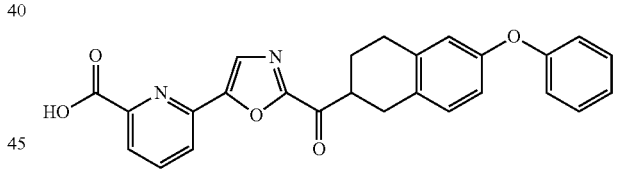

The title compound was prepared from methyl 6-(2-(6-phenoxy-1,2,3,4-tetrahydronaphthalene-2-carbonyl)oxazol-5-yl)picolinate (13, 5 mg, 0.010 mmol) following general procedure F. Each pure enantiomer of the methyl esters were converted to their corresponding carboxylic acid using general procedure G. Flash chromatography (SiO$_2$, 5% HOAc-EtOAc) yielded the title compound (3 mg, 70%) as a yellow solid: $^1$H NMR (CDCl$_3$+0.1% TFA, 600 MHz) δ 8.34 (d, 1H, J=6.0 Hz), 8.22-8.19 (m, 2H), 7.36 (t, 2H, J=8.0 Hz), 7.13-7.10 (m, 2H), 7.03 (d, 2H, J=7.8 Hz), 6.85-6.78 (m, 2H), 3.85-3.84 (m, 1H), 3.13-3.09 (m, 2H), 2.96-2.90 (m, 2H), 2.34-2.31 (m, 1H), 1.97-1.94 (m, 1H); $^{13}$C NMR (CDCl$_3$+0.1% TFA, 150 MHz) δ 191.0, 157.2, 156.8, 155.3, 151.2, 145.0, 140.5, 136.8, 130.2, 129.7 (2C), 128.9, 127.9, 125.8, 125.2, 123.2, 118.9 (2C), 118.6, 117.1, 43.9, 30.2, 28.5, 25.7; HRMS-ESI-TOF m/z 441.1451 ([M+H]$^+$, C$_{26}$H$_{20}$N$_2$O$_5$ requires 441.1445).

(S)-14: [α]$^{23}_D$ −4.5 (c 0.7, THF).

(R)-14: [α]$^{23}_D$ +5.4 (c 0.6, THF).

Methyl 6-(Benzyloxy)-1,2,3,4-tetrahydronaphthalene-2-carboxylate (S36)

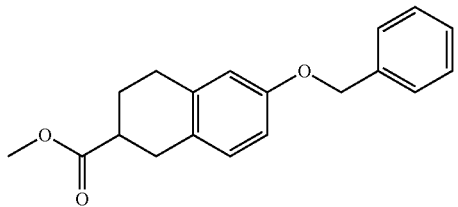 [SMILES: COC(=O)C1CCc2cc(OCc3ccccc3)ccc2C1]

A sample of methyl 1,2,3,4-tetrahydro-6-hydroxynaphthalene-2-carboxylate (S4, 4.0 g, 19.39 mmol), benzyl alcohol (2.2 mL, 21.3 mmol) and triphenylphosphine (6.60 g, 25.2 mmol) were dissolved in anhydrous THF (100 mL). The reaction mixture was cooled to 0° C. before diethyl azodicarboxylate (4 mL, 25.2 mmol) was added dropwise. The reaction mixture was stirred at room temperature for 17 h under Ar. The mixture was diluted with EtOAc, washed with saturated aqueous NaCl, and dried over $Na_2SO_4$. Evaporation in vacuo yielded the crude product that was purified by flash chromatography ($SiO_2$, 10% EtOAc-hexanes) to provide the title compound (4.3 g, 75%) as a colorless oil: $^1$H NMR ($CDCl_3$, 500 MHz) δ 7.49 (d, 2H, J=7.0 Hz), 7.44 (t, 2H, J=7.5 Hz), 7.38 (t, 1H, J=7.5 Hz), 7.07 (d, 1H, J=8.5 Hz), 6.84 (dd, 1H, J=2.5, 8.5 Hz), 6.78 (d, 1H, J=2.5 Hz), 5.07 (s, 2H), 3.78 (s, 3H), 3.03-3.00 (m, 2H), 2.90-2.86 (m, 2H), 2.79-2.75 (m, 1H), 2.27-2.23 (m, 1H), 1.94-1.90 (m, 1H); $^{13}$C NMR ($CDCl_3$, 125 MHz) δ 175.5, 156.7, 137.0, 136.5, 129.6 (2C), 128.2, 127.5, 127.1 (2C), 127.0, 114.2, 112.7, 69.6, 51.4, 39.8, 30.7, 28.5, 25.5.

(6-(Benzyloxy)-1,2,3,4-tetrahydronaphthalen-2-yl)methanol (S37)

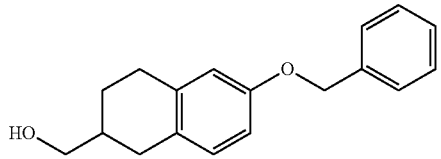 [SMILES: OCC1CCc2cc(OCc3ccccc3)ccc2C1]

The title compound was prepared from methyl 6-(benzyloxy)-1,2,3,4-tetrahydronaphthalene-2-carboxylate (S36, 4.30 g, 14.5 mmol) following general procedure A. Flash chromatography ($SiO_2$, 50% EtOAc-hexanes) afforded the title compound (4.10 g, 98%) as a colorless oil: $^1$H NMR ($CDCl_3$, 400 MHz) δ7.53 (d, 2H, J=6.8 Hz), 7.48 (t, 2H, J=6.8 Hz), 7.41 (t, 1H, J=7.2 Hz), 7.09 (d, 1H, J=8.4 Hz), 6.89-6.83 (m, 2H), 5.10 (s, 2H), 3.67 (d, 2H, J=5.2 Hz), 2.94-2.85 (m, 4H), 2.54-2.47 (m, 1H), 2.09-1.98 (m, 2H), 1.54-1.49 (m, 1H); $^{13}$C NMR ($CDCl_3$, 100 MHz) δ 156.5, 137.6, 137.0, 129.8, 128.3, 128.2 (2C), 128.1, 127.6, 114.3, 114.2, 112.6, 112.4, 69.7, 67.3, 37.0, 31.4, 28.8, 25.6.

6-(Benzyloxy)-1,2,3,4-tetrahydronaphthalene-2-carboxaldehyde (S38)

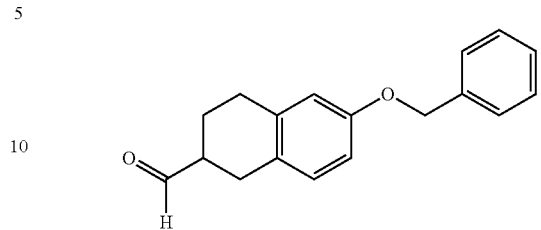

The title compound was prepared from (6-(benzyloxy)-1,2,3,4-tetrahydronaphthalen-2-yl)methanol (S37, 4.10 g, 15.27 mmol) following general procedure B. Flash chromatography ($SiO_2$, 10% EtOAc-hexanes) afforded the title compound (3.13 g, 77%) as a white solid: $^1$H NMR ($CDCl_3$, 500 MHz) δ 9.79 (s, 1H), 7.46 (d, 2H, J=7.0 Hz), 7.42 (t, 2H, J=7.0 Hz), 7.35 (t, 1H, J=7.5 Hz), 7.09 (d, 1H, J=8.0 Hz), 6.82 (dd, 1H, J=2.5, 8.5 Hz), 6.76 (d, 1H, J=2.5 Hz), 5.06 (s, 2H), 2.98-2.81 (m, 4H), 2.69-2.67 (m, 1H), 2.22-2.19 (m, 1H), 1.84-1.78 (m, 1H); $^{13}$C NMR ($CDCl_3$, 125 MHz) δ 203.7, 156.9, 137.0, 136.9, 129.9 (2C), 128.4, 127.7, 127.2, 126.5, 114.4, 113.0, 69.8, 46.9, 28.2, 27.6, 22.7.

(6-(Benzyloxy)-1,2,3,4-tetrahydronaphthalen-2-yl)(oxazol-2-yl)methanol (S39)

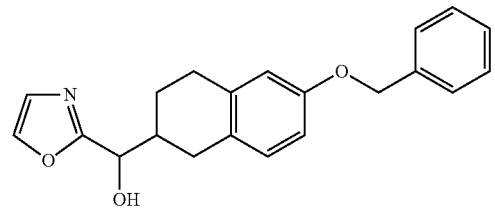 [SMILES: OC(c1ncco1)C1CCc2cc(OCc3ccccc3)ccc2C1]

Oxazole (0.815 mL, 12.4 mmol) in anhydrous THF (100 mL) was treated with $BH_3$.THF (1 M, 13.5 mL, 13.5 mmol) and the solution was stirred at room temperature for 1 h before being cooled to −78° C. and treated with 1.7 M n-BuLi (10 mL, 16.2 mmol) dropwise. The reaction mixture was stirred at −78° C. for 40 min before a solution of 6-(benzyloxy)-1,2,3,4-tetrahydronaphthalene-2-carboxaldehyde (S38, 3.13 g, 12.4 mmol) in THF (40 mL) was added. The reaction mixture was stirred at −78° C. for 2 h before being warmed to room temperature. A 5% HOAc-EtOH solution (100 mL) was added and this mixture was stirred at room temperature for 12 h. The solvent was removed under reduced pressure and the residue was dissolved in EtOAc, and washed with $H_2O$, saturated aqueous $NaHCO_3$, and saturated aqueous NaCl before the organic layer was dried over $MgSO_4$. The solvent was removed under reduced pressure. Flash chromatography ($SiO_2$, 50% EtOAc-hexanes) afforded the title compound (3.5 g, 84%) as white solid: $^1$H NMR ($CDCl_3$, 500 MHz) δ 7.64 (s, 1H), 7.43 (d, 2H, J=7.5 Hz), 7.38 (t, 2H, J=7.0 Hz), 7.31 (t, 1H, J=7.5 Hz), 7.10 (s, 1H), 7.00 (d, 0.5H, J=8.5 Hz), 6.93 (d, 0.5H, J=8.5 Hz), 6.77-6.71 (m, 2H), 5.02 (s, 2H), 4.76-4.72 (m, 1H), 3.66 (s, 1H), 2.84-2.69 (m, 2H), 2.56 (d, 1H, J=8.0 Hz), 2.36-2.31 (m, 1H), 2.13-2.10 (m, 1H), 1.81-1.78 (m, 1H), 1.60-1.52 (m, 1H); $^{13}$C NMR ($CDCl_3$, 125 MHz) δ 165.2, 156.8, 138.9, 137.5, 137.3, 137.2, 130.0, 129.9, 128.4 (2C), 127.9, 127.7 (2C), 127.3, 126.6, 114.4, 112.86, 112.84, 71.3, 71.2, 69.9, 40.0, 39.9, 30.6, 30.0, 29.0, 25.2, 24.5.

(6-(Benzyloxy)-1,2,3,4-tetrahydronaphthalen-2-yl)(oxazol-2-yl)methanone (15)

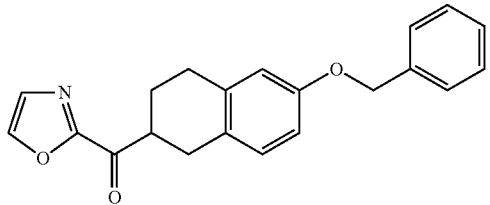 [SMILES: O=C(c1ncco1)C1CCc2cc(OCc3ccccc3)ccc2C1]

The title compound was prepared from (6-(benzyloxy)-1,2,3,4-tetrahydronaphthalen-2-yl)(oxazol-2-yl)methanol (S39, 40 mg, 0.119 mmol) following general procedure E. Flash chromatography (SiO$_2$, 20% EtOAc-hexanes) yielded the title compound (35 mg, 88%) as a white solid: $^1$H NMR (CDCl$_3$, 600 MHz) δ 7.84 (s, 1H), 7.43 (d, 2H, J=7.2 Hz), 7.39 (t, 2H, J=7.8 Hz), 7.37 (s, 1H), 7.30 (t, 1H, J=7.2 Hz), 7.02 (d, 1H, J=8.4 Hz), 6.77 (dd, 1H, J=2.4, 8.4 Hz), 6.748-6.744 (m, 1H), 5.04 (s, 2H), 3.85-3.80 (m, 1H), 3.03 (d, 2H, J=8.4 Hz), 2.95-2.90 (m, 2H), 2.28-2.25 (m, 1H), 1.91-1.87 (m, 1H); $^{13}$C NMR (CDCl$_3$, 150 MHz) δ 190.6, 157.5, 157.0, 141.6, 137.1, 136.7, 129.9, 129.0, 128.5 (2C), 127.8, 127.4 (2C), 127.1, 114.4, 113.0, 70.0, 43.7, 30.3, 29.0, 25.7; HRMS-ESI-TOF m/z 334.1442 ([M+H]$^+$, C$_{21}$H$_{19}$NO$_3$ requires 334.1438). The enantiomers were separated using a semipreparative chiral phase HPLC column (Daicel ChiraCel OD, 10 μm, 2×25 cm, 1% EtOH-hexanes, 7 mL/min, α=1.12).
(S)-15: [α]$^{23}_D$ −19 (c 0.2, THF).
(R)-15: [α]$^{23}_D$ +20 (c 0.2, THF).

2-((6-(Benzyloxy)-1,2,3,4-tetrahydronaphthalen-2-yl)(tert-butyldimethylsilyloxy)methyl)oxazole (S40)

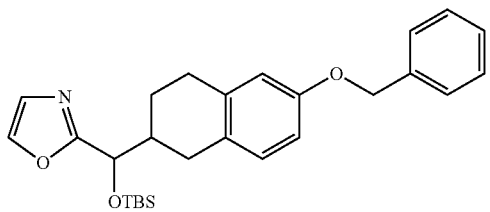 [SMILES: CC(C)(C)[Si](C)(C)OC(c1ncco1)C1CCc2cc(OCc3ccccc3)ccc2C1]

A solution of (6-(benzyloxy)-1,2,3,4-tetrahydronaphthalen-2-yl)(oxazol-2-yl)methanol (S39, 3.34 g, 9.95 mmol), TBSCl (3.6 g, 23.89 mmol) and imidazole (3.30 g, 49.75 mmol) in DMF (60 mL) was stirred at room temperature for 16 h before it was diluted with EtOAc, washed with H$_2$O, and saturated aqueous NaCl. The organic layer was dried over MgSO$_4$ and the solvent was removed under reduced pressure. Flash chromatography (SiO$_2$, 5% EtOAc-hexanes) yielded the title compound (5.10 g, 98%) as a thick colorless oil: $^1$H NMR (CDCl$_3$, 600 MHz) δ 7.65 (s, 1H), 7.43 (d, 2H, J=6.0 Hz), 7.38 (t, 2H, J=7.2 Hz), 7.31 (t, 1H, J=7.2 Hz), 7.10 (d, 1H, J=6.0 Hz), 7.01 (d, 0.5H, J=8.4 Hz), 6.92 (d, 0.5H, J=8.4 Hz), 6.77-6.70 (m, 2H), 5.02 (s, 2H), 4.76 (d, 0.5H, J=7.2 Hz), 4.68 (d, 0.5H, J=7.2 Hz), 2.91-2.65 (m, 1.5H), 2.50-2.40 (m, 1H), 2.31-2.22 (m, 1.5H), 1.69-1.68 (m, 1H), 1.49-1.43 (m, 2H), 0.89 (s, 9H), 0.09 (s, 1.5H), 0.07 (s, 1.5H), −0.09 (s, 1.5H), −0.10 (s, 1.5H); $^{13}$C NMR (CDCl$_3$, 150 MHz) δ 164.6, 164.5, 156.77, 156.74, 138.5, 138.4, 137.6, 137.4, 137.2, 130.1, 129.9, 128.4 (2C), 128.2, 127.9, 127.7, 127.3, 126.7, 114.4, 114.3, 112.8, 112.7, 72.4, 72.3, 69.9, 40.6, 40.5, 30.5, 29.1, 29.0, 25.6 (3C), 25.3, 25.0, 18.1, −5.2, −5.31, −5.34, −5.37.

2-((6-(Benzyloxy)-1,2,3,4-tetrahydronaphthalen-2-yl)(tert-butyldimethylsilyloxy)methyl)-5-(tributylstannyl)oxazole (S41)

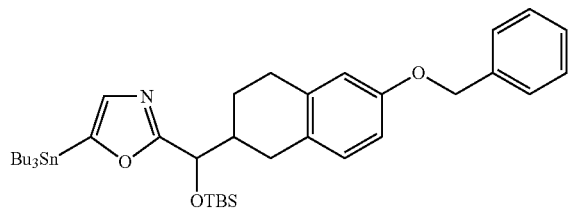

A solution of 2-((6-(benzyloxy)-1,2,3,4-tetrahydronaphthalen-2-yl)(tert-butyldimethylsilyloxy)methyl)oxazole (S40, 500 mg, 1.1 mmol) in THF (20 mL) was cooled to −78° C. before it was treated with 2.16 M n-BuLi (0.60 mL, 1.2 mmol) dropwise. The reaction mixture was stirred at −78° C. for 2 h, and treated with a solution of Bu$_3$SnCl (0.60 mL, 2.2 mmol) and stirred for 5 min. The solution was warmed to room temperature and diluted with EtOAc, and washed with saturated aqueous NaCl. The organic layer was dried over MgSO$_4$ and the solvent was removed under reduced pressure. Flash chromatography (SiO$_2$, 0-5% EtOAc-hexanes) yielded the title compound (499 mg, 62%) as a thick colorless oil: $^1$H NMR (CDCl$_3$, 500 MHz) δ 7.43 (d, 2H, J=7.5 Hz), 7.38 (t, 2H, J=7.5 Hz), 7.32 (t, 1H, J=7.0 Hz), 7.15 (s, 0.5H), 7.14 (s, 0.5H), 7.02 (d, 0.5H, J=8.5 Hz), 6.92 (d, 0.5H, J=8.5 Hz), 6.79-6.70 (m, 2H), 5.02 (s, 2H), 4.80 (d, 0.5H, J=7.5 Hz), 4.75 (d, 0.5H, J=7.5 Hz), 2.95-2.67 (m, 3H), 2.51-2.24 (m, 2H), 1.62-1.57 (m, 8H), 1.39-1.33 (m, 6H), 1.17-1.31 (m, 6H), 0.94-0.90 (m, 18H), 0.09 (s, 1.5H), 0.08 (s, 1.5H), −0.09 (s, 1.5H), −0.10 (s, 1.5H); $^{13}$C NMR (CDCl$_3$, 125 MHz) δ 168.5, 168.4, 156.6, 154.8, 154.7, 137.7, 137.4, 137.2, 137.1, 130.1, 129.9, 128.49, 128.42 (2C), 128.1, 127.7, 127.3 (2C), 114.37, 114.31, 112.7, 112.6, 72.5, 72.4, 69.9, 40.7, 40.6, 30.6, 30.5, 29.2, 29.1, 28.9 (3C), 28.8, 28.7, 27.3, 27.2 (3C), 27.0, 26.8, 25.6 (3C), 25.3, 25.1, 18.1, 13.6 (3C), 13.5, 11.6, 11.5 (3C), 10.1, 8.76, 8.70, −5.33, −5.36, −5.37, −5.40.

Methyl 2-((6-(Benzyloxy)-1,2,3,4-tetrahydronaphthalen-2-yl)(tert-butyldimethylsilyloxy)methyl)oxazole-5-carboxylate (S42)

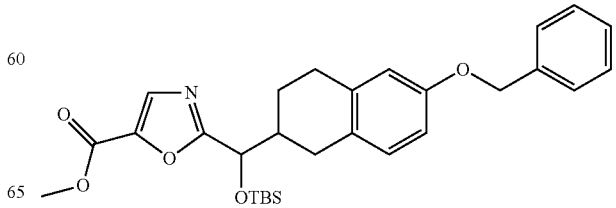

A solution of 2-((6-(benzyloxy)-1,2,3,4-tetrahydronaphthalen-2-yl)(tert-butyldimethylsilyloxy)methyl)oxazole (S40, 200 mg, 0.44 mmol) in THF (4 mL) was cooled to −78° C. before it was treated with 2.16 M n-BuLi (0.30 mL, 0.53 mmol) dropwise. The reaction mixture was stirred at −78° C. for 2 h, and treated with a solution of Mander's reagent (MeO$_2$CCN, 0.175 mL, 2.2 mmol) in THF (2 mL) and stirred for 5 min. The solution was warmed to room temperature and diluted with EtOAc and washed with saturated aqueous NaCl. The organic layer was dried over MgSO$_4$ and the solvent was removed under reduced pressure. Flash chromatography (SiO$_2$, 10% EtOAc-hexanes) yielded the title compound (134 mg, 59%) as a yellow oil: $^1$H NMR (CDCl$_3$, 600 MHz) δ 7.75-7.73 (m, 1H), 7.42 (d, 2H, J=7.8 Hz), 7.37 (t, 2H, J=7.8 Hz), 7.31 (t, 1H, J=7.2 Hz), 6.99 (d, 1H, J=8.4 Hz), 6.91 (d, 1H, J=8.4 Hz), 6.76-6.69 (m, 2H), 5.02 (s, 2H), 4.79 (d, 0.5H, J=6.6 Hz), 4.73 (d, 0.5H, J=7.8 Hz), 3.92 (s, 3H), 2.83-2.79 (m, 2H), 2.50-2.48 (m, 1H), 2.35-2.33 (m, 1H), 2.22-2.20 (m, 0.5H), 1.75-1.73 (m, 0.5H), 1.52-1.47 (m, 1H), 0.90 (s, 9H), 0.09 (s, 1.5H), 0.07 (s, 1.5H), −0.05 (s, 1.5H), −0.06 (s, 1.5H); $^{13}$C NMR (CDCl$_3$, 150 MHz) δ 167.8, 167.6, 158.0, 156.82, 156.80, 156.7, 142.2, 142.1, 137.5, 137.2, 134.0, 133.9, 130.1, 129.9, 128.4 (2C), 127.9, 127.7, 127.3 (2C), 114.4, 114.3, 112.8, 112.7, 72.45, 72.41, 72.3, 69.9, 52.1, 40.6, 39.0, 30.6, 30.0, 29.3, 26.0 (3C), 24.7, 18.1, 13.7, −5.1, −5.30, −5.33.

Methyl 2-((6-(Benzyloxy)-1,2,3,4-tetrahydronaphthalen-2-yl)(hydroxy)methyl)oxazole-5-carboxylate (S43)

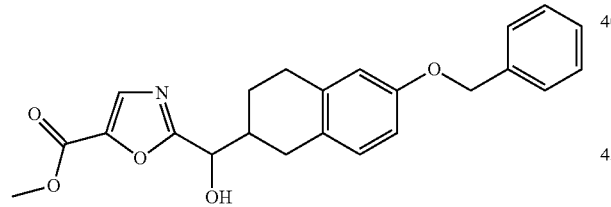

The title compound was prepared from methyl 2-((6-(benzyloxy)-1,2,3,4-tetrahydronaphthalen-2-yl)(tert-butyldimethylsilyloxy)methyl)oxazole-5-carboxylate (S42, 70 mg, 0.13 mmol) following general procedure D. Flash chromatography (SiO$_2$, 50% EtOAc-hexanes) yielded the title compound (33.5 mg, 62%) as a colorless oil: $^1$H NMR (CDCl$_3$, 600 MHz) δ 7.75 (s, 1H), 7.42 (d, 2H, J=7.8 Hz), 7.37 (t, 2H, J=7.8 Hz), 7.31 (t, 1H, J=7.2 Hz), 6.98 (d, 0.5H, J=8.4 Hz), 6.92 (d, 0.5H, J=8.4 Hz), 6.75-6.70 (m, 2H), 5.02 (s, 2H), 4.82 (d, 0.5H, J=6.6 Hz), 4.77 (d, 0.5H, J=7.8 Hz), 3.92 (s, 3H), 2.84-2.74 (m, 3H), 2.38-2.35 (m, 2H), 2.22-2.20 (m, 1H), 1.85-1.83 (m, 1H), 1.61-1.47 (m, 1H); $^{13}$C NMR (CDCl$_3$, 150 MHz) δ 157.9, 156.8, 137.3, 137.1, 133.7, 130.1, 129.9, 128.5 (2C), 127.8, 127.5, 127.4 (2C), 127.3, 114.4, 112.94, 112.91, 71.5, 71.4, 69.9, 52.3, 40.08, 40.01, 30.6, 29.6, 29.0, 25.3, 24.2.

Methyl 2-(6-(Benzyloxy)-1,2,3,4-tetrahydronaphthalene-2-carbonyl)oxazole-5-carboxylate (16)

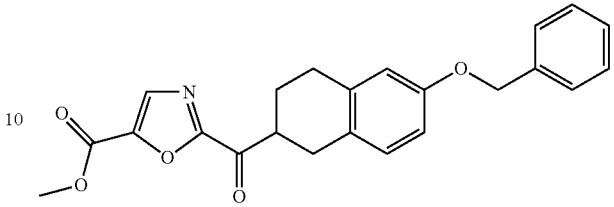

The title compound was prepared from methyl 2-((6-(benzyloxy)-1,2,3,4-tetrahydronaphthalen-2-yl)(hydroxy)methyl)oxazole-5-carboxylate (S43, 33.5 mg, 0.07 mmol) following general procedure E. Flash chromatography (SiO$_2$, 30% EtOAc-hexanes) yielded the title compound (21.3 mg, 70%) as a yellow oil: $^1$H NMR (CDCl$_3$, 600 MHz) δ 7.91 (s, 1H), 7.42 (d, 2H, J=7.8 Hz), 7.38 (t, 2H, J=7.8 Hz), 7.32 (t, 1H, J=7.2 Hz), 7.02 (d, 1H, J=8.4 Hz), 6.79-6.74 (m, 2H), 5.04 (s, 2H), 3.97 (s, 3H), 3.82-3.80 (m, 1H), 3.03-2.90 (m, 4H), 2.28-2.25 (m, 1H), 1.90-1.87 (m, 1H); $^{13}$C NMR (CDCl$_3$, 150 MHz) δ 190.3, 157.8, 157.4, 157.0, 143.8, 137.1, 136.6, 134.6, 129.8, 128.5 (2C), 127.8, 127.4, 126.8, 114.4, 113.1, 69.9, 52.7, 44.0, 30.2, 28.8, 25.5; HRMS-ESI-TOF m/z 392.1494 ([M+H]$^+$, C$_{23}$H$_{21}$NO$_5$ requires 392.1492). The enantiomers were separated using a semi-preparative chiral phase HPLC column (Daicel ChiraCel OD, 10 μm, 2×25 cm, 3% EtOH-hexanes, 7 mL/min, α=1.20).

(S)-16: [α]$^{23}_D$ −15 (c 0.1, THF).
(R)-16: [α]$^{23}_D$ +17 (c 0.1, THF).

2-((6-(Benzyloxy)-1,2,3,4-tetrahydronaphthalen-2-yl)(tert-butyldimethylsilyloxy)methyl)oxazole-5-carboxamide (S44)

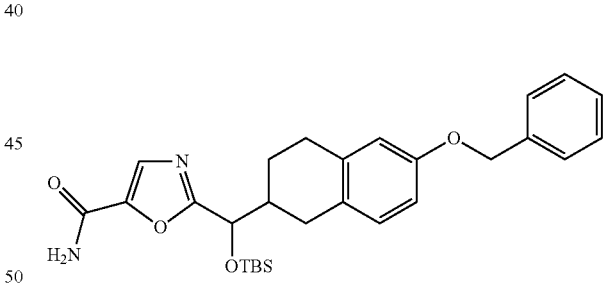

A solution of methyl 2-((6-(benzyloxy)-1,2,3,4-tetrahydronaphthalen-2-yl)(tert-butyldimethylsilyloxy)methyl)oxazole-5-carboxylate (S42, 75 mg, 0.14 mmol) was dissolved in a saturated solution of NH$_3$—CH$_3$OH (4 mL) and the mixture was stirred for 2 h at room temperature. Evaporation in vacuo yielded the crude carboxamide that was purified by flash chromatography (SiO$_2$, 50% EtOAc-hexanes) to provide the title compound (49.7 mg, 68%) as a colorless oil: $^1$H NMR (CDCl$_3$, 600 MHz) δ 7.71 (d, 1H, J=5.4 Hz), 7.42 (d, 2H, J=7.8 Hz), 7.37 (t, 2H, J=7.8 Hz), 7.30 (t, 1H, J=7.2 Hz), 6.99 (d, 0.5H, J=8.4 Hz), 6.91 (d, 0.5H, J=8.4 Hz), 6.77-6.70 (m, 2H), 6.18-6.17 (m, 2H), 5.02 (s, 2H), 4.77 (d, 0.5H, J=6.6 Hz), 4.70 (d, 0.5H, J=7.8 Hz), 2.85-2.76 (m, 2H), 2.68-2.66 (m, 1H), 2.49-2.45 (m, 1H), 2.31-2.05 (m, 2H), 1.51-1.48 (m, 1H), 0.89 (s, 9H), 0.10 (s, 1.5H), 0.08 (s, 1.5H), −0.06 (s, 1.5H), −0.07 (s, 1.5H); $^{13}$C NMR (CDCl$_3$, 150 MHz) δ 165.9, 165.8, 158.6, 158.5, 156.89, 156.85, 144.6, 144.5, 137.4, 137.1, 131.58, 131.56, 130.1, 129.9, 128.5 (2C), 127.8, 127.7, 127.4, 127.3 (2C), 114.4, 114.3, 112.9, 112.8, 72.5, 72.4, 69.9, 40.6, 30.6, 30.2, 29.0, 28.9, 25.6 (3C), 25.3, 24.9, 18.1, −5.18, −5.19, −5.22, −5.25.

2-((6-(Benzyloxy)-1,2,3,4-tetrahydronaphthalen-2-yl)(tert-butyldimethylsilyloxy)methyl)oxazole-5-carbonitrile (S45)

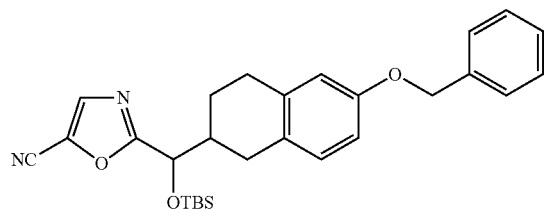 [SMILES: CC(C)(C)[Si](C)(C)OC(c1ncc(C#N)o1)C1CCc2cc(OCc3ccccc3)ccc2C1]

A solution of 2-((6-(benzyloxy)-1,2,3,4-tetrahydronaphthalen-2-yl)(tert-butyldimethylsilyloxy)methyl)oxazole-5-carboxamide (S44, 49.7 mg, 0.10 mmol) was dissolved in 1,4-dioxane (5 mL) and pyridine (0.020 mL, 0.25 mmol) and trifluoroacetic anhydride (0.018 mL, 0.13 mmol) were added. The reaction mixture was stirred for 2 h at room temperature. The mixture was diluted with CH$_2$Cl$_2$ and the organic layer was washed with saturated aqueous NaCl, and dried over Na$_2$SO$_4$. Evaporation in vacuo yielded the crude nitrile that was purified by flash chromatography (SiO$_2$, 10% EtOAc-hexanes) to afford the title compound (33.2 mg, 69%) as a white solid: $^1$H NMR (CDCl$_3$, 600 MHz) δ 7.70 (d, 1H, J=5.4 Hz), 7.42 (d, 2H, J=7.8 Hz), 7.37 (t, 2H, J=7.8 Hz), 7.31 (t, 1H, J=7.2 Hz), 7.00 (d, 0.5H, J=8.4 Hz), 6.92 (d, 0.5H, J=8.4 Hz), 6.77-6.70 (m, 2H), 5.02 (s, 2H), 4.80 (d, 0.5H, J=6.6 Hz), 4.74 (d, 0.5H, J=7.8 Hz), 2.83-2.76 (m, 2H), 2.69-2.66 (m, 1H), 2.50-2.47 (m, 1H), 2.31-2.28 (m, 1H), 2.13-2.11 (m, 0.5H), 1.74-1.72 (m, 0.5H), 1.58-1.48 (m, 1H), 0.88 (s, 9H), 0.10 (s, 1.5H), 0.08 (s, 1.5H), −0.06 (s, 1.5H), −0.07 (s, 1.5H); $^{13}$C NMR (CDCl$_3$, 150 MHz) δ 168.7, 168.5, 156.9, 156.8, 137.5, 137.3, 137.1, 137.0, 130.1, 129.9, 128.5 (2C), 127.8, 127.6, 127.4 (2C), 127.2, 124.49, 124.46, 114.4, 114.3, 112.9, 112.8, 109.09, 109.06, 72.3, 72.2, 69.9, 40.6, 30.5, 29.9, 28.99, 28.94, 25.5 (3C), 25.3, 24.6, 18.1, −5.22, −5.27, −5.29.

2-((6-(Benzyloxy)-1,2,3,4-tetrahydronaphthalen-2-yl)(hydroxy)methyl)oxazole-5-carbonitrile (S46)

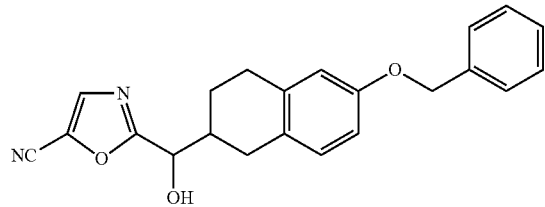 [SMILES: N#Cc1cnc(C(O)C2CCc3cc(OCc4ccccc4)ccc3C2)o1]

The title compound was prepared from 2-((6-(benzyloxy)-1,2,3,4-tetrahydronaphthalen-2-yl)(tert-butyldimethylsilyloxy)methyl)oxazole-5-carbonitrile (S45, 33.2 mg, 0.06 mmol) following general procedure D. Flash chromatography (SiO$_2$, 20% EtOAc-hexanes) yielded the title compound (8 mg, 32%) as a white solid: $^1$H NMR (CDCl$_3$, 600 MHz) δ 7.72 (d, 1H, J=5.4 Hz), 7.41 (d, 2H, J=7.8 Hz), 7.37 (t, 2H, J=7.8 Hz), 7.31 (t, 1H, J=7.2 Hz), 6.98 (d, 0.5H, J=8.4 Hz), 6.94 (d, 0.5H, J=8.4 Hz), 6.77-6.71 (m, 2H), 5.02 (s, 2H), 4.82-4.79 (m, 1H), 2.85-2.60 (m, 4H), 2.36-2.33 (m, 2H), 2.06-2.04 (m, 1H), 1.84-1.80 (m, 1H); $^{13}$C NMR (CDCl$_3$, 150 MHz) δ 168.5, 157.0, 137.45, 137.43, 137.17, 137.15, 137.0, 130.1, 129.9, 128.5 (2C), 127.8, 127.4 (2C), 127.1, 127.0, 125.0, 114.47, 114.45, 113.06, 113.02, 108.8, 71.5, 71.4, 70.0, 40.0, 39.9, 30.5, 29.6, 28.8, 25.2, 24.2.

2-(6-(Benzyloxy)-1,2,3,4-tetrahydronaphthalene-2-carbonyl)oxazole-5-carbonitrile (17)

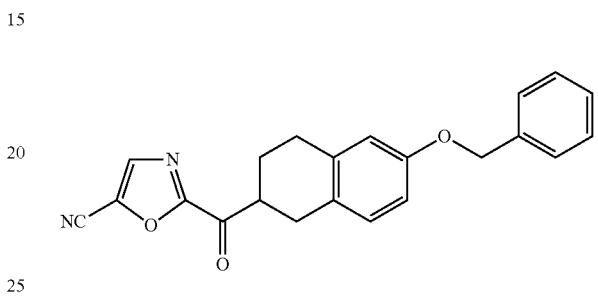

The title compound was prepared from 2-((6-(benzyloxy)-1,2,3,4-tetrahydronaphthalen-2-yl)(hydroxy)methyl)oxazole-5-carbonitrile (S46, 8 mg, 0.02 mmol) following general procedure E. Flash chromatography (SiO$_2$, 20% EtOAc-hexanes) yielded the title compound (7.2 mg, 95%) as a yellow oil: $^1$H NMR (CDCl$_3$, 600 MHz) δ 7.88 (s, 1H), 7.42 (d, 2H, J=6.6 Hz), 7.38 (t, 2H, J=7.2 Hz), 7.32 (t, 1H, J=7.2 Hz), 7.02 (d, 1H, J=8.4 Hz), 6.78 (dd, 1H, J=2.4, 8.4 Hz), 6.74 (s, 1H), 5.04 (s, 2H), 3.79-3.77 (m, 1H), 3.02 (d, 2H, J=7.2 Hz), 2.95-2.91 (m, 2H), 2.28-2.26 (m, 1H), 1.91-1.87 (m, 1H); $^{13}$C NMR (CDCl$_3$, 150 MHz) δ 189.4, 158.2, 157.1, 138.0, 137.0, 136.4, 129.8, 128.5 (2C), 127.9, 127.4 (2C), 126.57, 126.50, 114.5, 113.2, 108.1, 70.0, 44.3, 30.1, 28.8, 25.5; HRMS-ESI-TOF m/z 381.1220 ([M+Na]$^+$, C$_{22}$H$_{18}$N$_2$O$_3$ requires 381.1210). The enantiomers were separated using a semipreparative chiral phase HPLC column (Daicel ChiraCel OD, 10 μm, 2×25 cm, 10% EtOH-hexanes, 7 mL/min, α=1.24).

(S)-17: [α]$^{23}_D$ −19 (c 0.1, THF).
(R)-17: [α]$^{23}_D$ +21 (c 0.1, THF).

2-((6-(Benzyloxy)-1,2,3,4-tetrahydronaphthalen-2-yl)(tert-butyldimethylsilyloxy)methyl)-5-(pyridin-2-yl)oxazole (S47)

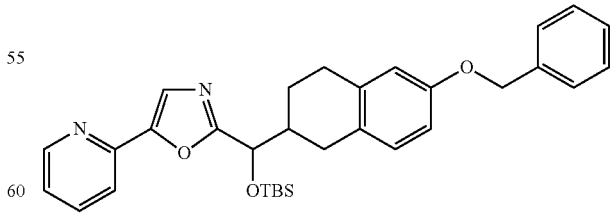

The title compound was prepared from 2-((6-(benzyloxy)-1,2,3,4-tetrahydronaphthalen-2-yl)(tert-butyldimethylsilyloxy)methyl)-5-(tributylstannyl)oxazole (S41, 250 mg, 0.33 mmol) and 2-bromopyridine following general procedure C. Flash chromatography (SiO$_2$, 20% EtOAc-hexanes)

yielded the title compound (129 mg, 74%) as a colorless oil: ¹H NMR (CDCl₃, 500 MHz) δ 8.64 (d, 1H, J=7.5 Hz), 7.77-7.66 (m, 2H), 7.43-7.41 (m, 2H), 7.39 (t, 2H, J=7.5 Hz), 7.36 (t, 1H, J=7.0 Hz), 7.23-7.20 (m, 1H), 7.03 (d, 0.5H, J=8.4 Hz), 6.95 (d, 0.5H, J=8.4 Hz), 6.76-6.63 (m, 2H), 5.028 (s, 1H), 5.023 (s, 1H), 4.81 (d, 0.5H, J=6.6 Hz), 4.76 (d, 0.5H, J=7.8 Hz), 2.91-2.65 (m, 3H), 2.58-2.52 (m, 1H), 2.44-2.39 (m, 1H), 2.36-2.26 (m, 0.5H), 1.80-1.79 (m, 0.5H), 1.68-1.63 (m, 2H), 1.67-1.63 (m, 2H), 1.58-1.55 (m, 2H), 0.93 (s, 3H), 0.91 (s, 3H), 0.13 (s, 1.5H), 0.11 (s, 1.5H), −0.02 (s, 1.5H), −0.03 (s, 1.5H): ¹³C NMR (CDCl₃, 125 MHz) δ 164.81, 164.71, 156.7, 150.8, 150.7, 149.8, 147.35, 147.32, 137.5, 137.3, 137.2, 136.8, 130.1, 129.9, 128.4 (2C), 128.1, 127.8, 127.7, 127.3, 125.1, 125.0, 122.7, 118.9, 114.4, 114.3, 112.8, 112.7, 72.5, 72.4, 69.9, 40.6, 30.7, 30.4, 29.1, 29.0, 27.7, 26.7, 25.6 (3C), 25.4, 24.9, 18.1, 17.4, 13.5, −5.1, −5.28, −5.31.

(6-(Benzyloxy)-1,2,3,4-tetrahydronaphthalen-2-yl) (5-(pyridin-2-yl)oxazol-2-yl)methanol (S48)

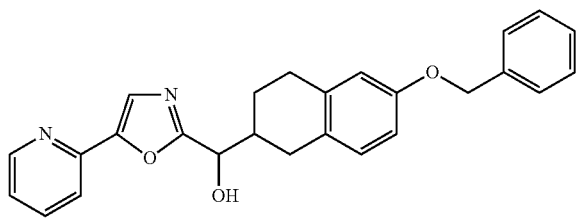 [SMILES: OC(c1ncc(-c2ccccn2)o1)C1CCc2cc(OCc3ccccc3)ccc2C1]

The title compound was prepared from 2-((6-(benzyloxy)-1,2,3,4-tetrahydronaphthalen-2-yl)(tert-butyldimethylsilyloxy)methyl)-5-(pyridin-2-yl)oxazole (S47, 128.6 mg, 0.24 mmol) following general procedure D. Flash chromatography (SiO₂, 50-100% EtOAc-hexanes) yielded the title compound (96.2 mg, 95%) as a white solid: ¹H NMR (CDCl₃, 500 MHz) δ 8.61 (d, 1H, J=7.5 Hz), 7.74-7.61 (m, 3H), 7.42-7.41 (m, 2H), 7.38 (t, 2H, J=7.5 Hz), 7.30 (t, 1H, J=7.0 Hz), 7.22-7.20 (m, 2H), 6.98 (d, 0.5H, J=8.4 Hz), 6.91 (d, 0.5H, J=8.4 Hz), 6.76-6.63 (m, 2H), 5.01 (s, 2H), 4.83 (d, 0.5H, J=6.6 Hz), 4.79 (d, 0.5H, J=7.8 Hz), 4.08 (s, 0.5H), 3.98 (s, 1H), 2.91-2.74 (m, 3H), 2.45-2.39 (m, 1H), 2.22-2.18 (m, 0.5H), 1.89-1.86 (m, 0.5H), 1.67-1.55 (m, 1H), 1.45-1.40 (m, 0.5H); ¹³C NMR (CDCl₃, 125 MHz) δ 165.4, 156.8, 151.0, 149.8, 146.9, 137.5, 137.3, 137.2, 136.8, 130.1, 129.9, 128.4 (2C), 127.9, 127.7, 127.3 (2C), 124.8, 122.9, 119.3, 114.4, 114.3, 112.85, 112.82, 71.4, 71.3, 69.9, 39.9, 30.8, 30.5, 29.8, 25.4, 24.5; HRMS-ESI-TOF m/z 413.1856 ([M+H]⁺, C₂₆H₂₄N₂O₃ requires 413.1860).

(6-(Benzyloxy)-1,2,3,4-tetrahydronaphthalen-2-yl) (5-(pyridin-2-yl)oxazol-2-yl)methanone (18)

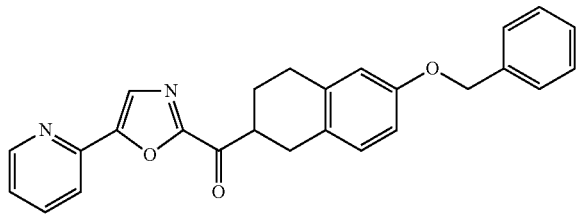 [SMILES: O=C(c1ncc(-c2ccccn2)o1)C1CCc2cc(OCc3ccccc3)ccc2C1]

The title compound was prepared from (6-(benzyloxy)-1,2,3,4-tetrahydronaphthalen-2-yl)(5-(pyridin-2-yl)oxazol-2-yl)methanol (S48, 96.2 mg, 0.23 mmol) following general procedure E. Flash chromatography (SiO₂, 20% EtOAc-hexanes) yielded the title compound (72 mg, 76%) as a yellow oil: ¹H NMR (CDCl₃, 600 MHz) δ 8.68 (d, 1H, J=7.5 Hz), 7.91 (s, 1H), 7.88 (d, 1H, J=7.5 Hz), 7.80 (td, 1H, J=2.5, 7.5 Hz), 7.43 (d, 2H, J=7.5 Hz), 7.38 (t, 2H, J=7.5 Hz), 7.31 (t, 2H, J=7.0 Hz), 7.03 (d, 1H J=8.4 Hz), 6.78 (d, 1H J=8.4 Hz), 6.76-6.74 (m, 1H), 5.04 (s, 2H), 3.91-3.86 (m, 1H), 3.06-2.89 (m, 4H), 2.32-2.28 (m, 1H), 1.95-1.86 (m, 1H); ¹³C NMR (CDCl₃, 150 MHz) δ 190.6, 156.9, 156.8, 153.3, 150.0, 146.2, 137.17, 137.12, 136.7, 129.8, 128.5 (2C), 127.8, 127.4 (2C), 127.1, 126.9, 124.1, 120.4, 114.4, 113.0, 69.9, 43.6, 30.4, 29.0, 25.8; HRMS-ESI-TOF m/z 411.1700 ([M+H]⁺, C₂₆H₂₂N₂O₃ requires 411.1703). The enantiomers were separated using a semipreparative chiral phase HPLC column (Daicel ChiraCel OD, 10 μm, 2×25 cm, 5% EtOH-hexanes, 7 mL/min, α=1.26).

(S)-18: [α]²³_D −3.2 (c 0.3. THF).

(R)-18: [α]²³_D +5.5 (c 0.2, THF).

Methyl 6-(2-((6-(Benzyloxy)-1,2,3,4-tetrahydronaphthalen-2-yl)(tert-butyldimethylsilyloxy) methyl)oxazol-5-yl)picolinate (S49)

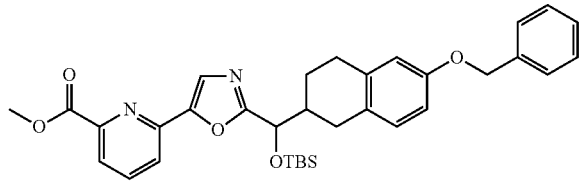 [SMILES: COC(=O)c1cccc(-c2cnc(C(O[Si](C)(C)C(C)(C)C)C3CCc4cc(OCc5ccccc5)ccc4C3)o2)n1]

The title compound was prepared from 2-((6-(benzyloxy)-1,2,3,4-tetrahydronaphthalen-2-yl)(tert-butyldimethylsilyloxy)methyl)-5-(tributylstannyl)oxazole (S41, 250 mg, 0.33 mmol) and methyl 6-bromopicolinate following general procedure C. Flash chromatography (SiO₂, 20% EtOAc-hexanes) yielded the title compound (160 mg, 67%) as a yellow oil: ¹H NMR (CDCl₃, 600 MHz) δ 8.04 (d, 1H, J=7.5 Hz), 7.90 (q, 1H, J=7.8 Hz), 7.84-7.81 (m, 2H), 7.42-7.40 (m, 2H), 7.37 (t, 2H, J=7.5 Hz), 7.30 (t, 1H, J=7.0 Hz), 7.00 (d, 0.5H, J=8.4 Hz), 6.90 (d, 0.5H, J=8.4 Hz), 6.76-6.69 (m, 1H), 5.018 (s, 1H), 5.013 (s, 1H), 4.80 (d, 0.5H, J=6.6 Hz), 4.75 (d, 0.5H, J=7.8 Hz), 4.02 (s, 3H), 2.91-2.70 (m, 2H), 2.54-2.49 (m, 1H), 2.39-2.34 (m, 1H), 2.27-2.24 (m, 1H), 1.66-1.62 (m, 1H), 1.54-1.52 (m, 1H), 1.38-1.28 (m, 1H), 0.90 (s, 4.5H), 0.88 (s, 4.5H), 0.11 (s, 1.5H), 0.09 (s, 1.5H), −0.05 (s, 1.5H), −0.06 (s, 1.5H); ¹³C NMR (CDCl₃, 150 MHz) δ 165.3, 165.2, 165.0, 156.79, 156.76, 150.0, 149.9, 148.2, 147.6, 147.5, 137.9, 137.5, 137.3, 137.2, 137.1, 130.1, 129.9, 128.4 (2C), 128.1, 127.7, 127.36, 127.34, 126.38, 126.32, 123.9, 123.8, 122.05, 122.02, 114.4, 114.3, 112.8, 112.7, 72.5, 72.4, 69.9, 52.9, 40.6, 30.7, 30.3, 29.1, 29.0, 27.7, 26.7, 25.6 (3C), 25.4, 25.0, 18.1, 17.4, 13.5, −5.14, −5.15, −5.25, −5.28.

Methyl 6-(2-((6-(Benzyloxy)-1,2,3,4-tetrahydronaphthalen-2-yl)(hydroxy)methyl)oxazol-5-yl)picolinate (S50)

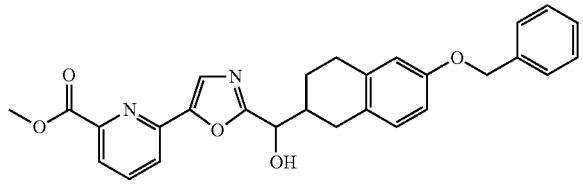 [SMILES: COC(=O)c1cccc(-c2cnc(C(O)C3CCc4cc(OCc5ccccc5)ccc4C3)o2)n1]

The title compound was prepared from methyl 6-(2-((6-(benzyloxy)-1,2,3,4-tetrahydronaphthalen-2-yl)(tert-butyldimethylsilyloxy)methyl)oxazol-5-yl)picolinate (S49, 160 mg, 0.28 mmol) following general procedure D. Flash chromatography (SiO$_2$, 50-100% EtOAc-hexanes) yielded the title compound (96.6 mg, 75%) as a yellow oil: $^1$H NMR (CDCl$_3$, 600 MHz) δ 8.03 (d, 1H, J=7.2 Hz), 7.88 (t, 1H, J=7.8 Hz), 7.78-7.76 (m, 3H), 7.41-7.35 (m, 2H), 7.36 (t, 1H, J=7.2 Hz), 7.30 (t, 1H, J=7.0 Hz), 6.98 (d, 0.5H, J=8.4 Hz), 6.90 (d, 0.5H, J=8.4 Hz), 6.74-6.69 (m, 2H), 5.00 (s, 2H), 4.85 (d, 0.5H, J=6.6 Hz), 4.79 (d, 0.5H, J=7.8 Hz), 4.01 (s, 3H), 3.74 (s, 1H), 2.86-2.73 (m, 4H), 2.42-2.39 (m, 1H), 1.87-1.85 (m, 1H), 1.64-1.57 (m, 1H); $^{13}$C NMR (CDCl$_3$, 150 MHz) δ 165.2, 156.8, 150.3, 148.1, 147.2, 137.9, 137.4, 137.2, 137.1, 130.0, 129.9, 128.4 (2C), 127.8, 127.7 (2C), 127.6, 127.3, 126.0, 124.0, 122.2, 114.39, 114.36, 112.84, 112.80, 71.4, 71.3, 69.9, 52.9, 39.95, 39.91, 30.7, 29.9, 29.06, 29.04, 25.3, 24.5; HRMS-ESI-TOF m/z 471.1922 ([M+H]$^+$, C$_{28}$H$_{26}$N$_2$O$_5$ requires 471.1914).

Methyl 6-(2-(6-(Benzyloxy)-1,2,3,4-tetrahydronaphthalene-2-carbonyl)oxazol-5-yl)picolinate (19)

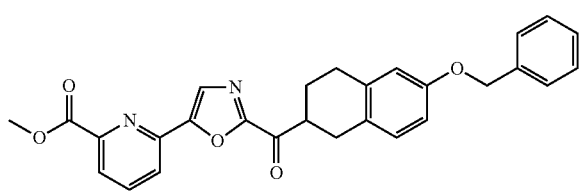 [SMILES: COC(=O)c1cccc(-c2cnc(C(=O)C3CCc4cc(OCc5ccccc5)ccc4C3)o2)n1]

The title compound was prepared from methyl 6-(2-((6-(benzyloxy)-1,2,3,4-tetrahydronaphthalen-2-yl)(hydroxy)methyl)oxazol-5-yl)picolinate (S50, 96.6 mg, 0.21 mmol) following general procedure E. Flash chromatography (SiO$_2$, 20% EtOAc-hexanes) yielded the title compound (26.5 mg, 48%) as a yellow oil: $^1$H NMR (CDCl$_3$, 600 MHz) δ 8.11 (dd, 1H, J=1.2, 9.0 Hz), 8.04 (s, 1H), 8.03 (dd, 1H, J=1.2, 9.0 Hz), 7.97 (t, 1H, J=7.8 Hz), 7.43 (d, 2H, J=7.8 Hz), 7.38 (t, 2H, J=7.8 Hz), 7.30 (t, 1H, J=7.0 Hz), 7.03 (d, 1H, J=8.4 Hz), 6.79 (dd, 1H, J=2.4, 8.4 Hz), 6.75-6.72 (m, 1H), 5.07 (s, 2H), 4.03 (s, 3H), 3.91-3.86 (m, 1H), 3.08-2.88 (m, 4H), 2.32-2.28 (m, 1H), 1.95-1.88 (m, 1H); $^{13}$C NMR (CDCl$_3$, 150 MHz) δ 190.6, 165.0, 157.0, 156.9, 152.4, 148.4, 146.5, 138.2, 137.1, 136.7, 129.8, 128.4 (2C), 127.9, 127.8 (2C), 127.3, 127.0, 125.1, 123.2, 114.4, 113.0, 69.9, 53.0, 43.6, 30.4, 28.9, 25.8; HRMS-ESI-TOF m/z 469.1760 ([M+H]$^+$, C$_{28}$H$_{24}$N$_2$O$_5$ requires 469.1758). The enantiomers were separated using a semipreparative chiral phase HPLC column (Daicel ChiraCel OD, 10 μm, 2×25 cm, 40% EtOH-hexanes, 7 mL/min, α=1.22).
(S)-19: [α]$^{23}$$_D$ −0.9 (c 1.2, THF).
(R)-19: [α]$^{23}$$_D$ +0.9 (c 1.2, THF).

6-(2-(6-(Benzyloxy)-1,2,3,4-tetrahydronaphthalene-2-carbonyl)oxazol-5-yl)picolinic acid (20)

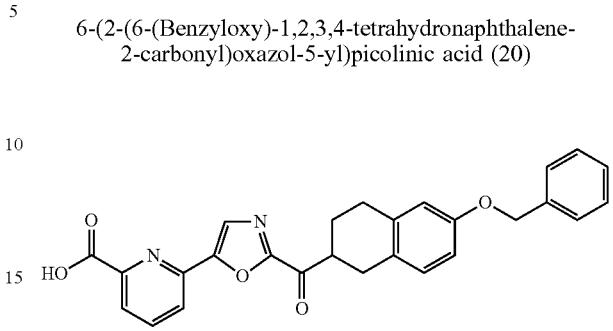

The title compound was prepared from methyl 6-(2-(6-(benzyloxy)-1,2,3,4-tetrahydronaphthalene-2-carbonyl)oxazol-5-yl)picolinate (19, 5 mg, 0.010 mmol) following general procedure G. Each pure enantiomer of the methyl esters were converted to their corresponding carboxylic acid using general procedure G. Flash chromatography (SiO$_2$, 5% MeOH—CH$_2$Cl$_2$) yielded the title compound (4 mg, 75%) as a white solid: $^1$H NMR (CDCl$_3$+0.1% TFA, 600 MHz) δ 10.05 (s, 1H), 8.32 (q, 1H, J=3.0 Hz), 8.16 (d, 3H, J=4.2 Hz), 7.42 (d, 2H, J=9.0 Hz), 7.39 (t, 2H, J=7.8 Hz), 7.33 (t, 1H, J=7.8 Hz), 7.06 (d, 1H, J=8.4 Hz), 6.82 (dd, 1H, J=2.4, 8.4 Hz), 6.78-6.75 (m, 1H), 5.08 (s, 2H), 3.85-3.80 (m, 1H), 3.09-2.92 (m, 4H), 2.33-2.30 (m, 1H), 1.97-1.91 (m, 1H); $^{13}$C NMR (CDCl$_3$+0.1% TFA, 150 MHz) δ 190.7, 166.0, 156.87, 156.80, 151.5, 146.0, 145.1, 140.1, 136.71, 136.54, 129.9, 128.6 (2C), 128.0, 127.7, 127.6 (2C), 126.8, 125.2, 124.9, 114.8, 113.3, 70.5, 44.0, 30.2, 28.7, 25.9; HRMS-ESI-TOF m/z 455.1604 ([M+H]$^+$, C$_{27}$H$_{22}$N$_2$O$_5$ requires 455.1601).
(S)-20: [α]$^{23}$$_D$ +4.2 (c 0.5, THF).
(R)-20: [α]$^{23}$$_D$ −4.8 (c 0.5, THF).

2-((6-(Benzyloxy)-1,2,3,4-tetrahydronaphthalen-2-yl)(tert-butyldimethylsilyloxy)methyl)-5-iodooxazole (S51)

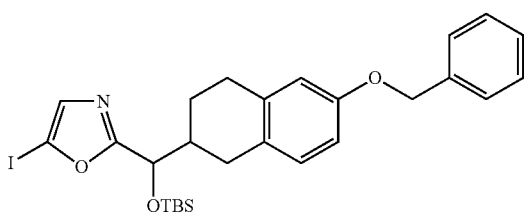 [SMILES: CC(C)(C)[Si](C)(C)OC(c1ncc(I)o1)C1CCc2cc(OCc3ccccc3)ccc2C1]

A solution of 2-((6-(benzyloxy)-1,2,3,4-tetrahydronaphthalen-2-yl)(tert-butyldimethylsilyloxy)methyl)oxazole (S40, 100 mg, 0.22 mmol) in THF (4 mL) was cooled to −78° C. before it was treated with 2.16 M n-BuLi (0.10 mL, 0.24 mmol) dropwise. The reaction mixture was stirred at −78° C. for 2 h, and treated with a solution of iodine (72 mg, 0.28 mmol) in THF (2 mL) and stirred for 5 min. The solution was warmed to room temperature and diluted with EtOAc, and washed with saturated aqueous NaCl. The organic layer was dried over MgSO$_4$ and the solvent was removed under reduced pressure. Flash chromatography (SiO$_2$, 5% EtOAc-hexanes) yielded the title compound (94.9 mg, 83%) as a yellow oil: $^1$H NMR (CDCl$_3$, 600 MHz) δ

7.43 (d, 2H, J=7.2 Hz), 7.39 (t, 2H, J=7.8 Hz), 7.30 (t, 1H, J=7.2 Hz), 7.12 (d, 1H, J=4.2 Hz), 7.02 (d, 0.5H, J=8.4 Hz), 6.95 (d, 0.5H, J=8.4 Hz), 6.78-6.71 (m, 2H), 5.04 (s, 2H), 4.73 (d, 0.5H, J=6.6 Hz), 4.66 (d, 0.5H, J=7.8 Hz), 2.91-2.78 (m, 2H), 2.70-2.66 (m, 1H), 2.50-2.48 (m, 1H), 2.34-2.29 (m, 1H), 2.22-2.20 (m, 0.5H), 1.75-1.73 (m, 0.5H), 1.52-1.47 (m, 1H), 0.91 (s, 9H), 0.09 (s, 1.5H), 0.05 (s, 1.5H), −0.05 (s, 1.5H), −0.06 (s, 1.5H); $^{13}$C NMR (CDCl$_3$, 150 MHz) δ 169.3, 169.2, 156.79, 156.75, 137.5, 137.3, 137.23, 137.21, 135.3, 135.2, 130.1, 129.9, 128.4 (2C), 128.0, 127.77 (2C), 127.73, 127.37, 127.36, 114.4, 114.3, 112.8, 112.7, 86.6, 86.4, 72.4, 72.3, 69.9, 40.4, 30.5, 30.3, 29.1, 28.9, 25.6 (3C), 25.3, 24.9, 18.4, −5.1, −5.2, −5.3.

(6-(Benzyloxy)-1,2,3,4-tetrahydronaphthalen-2-yl) (5-iodooxazol-2-yl)methanol (S52)

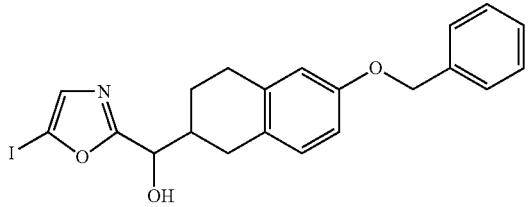 [SMILES: OC(c1ncc(I)o1)C1CCc2cc(OCc3ccccc3)ccc2C1]

The title compound was prepared from 2-((6-(benzyloxy)-1,2,3,4-tetrahydronaphthalen-2-yl)(tert-butyldimethylsilyloxy)methyl)-5-iodooxazole (S51, 94.9 mg, 0.16 mmol) following general procedure D. Flash chromatography (SiO$_2$, 50% EtOAc-hexanes) yielded the title compound (70 mg, 92%) as a white solid: $^1$H NMR (CDCl$_3$, 600 MHz) δ 7.42 (d, 2H, J=7.2 Hz), 7.37 (t, 2H, J=7.8 Hz), 7.31 (t, 1H, J=7.2 Hz), 7.25 (s, 1H), 7.12 (s, 1H), 6.98 (d, 0.5H, J=8.4 Hz), 6.94 (d, 0.5H, J=8.4 Hz), 6.76-6.70 (m, 2H), 5.02 (s, 2H), 4.76 (t, 0.5H, J=6.6 Hz), 4.71 (t, 0.5H, J=7.8 Hz), 2.84-2.70 (m, 2H), 2.33-2.30 (m, 1H), 2.17-2.04 (m, 1H), 1.84-1.82 (m, 1H), 1.62-1.53 (m, 2H); $^{13}$C NMR (CDCl$_3$, 150 MHz) δ 156.8, 137.4, 137.28, 137.21, 135.32, 135.30, 130.1, 130.0, 128.5 (2C), 127.8, 127.7, 127.6, 127.4 (2C), 114.4, 112.92, 112.90, 71.4, 71.3, 69.9, 39.9, 39.8, 30.6, 29.7, 29.0, 25.2, 24.3; HRMS-ESI-TOF m/z 462.0565 ([M+H]$^+$, C$_{21}$H$_{20}$INO$_3$ requires 462.0561).

(6-(Benzyloxy)-1,2,3,4-tetrahydronaphthalen-2-yl) (5-iodooxazol-2-yl)methanone (21)

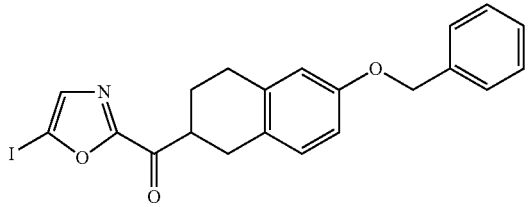 [SMILES: O=C(c1ncc(I)o1)C1CCc2cc(OCc3ccccc3)ccc2C1]

The title compound was prepared from (6-(benzyloxy)-1,2,3,4-tetrahydronaphthalen-2-yl)(5-iodooxazol-2-yl) methanol (S52, 62 mg, 0.13 mmol) following general procedure E. Flash chromatography (SiO$_2$, 20% EtOAc-hexanes) yielded the title compound (51.9 mg, 84%) as a white solid: $^1$H NMR (CDCl$_3$, 600 MHz) δ 7.42 (d, 2H, J=7.2 Hz), 7.39 (t, 2H, J=7.8 Hz), 7.37 (s, 1H), 7.31 (t, 2H, J=7.2 Hz), 7.02 (d, 1H, J=8.4 Hz), 6.79-6.74 (m, 2H), 5.04 (s, 2H), 3.79-3.75 (m, 1H), 3.01-2.90 (m, 3H), 2.25-2.22 (m, 1H), 1.90-1.87 (m, 1H); $^{13}$C NMR (CDCl$_3$, 150 MHz) δ 189.2, 162.0, 157.0, 137.4, 137.1, 136.6, 129.8, 128.5 (2C), 127.8, 127.4, 127.0 (2C), 114.4, 113.0, 93.9, 69.9, 43.3, 30.4, 28.9, 25.7; HRMS-ESI-TOF m/z 460.0403 ([M+H]$^+$, C$_{21}$H$_{18}$INO$_3$ requires 460.0404). The enantiomers were separated using a semipreparative chiral phase HPLC column (Daicel ChiraCel OD, 10 μm, 2×25 cm, 1% EtOH-hexanes, 7 mL/min, α=1.13).

(S)-21: [α]$^{23}_D$ −6.7 (c 2.9, THF).
(R)-21: [α]$^{23}_D$ +5.8 (c 2.0, THF).

The structure and absolute stereochemistry of (S)-21 (CCDC 790167) was confirmed with a single-crystal X-ray structure determination conducted on a colorless needle grown from MeOH.

Methyl 6-Methoxy-1-oxo-indan-2-carboxylate (S53)

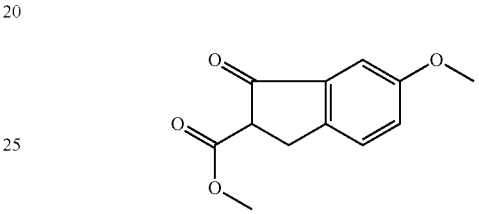

A solution of NaH (5.40 g, 122 mmol) in anhydrous THF (20 mL) was treated with dimethylcarbonate (6.6 mL, 81.3 mmol). The reaction mixture was cooled to 0° C. and a solution of 6-methoxyindanone (3.46 g, 21.33 mmol) in THF (10 mL) was added dropwise. The reaction mixture was warmed at reflux for 12 h before being quenched with the addition of HOAc (until pH=7) and diluted with EtOAc. The organic layer was washed with H$_2$O, saturated aqueous NaCl, and dried over Na$_2$SO$_4$. Evaporation in vacuo yielded the crude product that was purified by flash chromatography (SiO$_2$, 20-30% EtOAc-hexanes) to provide the title compound (3.14 g, 67%) as a purple solid: $^1$H NMR (CDCl$_3$, 500 MHz) δ 7.27 (d, 1H, J=8.5 Hz), 7.09 (dd, 1H, J=2.0, 8.5 Hz), 7.05 (d, 1H, J=2.5 Hz), 3.70 (s, 3H), 3.67 (s, 3H), 3.65-3.63 (m, 1H), 3.36-3.16 (m, 2H); $^{13}$C NMR (CDCl$_3$, 125 MHz) δ 199.0, 169.2, 159.3, 146.1, 136.0, 126.8, 124.4, 105.3, 55.2, 53.5, 52.3, 29.3.

Methyl 5-Methoxyindan-2-carboxylate (S54)

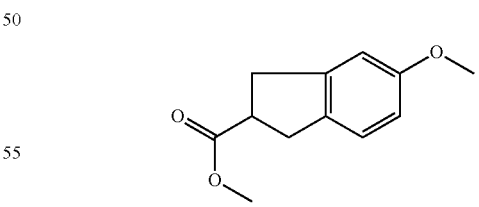

A sample of methyl 6-methoxy-1-oxo-indan-2-carboxylate (S53, 3.05 g, 13.87 mmol) was dissolved in acetic acid (60 mL), containing perchloric acid (0.5 mL) and 10% Pd/C (300 mg, 1.38 mmol). The mixture was flushed with H$_2$ and kept under an atmosphere of H$_2$ for 16 h. Upon completion, the reaction mixture was filtered through a pad of Celite and washed with EtOAc. The organic layer was washed with H$_2$O, saturated aqueous NaCl, and dried over Na$_2$SO$_4$. Evaporation in vacuo yielded the crude product that was purified by flash chromatography (SiO$_2$, 10% EtOAc-hexanes) to provide the title compound (921 mg, 32%) as a colorless oil: $^1$H NMR (CDCl$_3$, 500 MHz) δ 7.10 (d, 1H, J=8.5 Hz), 6.76 (s, 1H), 6.71 (dd, 1H, J=2.5, 8.0 Hz), 3.78 (s, 3H), 3.72 (s, 3H), 3.38-3.31 (m, 1H), 3.27-3.12 (m, 4H); $^{13}$C NMR (CDCl$_3$, 125 MHz) δ 175.6, 158.9, 143.0, 133.3, 124.7, 112.5, 109.6, 55.3, 51.8, 43.8, 36.2, 35.3.

5-Hydroxyindane-2-carboxylic Acid (S55)

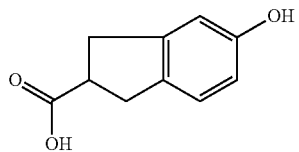 [SMILES: O=C(O)C1Cc2ccc(O)cc2C1]

A sample of methyl 5-methoxy-indan-2-carboxylate (S54, 667 mg, 3.03 mmol) was dissolved in acetic acid (5 mL) and aqueous 10% HBr (5 mL). The mixture was warmed at reflux under Ar for 2 h then cooled to room temperature and diluted with EtOAc. The organic layer was washed with H$_2$O, saturated aqueous NaCl, and dried over Na$_2$SO$_4$. Evaporation in vacuo yielded the crude product that was purified by flash chromatography (SiO$_2$, 50% EtOAc-hexanes) to provide the title compound (520 mg, 89%) as a white solid: $^1$H NMR (acetone-d, 600 MHz) δ 10.73 (brs, 1H), 8.04 (brs, 1H), 7.00 (d, 1H, J=8.5 Hz), 6.69 (s, 1H), 6.62 (dd, 1H, J=2.5, 8.0 Hz), 3.33-3.29 (m, 1H), 3.16-3.08 (m, 4H); $^{13}$C NMR (acetone-d$_6$, 150 MHz) δ 177.5, 158.3, 145.0, 134.0, 126.5, 115.4, 112.9, 45.2, 37.8, 36.9.

Methyl 5-Hydroxyindane-2-carboxylate (S56)

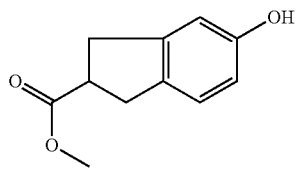

A sample of 5-hydroxyindane-2-carboxylic acid (S55, 270 mg, 1.51 mmol) was dissolved in MeOH (15 mL) and concentrated H$_2$SO$_4$ (3 mL). The mixture was warmed at reflux under Ar for 1 h then cooled to room temperature and diluted with EtOAc. The organic layer was washed with H$_2$O, saturated aqueous NaCl, and dried over Na$_2$SO$_4$. Evaporation in vacuo yielded the crude product that was purified by flash chromatography (SiO$_2$, 50% EtOAc-hexanes) to provide the title compound (120 mg, 41%) as a white solid: $^1$H NMR (acetone-d$_6$, 500 MHz) δ 8.04 (s, 1H), 6.99 (d, 1H, J=8.5 Hz), 6.69 (s, 1H), 6.62 (dd, 1H, J=2.5, 8.0 Hz), 3.65 (s, 3H), 3.32-3.29 (m, 1H), 3.11-3.05 (m, 4H); $^{13}$C NMR (acetone-d$_6$, 125 MHz) δ 176.9, 158.2, 144.8, 133.8, 126.4, 115.4, 112.9, 52.9, 45.3, 37.7, 36.8.

Methyl 5-(Trifluoromethanesulfonyloxy)indane-2-carboxylate (S57)

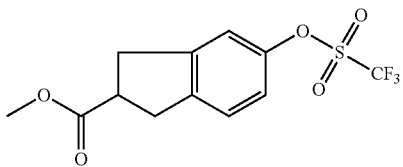 [SMILES: COC(=O)C1Cc2ccc(OS(=O)(=O)C(F)(F)F)cc2C1]

A sample of methyl 5-hydroxyindane-2-carboxylate (S56, 800 mg, 4.16 mmol) was dissolved in pyridine (15 mL) and the reaction mixture was cooled to 0° C. and triflic anhydride (1.1 mL, 6.24 mmol) was added slowly. The reaction mixture was warmed to room temperature and stirred for 3 h. The reaction mixture was diluted with CH$_2$Cl$_2$ and washed with saturated aqueous NaCl. The organic layer was dried over MgSO$_4$ and the solvent was removed under reduced pressure to give the title compound (1.34 g, 98%) as a white solid: $^1$H NMR (CDCl$_3$, 500 MHz) δ 7.19 (d, 1H, J=8.5 Hz), 7.07 (s, 1H), 7.00 (dd, 1H, J=2.0, 8.0 Hz), 3.67 (s, 3H), 3.83-3.31 (m, 1H), 3.27-3.13 (m, 4H); $^{13}$C NMR (CDCl$_3$, 125 MHz) δ 174.6, 148.4, 144.1, 141.9, 125.3, 119.3, 118.5 (q, CF$_3$, J=320 Hz), 117.1, 51.6, 43.3, 35.8, 35.3.

Methyl 5-Phenylindane-2-carboxylate (S58)

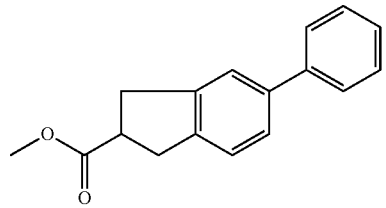 [SMILES: COC(=O)C1Cc2ccc(-c3ccccc3)cc2C1]

A sample of methyl 5-(trifluoromethylsulfonyloxyindane-2-carboxylate (S57, 1.34 g, 4.13 mmol), (Ph$_3$P)$_4$Pd (144 mg, 0.123 mmol), phenylboronic acid (604 mg, 4.95 mmol), and 2 M aqueous Na$_2$CO$_3$ (5 mL) were dissolved in anhydrous THF (20 mL) and the mixture was warmed at reflux for 16 h under Ar. The mixture was diluted with EtOAc, washed with saturated aqueous NH$_4$Cl, saturated aqueous NaCl, and dried over Na$_2$SO$_4$. Evaporation in vacuo yielded the crude coupling product. Flash chromatography (SiO$_2$, 10% EtOAc-hexanes) yielded the title compound (963 mg, 92%) as a colorless oil: $^1$H NMR (CDCl$_3$, 500 MHz) δ 7.68 (d, 2H, J=8.5 Hz), 7.54-7.51 (m, 4H), 7.44 (d, 1H, J=8.0 Hz), 7.36 (d, 1H, J=8.0 Hz), 3.83 (s, 3H), 3.49-3.40 (m, 3H), 3.37-3.15 (m, 2H); $^{13}$C NMR (CDCl$_3$, 125 MHz) δ 175.3, 142.0, 141.1, 140.4, 139.7, 128.5, 128.4, 126.8 (2C), 126.7, 125.5, 124.3, 122.8, 51.5, 43.3, 35.9, 35.6.

(5-Phenylindan-2-yl)methanol (S59)

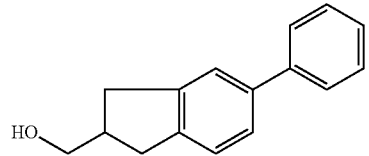 [SMILES: OCC1Cc2ccc(-c3ccccc3)cc2C1]

The title compound was prepared from methyl 5-phenylindane-2-carboxylate (S58, 963 mg, 3.81 mmol) following general procedure A. Flash chromatography (SiO$_2$, 50-100% EtOAc-hexanes) afforded the title compound (710 mg, 83%) as a white solid: $^1$H NMR (CDCl$_3$, 400 MHz) δ 7.72 (dd, 2H, J=1.6, 8.4 Hz), 7.57-7.43 (m, 5H), 7.38 (d, 1H, J=8.0 Hz), 3.77 (d, 2H, J=6.4 Hz), 3.27-3.19 (m, 3H), 2.95-2.85 (m, 3H); $^{13}$C NMR (CDCl$_3$, 100 MHz) δ 143.2, 141.7, 141.3, 139.3, 128.4 (2C), 126.8 (2C), 126.7, 125.2, 124.6, 123.1, 66.0, 41.4, 35.5, 35.2.

5-Phenylindane-2-carboxaldehyde (S60)

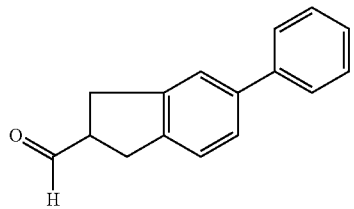 [SMILES: O=CC1Cc2ccc(-c3ccccc3)cc2C1]

The title compound was prepared from (5-phenylindan-2-yl)methanol (S59, 710 mg, 3.16 mmol) following general procedure B. Flash chromatography (SiO$_2$, 10% EtOAc-hexanes) afforded the title compound (404 mg, 57%) as a yellow oil: $^1$H NMR (CDCl$_3$, 600 MHz) δ 9.82 (s, 1H), 7.63 (d, 2H, J=8.4 Hz), 7.51-7.47 (m, 4H), 7.40 (t, 1H, J=7.2 Hz), 7.34 (d, 1H, J=7.8 Hz), 3.41-3.32 (m, 3H), 3.27-3.22 (m, 2H); $^{13}$C NMR (CDCl$_3$, 150 MHz) δ 202.5, 141.6, 141.0, 140.1, 139.9, 128.5 (2C), 126.94 (2C), 126.90, 125.7, 124.6, 123.1, 50.5, 32.6, 32.3.

Oxazol-2-yl(5-phenylindan-2-yl)methanol (S61)

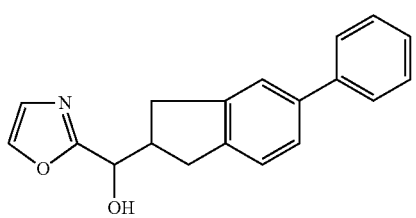 [SMILES: OC(c1ncco1)C1Cc2ccc(-c3ccccc3)cc2C1]

Oxazole (0.120 mL, 1.81 mmol) in anhydrous THF (7 mL) was treated with BH$_3$.THF (1 M, 1.9 mL, 1.97 mmol) and the solution was stirred at room temperature for 1 h before being cooled to –78° C. and treated with 2.41 M n-BuLi (0.80 mL, 1.97 mmol) dropwise. The reaction mixture was stirred at –78° C. for 40 min before a solution of 5-phenylindane-2-carboxaldehyde (S60, 404 mg, 1.81 mmol) in THF (2 mL) was added. The reaction mixture was stirred at –78° C. for 2 h before being warmed to room temperature. A 5% HOAc-EtOH solution (50 mL) was added and this mixture was stirred at room temperature for 12 h. The solvent was removed under reduced pressure and the residue was dissolved in EtOAc, washed with H$_2$O, saturated aqueous NaHCO$_3$, and saturated aqueous NaCl before the organic layer was dried over MgSO$_4$ and the solvent was removed under reduced pressure. Flash chromatography (SiO$_2$, 40% EtOAc-hexanes) afforded the title compound (310 mg, 58%) as colorless oil: $^1$H NMR (CDCl$_3$, 600 MHz) δ 7.63-7.60 (m, 3H), 7.49-7.36 (m, 5H), 7.34-7.28 (m, 1H), 7.10 (s, 1H), 5.08 (s, 1H), 4.88 (d, 1H, J=5.6 Hz), 3.26-3.18 (m, 4H), 3.07-2.85 (m, 1H); $^{13}$C NMR (CDCl$_3$, 150 MHz) δ 165.6, 142.9, 142.8, 141.4, 141.36, 141.32, 139.6, 139.5, 138.7, 128.5 (2C), 126.9 (2C), 126.8, 126.3, 125.4, 125.3, 124.6, 124.5, 123.1, 123.0, 70.08, 70.04, 44.2, 35.2, 35.0, 34.8, 34.7.

Oxazol-2-yl(5-phenylindan-2-yl)methanone (22)

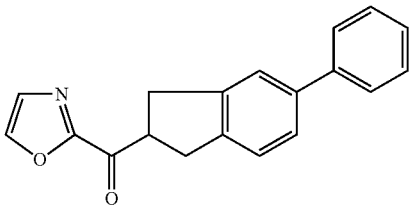 [SMILES: O=C(c1ncco1)C1Cc2ccc(-c3ccccc3)cc2C1]

The title compound was prepared from oxazol-2-yl(5-phenylindan-2-yl)methanol (S61, 20 mg, 0.068 mmol) following general procedure E. Flash chromatography (SiO$_2$, 20% EtOAc-hexanes) yielded the title compound (18 mg, 91%) as a white solid: $^1$H NMR (CDCl$_3$, 600 MHz) δ 7.86 (s, 1H), 7.56 (d, 2H, J=7.8 Hz), 7.45-7.41 (m, 4H), 7.39 (s, 1H), 7.34 (t, 1H, J=7.2 Hz), 7.29 (d, 1H, J=7.8 Hz), 4.48-4.42 (m, 1H), 3.47-3.40 (m, 4H); $^{13}$C NMR (CDCl$_3$, 150 MHz) δ 188.9, 157.7, 141.9, 141.6, 141.3, 140.3, 140.1, 129.1, 128.6 (2C), 127.1 (2C), 127.0, 125.9, 124.6, 123.1, 47.4, 35.5, 35.3: HRMS-ESI-TOF m/z 290.1179 ([M+H]$^+$, C$_{19}$H$_5$NO$_2$ requires 290.1175). The enantiomers were separated using a semipreparative chiral phase HPLC column (Daicel ChiraCel OD, 10 μm, 2×25 cm, 0.5% EtOH-hexanes, 7 mL/min, α=1.63).

(S)-22: [α]$^{23}_D$ –36 (c 0.1, THF).
(R)-22: [α]$^{23}_D$ +38 (c 0.1, THF).

2-((tert-Butyldimethylsllyloxy)(5-phenylindan-2-yl)methyl)oxazole (S62)

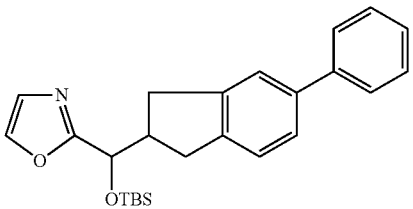 [SMILES: CC(C)(C)[Si](C)(C)OC(c1ncco1)C1Cc2ccc(-c3ccccc3)cc2C1]

A solution of oxazol-2-yl(5-phenylindan-2-yl)methanol (S61, 150 mg, 0.51 mmol), TBSCl (186 mg, 1.23 mmol) and imidazole (174 mg, 2.55 mmol) in DMF (2 mL) was stirred at room temperature for 16 h before it was diluted with EtOAc, washed with H$_2$O, and saturated aqueous NaCl. The organic layer was dried over MgSO$_4$ and the solvent was removed under reduced pressure. Flash chromatography (SiO$_2$, 10% EtOAc-hexanes) yielded the title compound (200 mg, 97%) as a thick colorless oil: $^1$H NMR (CDCl$_3$, 400 MHz) δ 7.67 (s, 1H), 7.64-7.60 (m, 3H), 7.50-7.32 (m, 6H), 7.15 (s, 1H), 4.89 (d, 1H, J=6.8 Hz), 3.26-3.13 (m, 2H), 2.99-2.82 (m, 2H), 0.95 (s, 9H), 0.16 (s, 3H), –0.02 (s, 3H); $^{13}$C NMR (CDCl$_3$, 100 MHz) δ 143.2, 142.9, 141.7, 141.5, 136.9, 139.5, 138.4, 128.5 (2C), 126.9, 126.8, 125.4, 125.3, 124.6, 124.5, 123.17, 123.13, 71.3, 45.3, 35.5, 35.2, 34.9, 34.6, 25.6 (3C), 18.0, −5.2, −5.3.

2-((tert-Butyldimethylsilyloxy)(5-phenylindan-2-yl)methyl)-5-(tributylstannyl)oxazole (S63)

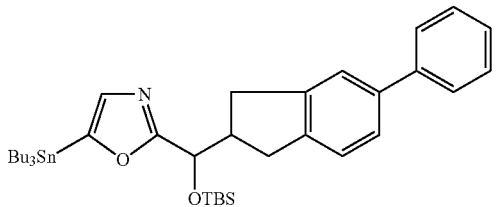

A solution of 2-((tert-butyldimethylsilyloxy)(5-phenylindan-2-yl)methyl)oxazole (S62, 100 mg, 0.24 mmol) in THF (3 mL) was cooled to −78° C. before it was treated with 2.16 M n-BuLi (0.150 mL, 0.27 mmol) dropwise. The reaction mixture was stirred at −78° C. for 2 h, and treated with a solution of Bu₃SnCl (0.140 mL, 0.48 mmol) and stirred for 5 min. The solution was warmed to room temperature and diluted with EtOAc and washed with saturated aqueous NaCl. The organic layer was dried over MgSO₄ and the solvent was removed under reduced pressure. Flash chromatography (SiO₂, 0-5% EtOAc-hexanes) yielded the title compound (300 mg, 65%) as a thick colorless oil: ¹H NMR (CDCl₃, 400 MHz) δ 7.58-7.54 (m, 2H), 7.43-7.27 (m, 7H), 7.12 (d, 1H, J=0.8 Hz), 4.87 (d, 1H, J=6.8 Hz), 3.14-3.08 (m, 3H), 2.89-2.78 (m, 2H), 1.70-1.56 (m, 10H), 1.42-1.25 (m, 13H), 0.96-0.88 (m, 12H), 0.85 (s, 9H), 0.07 (s, 3H), −0.11 (s, 3H); ¹³C NMR (CDCl₃, 100 MHz) δ 168.5, 154.8, 143.4, 143.1, 141.9, 141.7, 141.5, 139.5, 139.4, 137.1, 128.5 (2C), 126.9 (2C), 126.7, 125.3, 125.2, 124.56, 124.52, 123.1, 123.0, 71.4, 45.9, 35.5, 35.2, 35.0, 34.6, 28.8, 27.8 (3C), 27.7, 27.6, 27.3 (3C), 27.0, 26.7, 26.4, 25.5, 19.1 (3C), 19.0, 18.0, 17.4, 15.8, 15.7, 13.56 (3C), 13.50, 10.1, −5.3, −5.4.

2-((tert-Butyldimethylsilyloxy)(5-phenylindan-2-yl)methyl)-5-(pyridin-2-yl)oxazole (S64)

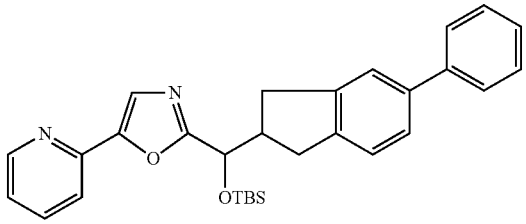 [SMILES: CC(C)(C)[Si](C)(C)OC(c1ncc(-c2ccccn2)o1)C1Cc2ccc(-c3ccccc3)cc2C1]

The title compound was prepared from 2-((tert-butyldimethylsilyloxy)(5-phenylindan-2-yl)methyl)-5-(tributylstannyl)oxazole (S63, 167 mg, 0.24 mmol) and 2-bromopyridine following general procedure C. Flash chromatography (SiO₂, 20% EtOAc-hexanes) yielded the title compound (26.1 mg, 22%) as a colorless oil: ¹H NMR (CDCl₃, 400 MHz) δ 8.64-8.62 (m, 1H), 7.79-7.73 (m, 1H), 7.68-7.65 (m, 2H), 7.56-7.51 (m, 2H), 7.44-7.25 (m, 7H), 4.87-4.86 (m, 1H), 3.19-3.13 (m, 3H), 2.96-2.85 (m, 2H), 0.96 (m, 9H), 0.10 (s, 3H), −0.05 (s, 3H); ¹³C NMR (CDCl₃, 100 MHz) δ 150.8, 149.8, 147.3, 141.7, 141.5, 136.8, 128.6 (2C), 127.0, 126.8 (2C), 125.5, 125.4, 125.1, 124.6, 123.2, 122.8, 119.0, 71.57, 71.54, 45.39, 45.36, 35.5, 35.1, 35.0, 34.8, 27.8, 26.8, 25.6 (3C), 18.1, 17.5, 13.5, −5.0, −5.2.

(5-Phenylindan-2-yl)(5-(pyridin-2-yl)oxazol-2-yl)methanol (S65)

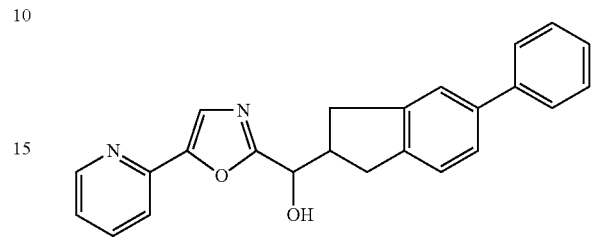

The title compound was prepared from 2-((tert-butyldimethylsilyloxy)(5-phenylindan-2-yl)methyl)-5-(pyridin-2-yl)oxazole (S64, 26.1 mg, 0.054 mmol) following general procedure D. Flash chromatography (SiO₂, 50-100% EtOAc-hexanes) yielded the title compound (20.9 mg, 98%) as a yellow oil: ¹H NMR (CDCl₃, 600 MHz) δ 8.62 (d, 1H, J=4.8 Hz), 7.75-7.72 (m, 1H), 7.64-7.61 (m, 2H), 7.53-7.51 (m, 2H), 7.42-7.23 (m, 7H), 4.92 (d, 1H, J=6.6 Hz), 3.22-3.16 (m, 3H), 3.08-2.95 (m, 2H); ¹³C NMR (CDCl₃, 150 MHz) δ 165.3, 151.0, 149.8, 146.9, 142.9, 142.8, 141.47, 141.45, 141.3, 139.77, 139.72, 136.9, 128.6 (2C), 127.0 (2C), 126.8, 125.59, 125.53, 124.9, 124.7, 124.6, 123.3, 123.2, 123.0, 119.3, 70.48, 70.45, 44.3, 35.2, 35.0, 34.8, 34.7.

(5-Phenylindan-2-yl)-(5-(pyridin-2-yl)oxazol-2-yl)methanone (23)

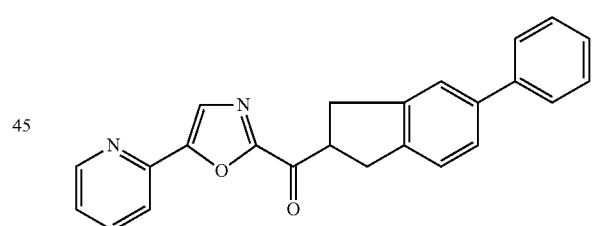

The title compound was prepared from (5-phenylindan-2-yl)(5-(pyridin-2-yl)oxazol-2-yl)methanol (S65, 20.9 mg, 0.056 mmol) following general procedure E. Flash chromatography (SiO₂, 20% EtOAc-hexanes) yielded the title compound (18 mg, 87%) as a white solid: ¹H NMR (CDCl₃, 600 MHz) δ 8.68 (d, 1H, J=4.2 Hz), 7.94 (s, 1H), 7.87 (d, 1H, J=7.8 Hz), 7.82 (t, 1H, J=7.8 Hz), 7.57 (d, 2H, J=7.8 Hz), 7.46-7.41 (m, 4H), 7.34-7.29 (m, 3H), 4.50 (q, 1H, J=7.8 Hz), 3.48-3.43 (m, 4H); ¹³C NMR (CDCl₃, 150 MHz) δ 188.9, 157.1, 153.4, 150.1, 146.2, 141.9, 141.3, 140.4, 140.1, 137.1, 128.6 (2C), 127.1 (3C), 127.0, 125.9, 124.6, 124.1, 123.1, 120.4, 47.4, 35.7, 35.4; HRMS-ESI-TOF m/z 367.1444 ([M+H]⁺, C₂₄H₁₈N₂O₂ requires 367.1441). The enantiomers were separated using a semipreparative chiral phase HPLC column (Daicel ChiraCel OD, 10 μm, 2×25 cm, 10% EtOH-hexanes, 7 mL/min, α=2.08).

(S)-23: [α]$^{23}_D$ −58 (c 0.2, THF).
(R)-23: [α]$^{23}_D$ +60 (c 0.3, THF).

Methyl 6-{2-[(tert-Butyldimethylsilyloxy)-(5-phenylindan-2-yl)methyl]oxazol-5-yl}-pyridine-2-carboxylate (S66)

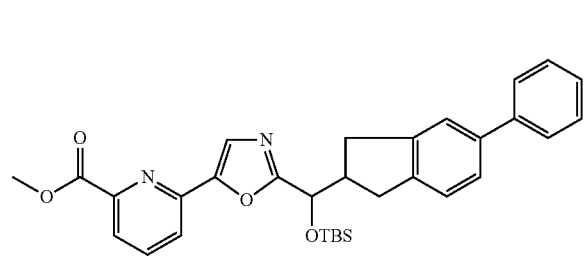 [SMILES: COC(=O)c1cccc(-c2cnc(C(O[Si](C)(C)C(C)(C)C)C3Cc4ccc(-c5ccccc5)cc4C3)o2)n1]

The title compound was prepared from 2-((tert-butyldimethylsilyloxy)(5-phenylindan-2-yl)methyl)-5-(tributylstannyl)oxazole (S63, 222 mg, 0.44 mmol) and methyl 6-bromopicolinate following general procedure C. Flash chromatography (SiO$_2$, 20% EtOAc-hexanes) yielded the title compound (216 mg, 90%) as a yellow solid: $^1$H NMR (CDCl$_3$, 600 MHz) δ 8.08-8.01 (m, 2H), 7.92-7.80 (m, 3H), 7.69-7.64 (m, 2H), 7.43-7.19 (m, 3H), 4.87-4.86 (m, 1H), 3.98 (s, 3H), 3.19-3.09 (m, 3H), 2.97-2.85 (m, 2H), 1.36-1.23 (m, 2H), 0.87 (m, 9H), 0.09 (s, 3H), −0.06 (s, 3H); $^{13}$C NMR (CDCl$_3$, 150 MHz) δ 165.2, 165.1, 164.3, 149.9, 148.5, 148.1, 147.5, 143.1, 142.9, 141.9, 141.5, 141.4, 141.3, 139.5, 139.1, 137.98, 137.96, 131.7, 128.55, 128.53, 126.99, 126.95, 126.8, 126.7, 126.35, 126.31, 125.4, 125.3, 124.64, 124.62, 123.9, 123.8, 123.18, 123.15, 121.9, 71.48, 71.44, 53.0, 52.8, 45.28, 45.23, 35.4, 35.0, 34.9, 34.7, 27.7, 26.7, 25.5 (3C), 18.0, 17.4, 13.5, −5.1, −5.2.

Methyl 6-{2-[Hydroxy-(5-phenylindan-2-yl)methyl]oxazol-5-yl}pyridine-2-carboxylate (S67)

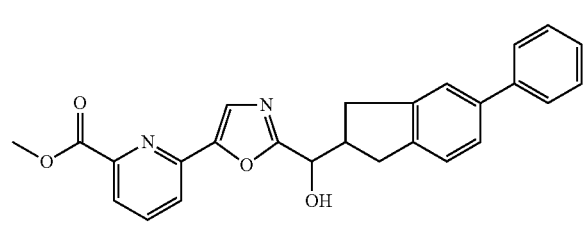 [SMILES: COC(=O)c1cccc(-c2cnc(C(O)C3Cc4ccc(-c5ccccc5)cc4C3)o2)n1]

The title compound was prepared from methyl 6-{2-[(tert-butyldimethylsilyloxy)-(5-phenylindan-2-yl)-methyl]-oxazol-5-yl}-pyridine-2-carboxylic (S66, 216 mg, 0.39 mmol) and methyl 6-bromopicolinate following general procedure C. Flash chromatography (SiO$_2$, 50-100% EtOAc-hexanes) yielded the title compound (108 mg, 64%) as a colorless oil: $^1$H NMR (CDCl$_3$, 600 MHz) δ 8.00 (d, 1H, J=7.8 Hz), 7.85-7.82 (td, 1H, J=2.4, 7.8 Hz), 7.76-7.75 (m, 2H), 7.52-7.50 (m, 2H), 7.40-7.18 (m, 6H), 4.92 (d, 1H, J=6.0 Hz), 4.66 (s, 1H, OH), 3.99 (s, 3H), 3.22-3.15 (m, 3H), 3.05-3.01 (m, 1H), 2.94-2.90 (m, 1H); $^{13}$C NMR (CDCl$_3$, 150 MHz) δ 171.3, 165.9, 165.1, 150.0, 147.9, 147.0, 142.9, 142.7, 141.4, 141.27, 141.23, 139.59, 139.53, 137.9, 128.5 (2C), 126.9 (2C), 126.8, 125.9, 126.8, 125.9, 125.48, 125.40, 127.7, 124.6, 124.0, 123.2, 123.1, 122.3, 70.3, 70.2, 44.1, 35.1, 35.0, 34.8, 34.7.

Methyl 6-[2-(5-Phenylindane-2-carbonyl)oxazol-5-yl]pyridine-2-carboxylate (24)

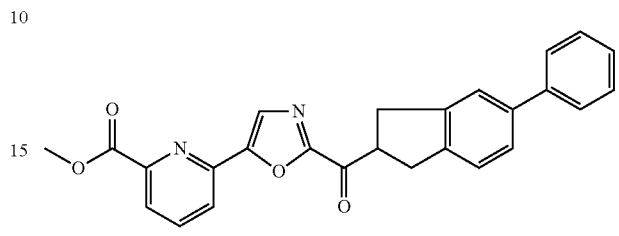

The title compound was prepared from methyl 6-{2-[hydroxy-(5-phenylindan-2-yl)methyl]oxazol-5-yl}-pyridine-2-carboxylic (S67, 107.6 mg, 0.25 mmol) following general procedure E. Flash chromatography (SiO$_2$, 30% EtOAc-hexanes) yielded the title compound (76.6 mg, 72%) as a white solid: $^1$H NMR (CDCl$_3$, 600 MHz) δ 8.13 (d, 1H, J=7.8 Hz), 8.08 (s, 1H), 8.03 (d, 1H, J=7.8 Hz), 7.97 (t, 1H, J=7.8 Hz), 7.57 (d, 2H, J=7.8 Hz), 7.45-7.41 (m, 4H), 7.34-7.29 (m, 2H), 4.50 (q, 1H, J=7.8 Hz), 4.04 (s, 3H), 3.47-3.43 (m, 4H); $^{13}$C NMR (CDCl$_3$, 150 MHz) δ 188.8, 165.0, 157.1, 152.3, 148.3, 146.4, 141.8, 141.2, 140.3, 140.0, 138.2, 128.6 (2C), 128.0, 127.0 (2C), 126.9, 125.8, 125.1, 124.6, 123.3, 123.1, 53.0, 47.3, 35.5, 35.3; HRMS-ESI-TOF m/z 425.1500 ([M+H]$^+$, C$_{26}$H$_{20}$N$_2$O$_4$ requires 425.1496). The enantiomers could not be separated using chiral phase HPLC.

6-[2-(5-Phenylindane-2-carbonyl)oxazol-5-yl]pyridine-2-carboxylic Acid (25)

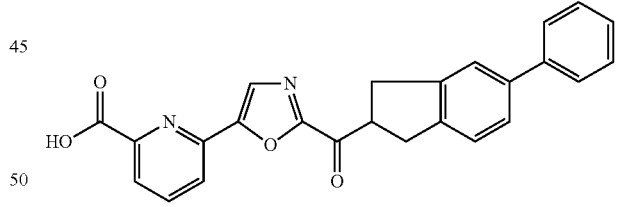

The title compound was prepared from methyl 6-[2-(5-phenylindane-2-carbonyl)oxazol-5-yl]pyridine-2-carboxylate (24, 5 mg, 0.011 mmol) following general procedure G. Flash chromatography (SiO$_2$, 5% HOAc-EtOAc) yielded the title compound (3.9 mg, 86%) as a yellow solid: $^1$H NMR (THF-d, 600 MHz) δ 8.13-8.08 (m, 4H), 7.58 (dd, 2H, J=1.2, 8.4 Hz), 7.48 (s, 1H), 7.42-7.36 (m, 3H), 7.33 (t, 1H, J=7.8 Hz), 7.14 (d, 1H, J=7.8 Hz), 6.88 (d, 1H, J=2.4 Hz), 6.84 (dd, 1H, J=2.4, 7.8 Hz), 7.28-7.26 (m, 2H), 4.51-4.45 (m, 1H), 3.42-3.38 (m, 4H); $^{13}$C NMR (THF-d$_8$, 150 MHz) δ 188.9, 165.6, 158.8, 153.7, 150.1, 147.2, 143.3, 142.5, 141.8, 141.0, 139.7, 129.5 (2C), 128.8, 127.8 (2C), 126.6, 125.5, 125.4, 123.8, 123.7, 48.6, 36.5, 36.2; HRMS-ESI-TOF m/z 411.1342 ([M+H]$^+$, C$_{25}$H$_{18}$N$_2$O$_4$ requires 411.1339).

Methyl 5-Phenoxylindane-2-carboxylate (S68)

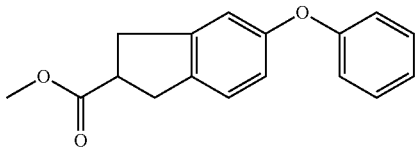 [SMILES: COC(=O)C1Cc2ccc(Oc3ccccc3)cc2C1]

A sample of methyl 5-hydroxyindane-2-carboxylate (S56, 400 mg, 2.08 mmol), phenylboronic acid (507 mg, 4.16 mmol), Cu(OAc)$_2$ (377 mg, 2.08 mmol), and 4 Å MS (400 mg) were placed in anhydrous CH$_2$Cl$_2$ (30 mL). The reaction mixture was stirred at room temperature for 15 min before Et$_3$N (0.584 mL, 4.16 mmol) was added dropwise. The reaction mixture was stirred at room temperature for 17 h under Ar. The mixture was diluted with EtOAc, washed with saturated aqueous NH$_4$Cl, saturated aqueous NaCl, and dried over Na$_2$SO$_4$. Evaporation in vacuo yielded the crude product that was purified by flash chromatography (SiO$_2$, 10% EtOAc-hexanes) to provide the title compound (263 mg, 47%) as a colorless oil: $^1$H NMR (CDCl$_3$, 600 MHz) δ 7.31 (t, 2H, J=7.8 Hz), 7.15 (d, 1H, J=7.2 Hz), 7.07 (t, 1H, J=7.2 Hz), 6.98 (d, 2H, J=8.4 Hz), 6.82 (dd, 2H, J=2.4, 8.4 Hz), 3.73 (s, 3H), 3.40-3.34 (m, 1H), 3.25-3.14 (m, 4H); $^{13}$C NMR (CDCl$_3$, 150 MHz) δ 175.5, 157.7, 156.1, 143.4, 136.4, 129.6 (2C), 125.1, 122.8, 118.5 (2C), 117.7, 115.1, 51.9, 43.8, 36.2, 35.5.

(5-Phenoxyindan-2-yl)methanol (S69)

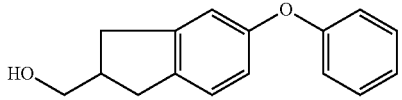 [SMILES: OCC1Cc2ccc(Oc3ccccc3)cc2C1]

The title compound was prepared from methyl 5-phenoxyindan-2-carboxylate (S68, 242 mg, 0.90 mmol) following general procedure A. Flash chromatography (SiO$_2$, 30% EtOAc-hexanes) afforded the title compound (214 mg, 97%) as a colorless oil: $^1$H NMR (CDCl$_3$, 500 MHz) δ 7.34 (t, 2H, J=7.8 Hz), 7.17 (d, 1H, J=7.2 Hz), 7.10 (t, 1H, J=7.2 Hz), 7.04 (d, 2H, J=8.4 Hz), 6.91 (s, 1H), 6.85 (dd, 1H, J=2.4, 8.4 Hz), 3.67 (d, 2H, J=6.5 Hz), 3.07-3.03 (m, 2H), 2.77-2.72 (m, 3H), 2.58 (s, 1H); $^{13}$C NMR (CDCl$_3$, 125 MHz) δ 157.7, 155.6, 144.4, 137.5, 129.4 (2C), 125.2, 122.6, 118.2 (2C), 117.2, 115.4, 66.1, 41.7, 35.7, 34.8.

5-Phenoxyindane-2-carboxaldehyde (S70)

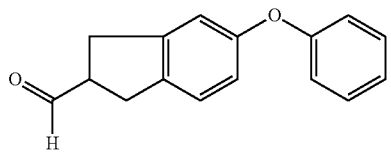 [SMILES: O=CC1Cc2ccc(Oc3ccccc3)cc2C1]

The title compound was prepared from (5-phenoxyindan-2-yl)methanol (S69, 214 mg, 0.89 mmol) following general procedure B. Flash chromatography (SiO$_2$, 30% EtOAc-hexanes) afforded the title compound (163 mg, 76%) as a colorless oil: $^1$H NMR (CDCl$_3$, 500 MHz) δ 9.77 (s, 1H), 7.34 (t, 2H, J=7.8 Hz), 7.18 (d, 1H, J=7.2 Hz), 7.09 (t, 1H, J=7.2 Hz), 7.00 (d, 2H, J=8.4 Hz), 6.90 (s, 1H), 6.86 (dd, 1H, J=2.4, 8.4 Hz), 3.32-3.26 (m, 3H), 3.19-3.12 (m, 2H); $^{13}$C NMR (CDCl$_3$, 125 MHz) δ 202.3, 157.5, 156.2, 142.9, 135.7, 129.5 (2C), 125.3, 122.8, 118.4 (2C), 117.7, 115.2, 50.8, 32.8, 32.0.

Oxazol-2-yl(5-phenoxyindan-2-yl)methanol (S71)

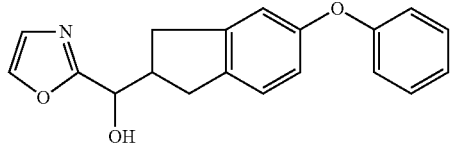 [SMILES: OC(c1ncco1)C1Cc2ccc(Oc3ccccc3)cc2C1]

Oxazole (0.027 mL, 0.41 mmol) in anhydrous THF (5 mL) was treated with BH$_3$.THF (1 M, 0.50 mL, 0.44 mmol) and the solution was stirred at room temperature for 1 h before being cooled to −78° C. and treated with 1.7 M t-BuLi (0.40 mL, 0.53 mmol) dropwise. The reaction mixture was stirred at −78° C. for 40 min before a solution of 5-phenoxyindane-2-carboxaldehyde (S70, 98 mg, 0.41 mmol) in THF (2 mL) was added. The reaction mixture was stirred at −78° C. for 2 h before being warmed to room temperature. A 5% HOAc-EtOH solution (50 mL) was added and this mixture was stirred at room temperature for 12 h. The solvent was removed under reduced pressure and the residue was dissolved in EtOAc, washed with H$_2$O, saturated aqueous NaHCO$_3$, and saturated aqueous NaCl before the organic layer was dried over MgSO$_4$ and the solvent was removed under reduced pressure. Flash chromatography (SiO$_2$, 50% EtOAc-hexanes) afforded the title compound (60.4 mg, 47%) as colorless oil: $^1$H NMR (CDCl$_3$, 500 MHz) δ 7.61 (d, 1H, J=2.5 Hz), 7.32 (t, 2H, J=7.8 Hz), 7.14-7.04 (m, 3H), 6.98-6.96 (m, 2H), 6.85-6.75 (m, 2H), 4.80 (d, 1H, J=7.0 Hz), 3.48 (brs, 1H, OH), 3.12-3.02 (m, 3H), 2.95-2.75 (m, 2H); $^{13}$C NMR (CDCl$_3$, 125 MHz) δ 157.7, 155.8, 144.1, 144.0, 138.9, 137.2, 137.1, 129.5 (2C), 126.6, 125.2, 125.1, 122.7, 118.3, 117.5, 117.4, 115.4, 115.3, 70.1, 44.6, 35.1, 34.3.

Oxazol-2-yl(5-phenoxyindan-2-yl)methanone (26)

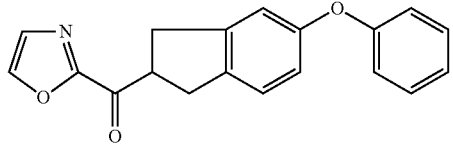 [SMILES: O=C(c1ncco1)C1Cc2ccc(Oc3ccccc3)cc2C1]

The title compound was prepared from oxazol-2-yl(5-phenoxyindan-2-yl)methanol (S71, 5 mg, 0.016 mmol) following general procedure E. Flash chromatography (SiO$_2$, 20% EtOAc-hexanes) yielded the title compound (4.7 mg, 96%) as a white solid: $^1$H NMR (CDCl$_3$, 600 MHz) δ 7.85 (s, 1H), 7.37 (s, 1H), 7.32 (t, 2H, J=7.0 Hz), 7.16 (d, 1H, J=7.2 Hz), 7.07 (t, 1H, J=7.1 Hz), 6.98 (d, 2H, J=7.0 Hz), 6.87-6.83 (m, 2H), 4.45-4.39 (m, 1H), 3.38-3.28 (m, 4H); $^{13}$C NMR (CDCl$_3$, 150 MHz) δ 188.7, 157.77, 157.71, 156.2, 143.1, 141.6, 136.0, 129.6 (2C), 129.1, 125.2, 122.8, 118.5 (2C), 117.8, 115.2, 47.7, 35.5, 35.0; HRMS-ESI-TOF m/z 306.1120 ([M+H]⁺, $C_{19}H_{15}NO_3$ requires 306.1125). The enantiomers were separated using a semipreparative chiral phase HPLC column (Daicel ChiraCel OD, 10 μm, 2×25 cm, 1% EtOH-hexanes, 7 mL/min, α=1.1).

(S)-26: $[\alpha]^{23}_D$ −12 (c 0.1, THF).
(R)-26: $[\alpha]^{23}_D$ +13 (c 0.1, THF).

2-((tert-Butyldimethylsilyloxy)(5-phenoxyindan-2-yl)methyl)oxazole (S72)

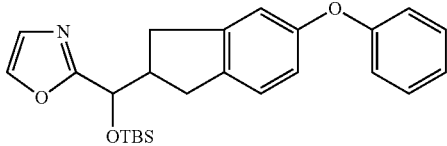 [SMILES: CC(C)(C)[Si](C)(C)OC(c1ncco1)C1Cc2ccc(Oc3ccccc3)cc2C1]

A solution of oxazol-2-yl(5-phenoxyindan-2-yl)methanol (S71, 60.4 mg, 0.19 mmol), TBSCl (72 mg, 0.47 mmol) and imidazole (54 mg, 0.78 mmol) in DMF (4 mL) was stirred at room temperature for 16 h before it was diluted with EtOAc, washed with $H_2O$, and saturated aqueous NaCl. The organic layer was dried over $MgSO_4$ and the solvent was removed under reduced pressure. Flash chromatography ($SiO_2$, 10% EtOAc-hexanes) yielded the title compound (38.2 mg, 47%) as a thick colorless oil: ¹H NMR (CDCl₃, 500 MHz) δ 7.62 (d, 1H, J=2.5 Hz), 7.30 (t, 2H, J=7.8 Hz), 7.14-7.04 (m, 2H), 6.98-6.96 (m, 2H), 6.85-6.78 (m, 2H), 4.80 (d, 1H, J=7.0 Hz), 4.79-4.77 (m, 2H), 3.09-2.98 (m, 3H), 2.82-2.74 (m, 3H), 0.90 (s, 4.5H), 0.85 (s, 4.5H), 0.07 (s, 1.5H), 0.05 (s, 1.5H), −0.112 (s, 1.5H), −0.116 (s, 1.5H); ¹³C NMR (CDCl₃, 125 MHz) δ 157.9, 157.8, 155.8, 155.7, 144.4, 144.2, 138.5, 137.5, 137.3, 129.5 (2C), 126.8, 125.1, 122.6, 118.4, 118.3, 117.4, 115.4, 115.3, 71.4, 45.6, 35.7, 35.1, 34.8, 34.3, 25.6 (3C), 18.1, −5.2, −5.3.

2-(tert-Butyldimethylsilyloxy)(5-phenoxyindan-2-yl)methyl)-5-(tributylstannyl)oxazole (S73)

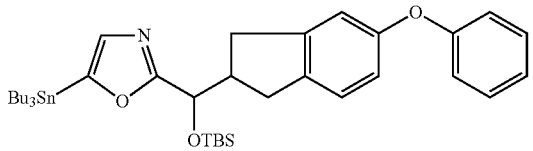

A solution of 2-((tert-butyldimethylsilyloxy)(5-phenoxyindan-2-yl)methyl)oxazole (S72, 38.2 mg, 0.09 mmol) in THF (3 mL) was cooled to −78° C. before it was treated with 2.35 M n-BuLi (0.045 mL, 0.09 mmol) dropwise. The reaction mixture was stirred at −78° C. for 2 h, and treated with a solution of $Bu_3SnCl$ (0.05 mL, 0.18 mmol) and stirred for 5 min. The solution was warmed to room temperature and diluted with EtOAc, and washed with saturated aqueous NaCl. The organic layer was dried over $MgSO_4$ and the solvent was removed under reduced pressure. Flash chromatography ($SiO_2$, 0-5% EtOAc-hexanes) yielded the title compound (21.8 mg, 34%) as a thick colorless oil: ¹H NMR (CDCl₃, 600 MHz) δ 7.42 (t, 2H, J=7.8 Hz), 7.39-7.30 (m, 3H), 7.09-7.00 (m, 2H), 6.84-6.73 (m, 2H), 5.02 (d, 2H, J=7.0 Hz), 4.80 (d, 1H, J=7.2 Hz), 3.06-2.95 (m, 3H), 2.75-2.64 (m, 2H), 1.57-1.53 (m, 6H), 1.35-1.30 (m, 7H), 1.13-1.08 (m, 6H), 0.89 (t, 6H, J=7.0 Hz), 0.84 (s, 9H), 0.03 (s, 3H), 0.05 (s, 1.5H), −0.15 (s, 1.5H); ¹³C NMR (CDCl₃, 150 MHz) δ 168.6, 157.86, 157.80, 154.9, 144.3, 144.0, 137.33, 137.32, 137.1, 135.1, 134.8, 128.5 (2C), 127.7, 127.3 (2C), 124.88, 124.85, 113.03, 113.02, 110.9, 71.55, 71.51, 70.1, 45.84, 45.81, 35.9, 35.2, 34.8, 34.1, 28.8 (3C), 27.2 (3C), 25.6 (3C), 18.1 (3C), 13.6, 10.1 (3C), −5.2, −5.3.

2-((tert-Butyldimethylsilyloxy)(5-phenoxyindan-2-yl)methyl)-5-(pyridin-2-yl)oxazole (S74)

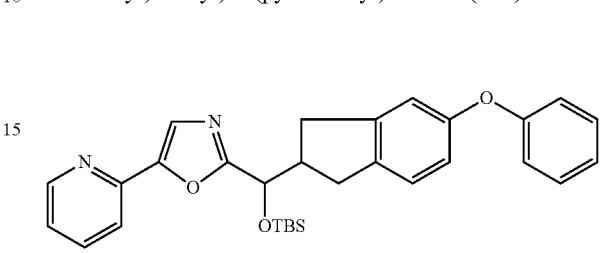

The title compound was prepared from 2-((tert-butyldimethylsilyloxy)(5-phenoxyindan-2-yl)methyl)-5-(tributylstannyl)oxazole (S73, 740 mg, 1.04 mmol) and 2-bromopyridine following general procedure C. Flash chromatography ($SiO_2$, 20% EtOAc-hexanes) yielded the title compound (153 mg, 30%) as a colorless oil: ¹H NMR (CDCl₃, 500 MHz) δ 8.62 (d, 1H, J=4.5 Hz), 7.76 (t, 1H, J=7.8 Hz), 7.66-7.64 (m, 2H), 7.31-7.21 (m, 4H), 7.15-7.03 (m, 2H), 6.97-6.95 (m, 1H), 6.90-6.82 (m, 1H), 4.84 (dd, 1H, J=2.5, 7.5 Hz), 3.17-3.04 (m, 2H), 2.91-2.79 (m, 4H), 0.89 (s, 9H), 0.10 (s, 1.5H), 0.09 (s, 1.5H), −0.04 (s, 1.5H), −0.05 (s, 1.5H); ¹³C NMR (CDCl₃, 125 MHz) δ 164.7, 157.8, 155.7, 150.8, 149.8, 147.3, 144.3, 137.3, 136.8, 129.5 (2C), 125.18, 125.13, 122.8, 122.69, 122.65, 119.0 (2C), 118.38, 118.30, 117.4, 117.3, 115.4, 115.3, 71.4, 45.5, 35.5, 35.1, 34.7, 34.3, 26.7, 25.6 (3C), 18.1, 13.5, −5.0, −5.2.

(5-Phenoxyindan-2-yl)(5-(pyridin-2-yl)oxazol-2-yl)methanol (S75)

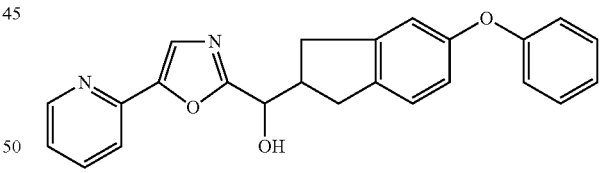

The title compound was prepared from 2-((tert-butyldimethylsilyloxy)(5-phenoxyindan-2-yl)methyl)-5-(pyridin-2-yl)oxazole (S74, 153 mg, 0.30 mmol) following general procedure D. Flash chromatography ($SiO_2$, 50% EtOAc-hexanes) yielded the title compound (109 mg, 95%) as a yellow oil: ¹H NMR (CDCl₃, 500 MHz) δ 8.58 (d, 1H, J=4.5 Hz), 7.79 (t, 1H, J=7.8 Hz), 7.29-7.26 (m, 2H), 7.21-7.18 (m, 4H), 7.12-7.02 (m, 2H), 6.95-6.91 (m, 2H), 6.88-6.82 (m, 1H), 4.90 (dd, 1H, J=2.5, 7.5 Hz), 4.64 (brs, 1H, OH), 3.21-3.09 (m, 3H), 2.98-2.83 (m, 2H); ¹³C NMR (CDCl₃, 125 MHz) δ 165.5, 157.7, 155.8, 155.7, 150.8, 149.7, 146.8, 144.1, 143.9, 137.2, 137.0, 136.8, 129.5 (2C), 125.2, 125.1, 124.8, 122.9, 122.6, 119.2, 118.2 (2C), 117.45, 117.40, 115.4, 115.3, 70.2, 44.55, 44.52, 35.2, 34.4.

(5-Phenoxyindan-2-yl)(5-(pyridin-2-yl)oxazol-2-yl)methanone (27)

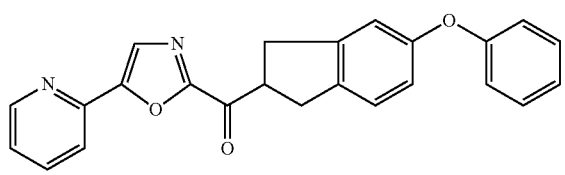 [SMILES: O=C(c1ncc(-c2ccccn2)o1)C1Cc2ccc(Oc3ccccc3)cc2C1]

The title compound was prepared from (5-phenoxyindan-2-yl)(5-(pyridin-2-yl)oxazol-2-yl)methanol (S75, 109.3 mg, 0.28 mmol) following general procedure E. Flash chromatography (SiO$_2$, 20% EtOAc-hexanes) yielded the title compound (77 mg, 72%) as a yellow oil: $^1$H NMR (CDCl$_3$, 600 MHz) δ 8.67 (d, 1H, J=4.5 Hz), 7.92 (s, 1H), 7.86 (d, 1H, J=7.8 Hz), 7.80 (t, 1H, J=7.8 Hz), 7.33-7.30 (m, 3H), 7.16 (d, 1H, J=8.4 Hz), 7.07 (t, 1H, J=7.2 Hz), 6.98 (d, 2H, J=7.8 Hz), 6.87-6.83 (m, 2H), 4.50-4.45 (m, 1H), 3.41-3.30 (m, 4H); $^{13}$C NMR (CDCl$_3$, 150 MHz) δ 188.7, 157.5, 156.9, 156.1, 153.3, 150.0, 146.0, 143.0, 137.1, 136.0, 129.5 (2C), 126.9, 125.1, 124.1, 122.8, 120.3, 118.3 (2C), 117.7, 115.1, 47.5, 35.5, 35.0; HRMS-ESI-TOF m/z 383.1395 ([M+H]$^+$, C$_{24}$H$_{18}$N$_2$O$_3$ requires 383.1390). The enantiomers were separated using a semipreparative chiral phase HPLC column (Daicel ChiraCel OD, 10 μm, 2×25 cm, 10% EtOH-hexanes, 7 mL/min, α=1.21).

(S)-27: [α]$^{23}_D$ +78 (c 0.1, THF).

(R)-27: [α]$^{23}_D$ −68 (c 0.1, THF).

Methyl 6-(2-((tert-Butyldimethylsilyloxy)(5-phenoxyindan-2-yl)methyl)oxazol-5-yl)picolinate (S76)

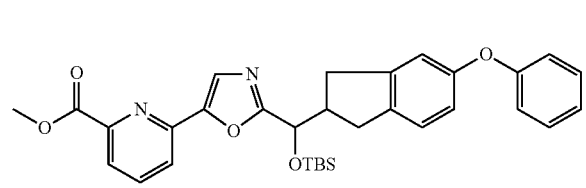 [SMILES: COC(=O)c1cccc(-c2cnc(C(O[Si](C)(C)C(C)(C)C)C3Cc4ccc(Oc5ccccc5)cc4C3)o2)n1]

The title compound was prepared from 2-((tert-butyldimethylsilyloxy)(5-phenoxyindan-2-yl)methyl)-5-(tributylstannyl)oxazole (S73, 21.8 mg, 0.03 mmol) and methyl 6-bromopicolinate following general procedure C. Flash chromatography (SiO$_2$, 20% EtOAc-hexanes) yielded the title compound (12.8 mg, 76%) as a colorless oil: $^1$H NMR (CDCl$_3$, 600 MHz) δ 8.03 (d, 1H, J=4.5 Hz), 7.92 (t, 1H, J=7.8 Hz), 7.82-7.79 (m, 2H), 7.42-7.35 (m, 4H), 7.32-7.30 (m, 1H), 7.09 (d, 0.5H, J=6.5 Hz), 7.02 (d, 0.5H, J=6.5 Hz), 6.84-6.72 (m, 2H), 5.02 (d, 1H, J=5.5 Hz), 4.81 (d, 1H, J=5.5 Hz), 4.02 (s, 3H), 3.17-2.97 (m, 2H), 2.86-2.70 (m, 2H), 0.87 (s, 9H), 0.08 (s, 3H), −0.07 (s, 3H); $^{13}$C NMR (CDCl$_3$, 150 MHz) δ 165.39, 165.31, 165.2, 157.9, 157.8, 149.9, 148.2, 147.6, 143.9, 143.7, 138.0, 137.27, 137.25, 134.7, 134.5, 132.1, 132.0, 128.5 (2C), 128.4, 127.8 (2C), 127.3, 126.4, 124.9, 123.9, 122.0, 113.2, 113.1, 110.99, 110.96, 71.57, 71.55, 70.1, 52.9, 45.64, 45.62, 35.7, 35.2, 34.7, 34.1, 29.6, 25.6 (3C), 18.1, −5.0, −5.2.

Methyl 6-(2-(Hydroxy(5-phenoxyindan-2-yl)methyl)oxazol-5-yl)picolinate (S77)

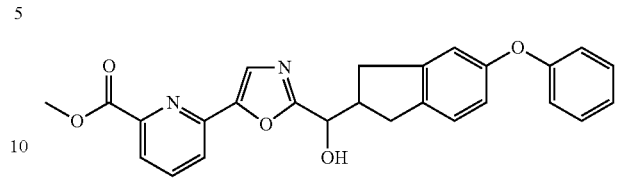

The title compound was prepared from methyl 6-(2-((tert-butyldimethylsilyloxy)(5-phenoxyindan-2-yl)methyl)oxazol-5-yl)picolinate (S76, 12.8 mg, 0.02 mmol) following general procedure D. Flash chromatography (SiO$_2$, 50% EtOAc-hexanes) yielded the title compound (7.4 mg, 76%) as a colorless oil: $^1$H NMR (CDCl$_3$, 600 MHz) δ 8.05 (d, 1H, J=4.5 Hz), 7.91 (t, 1H, J=7.8 Hz), 7.79-7.77 (m, 2H), 7.41-7.40 (m, 2H), 7.38-7.35 (m, 2H), 7.32-7.30 (m, 1H), 7.08 (d, 0.5H, J=6.5 Hz), 7.05 (d, 0.5H, J=6.5 Hz), 6.84-6.73 (m, 2H), 5.00 (s, 1H), 4.88 (d, 1H, J=5.5 Hz), 4.02 (s, 3H), 3.16-2.94 (m, 5H); $^{13}$C NMR (CDCl$_3$, 150 MHz) δ 165.6, 165.3, 158.0, 157.9, 150.3, 148.2, 147.3, 143.6, 143.5, 137.9, 137.2, 134.4, 134.3, 128.5 (2C), 127.8, 127.3 (2C), 126.2, 125.0, 124.9, 124.1, 122.3, 113.38, 113.31, 111.0, 110.9, 70.6, 70.1, 53.0, 44.6, 35.4, 35.1, 34.3, 34.0.

Methyl 6-(2-(5-Phenoxyidane-2-carbonyl)picolinate (28)

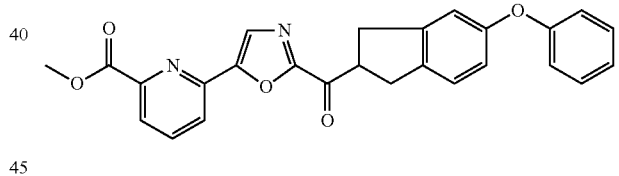

The title compound was prepared from methyl 6-(2-(hydroxy(5-phenoxyindan-2-yl)methyl)oxazol-5-yl)picolinate (S77, 119 mg, 0.26 mmol) following general procedure E. Flash chromatography (SiO$_2$, 20% EtOAc-hexanes) yielded the title compound (80 mg, 69%) as a colorless oil: $^1$H NMR (CDCl$_3$, 600 MHz) δ 8.11 (d, 1H, J=4.5 Hz), 8.06 (s, 1H), 8.04 (d, 2H, J=7.8 Hz), 7.97 (t, 1H, J=4.5 Hz), 7.32 (t, 1H, J=7.8 Hz), 7.17 (d, 1H, J=7.8 Hz), 7.07 (t, 1H, J=4.5 Hz), 6.98 (d, 2H, J=4.5 Hz), 6.88-6.84 (m, 2H), 4.51-4.45 (m, 1H), 3.04 (s, 3H), 3.41-3.31 (m, 4H); $^{13}$C NMR (CDCl$_3$, 150 MHz) 188.8, 165.0, 157.6, 157.2, 156.3, 152.4, 148.5, 146.5, 143.0, 138.3, 136.0, 129.6 (2C), 128.0, 125.2, 125.1, 123.3, 122.9, 118.5 (2C), 117.8, 115.2, 53.0, 47.7, 35.6, 35.1; HRMS-ESI-TOF m/z 441.1440 ([M+H]$^+$, C$_{26}$H$_{20}$N$_2$O$_5$ requires 441.1445). The enantiomers were separated using a semipreparative chiral phase HPLC column (Daicel ChiraCel OD, 10 μm, 2×25 cm, 40% EtOH-hexanes, 7 mL/min, α=1.17).

(S)-28: [α]$^{23}_D$ +28 (c 0.1, THF).

(R)-28: [α]$^{23}_D$ −30 (c 0.1, THF).

6-(2-(5-Phenoxyindane-2-carbonyl)oxazol-5-yl)picolinic acid (29)

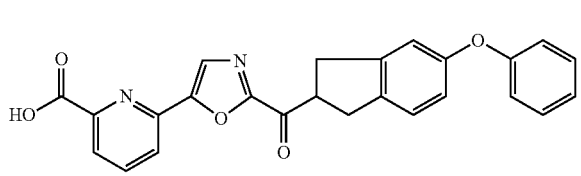 [SMILES: O=C(O)c1cccc(-c2cnc(C(=O)C3Cc4ccc(Oc5ccccc5)cc4C3)o2)n1]

The title compound was prepared from methyl 6-(2-(5-(benzyloxy)indane-2-carbonyl)oxazol-5-yl)picolinate (28, 5 mg, 0.011 mmol) following general procedure G. Each pure enantiomer of the methyl esters were converted to their corresponding carboxylic acid using general procedure G. Flash chromatography (SiO$_2$, 5% HOAc-EtOAc) yielded the title compound (4 mg, 85%) as a white solid: $^1$H NMR (CDCl$_3$+0.1% TFA, 600 MHz) δ 8.28 (d, 1H, J=4.2 Hz), 8.10 (d, 2H, J=7.8 Hz), 8.07 (s, 1H), 7.32 (t, 2H, J=7.8 Hz), 7.18 (d, 1H, J=7.8 Hz), 7.08 (t, 1H, J=4.5 Hz), 7.00 (d, 2H, J=4.5 Hz), 6.88-6.85 (m, 2H), 4.48-4.43 (m, 1H), 3.42-3.36 (m, 4H); $^{13}$C NMR (CDCl$_3$+0.1% TFA, 150 MHz) 188.9, 164.9, 157.5, 157.2, 156.4, 151.4, 146.3, 145.1, 142.7, 139.9, 135.6, 129.7 (2C), 127.9, 125.2, 124.8, 124.6, 123.0, 118.5 (2C), 117.9, 117.3, 115.1, 47.7, 35.5, 35.0; HRMS-ESI-TOF m/z 449.1106 ([M+Na]$^+$, C$_{25}$H$_{18}$N$_2$O$_5$ requires 449.1108).

(S)-29: [α]$^{23}_D$ +24 (c 0.1, THF).

(R)-29: [α]$^{23}_D$ −22 (c 0.1, THF).

Methyl 5-(Benzyloxy)indane-2-carboxylate (S78)

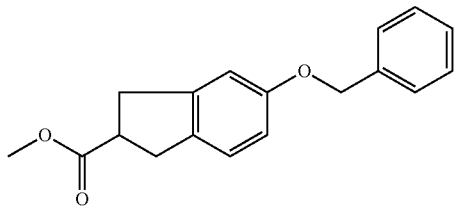 [SMILES: COC(=O)C1Cc2ccc(OCc3ccccc3)cc2C1]

A sample of methyl 5-hydroxyindane-2-carboxylate (S56, 120 mg, 0.62 mmol), benzyl alcohol (0.084 mL, 0.81 mmol) and triphenylphosphine (212 mg, 0.81 mmol) were dissolved in anhydrous THF (10 mL). The reaction mixture was cooled to 0° C. before diethyl azodicarboxylate (0.128 mL, 0.81 mmol) was added dropwise. The reaction mixture was stirred at room temperature for 17 h under Ar. The mixture was diluted with EtOAc, washed with saturated aqueous NaCl, and dried over Na$_2$SO$_4$. Evaporation in vacuo yielded the crude product that was purified by flash chromatography (SiO$_2$, 5% EtOAc-hexanes) to provide the title compound (82.9 mg, 47%) as a colorless oil: $^1$H NMR (CDCl$_3$, 600 MHz) δ 7.45 (d, 2H, J=7.2 Hz), 7.40 (t, 2H, J=7.2 Hz), 7.34 (t, 1H, J=7.2 Hz), 7.12 (d, 1H, J=8.4 Hz), 6.87 (s, 1H), 6.83 (dd, 1H, J=2.4, 8.4 Hz), 5.05 (s, 2H), 3.74 (s, 3H), 3.38-3.34 (m, 1H), 3.28-3.15 (m, 4H); $^{13}$C NMR (CDCl$_3$, 150 MHz) δ 175.5, 158.0, 143.0, 137.1, 133.6, 128.4 (2C), 127.7, 127.3 (2C), 124.7, 113.4, 110.7, 70.1, 51.8, 43.8, 36.2, 35.3.

(5-(Benzyloxy)indan-2-yl)methanol (S79)

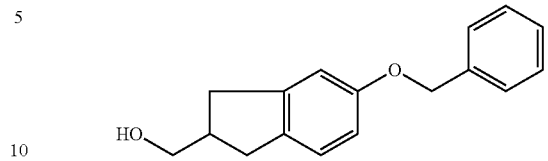

The title compound was prepared from methyl 5-(benzyloxy)indane-2-carboxylate (S78, 82.9 mg, 0.29 mmol) following general procedure A. Flash chromatography (SiO$_2$, 50% EtOAc-hexanes) afforded the title compound (82 mg, 98%) as a colorless oil: $^1$H NMR (CDCl$_3$, 400 MHz) δ 7.45 (d, 2H, J=7.2 Hz), 7.40 (t, 2H, J=7.2 Hz), 7.34 (t, 1H, J=7.2 Hz), 7.11 (d, 1H, J=8.4 Hz), 6.87 (s, 1H), 6.83 (dd, 1H, J=2.4, 8.4 Hz), 5.05 (s, 2H), 3.66 (d, 2H, J=6.4 Hz), 3.06-2.99 (m, 2H), 2.76-2.65 (m, 3H), 1.87 (s, 1H); $^{13}$C NMR (CDCl$_3$, 100 MHz) δ 157.8, 144.1, 137.2, 134.8, 128.4 (2C), 127.7, 127.3 (2C), 125.0, 113.0, 111.0, 70.1, 66.4, 41.8, 35.9, 34.7.

5-(Benzyloxy)indane-2-carboxaldehyde (S80)

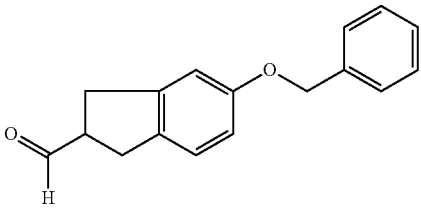 [SMILES: O=CC1Cc2ccc(OCc3ccccc3)cc2C1]

The title compound was prepared from (5-(benzyloxy)indan-2-yl)methanol (S79, 82 mg, 0.32 mmol) following general procedure B. Flash chromatography (SiO$_2$, 10% EtOAc-hexanes) afforded the title compound (50 mg, 62%) as a colorless oil: $^1$H NMR (CDCl$_3$, 600 MHz) δ 9.76 (s, 1H), 7.43 (d, 2H, J=7.2 Hz), 7.39 (t, 2H, J=7.2 Hz), 7.33 (t, 1H, J=7.2 Hz), 7.12 (d, 1H, J=8.4 Hz), 6.87 (s, 1H), 6.82 (dd, 1H, J=2.4, 8.4 Hz), 5.04 (s, 2H), 3.29-3.20 (m, 3H), 3.16-3.11 (m, 2H); $^{13}$C NMR (CDCl$_3$, 150 MHz) δ 202.7, 158.2, 142.6, 137.0, 133.2, 128.5 (2C), 127.8, 127.3 (2C), 125.0, 113.7, 110.9, 70.1, 51.0, 33.0, 32.1.

(5-(Benzyloxy)indan-2-yl)(oxazol-2-yl)methanol (S81)

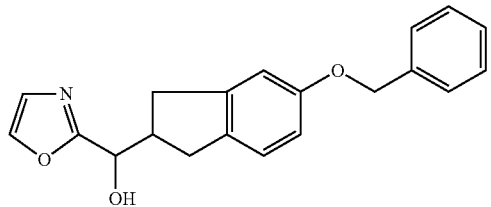 [SMILES: OC(c1ncco1)C1Cc2ccc(OCc3ccccc3)cc2C1]

Oxazole (0.052 mL, 0.79 mmol) in anhydrous THF (10 mL) was treated with BH$_3$.THF (1 M, 0.086 mL, 0.86 mmol) and the solution was stirred at room temperature for 1 h before being cooled to −78° C. and treated with 1.5 M t-BuLi (0.100 mL, 1.27 mmol) dropwise. The reaction mixture was stirred at −78° C. for 40 min before a solution of 5-(benzyloxy)indane-2-carboxaldehyde (S80, 249 mg, 0.79 mmol) in THF (4 mL) was added. The reaction mixture was stirred at −78° C. for 2 h before being warmed to room temperature. A 5% HOAc-EtOH solution (50 mL) was added and this mixture was stirred at room temperature for 12 h. The solvent was removed under reduced pressure and the residue was dissolved in EtOAc, washed with $H_2O$, saturated aqueous $NaHCO_3$, and saturated aqueous NaCl before the organic layer was dried over $MgSO_4$ and the solvent was removed under reduced pressure. Flash chromatography ($SiO_2$, 50% EtOAc-hexanes) afforded the title compound (160 mg, 63%) as colorless oil: $^1H$ NMR ($CDCl_3$, 600 MHz) δ 7.62 (s, 1H), 7.43-7.40 (m, 2H), 7.39-7.36 (m, 2H), 7.32-7.30 (m, 1H), 7.09-7.07 (m, 2H), 7.04 (d, 1H, J=7.8 Hz), 6.83 (d, 0.5H, J=2.4 Hz), 6.79-6.74 (m, 1H), 5.29 (s, 2H), 5.03 (d, 2H, J=5.4 Hz), 4.79-4.77 (m, 1H), 3.07-2.88 (m, 4H); $^{13}C$ NMR ($CDCl_3$, 150 MHz) δ 165.2, 157.97, 157.92, 143.7, 143.6, 138.9, 137.2, 134.5, 134.4, 128.5 (2C), 127.8, 127.3 (2C), 126.7, 124.99, 124.90, 113.29, 113.27, 110.98, 110.92, 70.4, 70.1, 53.4, 44.76, 44.74, 35.3, 35.2, 34.2, 34.1; HRMS-ESI-TOF m/z 322.1437 ([M+H]$^+$, $C_{20}H_{19}NO_3$ requires 322.1438).

(5-(Benzyloxy)indan-2-yl)(oxazol-2-yl)methanone (30)

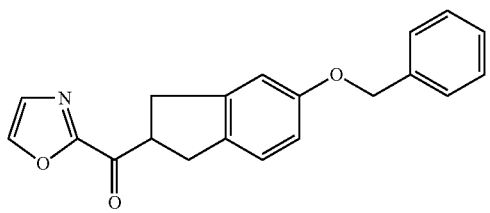 [SMILES: O=C(c1ncco1)C1Cc2ccc(OCc3ccccc3)cc2C1]

The title compound was prepared from (5-(benzyloxy)indan-2-yl)(oxazol-2-yl)methanol (S81, 10 mg, 0.031 mmol) following general procedure E. Flash chromatography ($SiO_2$, 5-20% EtOAc-hexanes) yielded the title compound (8 mg, 75%) as a white solid: $^1H$ NMR ($CDCl_3$, 600 MHz) δ 7.43 (s, 1H), 7.42 (d, 2H, J=6.6 Hz), 7.39 (m, 3H), 7.32 (t, 1H, J=7.2 Hz), 7.11 (d, 1H, J=7.8 Hz), 6.85 (d, 1H, J=7.8 Hz), 6.80 (d, 1H, J=2.4 Hz), 5.04 (s, 2H), 4.41-4.38 (m, 1H), 3.39-3.26 (m, 4H); $^{13}C$ NMR ($CDCl_3$, 150 MHz) δ 188.9, 158.2, 157.8, 142.7, 141.6, 137.1, 133.3, 129.1, 128.5 (2C), 127.8, 127.4 (2C), 124.9, 113.7, 110.8, 70.2, 47.7, 35.6, 34.9; HRMS-ESI-TOF m/z 320.1277 ([M+H]$^+$, $C_{20}H_{17}NO_3$ requires 320.1281). The enantiomers could not be separated using chiral phase HPLC.

2-((5-(Benzyloxy)indan-2-yl)(tert-butyldimethylsilyloxy)methyl)oxazole (S82)

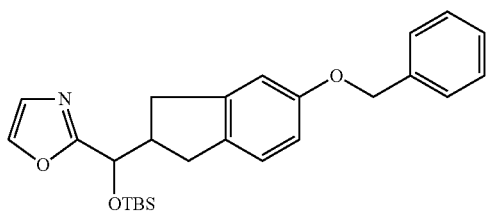 [SMILES: CC(C)(C)[Si](C)(C)OC(c1ncco1)C1Cc2ccc(OCc3ccccc3)cc2C1]

A solution of (5-(benzyloxy)indan-2-yl)(oxazol-2-yl)methanone (S81, 130 mg, 0.40 mmol), TBSCl (147 mg, 0.97 mmol) and imidazole (137 mg, 2 mmol) in DMF (10 mL) was stirred at room temperature for 16 h before it was diluted with EtOAc, washed with $H_2O$, and saturated aqueous NaCl. The organic layer was dried over $MgSO_4$ and the solvent was removed under reduced pressure. Flash chromatography ($SiO_2$, 10% EtOAc-hexanes) yielded the title compound (155 mg, 89%) as a thick colorless oil: $^1H$ NMR ($CDCl_3$, 400 MHz) δ 7.64 (s, 1H), 7.46-7.33 (m, 5H), 7.13-7.10 (m, 1H), 7.04 (d, 1H, J=7.8 Hz), 6.88 (d, 1H, J=2.4 Hz), 6.81-6.77 (m, 2H), 5.05 (d, 2H, J=7.2 Hz), 4.80 (d, 1H, J=5.4 Hz), 3.12-2.97 (m, 2H), 2.84-2.64 (m, 2H), 0.92 (s, 9H), 0.01 (s, 3H), −0.07 (s, 3H); $^{13}C$ NMR ($CDCl_3$, 100 MHz) δ 164.6, 157.8, 157.7, 143.9, 143.7, 138.49, 138.41, 137.2, 134.7, 134.5, 128.4 (2C), 127.7, 127.3 (2C), 126.7, 124.8, 113.0, 110.9, 110.8, 99.8, 71.4, 71.2, 70.0, 69.9, 45.5, 35.8, 35.1, 34.7, 34.0, 25.5 (3C), 18.0, −5.2.

2-((5-(Benzyloxy)indan-2-yl)(tert-butyldimethylsilyloxy)methyl)-5-(tributylstannyl)oxazole (S83)

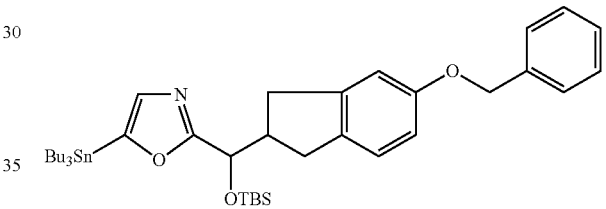

A solution of 2-((5-(benzyloxy)indan-2-yl)(tert-butyldimethylsilyloxy)methyl)oxazole (S82, 155 mg, 0.35 mmol) in THF (10 mL) was cooled to −78° C. before it was treated with 2.29 M n-BuLi (0.20 mL, 0.39 mmol) dropwise. The reaction mixture was stirred at −78° C. for 2 h, treated with a solution of $Bu_3SnCl$ (0.20 mL, 0.7 mmol), and stirred for 5 min. The solution was warmed to room temperature and diluted with EtOAc and washed with saturated aqueous NaCl. The organic layer was dried over $MgSO_4$ and the solvent was removed under reduced pressure. Flash chromatography ($SiO_2$, 0-5% EtOAc-hexanes) yielded the title compound (181 mg, 72%) as a thick colorless oil: $^1H$ NMR ($CDCl_3$, 500 MHz) δ 7.45-7.43 (m, 2H), 7.40-7.37 (m, 2H), 7.34-7.31 (m, 1H), 7.14 (s, 1H), 7.11 (d, 0.5H, J=7.8 Hz), 7.04 (d, 0.5H, J=7.8 Hz), 6.87 (d, 0.5H, J=2.4 Hz), 6.80-6.76 (m, 1.5H), 5.04 (d, 2H, J=7.2 Hz), 4.84 (d, 1H, J=5.4 Hz), 3.12-2.99 (m, 3H), 2.78-2.69 (m, 2H), 1.62-1.57 (m, 6H), 1.40-1.35 (m, 6H), 1.17-1.14 (m, 6H), 0.95-0.92 (m, 9H), 0.89 (s, 9H), 0.08 (s, 3H), −0.10 (s, 3H); $^{13}C$ NMR ($CDCl_3$, 125 MHz) δ 168.6, 157.8, 157.7, 154.8, 144.2, 143.9, 137.34, 137.30, 137.1, 135.0, 134.8, 128.4 (2C), 127.6, 127.2, 124.8 (2C), 124.7, 112.9, 110.9, 71.5, 71.4, 70.1, 45.7, 35.8, 35.2, 34.8, 34.1, 28.8 (3C), 27.2 (3C), 25.6 (3C), 18.0, 13.5 (3C), 10.1 (3C), −5.27, −5.37.

2-((5-(Benzyloxy)indan-2-yl)(tert-butyldimethylsilyloxy)methyl)-5-(pyridin-2-yl)oxazole (S84)

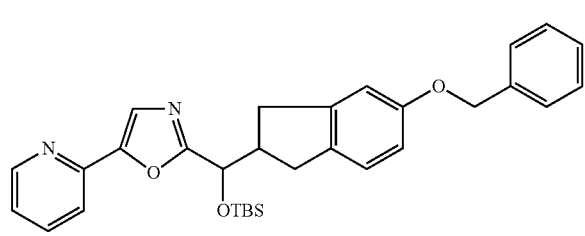 [SMILES: CC(C)(C)[Si](C)(C)OC(c1ncc(-c2ccccn2)o1)C1Cc2ccc(OCc3ccccc3)cc2C1]

The title compound was prepared from 2-((5-(benzyloxy)indan-2-yl)(tert-butyldimethylsilyloxy)methyl)-5-(tributylstannyl)oxazole (S83, 167 mg, 0.22 mmol) and 2-bromopyridine following general procedure C. Flash chromatography (SiO$_2$, 20% EtOAc-hexanes) yielded the title compound (66.8 mg, 59%) as a colorless oil: $^1$H NMR (CDCl$_3$, 500 MHz) δ 8.63 (d, 1H, J=7.2 Hz), 7.76 (t, 1H, J=7.8 Hz), 7.67-7.65 (m, 2H), 7.43-7.35 (m, 4H), 7.33-7.30 (m, 1H), 7.25-7.21 (m, 1H), 7.23-7.21 (m, 1H), 7.08 (d, 0.5H, J=7.8 Hz), 7.04 (d, 0.5H, J=7.8 Hz), 6.84 (d, 1H, J=2.4 Hz), 6.78-6.73 (m, 1H), 5.02 (d, 2H, J=7.2 Hz), 4.82 (d, 1H, J=5.4 Hz), 3.14-2.99 (m, 2H), 2.85-2.72 (m, 2H), 0.89 (s, 9H), 0.09 (s, 3H), −0.05 (s, 3H): $^{13}$C NMR (CDCl$_3$, 125 MHz) δ 164.93, 164.90, 157.9, 157.8, 150.7, 149.8, 147.3, 144.0, 143.8, 137.2, 136.8, 134.7, 134.6, 128.4 (2C), 127.7, 127.3 (2C), 125.1, 124.9, 122.8, 119.0, 113.18, 113.14, 110.98, 110.95, 71.5, 70.1, 45.6, 35.7, 35.2, 34.7, 34.2, 25.6 (3C), 18.1, −5.03, −5.22.

(5-(Benzyloxy)indan-2-yl)(5-(pyridin-2-yl)oxazol-2-yl)methanol (S85)

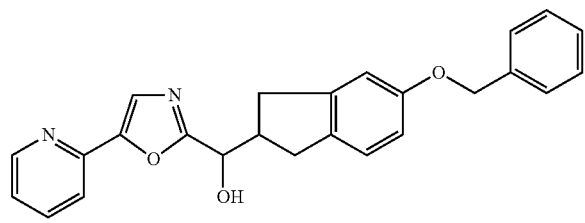 [SMILES: OC(c1ncc(-c2ccccn2)o1)C1Cc2ccc(OCc3ccccc3)cc2C1]

The title compound was prepared from 2-((5-(benzyloxy)indan-2-yl)(tert-butyldimethylsilyloxy)methyl)-5-(pyridin-2-yl)oxazole (S84, 66.8 mg, 0.13 mmol) following general procedure D. Flash chromatography (SiO$_2$, 50-100% EtOAc-hexanes) yielded the title compound (56.8 mg, 98%) as a colorless oil: $^1$H NMR (CDCl$_3$, 600 MHz) δ 8.60 (d, 1H, J=7.2 Hz), 7.72 (t, 1H, J=7.8 Hz), 7.61-7.62 (m, 2H), 7.42-7.35 (m, 4H), 7.32-7.30 (m, 1H), 7.22-7.20 (m, 1H), 7.23-7.21 (m, 1H), 7.07 (d, 0.5H, J=7.8 Hz), 7.03 (d, 0.5H, J=7.8 Hz), 6.83 (d, 1H, J=2.4 Hz), 6.78-6.73 (m, 1H), 4.99 (d, 2H, J=7.2 Hz), 4.86 (d, 1H, J=5.4 Hz), 3.18-3.05 (m, 3H), 2.96-2.90 (m, 2H); $^{13}$C NMR (CDCl$_3$, 150 MHz) δ 165.5, 157.88, 157.83, 150.8, 149.7, 146.8, 143.7, 143.6, 137.1, 136.9, 134.5, 134.3, 128.4 (2C), 127.7, 127.3 (2C), 124.9, 124.88, 124.85, 122.9, 119.3, 113.2, 113.1, 110.9, 110.8, 70.3, 70.0, 44.57, 44.55, 35.4, 34.3.

(5-(Benzyloxy)indan-2-yl)(5-(pyridin-2-yl)oxazol-2-yl)methanone (31)

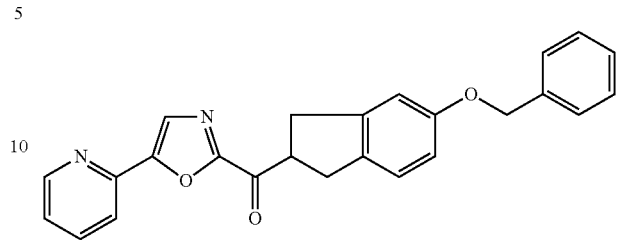

The title compound was prepared from (5-(benzyloxy)indan-2-yl)(5-(pyridin-2-yl)oxazol-2-yl)methanol (S85, 56.8 mg, 0.14 mmol) following general procedure E. Flash chromatography (SiO$_2$, 20% EtOAc-hexanes) yielded the title compound (26.5 mg, 48%) as a yellow oil: $^1$H NMR (CDCl$_3$, 600 MHz) δ 8.67 (d, 1H, J=7.2 Hz), 7.92 (s, 1H), 7.87 (d, 1H, J=7.8 Hz), 7.81 (t, 1H, J=7.8 Hz), 7.43 (d, 2H, J=7.8 Hz), 7.38 (t, 1H, J=7.8 Hz), 7.32 (t, 2H, J=7.8 Hz), 7.11 (d, 1H, J=7.8 Hz), 7.03 (d, 1H, J=7.8 Hz), 6.82 (d, 1H, J=2.4 Hz), 6.81 (d, 1H, J=7.8 Hz), 5.04 (d, 2H, J=7.2 Hz), 4.48-4.42 (m, 1H), 3.39-3.28 (m, 4H); $^{13}$C NMR (CDCl$_3$, 150 MHz) δ 188.9, 158.2, 157.0, 153.3, 150.0, 146.2, 142.7, 137.13, 137.10, 133.4, 128.5 (2C), 127.8, 127.3 (2C), 126.9, 124.8, 124.1, 120.4, 113.6, 110.7, 70.1, 47.7, 35.7, 35.0; HRMS-ESI-TOF m/z 397.1550 ([M+H]$^+$, C$_{25}$H$_{20}$N$_2$O$_3$ requires 397.1547). The enantiomers were separated using a semipreparative chiral phase HPLC column (Daicel ChiraCel OD, 10 μm, 2×25 cm, 1% EtOH-hexanes, 7 mL/min, α=1.12).

(S)-31: [α]$^{23}_D$ −22 (c 0.1, THF).
(R)-31: [α]$^{23}_D$ +24 (c 0.1, THF).

Methyl 6-(2-((5-(Benzyloxy)indan-2-yl)(tert-butyldimethylsilyloxy)methyl)oxazol-5-yl)picolinate (S86)

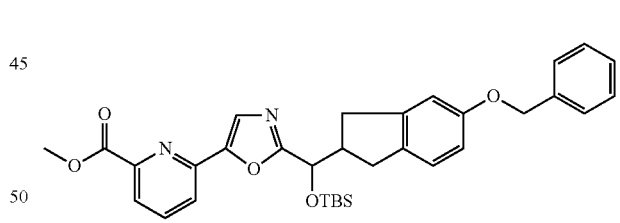

The title compound was prepared from 2-((5-(benzyloxy)indan-2-yl)(tert-butyldimethylsilyloxy)methyl)-5-(tributylstannyl)oxazole (S83, 60 mg, 0.082 mmol) and methyl 6-chloropicolinate following general procedure C. Flash chromatography (SiO$_2$, 30% EtOAc-hexanes) yielded the title compound (31.8 mg, 67%) as a yellow oil: $^1$H NMR (CDCl$_3$, 600 MHz) δ 8.04 (d, 1H, J=7.2 Hz), 7.90 (t, 1H, J=7.8 Hz), 7.82 (m, 2H), 7.42-7.30 (m, 4H), 7.08 (d, 0.5H, J=7.8 Hz), 7.03 (d, 0.5H, J=7.8 Hz), 6.84 (d, 1H, J=2.4 Hz), 6.78-6.73 (m, 1H), 5.02 (d, 2H, J=7.2 Hz), 4.82 (d, 1H, J=5.4 Hz), 4.01 (s, 3H), 3.10-2.98 (m, 4H), 2.86-2.70 (m, 2H), 0.87 (s, 9H), 0.08 (s, 3H), −0.07 (s, 3H); $^{13}$C NMR (CDCl$_3$, 150 MHz) δ 165.3, 165.29, 165.27, 157.9, 157.8, 149.9, 148.2, 147.6, 143.9, 143.7, 138.0, 137.26, 137.24, 134.6, 134.5, 128.4 (2C), 127.7, 127.3 (2C), 126.4, 124.9, 123.9, 122.0, 113.2, 113.1, 110.98, 110.95, 71.56, 71.54, 70.1, 52.9, 45.62, 45.60, 35.7, 35.2, 34.7, 34.1, 25.6 (3C), 18.1, 13.5, −5.05, −5.21.

Methyl 6-(2-((5-(Benzyloxy)indan-2-yl)(hydroxy)methyl)oxazol-5-yl)picolinate (S87)

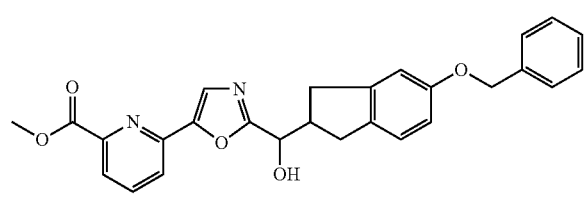 [SMILES: COC(=O)c1cccc(-c2cnc(C(O)C3Cc4ccc(OCc5ccccc5)cc4C3)o2)n1]

The title compound was prepared from methyl 6-(2-((5-(benzyloxy)indan-2-yl)(tert-butyldimethylsilyloxy)methyl)oxazol-5-yl)picolinate (S86, 31.8 mg, 0.055 mmol) following general procedure D. Flash chromatography (SiO$_2$, 60% EtOAc-hexanes) yielded the title compound (21.7 mg, 86%) as a colorless oil: $^1$H NMR (CDCl$_3$, 600 MHz) δ 8.04 (d, 1H, J=7.2 Hz), 7.89 (t, 1H, J=7.8 Hz), 7.77 (m, 2H), 7.41-7.30 (m, 4H), 7.08 (d, 1H, J=7.8 Hz), 7.04 (d, 0.5H, J=7.8 Hz), 6.84 (d, 0.5H, J=2.4 Hz), 6.76-6.72 (m, 2H), 5.00 (d, 2H, J=7.2 Hz), 4.88 (d, 1H, J=5.4 Hz), 4.01 (s, 3H), 3.16-2.93 (m, 4H), 2.89-2.70 (m, 2H); $^{13}$C NMR (CDCl$_3$, 150 MHz) δ 165.2, 157.98, 157.94, 148.2, 147.3, 143.7, 143.5, 137.9, 137.2, 134.4, 134.3, 128.5 (2C), 127.8, 127.3 (2C), 126.1, 125.0, 124.9, 124.0, 122.3, 113.3, 113.2, 110.98, 110.91, 70.5, 70.1, 52.9, 44.6, 35.4, 35.2, 34.3, 34.1.

Methyl 6-(2-(5-(Benzyloxy)indane-2-carbonyl)oxazol-5-yl)picolinate (32)

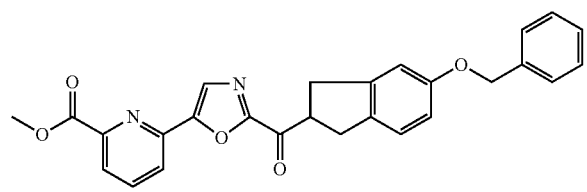 [SMILES: COC(=O)c1cccc(-c2cnc(C(=O)C3Cc4ccc(OCc5ccccc5)cc4C3)o2)n1]

The title compound was prepared from methyl 6-(2-((5-(benzyloxy)indan-2-yl)(hydroxy)methyl)oxazol-5-yl)picolinate (S87, 21.7 mg, 0.047 mmol) following general procedure E. Flash chromatography (SiO$_2$, 30% EtOAc-hexanes) yielded the title compound (16.2 mg, 75%) as a yellow oil: $^1$H NMR (CDCl$_3$, 600 MHz) δ 8.12 (d, 1H, J=7.2 Hz), 8.05 (s, 1H), 8.04 (d, 1H, J=7.8 Hz), 7.97 (t, 1H, J=7.8 Hz), 7.43 (d, 2H, J=7.2 Hz), 7.38 (t, 2H, J=7.8 Hz), 7.30 (t, 1H, J=7.8 Hz), 7.11 (d, 1H, J=7.8 Hz), 6.86 (d, 1H, J=2.4 Hz), 6.81 (dd, 1H, J=2.4, 7.8 Hz), 5.04 (s, 2H), 4.48-4.38 (m, 1H), 4.04 (s, 3H), 3.41-3.30 (m, 4H); $^{13}$C NMR (CDCl$_3$, 150 MHz) δ 188.9, 165.0, 158.2, 157.3, 152.4, 148.5, 146.5, 142.7, 138.2, 137.1, 133.3, 128.5 (2C), 128.0, 127.8 (2C), 127.4, 125.1, 124.9, 123.3, 113.7, 110.8, 70.2, 53.0, 47.7, 35.7, 35.0; HRMS-ESI-TOF m/z 455.1602 ([M+H]$^+$, C$_{27}$H$_{22}$N$_2$O$_5$ requires 455.1601). The enantiomers were separated using a semipreparative chiral phase HPLC column (Daicel ChiraCel OD, 10 μm, 2×25 cm, 20% EtOH-hexanes, 7 mL/min, α=1.09).
(S)-32: [α]$^{23}_D$ +84 (c 0.1, THF).
(R)-32: [α]$^{23}_D$ −88 (c 0.1, THF).

6-(2-(5-(Benzyloxy)indane-2-carbonyl)oxazol-5-yl)picolinic acid (33)

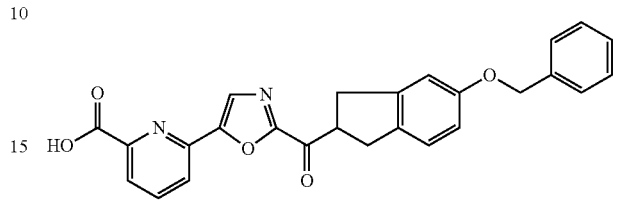

The title compound was prepared from methyl 6-(2-(5-(benzyloxy)indane-2-carbonyl)oxazol-5-yl)picolinate (32, 1.88 mg, 0.004 mmol) following general procedure G. Each pure enantiomer of the methyl esters were converted to their corresponding carboxylic acid using general procedure G. Flash chromatography (SiO$_2$, 5% HOAc-EtOAc) yielded the title compound (1.3 mg, 73%) as a white solid: $^1$H NMR (CDCl$_3$+0.1% TFA, 600 MHz) δ 8.31 (d, 1H, J=7.2 Hz), 8.17 (m, 3H), 7.43 (d, 2H, J=7.2 Hz), 7.38 (t, 2H, J=7.8 Hz), 7.33 (t, 1H, J=7.8 Hz), 7.14 (d, 1H, J=7.8 Hz), 6.88 (d, 1H, J=2.4 Hz), 6.84 (dd, 1H, J=2.4, 7.8 Hz), 5.08 (s, 2H), 4.41-4.38 (m, 1H), 3.43-3.31 (m, 4H); $^{13}$C NMR (CDCl$_3$+0.1% TFA, 150 MHz) 200.1, 189.1, 158.0, 157.1, 145.1, 142.2, 140.3, 136.6, 133.2, 128.6 (2C), 128.1, 127.8 (2C), 127.6, 125.4, 125.1, 125.0, 114.3, 111.2, 70.8, 53.4, 47.7, 35.5, 34.9, 14.2; HRMS-ESI-TOF m/z 441.1445 ([M+H]$^+$, C$_{26}$H$_{20}$N$_2$O$_5$ requires 441.1445).
(S)-33: [α]$^{23}_D$ −80 (c 0.1, THF).
(R)-33: [α]$^{23}_D$ +72 (c 0.1, THF).

2-Hydroxy-2-(6-phenoxy-1,2,3,4-tetrahydronaphthalen-2-yl)acetonitrile (S88)

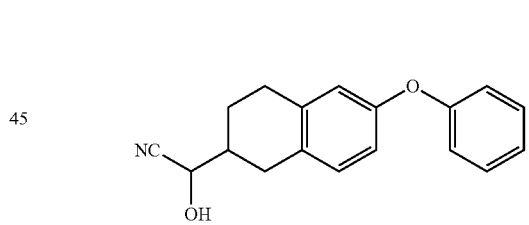

A solution of 6-phenoxy-1,2,3,4-tetrahydronaphthalene-2-carboxaldehyde (S23, 470 mg, 1.86 mmol) and KCN (912 mg, 18.6 mmol) in a mixture of THF/H$_2$O (10/10 mL) was stirred at room temperature for 16 h before it was diluted with EtOAc, washed with H$_2$O, and saturated aqueous NaCl. The organic layer was dried over MgSO$_4$ and the solvent was removed under reduced pressure. Flash chromatography (SiO$_2$, 20% EtOAc-hexanes) yielded the title compound (410 mg, 79%) as a colorless oil: $^1$H NMR (CDCl$_3$, 500 MHz) δ 7.34 (t, 2H, J=7.2 Hz), 7.11-7.06 (m, 2H), 7.02 (d, 2H, J=8.0 Hz), 6.82-6.77 (m, 2H), 4.45-4.43 (m, 1H), 3.96 (s, 1H), 3.03-2.96 (m, 1H), 2.85-2.81 (m, 2H), 2.74-2.68 (m, 1H), 2.24-2.19 (m, 2H), 1.67-1.62 (m, 1H): $^{13}$C NMR (CDCl$_3$, 125 MHz) δ 157.3, 155.1, 137.3, 130.3, 130.2, 129.6 (2C), 129.25, 129.21, 122.9, 119.2, 118.7, 118.5 (2C), 116.9, 67.9, 65.2, 65.1, 39.2, 39.1, 30.3, 30.2, 28.3, 25.4, 24.4, 24.3.

Methyl 2-Hydroxy-2-(6-phenoxy-1,2,3,4-tetrahydronaphthalen-2-yl)acetate (S89)

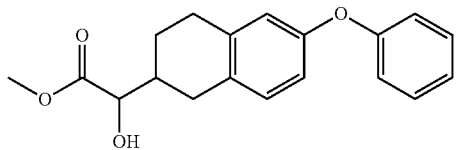 [SMILES: COC(=O)C(O)C1CCc2cc(Oc3ccccc3)ccc2C1]

A sample of 2-hydroxy-2-(6-phenoxy-1,2,3,4-tetrahydronaphthalen-2-yl)acetonitrile (S88, 310 mg, 1.10 mmol) was dissolved in a solution of 4 N HCl/EtOAc (4 mL) and MeOH (4 mL) and the mixture was warmed at reflux for 16 h under Ar. The mixture was diluted with EtOAc, and washed with saturated aqueous NaCl. The organic layer was dried over MgSO$_4$ and the solvent was removed under reduced pressure. Flash chromatography (SiO$_2$, 30% EtOAc-hexanes) yielded the title compound (263 mg, 73%) as a yellow oil: $^1$H NMR (CDCl$_3$, 600 MHz) δ 7.32 (t, 2H, J=7.2 Hz), 7.10-7.02 (m, 2.5H), 6.99 (d, 2H, J=8.0 Hz), 6.81-6.73 (m, 2.5H), 4.26 (t, 1H, J=7.2 Hz), 4.22 (t, 0.5H, J=7.2 Hz), 3.83 (s, 3H), 2.83-2.67 (m, 5H), 2.53-2.49 (m, 0.5H), 2.22-2.17 (m, 1.5H); $^{13}$C NMR (CDCl$_3$, 150 MHz) δ 175.09, 175.05, 157.6, 154.8, 137.73, 173.70, 130.8, 130.5, 130.39, 130.36, 130.2, 129.66, 129.61 (2C), 129.1, 123.0, 122.8, 118.9, 118.86, 118.82, 118.6, 118.4 (2C), 117.0, 116.81, 116.80, 73.9, 73.8, 65.4, 65.3, 52.64, 52.62, 39.4, 39.2, 38.8, 38.5, 31.1, 30.3, 30.2, 29.6, 29.4, 29.2, 28.45, 28.43, 25.6, 24.49, 24.42, 23.3.

Methyl 2-(tert-Butyldimethylsilyloxy)-2-(6-phenoxy-1,2,3,4-tetrahydronaphthalen-2-yl)acetate (S90)

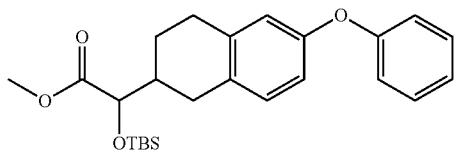 [SMILES: COC(=O)C(O[Si](C)(C)C(C)(C)C)C1CCc2cc(Oc3ccccc3)ccc2C1]

A solution of methyl 2-hydroxy-2-(6-phenoxy-1,2,3,4-tetrahydronaphthalen-2-yl)acetate (S89, 410 mg, 1.31 mmol), TBSCl (474 mg, 3.15 mmol) and imidazole (450 mg, 6.55 mmol) in DMF (5 mL) was stirred at room temperature for 16 h before it was diluted with EtOAc, washed with H$_2$O, and saturated aqueous NaCl. The organic layer was dried over MgSO$_4$ and the solvent was removed under reduced pressure. Flash chromatography (SiO$_2$, 5% EtOAc-hexanes) yielded the title compound (380 mg, 67%) as a thick colorless oil: $^1$H NMR (CDCl$_3$, 600 MHz) δ 7.32 (t, 2H, J=7.2 Hz), 7.08-7.03 (m, 2H), 6.99-6.97 (m, 2H), 6.78-6.73 (m, 2H), 4.23 (d, 0.5H, J=7.2 Hz), 4.16 (d, 0.5H, J=7.2 Hz), 3.76 (s, 1.5H), 3.75 (s, 1.5H), 2.82-2.74 (m, 2.5H), 2.68-2.64 (m, 2H), 2.22-2.14 (m, 1H), 1.93-1.90 (m, 1H), 1.83-1.80 (m, 0.5H), 0.91 (s, 9H), 0.08 (s, 3H), 0.05 (s, 3H); $^{13}$C NMR (CDCl$_3$, 150 MHz) δ 173.67, 173.62, 157.6, 157.5, 154.7, 154.6, 138.0, 137.6, 131.0, 130.8, 130.4, 130.2, 129.5 (2C), 122.78, 122.74, 118.9, 118.8, 118.4 (2C), 118.3, 116.7, 116.6, 75.8, 75.4, 51.7, 39.1, 39.0, 31.2, 29.3, 29.1, 28.9, 26.1, 25.7 (3C), 23.9, 18.3, −4.9, −5.0, −5.32, −5.39.

2-(tert-Butyldimethylsilyloxy)-2-(6-phenoxy-1,2,3,4-tetrahydronaphthalen-2-yl)acetic acid (S91)

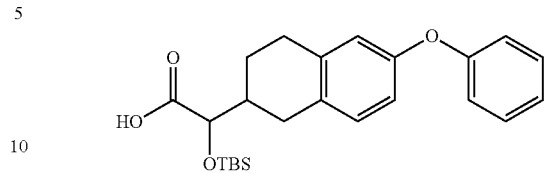

A sample of methyl 2-(tert-butyldimethylsilyloxy)-2-(6-phenoxy-1,2,3,4-tetrahydronaphthalen-2-yl)acetate (S90, 380 mg, 0.89 mmol) was dissolved in a mixture of 3:2:1 THF/H$_2$O/MeOH (4:2:2 mL) and LiOH (75 mg, 1.78 mmol) was added. The reaction mixture was stirred for 16 h at room temperature before the mixture was diluted with EtOAc, washed with aqueous 0.01 N KHSO$_4$, saturated aqueous NaCl, and dried over Na$_2$SO$_4$. Evaporation in vacuo yielded the crude acid that was purified by chromatography (SiO$_2$, 10% EtOAc-hexanes) yielding the title compound (258 mg, 70%) as a thick colorless oil: $^1$H NMR (CDCl$_3$, 600 MHz) δ 7.31 (t, 2H, J=7.2 Hz), 7.08-7.02 (m, 2H), 6.99-6.97 (m, 2H), 6.78-6.73 (m, 2H), 4.29 (d, 0.5H, J=7.2 Hz), 4.25 (d, 0.5H, J=7.2 Hz), 2.86-2.76 (m, 3H), 2.69-2.64 (m, 1H), 2.23-2.19 (m, 1H), 1.91-1.90 (m, 0.5H), 1.65-1.60 (m, 1.5H), 0.95 (s, 9H), 0.16 (s, 3H), 0.14 (s, 3H); $^{13}$C NMR (CDCl$_3$, 150 MHz) δ 177.5, 177.4, 157.59, 157.53, 155.0, 154.8, 137.6, 137.4, 130.48, 130.43, 130.3, 130.2, 129.6 (2C), 122.88, 122.84, 118.8, 118.5, 118.4 (2C), 116.8, 116.7, 75.8, 75.4, 39.3, 39.2, 31.1, 29.6, 29.3, 29.2, 28.9, 25.7 (3C), 25.6, 23.9, 18.1, −4.9, −5.16, −5.19.

Methyl {N'-[2-(tert-Butyldimethylsilyloxy)-2-(6-phenoxy-1,2,3,4-tetrahydronaphthalen-2-yl)-acetyl]hydrazino}-2-oxo-acetate (S92)

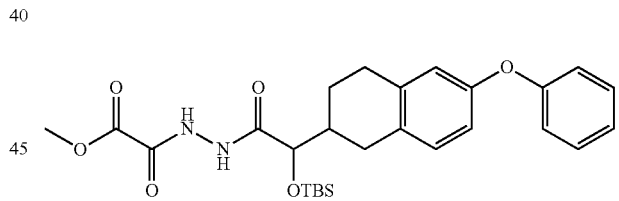

A sample of 2-(tert-butyldimethylsilyloxy)-2-(6-phenoxy-1,2,3,4-tetrahydronaphthalen-2-yl)acetic acid (S91, 60 mg, 0.14 mmol) and methyl oxalylhydrazide (18 mg, 0.14 mmol) were dissolved in CH$_2$Cl$_2$ (2 mL). EDCI (27 mg, 0.14 mmol) was added as a solid. The reaction mixture was stirred at room temperature for 16 h. The solvent was evaporated in vacuo and the residue was dissolved in EtOAc, washed with 1 N aqueous HCl, 5% aqueous NaHCO$_3$, saturated aqueous NaCl, and dried over Na$_2$SO$_4$. The solvent was removed under reduced pressure and flash chromatography (SiO$_2$, 5% MeOH-EtOAc) afforded the title compound (72.7 mg, 98%) as a colorless oil: $^1$H NMR (CDCl$_3$, 600 MHz) δ 9.11 (brs, 1H, NH), 9.02 (brs, 1H, NH), 7.31 (t, 2H, J=7.2 Hz), 7.06-7.01 (m, 2H), 6.97-6.95 (m, 2H), 6.76-6.73 (m, 2H), 4.30 (d, 0.5H, J=7.2 Hz), 4.26 (d, 0.5H, J=7.2 Hz), 3.93 (s, 1.5H), 3.88 (s, 1.5H), 2.82-2.66 (m, 3H), 2.69-2.64 (m, 1H), 2.23-2.19 (m, 1H), 1.91-1.90 (m, 2H), 1.65-1.60 (m, 2H), 0.95 (s, 9H), 0.16 (s, 3H), 0.14 (s, 3H).

Methyl 5-((tert-Butyldimethylsilyloxy)(6-phenoxy-1,2,3,4-tetrahydronaphthalen-2-yl)methyl)-1,3,4-oxadiazole-2-carboxylate (S93)

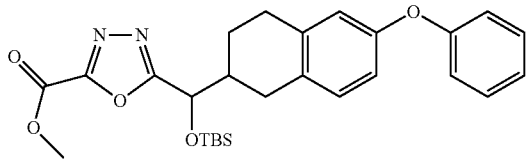 [SMILES: COC(=O)c1nnc(C(O[Si](C)(C)C(C)(C)C)C2CCc3cc(Oc4ccccc4)ccc3C2)o1]

A sample of {NV-[2-(tert-butyldimethylsilyloxy)-2-(6-phenoxy-1,2,3,4-tetrahydronaphthalen-2-yl)-acetyl]-hydrazino}-2-oxo-acetate (S92, 72.7 mg, 0.14 mmol) was dissolved in CH$_2$Cl$_2$ (3 mL). TsCl (82 mg, 0.42 mmol) and Et$_3$N (0.060 mL, 0.42 mmol) were added. The reaction mixture was stirred at room temperature for 16 h. The solvent was evaporated in vacuo and the residue was dissolved in EtOAc, washed with saturated aqueous NaCl, and dried over Na$_2$SO$_4$. The solvent was removed under reduced pressure. Purification by flash chromatography (SiO$_2$, 20% EtOAc-hexanes) afforded the title compound (17.9 mg, 26%) as a colorless oil: $^1$H NMR (CDCl$_3$, 600 MHz) δ 7.69 (d, 2H, J=8.4 Hz), 7.31 (t, 2H, J=7.2 Hz), 7.08-7.03 (m, 1H), 6.98-6.95 (m, 2H), 6.78-6.72 (m, 2H), 4.99 (d, 0.5H, J=7.2 Hz), 4.93 (d, 0.5H, J=7.2 Hz), 4.06 (s, 1.5H), 4.05 (s, 1.5H), 2.85-2.74 (m, 2.5H), 2.69-2.64 (m, 1H), 2.23-2.19 (m, 1H), 1.91-1.90 (m, 1H), 1.65-1.60 (m, 1.5H), 0.95 (s, 9H), 0.16 (s, 3H), 0.14 (s, 3H); $^{13}$C NMR (CDCl$_3$, 150 MHz) δ 169.1, 169.0, 157.57, 157.51, 156.8, 156.7, 155.0, 154.9, 154.6, 154.5, 146.7, 142.8, 141.6, 137.7, 137.4, 137.3, 130.4, 130.2, 130.1, 130.0, 129.68, 129.65 (2C), 129.5, 127.03, 127.0, 126.9 (2C), 122.88, 122.84, 118.8, 118.5, 118.4, 116.9, 116.8, 70.4, 70.2, 52.8, 41.9, 40.1, 40.0, 30.7, 30.1, 29.6, 28.8, 25.5 (3C), 25.2, 24.5, 21.8, 21.4, 18.1, 14.1, −5.15, −5.17, −5.23, −5.26.

(1,3,4-Oxadiazol-2-yl)(6-phenoxy-1,2,3,4-tetrahydronaphthalen-2-yl)methanol (S94)

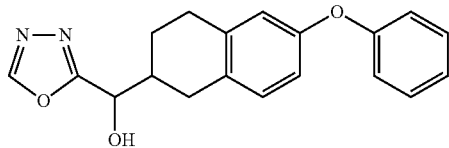 [SMILES: OC(c1nnco1)C1CCc2cc(Oc3ccccc3)ccc2C1]

The title compound was prepared from methyl 5-((tert-butyldimethylsilyloxy)(6-phenoxy-1,2,3,4-tetrahydronaphthalen-2-yl)methyl)-1,3,4-oxadiazole-2-carboxylate (S93, 17.9 mg, 0.036 mmol) following general procedure D. Flash chromatography (SiO$_2$, 50-100% EtOAc-hexanes) yielded the title compound (15.9 mg, 98%) as a white solid: $^1$H NMR (CDCl$_3$, 600 MHz) δ 8.44 (d, 1H, J=1.8 Hz), 7.69 (d, 1H, J=8.4 Hz), 7.32-7.27 (m, 2H), 7.08-7.04 (m, 2H), 6.98-6.96 (m, 2H), 6.79-6.72 (m, 2H), 4.99 (t, 0.5H, J=6.0 Hz), 4.95 (t, 0.5H, J=6.0 Hz), 2.98-2.62 (m, 2H), 2.41-2.38 (m, 1H), 2.17-2.15 (m, 1H), 1.84-1.81 (m, 1H), 1.65-1.55 (m, 2H); $^{13}$C NMR (CDCl$_3$, 150 MHz) δ 157.49, 157.47, 155.0, 153.2, 142.8, 137.7, 137.5, 130.4, 130.2, 129.8, 129.66, 129.63 (2C), 129.5, 127.0, 122.9, 118.85, 118.82, 118.59 (2C), 118.53, 116.9, 116.8, 69.5, 69.4, 41.9, 39.35, 39.30, 31.9, 30.7, 30.1, 29.69, 29.64, 29.3, 28.7, 28.6, 25.1, 24.2, 22.6, 21.4, 14.1.

(1,3,4-Oxadiazol-2-yl)(6-phenoxy-1,2,3,4-tetrahydronaphthalen-2-yl)methanone (34)

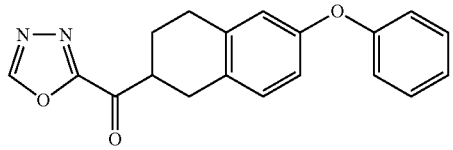

The title compound was prepared from (1,3,4-oxadiazol-2-yl)(6-phenoxy-1,2,3,4-tetrahydronaphthalen-2-yl)methanol (S94, 15.9 mg, 0.049 mmol) following general procedure E. Flash chromatography (SiO$_2$, 20% EtOAc-hexanes) yielded the title compound (5 mg, 32%) as a white solid: $^1$H NMR (CDCl$_3$, 600 MHz) δ 8.59 (s, 1H), 7.33 (t, 2H, J=7.2 Hz), 7.09 (t, 2H, J=6.6 Hz), 7.00 (d, 2H, J=9.0 Hz), 6.82-6.78 (m, 2H), 3.91-3.87 (m, 1H), 3.12-3.09 (m, 2H), 2.96-2.90 (m, 2H), 2.37-2.34 (m, 1H), 1.97-1.91 (m, 1H); $^{13}$C NMR (CDCl$_3$, 150 MHz) δ 189.2, 160.2, 157.4, 155.3, 154.2, 136.9, 130.1, 129.6 (2C), 128.9, 123.0, 118.8, 118.6 (2C), 117.0, 44.8, 30.1, 28.6, 25.4; HRMS-ESI-TOF m/z 321.1233 ([M+H]$^+$, C$_{19}$H$_{16}$N$_2$O$_3$ requires 321.1234). The enantiomers were separated using a semipreparative chiral phase HPLC column (Daicel ChiraCel OD, 10 μm, 2×25 cm, 40% EtOH-hexanes, 7 mL/min, α=1.23).

(S)-34: [α]$^{23}_D$ −16 (c 0.1, THF).
(R)-34: [α]$^{23}_D$ +20 (c 0.1, THF).

Methyl 5-[Hydroxy-(6-phenoxy-1,2,3,4-tetrahydronaphthalen-2-yl)methyl]-[1,3,4]oxadiazole-2-carboxylate (S95)

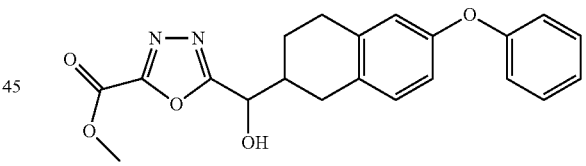

A sample of methyl 5-((tert-butyldimethylsilyloxy)(6-phenoxy-1,2,3,4-tetrahydronaphthalen-2-yl)methyl)-1,3,4-oxadiazole-2-carboxylate (S93, 62.5 mg, 0.12 mmol) was dissolved in THF (2 mL), and TASF$^2$ (35 mg, 0.12 mmol) was added as a solid. The reaction mixture was stirred at room temperature for 1 h under Ar. The reaction mixture was diluted with EtOAc, washed with saturated aqueous NaCl, and dried over Na$_2$SO$_4$. Flash chromatography (SiO$_2$, 50% EtOAc-hexanes) yielded the title compound (18.9 mg, 41%) as a colorless oil: $^1$H NMR (CDCl$_3$, 600 MHz) δ 7.31 (t, 2H, J=7.8 Hz), 7.08-7.03 (m, 2H), 6.98 (d, 2H, J=7.8 Hz), 6.79 (m, 2H), 5.01 (t, 0.5H, J=7.0 Hz), 4.97 (t, 0.5H, J=7.0 Hz), 4.06 (s, 3H), 2.88-2.77 (m, 3H), 2.45-2.41 (m, 1H), 2.17-2.04 (m, 1H), 1.87-1.58 (m, 3H); $^{13}$C NMR (CDCl$_3$, 150 MHz) δ 157.4, 155.1, 154.5, 137.6, 137.4, 130.4, 130.2, 129.6 (2C), 129.4, 122.9, 118.85, 118.82 (2C), 118.5, 116.97, 116.93, 69.8, 69.6, 53.9, 39.38, 39.33, 30.7, 29.9, 28.6, 28.5, 25.1, 24.1.

Methyl 5-(6-Phenoxy-1,2,3,4-tetrahydronaphthalene-2-carbonyl)-[1,3,4]oxadiazole-2-carboxylate (35)

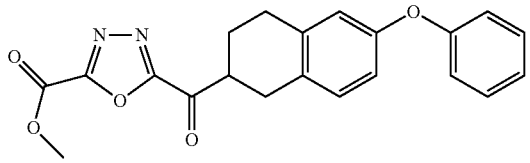 [SMILES: COC(=O)c1nnc(C(=O)C2CCc3cc(Oc4ccccc4)ccc3C2)o1]

The title compound was prepared from methyl 5-[hydroxy-(6-phenoxy-1,2,3,4-tetrahydronaphthalen-2-yl)methyl]-[1,3,4]oxadiazole-2-carboxylate (S95, 18.9 mg, 0.049 mmol) following general procedure E. Flash chromatography (SiO$_2$, 20% EtOAc-hexanes) yielded the title compound (14 mg, 75%) as a yellow solid: $^1$H NMR (CDCl$_3$, 600 MHz) δ 7.33 (t, 2H, J=7.8 Hz), 7.09 (t, 2H, J=7.8 Hz), 7.00 (d, 2H, J=8.4 Hz), 6.82-6.77 (m, 2H), 4.10 (s, 3H), 3.90-3.86 (m, 1H), 3.12-3.10 (m, 2H), 2.95-2.90 (m, 2H), 2.36-2.33 (m, 1H), 1.98-1.90 (m, 1H); $^{13}$C NMR (CDCl$_3$, 150 MHz) δ 188.8, 160.6, 157.4, 157.1, 155.3, 153.9, 136.8, 130.1, 129.6 (2C), 128.7, 123.0, 118.8, 118.6 (2C), 117.1, 54.2, 44.9, 30.0, 28.5, 25.3; HRMS-ESI-TOF m/z 379.1292 ([M+H]$^+$, C$_{21}$H$_{18}$N$_2$O$_5$ requires 379.1288). The enantiomers were separated using a semipreparative chiral phase HPLC column (Daicel ChiraCel OD, 10 μm, 2×25 cm, 40% EtOH-hexanes, 7 mL/min, α=1.05).

(S)-35: [α]$^{23}_D$ −46 (c 0.1, THF).
(R)-35: [α]$^{23}_D$ +36 (c 0.1, THF).

N'-(2-(tert-Butyldimethylsilyloxy)-2-(6-phenoxy-1,2,3,4-tetrahydronaphthalen-2-yl)acetyl)picolinohydrazide (S96)

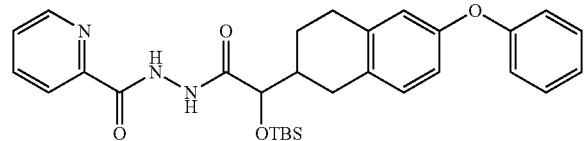 [SMILES: CC(C)(C)[Si](C)(C)OC(C(=O)NNC(=O)c1ccccn1)C1CCc2cc(Oc3ccccc3)ccc2C1]

A sample of 2-(tert-butyldimethylsilyloxy)-2-(6-phenoxy-1,2,3,4-tetrahydronaphthalen-2-yl)acetic acid (S91, 62 mg, 0.15 mmol) and pyridine-2-carboxylic acid hydrazide (21 mg, 0.15 mmol) were dissolved in CH$_2$Cl$_2$ (2 mL). EDCl (29 mg, 0.15 mmol) was added as a solid. The reaction mixture was stirred at room temperature for 16 h. The solvent was evaporated in vacuo and the residue was dissolved in EtOAc, washed with 1 N aqueous HCl, 5% aqueous NaHCO$_3$, saturated aqueous NaCl, and dried over Na$_2$SO$_4$. The solvent was removed under reduced pressure and flash chromatography (SiO$_2$, 10% MeOH—CH$_2$Cl$_2$) afforded the title compound (85.6 mg, 98%) as a colorless oil: $^1$H NMR (CDCl$_3$, 600 MHz) δ 9.10 (s, 1H), 9.07 (s, 1H), 8.58-8.53 (m, 1H), 8.29-8.13 (m, 1H), 7.87-7.83 (m, 1H), 7.47-7.40 (m, 1H), 7.30-7.27 (m, 3H), 7.06-6.80 (m, 4H), 6.75-7.67 (m, 3H), 4.35 (d, 0.5H, J=7.2 Hz), 4.31 (d, 0.5H, J=7.2 Hz), 1.67-1.63 (m, 3H), 1.24-1.14 (m, 2H), 0.95 (s, 9H), 0.16 (s, 3H), 0.14 (s, 3H); $^{13}$C NMR (CDCl$_3$, 150 MHz) δ 168.8, 168.7, 160.3, 160.2, 157.58, 157.54, 154.7, 154.6, 148.4, 148.2, 147.97, 147.96, 137.7, 137.5, 137.4, 137.2, 130.84, 130.82, 130.4, 130.1, 129.5 (2C), 126.8, 126.4, 126.3, 122.7, 122.6, 122.3, 122.1, 118.8, 118.4, 118.38, 118.35, 118.30, 116.7, 116.6, 76.4, 76.3, 39.6, 39.3, 31.3, 29.6, 29.4, 29.3, 28.5, 26.0, 25.7 (3C), 25.49, 25.47, 23.5, 18.2, 17.9, 14.6, −4.95, −4.99, −5.08.

2-((tert-Butyldimethylsilyloxy)(6-pheoxy-1,2,3,4-tetrahydrooaphthalen-2-yl)methyl)-5-(pyridin-2-yl)-1,3,4-oxadiazole (S97)

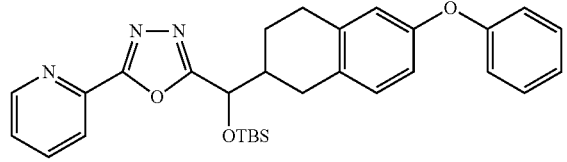 [SMILES: CC(C)(C)[Si](C)(C)OC(c1nnc(-c2ccccn2)o1)C1CCc2cc(Oc3ccccc3)ccc2C1]

A sample of N-(2-(tert-butyldimethylsilyloxy)-2-(6-phenoxy-1,2,3,4-tetrahydronaphthalen-2-yl)acetyl)picolinohydrazide (S96, 85.6 mg, 0.16 mmol) was dissolved in CH$_2$Cl$_2$ (3 mL). TsCl (92 mg, 0.48 mmol) and Et$_3$N (0.068 mL, 0.48 mmol) were added. The reaction mixture was stirred at room temperature for 16 h. The solvent was evaporated in vacuo and the residue was dissolved in EtOAc, washed with saturated aqueous NaCl, and dried over Na$_2$SO$_4$. The solvent was removed under reduced pressure. Purification by flash chromatography (SiO$_2$, 20% EtOAc-hexanes) afforded the title compound (53 mg, 64%) as a colorless oil: $^1$H NMR (CDCl$_3$, 600 MHz) δ 8.80 (s, 1H), 8.23 (d, 1H, J=8.4 Hz), 7.88 (t, 1H, J=8.4 Hz), 7.46 (t, 1H, J=7.2 Hz), 7.30 (t, 2H, J=7.2 Hz), 7.05 (t, 2H, J=7.2 Hz), 6.97-6.94 (m, 2H), 6.78-6.72 (m, 2H), 5.00 (d, 1H, J=7.2 Hz), 4.94 (d, 1H, J=7.2 Hz), 2.95-2.76 (m, 2H), 2.60-2.44 (m, 2H), 1.82-1.80 (m, 1H), 1.62-1.53 (m, 1H), 0.91 (s, 9H), 0.14 (s, 1.5H), 0.11 (s, 1.5H), −0.01 (s, 3H); $^{13}$C NMR (CDCl$_{13}$, 150 MHz) δ 167.7, 167.6, 164.2, 164.1, 157.6, 157.5, 154.88, 154.81, 143.43, 143.40, 137.9, 137.6, 137.1, 130.4, 130.3, 130.2, 129.9, 129.5 (2C), 125.86, 125.84, 123.0, 122.78, 122.74, 118.8, 118.4, 118.3, 116.8, 116.7, 70.5, 70.4, 39.99, 39.96, 30.8, 30.3, 29.6, 28.8, 28.6, 25.6 (3C), 25.3, 24.7, 18.14, 18.12, −5.06, −5.25, −5.28.

(6-Phenoxy-1,2,3,4-tetrahydronaphthalen-2-yl)(5-(pyridin-2-yl)-1,3,4-oxadiazol-2-yl)methanol (S98)

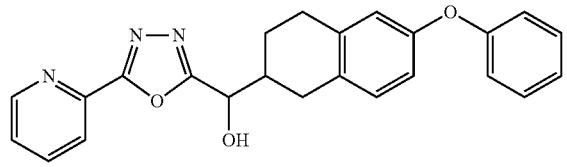 [SMILES: OC(c1nnc(-c2ccccn2)o1)C1CCc2cc(Oc3ccccc3)ccc2C1]

The title compound was prepared from 2-((tert-butyldimethylsilyloxy)(6-phenoxy-1,2,3,4-tetrahydronaphthalen-2-yl)methyl)-5-(pyridin-2-yl)-1,3,4-oxadiazole (S97, 53 mg, 0.10 mmol) following general procedure D. Flash chromatography (SiO$_2$, 50-100% EtOAc-hexanes) yielded the title compound (48 mg, 98%) as a yellow solid: $^1$H NMR (CDCl$_3$, 600 MHz) δ 8.75 (d, 1H, J=8.4 Hz), 8.23 (d, 1H J=8.4 Hz), 7.87 (t, 1H, J=8.4 Hz), 7.46 (t, 1H, J=7.2 Hz), 7.29 (t, 2H, J=7.2 Hz), 7.05 (t, 2H, J=7.2 Hz), 6.97-6.95 (, 2H), 6.76-6.72 (m, 2H), 5.00 (t, 0.5H, J=8.0 Hz), 5.01 (t, 0.5H, J=8.0 Hz), 4.20-4.17 (m, 1H), 2.99-2.76 (m, 1H), 2.53-2.49 (m, 1H), 2.27-2.24 (m, 1H), 2.06-1.90 (m, 2H), 1.68-1.54 (m, 2H); $^{13}$C NMR (CDCl$_3$, 150 MHz) δ 168.1, 168.0, 164.1, 157.5, 154.8, 150.1, 143.1, 137.8, 137.6, 137.3, 130.3, 130.2, 130.1, 129.9, 129.5 (2C), 126.0, 123.2, 122.7, 118.86, 118.81, 118.4 (2C), 116.85, 116.81, 69.7, 69.5, 39.38, 39.26, 30.9, 30.1, 28.75, 28.72, 25.6, 25.3, 24.3, 17.9.

(6-Phenoxy-1,2,3,4-tetrahydronaphthalen-2-yl)(5-(pyridin-2-yl)-1,3,4-oxadiazol-2-yl)methanone (36)

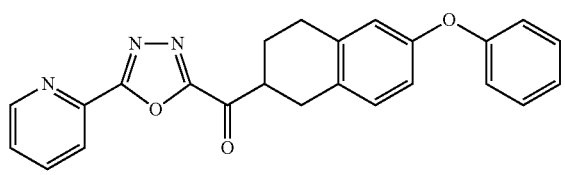 [SMILES: O=C(c1nnc(-c2ccccn2)o1)C1CCc2cc(Oc3ccccc3)ccc2C1]

The title compound was prepared from (6-phenoxy-1,2,3,4-tetrahydronaphthalen-2-yl)(5-(pyridin-2-yl)-1,3,4-oxadiazol-2-yl)methanol (S98, 48 mg, 0.12 mmol) following general procedure E. Flash chromatography (SiO$_2$, 20% EtOAc-hexanes) yielded the title compound (15 mg, 31%) as a yellow solid: $^1$H NMR (CDCl$_3$, 600 MHz) δ 8.85 (s, 1H), 8.30 (d, 1H, J=7.2 Hz), 7.93 (t, 2H, J=6.6 Hz), 7.54 (t, 2H, J=6.6 Hz), 7.33 (t, 2H, J=9.0 Hz), 7.09-6.99 (m, 4H), 6.82-6.78 (m, 2H), 3.96-3.91 (m, 1H), 3.14-2.88 (m, 4H), 2.38-2.35 (m, 1H), 1.99-1.94 (m, 1H); $^{13}$C NMR (CDCl$_3$, 150 MHz) δ 189.2, 165.1, 160.7, 157.4, 155.2, 150.7, 142.5, 137.3, 137.0, 130.1, 129.6 (2C), 129.1, 126.7, 124.0, 122.9, 118.8, 118.5 (2C), 117.0, 44.5, 30.2, 28.6, 25.5; HRMS-ESI-TOF m/z 398.1502 ([M+H]$^+$, C$_{24}$H$_9$N$_3$O$_3$ requires 398.1499). The enantiomers were separated using a semi-preparative chiral phase HPLC column (Daicel ChiraCel OD, 10 μm, 2×25 cm, 40% EtOH-hexanes, 7 mL/min, α=1.08).

(S)-36: [α]$^{23}_D$ −14 (c 0.1, THF).
(R)-36: [α]$^{23}_D$ +18 (c 0.1, THF).

Oxazol-2-yl-1,2,3,4-tetrahydronaphthalen-2-yl)methanol (S99)

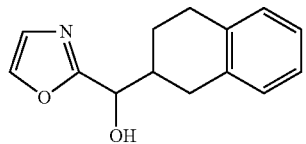 [SMILES: OC(c1ncco1)C1CCc2ccccc2C1]

Oxazole (0.205 mL, 3.12 mmol) in anhydrous THF (10 mL) was treated with BH$_3$·THF (1 M, 3.4 mL, 3.40 mmol) and the solution was stirred at room temperature for 1 h before being cooled to −78° C. and treated with 2.41 M n-BuLi (1.7 mL, 4.05 mmol) dropwise. The reaction mixture was stirred at −78° C. for 40 min before a solution of commercially available 1,2,3,4-tetrahydronaphthalene-2-carboxaldehyde (500 mg, 3.12 mmol) in THF (3 mL) was added. The reaction mixture was stirred at −78° C. for 2 h before being warmed to room temperature. A 5% HOAc-EtOH solution (50 mL) was added and this mixture was stirred at room temperature for 12 h. The solvent was removed under reduced pressure and the residue was dissolved in EtOAc, and washed with H$_2$O, saturated aqueous NaHCO$_3$, and saturated aqueous NaCl. The organic layer was dried over MgSO$_4$ and the solvent was removed under reduced pressure. Flash chromatography (SiO$_2$, 40% EtOAc-hexanes) afforded the title compound (264 mg, 37%) as a white solid: $^1$H NMR (CDCl$_3$, 400 MHz) δ 7.62 (s, 1H), 7.12-7.00 (m, 5H), 5.22 (brs, 1H), 4.78 (d, 0.5H, J=5.6 Hz), 4.75 (d, 0.5H, J=5.6 Hz), 3.49-2.63 (m, 2H), 2.63-2.60 (m, 1H), 2.42-2.36 (m, 2H), 2.22-2.19 (m, 1H), 1.79-1.76 (m, 1H); $^{13}$C NMR (CDCl$_3$, 100 MHz) δ 165.4, 138.6, 136.2, 136.0, 135.4, 135.2, 129.0, 128.9, 128.57, 128.51, 126.2, 125.45 (2C), 125.40, 70.9, 70.7, 39.46, 39.41, 31.3, 31.0, 28.6, 28.5, 25.1, 24.6.

Oxazol-2-yl(1,2,3,4-tetrahydronaphthalen-2-yl)methanone (37)

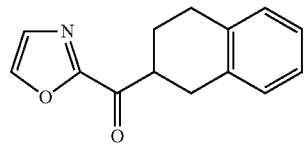 [SMILES: O=C(c1ncco1)C1CCc2ccccc2C1]

The title compound was prepared from oxazol-2-yl-1,2,3,4-tetrahydronaphthalen-2-yl)methanol (S99, 45 mg, 0.196 mmol) following general procedure E. Flash chromatography (SiO$_2$, 30% EtOAc-hexanes) yielded the title compound (37.8 mg, 84%) as a white solid: $^1$H NMR (CDCl$_3$, 600 MHz) δ 7.85 (s, 1H), 7.36 (s, 1H), 7.12-7.10 (m, 4H), 3.88-3.83 (m, 1H), 3.14-3.06 (m, 2H), 2.98-2.92 (m, 2H), 2.32-2.28 (m, 1H), 1.94-1.86 (m, 1H); $^{13}$C NMR (CDCl$_3$, 150 MHz) δ 190.5, 157.5, 141.6, 135.6, 134.7, 129.05, 129.02, 128.7, 125.9, 125.8, 43.4, 30.9, 28.6, 25.8; HRMS-ESI-TOF ml/228.1016 ([M+H]$^+$, C$_{14}$H$_{13}$NO$_2$ requires 228.1019). The enantiomers were separated using a semi-preparative chiral phase HPLC column (Daicel ChiraCel OD, 10 μm, 2×25 cm, 0.5% EtOH-hexanes, 7 mL/min, α=1.21).

(S)-37: [α]$^{23}_D$ −46 (c 0.1, THF).
(R)-37: [α]$^{23}_D$ +50 (c 0.1, THF).

2-((tert-Butyldimethylsilyloxy)-(1,2,3,4-tetrahydronaphthalen-2-yl)methyl)oxazole (S100)

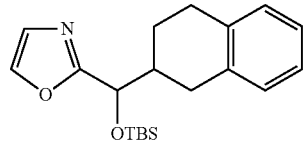 [SMILES: CC(C)(C)[Si](C)(C)OC(c1ncco1)C1CCc2ccccc2C1]

A solution of oxazol-2-yl-(1,2,3,4-tetrahydronaphthalen-2-yl)methanol (S99, 215 mg, 0.93 mmol), TBSCl (339 mg, 2.24 mmol) and imidazole (316 mg, 4.65 mmol) in DMF (3 mL) was stirred at room temperature for 16 h before it was diluted with EtOAc, washed with H$_2$O, and saturated aqueous NaCl. The organic layer was dried over MgSO$_4$ and the solvent was removed under reduced pressure. Flash chromatography (SiO$_2$, 10% EtOAc-hexanes) yielded the title compound (184 mg, 57%) as a thick colorless oil: $^1$H NMR (CDCl$_3$, 500 MHz) δ 7.66 (s, 1H), 7.13-7.02 (m, 5H), 4.78

(d, 0.5H, J=5.6 Hz), 4.74 (d, 0.5H, J=5.6 Hz), 2.90-2.76 (m, 3H), 2.59-2.53 (m, 2H), 2.37-2.26 (m, 1H), 1.76-1.73 (m, 1H), 0.96 (s, 9H), 0.12 (s, 1.5H), 0.10 (s, 1.5H), −0.05 (s, 1.5H), −0.07 (s, 1.5H); $^{13}$C NMR (CDCl$_3$, 125 MHz) δ 164.5, 164.4, 138.46, 138.40, 136.4, 136.2, 135.7, 135.4, 129.2, 129.0, 128.67, 128.61, 126.7, 125.54, 125.50, 72.37, 72.30, 40.3, 31.29, 31.25, 28.8, 28.7, 25.6 (3C), 25.3, 25.0, 18.1, −5.35, −5.39, −5.4.

2-((tert-Butyldimethylsilyloxy)-(1,2,3,4-tetrahydronaphthalen-2-yl)methyl)-5-(tributylstannyl)oxazole (S101)

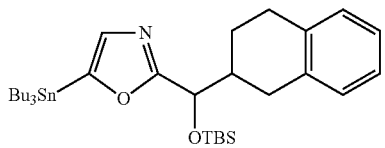

A solution of 2-((tert-butyldimetylsilyloxy)-1,2,3,4-tetrahydronaphthalen-2-yl)methyl)oxazole (S100, 184 mg, 0.53 mmol) in THF (5 mL) was cooled to −78° C. before it was treated with 2.41 M n-BuLi (0.25 mL, 0.58 mmol) dropwise. The reaction mixture was stirred at −78° C. for 2 h, treated with a solution of Bu$_3$SnCl (0.30 mL, 1.06 mmol) and stirred for 5 min. The solution was warmed to room temperature and diluted with EtOAc and washed with saturated aqueous NaCl. The organic layer was dried over MgSO$_4$ and the solvent was removed under reduced pressure. Flash chromatography (SiO$_2$, 10% EtOAc-hexanes) yielded the title compound (332 mg, 65%) as a colorless oil: $^1$H NMR (CDCl$_3$, 600 MHz) δ 7.13 (s, 1H), 7.09-7.00 (m, 3H), 6.99-6.80 (m, 1H), 4.78 (d, 0.5H, J=5.6 Hz), 4.74 (d, 0.5H, J=5.6 Hz), 2.85-2.75 (m, 3H), 2.56-2.48 (m, 1H), 2.36-2.24 (m, 2H), 1.69-1.56 (m, 27H), 1.36-1.33 (s, 9H), 0.09 (s, 1.5H), 0.05 (s, 1.5H), −0.12 (s, 1.5H), −0.13 (s, 1.5H); $^{13}$C NMR (CDCl$_3$, 150 MHz) δ 168.5, 154.6, 137.0, 136.3, 136.0, 135.7, 129.2, 129.0, 128.6, 128.5, 125.4, 125.3, 72.4, 40.5, 31.3, 28.88, 28.81 (3C), 27.7, 27.0, 26.7, 25.6 (3C), 25.4 (3C), 18.0, 17.4, 13.55 (3C), 13.53, 13.52, 10.1 (3C), −5.38, −5.40, −5.42, −5.44.

2-((tert-Butyldimethylsilyloxy)-(1,2,3,4-tetrahydronaphthalen-2-yl)methyl)-5-(pyridin-2-yl)oxazole (S102)

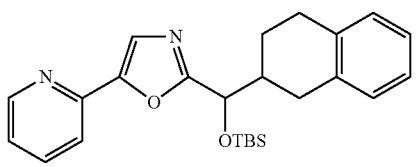 [SMILES: CC(C)(C)[Si](C)(C)OC(c1ncc(-c2ccccn2)o1)C1CCc2ccccc2C1]

The title compound was prepared from 2-((tert-butyldimethylsilyloxy)-(1,2,3,4-tetrahydronaphthalen-2-yl)methyl)-5-(tributylstannyl)oxazole (S101, 332 mg, 0.52 mmol) and 2-bromopyridine following general procedure C. Flash chromatography (SiO$_2$, 20% EtOAc-hexanes) yielded the title compound (128 mg, 59%) as a colorless oil: $^1$H NMR (CDCl$_3$, 600 MHz) δ 8.63 (d, 1H, J=4.2 Hz), 7.77-7.66 (m, 2H), 7.23-7.21 (m, 1H), 7.09-7.00 (m, 3H), 4.82 (d, 0.5H, J=5.6 Hz), 4.76 (d, 0.5H, J=5.6 Hz), 2.88-2.79 (m, 3H), 2.67-2.57 (m, 1H), 2.42-2.27 (m, 2H), 1.83-1.81 (m, 3H), 0.98 (s, 9H), 0.11 (s, 1.5H), 0.05 (s, 1.5H), −0.12 (s, 1.5H), −0.13 (s, 1.5H); $^{13}$C NMR (CDCl$_3$, 150 MHz) δ 164.8, 164.6, 150.8, 150.7, 149.8, 147.34, 147.30, 136.8, 136.4, 136.2, 135.7, 135.4, 129.2, 129.1, 128.7, 128.6, 125.58, 125.53, 125.51, 125.1, 125.0, 122.77, 122.75, 119.0, 118.9, 72.5, 72.4, 40.38, 40.35, 31.4, 31.1, 28.8, 28.7, 26.7, 25.6 (3C), 25.5, 25.0, 18.3, 13.5, −5.14, −5.28, −5.32.

(5-(Pyridin-2-yl)oxazol-2-yl)(-1,2,3,4-tetrahydronaphthalen-2-yl)methanol (S103)

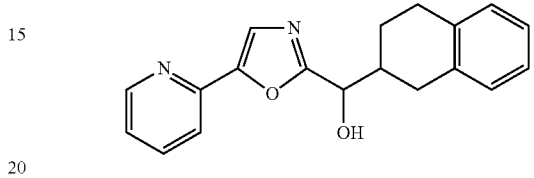

The title compound was prepared from 2-((tert-butyldimethylsilyloxy)-1,2,3,4-tetrahydronaphthalen-2-yl)methyl)-5-(pyridin-2-yl)oxazole (S102, 128 mg, 0.30 mmol) following general procedure D. Flash chromatography (SiO$_2$, 50-100% EtOAc-hexanes) yielded the title compound (84.4 mg, 92%) as a yellow oil: $^1$H NMR (CDCl$_3$, 600 MHz) δ 8.62 (d, 1H, J=4.2 Hz), 7.74 (t, 1H, J=7.0 Hz), 7.65 (s, 1H), 7.62 (d, 1H, J=7.5 Hz), 7.23-7.21 (m, 1H), 7.09-7.01 (m, 3H), 4.86 (d, 0.5H, J=5.6 Hz), 4.82 (d, 0.5H, J=5.6 Hz), 3.64 (s, 0.5H), 3.61 (s, 0.5H), 2.92-2.81 (m, 2H), 2.72-2.70 (m, 2H), 2.46-2.44 (m, 1H), 2.21-2.18 (m, 1H), 1.92-1.90 (m, 1H), 1.67-1.60 (m, 1H); $^{13}$C NMR (CDCl$_3$, 150 MHz) δ 165.3, 165.2, 151.1, 149.8, 147.03, 147.01, 136.9, 136.3, 136.2, 135.5, 135.3, 129.3, 129.1, 128.76, 128.73, 125.7, 125.68, 125.66, 125.62, 124.93, 124.91, 123.0, 119.3, 71.5, 71.3, 39.79, 39.75, 31.5, 30.7, 28.84, 28.81, 25.5, 24.5.

(5-(Pyridin-2-yl)oxazol-2-yl)(1,2,3,4-tetrahydronaphthalen-2-yl)methanone (38)

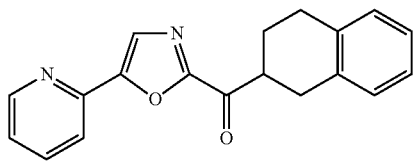 [SMILES: O=C(c1ncc(-c2ccccn2)o1)C1CCc2ccccc2C1]

The title compound was prepared from (5-(pyridin-2-yl)oxazol-2-yl)(1,2,3,4-tetrahydronaphthalen-2-yl)methanol (S103, 84.4 mg, 0.27 mmol) following general procedure E. Flash chromatography (SiO$_2$, 20% EtOAc-hexanes) yielded the title compound (78.6 mg, 96%) as a white solid: $^1$H NMR (CDCl$_3$, 600 MHz) δ 8.67 (d, 1H, J=4.2 Hz), 7.91 (s, 1H), 7.87 (d, 1H, J=7.0 Hz), 7.81 (t, 1H, J=7.0 Hz), 7.32-7.30 (m, 1H), 7.13-7.10 (m, 4H), 3.93-3.88 (m, 1H), 3.17-3.07 (m, 2H), 3.02-2.92 (m, 2H), 2.34-2.30 (m, 1H), 1.99-1.93 (m, 1H); $^{13}$C NMR (CDCl$_3$, 150 MHz) δ 190.4, 156.8, 153.3, 150.0, 146.2, 137.0, 135.5, 134.7, 129.0, 128.7, 126.9, 125.8, 125.7, 124.0, 120.3, 43.3, 31.0, 28.6, 25.9; HRMS-ESI-TOF m/z 305.1289 ([M+H]$^+$, C$_{19}$H$_{16}$N$_2$O$_2$ requires 305.1284). The enantiomers were separated using a semipreparative chiral phase HPLC column (Daicel ChiraCel OD, 10 μm, 2×25 cm, 0.5% EtOH-hexanes, 7 mL/min, α=1.15).

(S)-38: [α]$^{23}_D$ −18 (c 0.1, THF).
(R)-38: [α]$^{23}_D$ +24 (c 0.1, THF).

(Indan-2-yl)methanol (S104)

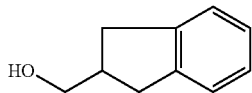 [SMILES: OCC1Cc2ccccc2C1]

A solution of indane-2-carboxylic acid (800 mg, 4.93 mmol) was dissolved in anhydrous THF (20 mL) and cooled to 0° C. and LiAlH$_4$ (187 mg, 4.93 mmol) was added portion wise. The reaction mixture was stirred for 1 h at 0° C. The solution was warmed to room temperature and diluted with EtOAc and washed with saturated aqueous NaCl. The organic layer was dried over MgSO$_4$ and the solvent was removed under reduced pressure. Flash chromatography (SiO$_2$, 20% EtOAc-hexanes) yielded the title compound (481 mg, 66%) as a colorless oil: $^1$H NMR (CDCl$_3$, 400 MHz) δ 7.29-7.26 (m, 2H), 7.23-7.19 (m, 2H), 3.69 (d, 2H, J=6.4 Hz), 3.16-3.09 (m, 2H), 2.83-2.67 (m, 4H), 2.67 (s, 1H); $^{13}$C NMR (CDCl$_3$, 100 MHz) δ 142.5 (2C), 126.1 (2C), 124.5 (2C), 66.2, 41.2, 35.6 (2C).

Indane-2-carboxaldehyde (S105)

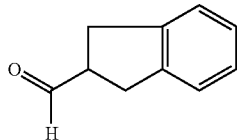 [SMILES: O=CC1Cc2ccccc2C1]

The title compound was prepared from (indan-2-yl)methanol (S104, 300 mg, 2.02 mmol) following general procedure B. Following fast filtration through Florisil, the solvent was removed under reduced pressure to afford the title compound (300 mg, 88%) as a yellow oil: $^1$H NMR (CDCl$_3$, 400 MHz) δ9.78 (s, 1H), 7.26-7.18 (m, 4H), 3.33-3.18 (m, 5H); $^{13}$C NMR (CDCl$_3$, 100 MHz) δ 202.4, 140.7 (2C), 126.3 (2C), 124.2 (2C), 50.2, 32.5 (2C).

(Indan-2-yl)(oxazol-2-yl)methanol (S106)

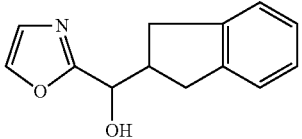 [SMILES: OC(c1ncco1)C1Cc2ccccc2C1]

Oxazole (0.135 mL, 2.05 mmol) in anhydrous THF (7 mL) was treated with BH$_3$-THF (1 M, 2.3 mL, 2.23 mmol) and the solution was stirred at room temperature for 1 h before being cooled to −78° C. and treated with 2.41 M n-BuLi (1.1 mL, 2.66 mmol) dropwise. The reaction mixture was stirred at −78° C. for 40 min before a solution of indane-2-carboxaldehyde (S105, 300 mg, 2.05 mmol) in THF (2 mL) was added. The reaction mixture was stirred at −78° C. for 2 h before being warmed to room temperature. A 5% HOAc-EtOH solution (50 mL) was added and the mixture was stirred at room temperature for 12 h. The solvent was removed under reduced pressure and the residue was dissolved in EtOAc, washed with H$_2$O, saturated aqueous NaHCO$_3$, and saturated aqueous NaCl. The organic layer was dried over MgSO$_4$ and the solvent was removed under reduced pressure. Flash chromatography (SiO$_2$, 20% EtOAc-hexanes) afforded the title compound (161 mg, 35%) as white solid: $^1$H NMR (CDCl$_3$, 400 MHz) δ 7.59 (s, 1H), 7.26-7.12 (m, 3H), 7.05 (s, 1H), 4.78 (d, 1H, J=6.8 Hz), 4.51 (s, 1H), 3.14-3.04 (m, 3H), 2.96-2.75 (m, 2H); $^{13}$C NMR (CDCl$_3$, 100 MHz) δ 165.6, 142.2, 142.1, 138.7, 126.4, 126.28, 126.22, 124.4, 124.3, 70.1, 44.0, 35.2, 35.0.

(Indan-2-yl)(oxazol-2-yl)methanone (39)

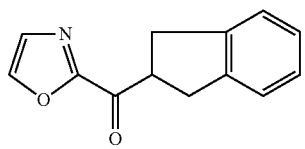 [SMILES: O=C(c1ncco1)C1Cc2ccccc2C1]

The title compound was prepared from (indan-2-yl)(oxazol-2-yl)methanol (S106, 20 mg, 0.092 mmol) following general procedure E. Flash chromatography (SiO$_2$, 20% EtOAc-hexanes) yielded the title compound (15.2 mg, 77%) as a white solid: $^1$H NMR (CDCl$_3$, 600 MHz) δ 7.85 (s, 1H), 7.37 (s, 1H), 7.23-7.21 (m, 2H), 7.19-7.16 (m, 2H), 4.42-4.37 (m, 1H), 3.41-3.30 (m, 4H); $^{13}$C NMR (CDCl$_3$, 150 MHz) δ 188.9, 157.8, 141.6, 141.1, 129.1 (2C), 126.7 (2C), 124.3 (2C), 47.3, 35.5 (2C); HRMS-ESI-TOF m/z 214.0862 ([M+H]$^+$, C$_{13}$H$_{11}$NO$_2$ requires 214.0863).

2-((tert-Butyldimethylsilyloxy)(indan-2-yl)methyl) oxazole (S107)

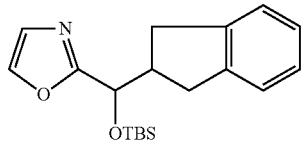 [SMILES: CC(C)(C)[Si](C)(C)OC(c1ncco1)C1Cc2ccccc2C1]

A solution of (indan-2-yl)(oxazol-2-yl)methanol (S105, 100 mg, 0.46 mmol), TBSCl (168 mg, 1.11 mmol) and imidazole (156 mg, 2.3 mmol) in DMF (1 mL) was stirred at room temperature for 16 h before it was diluted with EtOAc, and washed with H$_2$O, and saturated aqueous NaCl. The organic layer was dried over MgSO$_4$ and the solvent was removed under reduced pressure. Flash chromatography (SiO$_2$, 10% EtOAc-hexanes) yielded the title compound (43.2 mg, 28%) as a thick colorless oil: $^1$H NMR (CDCl$_3$, 600 MHz) δ 7.63 (s, 1H), 7.20-7.19 (m, 1H), 7.13-7.11 (m, 3H), 7.08 (s, 1H), 4.78 (d, 1H, J=6.8 Hz), 3.12-3.01 (m, 3H), 2.84-2.70 (m, 2H), 0.86 (s, 9H), 0.06 (s, 3H), −0.11 (s, 3H): $^{13}$C NMR (CDCl$_3$, 150 MHz) δ 164.7, 142.5, 142.3, 138.5, 126.8, 126.2, 126.1, 124.44, 124.40, 71.4, 45.1, 35.6, 34.9, 25.6 (3C), 18.1, −5.2, −5.3.

2-((tert-Butyldimethylsilyloxy)(indan-2-yl)methyl)-5-(tributylstannyl)oxazole (S108)

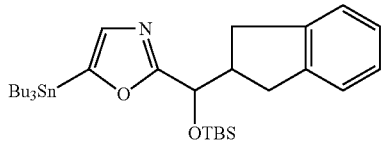

A solution of 2-((tert-butyldimethylsilyloxy)(indan-2-yl)methyl)oxazole (S107, 43.2 mg, 0.13 mmol) in THF (1 mL) was cooled to −78° C. before it was treated with 2.16 M n-BuLi (0.10 mL, 0.14 mmol) dropwise. The reaction mixture was stirred at −78° C. for 2 h, and treated with a solution of Bu$_3$SnCl (0.07 mL, 0.26 mmol) and stirred for 5 min. The solution was warmed to room temperature and diluted with EtOAc and washed with saturated aqueous NaCl. The organic layer was dried over MgSO$_4$ and the solvent was removed under reduced pressure. Flash chromatography (SiO$_2$, 0-10% EtOAc-hexanes) yielded the title compound (80.5 mg, 65%) as a thick colorless oil: $^1$H NMR (CDCl$_3$, 500 MHz) δ 7.19-7.09 (m, 5H), 4.81 (d, 1H, J=6.8 Hz), 3.10-3.01 (m, 3H), 2.82-2.69 (m, 2H), 1.66-1.62 (m, 6H), 1.38-1.27 (m, 6H), 1.12-1.09 (m, 6H), 0.94-0.85 (m, 9H), 0.80 (s, 9H), 0.03 (s, 3H), −0.14 (s, 3H); $^{13}$C NMR (CDCl$_3$, 125 MHz) δ 168.6, 154.9, 142.5, 137.2, 126.1 (2C), 126.0, 124.4 (2C), 124.3, 99.5, 71.5, 45.3, 35.6, 35.0, 28.8, 27.8, 27.0, 26.8, 25.6 (3C), 17.5, 13.6, 13.5, 10.2, −5.2, −5.3.

2-((tert-Butyldimethylsilyloxy)(indan-2-yl)methyl)-5-(pyridin-2-yl)oxazole (S109)

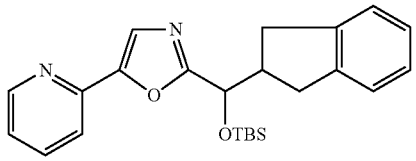 [SMILES: CC(C)(C)[Si](C)(C)OC(c1ncc(-c2ccccn2)o1)C1Cc2ccccc2C1]

The title compound was prepared from 2-((tert-butyldimethylsilyloxy)(indan-2-yl)methyl)-5-(tributylstannyl)oxazole (S108, 80 mg, 0.12 mmol) and 2-bromopyridine following general procedure C. Flash chromatography (SiO$_2$, 30% EtOAc-hexanes) yielded the title compound (28.7 mg, 59%) as a colorless oil: $^1$H NMR (CDCl$_3$, 600 MHz) δ 8.63 (d, 1H, J=4.8 Hz), 7.76 (t, 1H, J=7.8 Hz), 7.67-7.64 (m, 2H), 7.24-7.10 (m, 5H), 4.82 (d, 1H, J=6.8 Hz), 3.14-3.07 (m, 3H), 2.91-2.78 (m, 2H), 0.88 (s, 9H), 0.09 (s, 3H), −0.06 (s, 3H); $^{13}$C NMR (CDCl$_3$, 150 MHz) δ 164.9, 150.8, 149.8, 147.3, 142.5, 142.3, 136.8, 126.2, 126.1, 125.1, 124.46, 124.44, 122.8, 119.0, 71.5, 45.1, 35.5, 35.0, 25.6 (3C), 18.1, −5.0, −5.2.

(Indan-2-yl)(5-(pyridin-2-yl)oxazol-2-yl)methanol (S110)

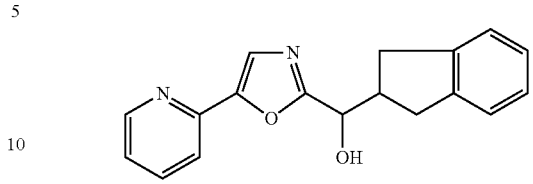

The title compound was prepared from 2-((tert-butyldimethylsilyloxy)(indan-2-yl)methyl)-5-(pyridin-2-yl)oxazole (S109, 28.7 mg, 0.07 mmol) following general procedure D. Flash chromatography (SiO$_2$, 50-100% EtOAc-hexanes) yielded the title compound (20.9 mg, 98%) as a colorless oil: $^1$H NMR (CDCl$_3$, 600 MHz) δ 8.63 (d, 1H, J=4.8 Hz), 7.74 (t, 1H, J=7.8 Hz), 7.62-7.60 (m, 2H), 7.24-7.10 (m, 5H), 4.88 (d, 1H, J=6.8 Hz), 3.91 (s, 1H), 3.16-3.11 (m, 3H), 3.03-2.88 (m, 2H); $^{13}$C NMR (CDCl$_3$, 150 MHz) δ 165.4, 151.0, 149.8, 146.9, 142.2, 142.1, 136.9, 126.35, 126.30, 124.9, 124.5, 124.4, 123.0, 119.3, 70.4, 44.1, 35.2, 35.1.

(Indan-2-yl)(5-(pyridin-2-yl)oxazol-2-yl)methanone (40)

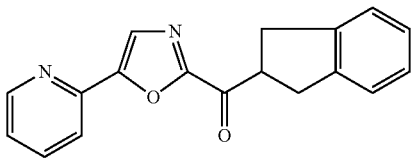 [SMILES: O=C(c1ncc(-c2ccccn2)o1)C1Cc2ccccc2C1]

The title compound was prepared from (indan-2-yl)(5-(pyridin-2-yl)oxazol-2-yl)methanol (S110, 20.9 mg, 0.071 mmol) following general procedure E. Flash chromatography (SiO$_2$, 30% EtOAc-hexanes) yielded the title compound (15.5 mg, 75%) as a white solid: $^1$H NMR (CDCl$_3$, 600 MHz) δ 8.67 (d, 1H, J=4.8 Hz), 7.93 (s, 1H), 7.88 (d, 1H, J=7.8 Hz), 7.82 (t, 1H, J=7.8 Hz), 7.33-7.31 (m, 1H), 7.24-7.16 (m, 4H), 4.48-4.42 (m, 1H), 3.44-3.37 (m, 4H); $^{13}$C NMR (CDCl$_3$, 150 MHz) δ 189.0, 157.1, 153.3, 150.1, 146.2, 141.2, 137.1, 126.9, 126.7 (2C), 124.4 (2C), 124.1, 120.4, 47.3, 35.7 (2C); HRMS-ESI-TOF m/z 291.1129 ([M+H]$^+$, C$_{18}$H$_{14}$N$_2$O$_2$ requires 291.1128).

TABLE 11

Data processing and refinement statistics for FAAH-12 X-Ray crystal structure

| Data collection | |
|---|---|
| Space group | P3$_2$21 |
| Cell dimensions | |
| a, b, c (Å) | 103.30, 103.30, 253.36 |
| α, β, γ (°) | 90, 90, 120 |
| Resolution (Å) | 30-1.90 (1.96-1.90) |
| R$_{merge}$ (%) | 9.4 (62.0) |
| I/σI | 12.9 (2.6) |
| Completeness (%) | 95.6 (87.4) |
| Redundancy | 6.2 (5.7) |

TABLE 11-continued

Data processing and refinement statistics for FAAH-12 X-Ray crystal structure

| Refinement | |
|---|---|
| Resolution (Å) | 1.90(1.92-1.90) |
| No. reflections | 118622 |
| $R_{work}/R_{free}$ (%) | 15.4(21.6)/18.5(25.0) |
| No. atoms | 9527 |
| Protein | 8481 |
| Ligand/ion | 61 |
| Water | 985 |
| B-factors | |
| Protein | 25.65 |
| Ligand/ion | 24.4 |
| Water | 19.5 |
| R.m.s. deviations | 36.5 |
| Bond lengths (Å) | 0.013 |
| Bond angles (°) | 1.644 |

TABLE 12

Enantionmeric Purity Analysis[a]

| Compd | Purity |
|---|---|
| (S)-3 | 98 |
| (R)-3 | 98 |
| (S)-4 | 98 |
| (R)-4 | 98 |
| (S)-5 | 98 |
| (R)-5 | 98 |
| (S)-6 | 98 |
| (R)-6 | 98 |
| (S)-7 | >99 |
| (R)-7 | >99 |
| (S)-8 | 98 |
| (R)-8 | 98 |
| (S)-9 | 98 |
| (R)-9 | 98 |
| (S)-10 | 99 |
| (R)-10 | 99 |
| (S)-11 | 98 |
| (R)-11 | 98 |
| (S)-12 | 98 |
| (R)-12 | 98 |
| (S)-13 | 98 |
| (R)-13 | 98 |
| (S)-14 | 98 |
| (R)-14 | 98 |
| (S)-15 | 98 |
| (R)-15 | 98 |
| (S)-16 | 98 |
| (R)-16 | 98 |
| (S)-17 | 95 |
| (R)-17 | 95 |
| (S)-18 | 98 |
| (R)-18 | 98 |
| (S)-19 | 98 |
| (R)-19 | 98 |
| (S)-20 | 98 |
| (R)-20 | 95 |
| (S)-21 | 98 |
| (R)-21 | 98 |
| (S)-22 | 98 |
| (R)-22 | 98 |
| (S)-23 | 95 |
| (R)-23 | 95 |
| 24 | 98 |
| 25 | 98 |
| (S)-26 | 95 |
| (R)-26 | 95 |
| (S)-27 | 95 |
| (R)-27 | 95 |
| (S)-28 | 98 |
| (R)-28 | 98 |
| (S)-29 | 98 |
| (R)-29 | 98 |
| 30 | 98 |
| (S)-31 | 95 |
| (R)-31 | 95 |
| (S)-32 | 98 |
| (R)-32 | 98 |
| (S)-33 | 98 |
| (R)-33 | 98 |
| (S)-34 | 98 |
| (R)-34 | 95 |
| (S)-35 | 95 |
| (R)-35 | 95 |
| (S)-36 | 98 |
| (R)-36 | 98 |
| (S)-37 | 98 |
| (R)-37 | 98 |
| (S)-38 | 95 |
| (R)-38 | 95 |
| 39 | 99 |
| 40 | 98 |

[a]Purity of each compound was determined on an Agilent 1100 LC/MS instrument on a ZORBAX® SB-C18, 3.5 mm, 4.6 × 50, a flow rate of 0.75 mL/min, detection at 220 and 254 nm, with a 10-98% acetonitrile/water/0.1% formic acid gradient and a 50-98% acetonitrile/water/0.1% formic acid gradient.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A compound of formula (I)

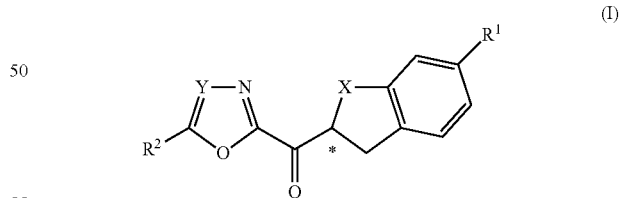

wherein:

$R^2$ is hydrogen, halo, haloalkyl, nitrile, C(O)OR', C(O)N(R')$_2$, aryl, or heteroaryl, wherein the aryl or heteroaryl is optionally mono- or independently multisubstituted with J;

X is CH$_2$ or CH$_2$CH$_2$;

Y is CH or N;

$R^1$ is selected from the group consisting of H, aryl, —Z-aryl, heteroaryl, and —Z-heteroaryl, wherein Z is selected from C$_{1-6}$alkylene, oxy, —O—C$_{1-6}$alkylene, —S(O)$_w$, —S(O)$_w$—C$_{1-6}$alkylene, wherein w is 0, 1 or 2, NR', and alkyleneNR', wherein aryl or heteroaryl can be mono- or independently multi-substituted with J, or can be fused with a 5-7 membered cycloalkyl, heterocyclyl, aryl, or heteroaryl optionally further mono- or independently multi-substituted with J, or both;

* indicates a chiral carbon atom which can be of the S absolute configuration, the R absolute configuration, or any mixture thereof, including a racemic mixture;

J is selected from the group consisting of F, Cl, Br, I, OR', OC(O)N(R')$_2$, CN, NO, NO$_2$, ONO$_2$, N$_3$, CF$_3$, OCF$_3$, R', methylenedioxy, ethylenedioxy, N(R')$_2$, SR', SOR', SO$_2$R', SO$_2$N(R')$_2$, SO$_3$R', C(O)R',C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', and C(=NOR')R'; R' is selected, independently for each occurrence, from the group consisting of hydrogen, C$_{1-6}$alkyl, acyl, C$_{3-6}$cycloalkyl, C$_{2-6}$alkenyl, phenyl, heterocyclyl, heteroaryl, and heteroarylalkyl, wherein alkyl, acyl, cycloalkyl, phenyl, heterocyclyl, heteroaryl, or heteroarylalkyl is optionally substituted with one, two or three substituents selected from the group consisting of halogen, cyano, hydroxyl, phenyl, and heterocyclyl, or wherein two R' groups, when bonded to a nitrogen atom or to two adjacent nitrogen atoms can together with the nitrogen atom or atoms form a heterocyclyl, which can be mono- or independently multi-substituted with one, two or three substitutents selected from the group consisting of halogen, hydroxyl, cyano, C$_{1-6}$alkyl, acyl, C$_{3-6}$cycloalkyl, C$_{2-6}$alkenyl, phenyl, and heterocyclyl;

or a pharmaceutically acceptable salt thereof.

2. The compound of claim 1 wherein R$^2$ is heteroaryl.

3. The compound of claim 1 wherein R$^2$ is a 2-, 3-, or 4-pyridyl, wherein the pyridyl is optionally mono- or independently multi-substituted with J, and wherein any pyridyl is optionally fused with a 5-7 membered cycloalkyl, heterocyclyl, aryl, or heteroaryl, any of which cycloalkyl, heterocyclyl, aryl, or heteroaryl can be further mono- or independently multi-substituted with J.

4. The compound of claim 1 wherein R$^2$ is 2-pyridyl, optionally mono- or independently multi-substituted with J.

5. The compound of claim 4 wherein the 2-pyridyl is unsubstituted or is substituted with carboxylic acid, alkoxycarbonyl or carboxamido group.

6. The compound of claim 4, wherein R$^2$ is

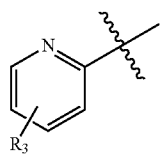

wherein R$^3$ is selected from the group consisting of hydrogen, hydroxyl, cyano, and —C(O)O—R$^4$, wherein R$^4$ is H or C$_{1-4}$alkyl., and wherein a wavy line indicates a point of bonding.

7. The compound of claim 6 wherein R$^2$ is selected from the set consisting of

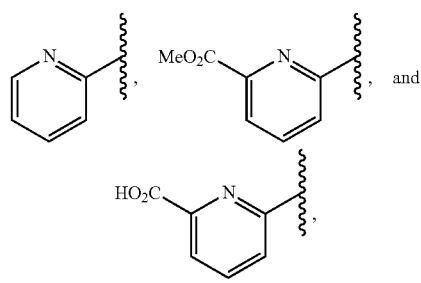

wherein a wavy line indicates a point of attachment.

8. The compound of claim 1 wherein R$^1$ is aryl, aralkyl, aryloxy, or aralkoxy, and of which aryl, aralkyl, aryloxy, or aralkoxy is optionally mono- or independently multi-substituted with J.

9. The compound of claim 8 wherein R$^1$ is phenyl, phenoxy, or benzyloxy, any of which optionally mono- or independently multi-substituted with J.

10. The compound of claim 1 wherein the chiral center is of the S absolute configuration.

11. A compound of claim 1 wherein the compound inhibits the bioactivity of a fatty acid amide hydrolase (FAAH) at a therapeutically achievable concentration.

12. A pharmaceutical composition comprising the compound of claim 1 and a pharmaceutically acceptable excipient.

13. The composition of claim 12 adapted for oral administration.

14. A compound selected from one of the following

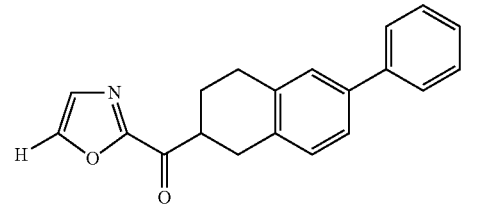

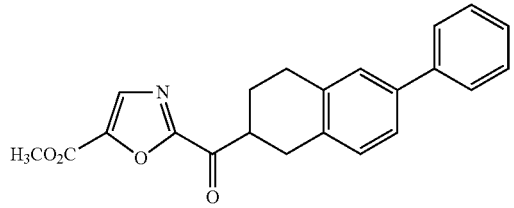

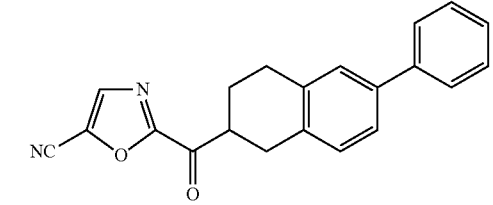

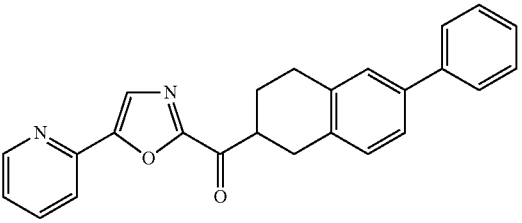

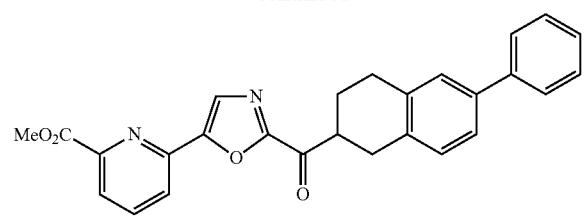
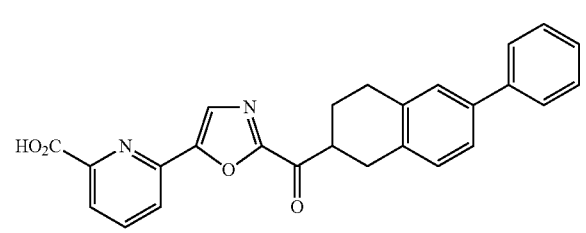
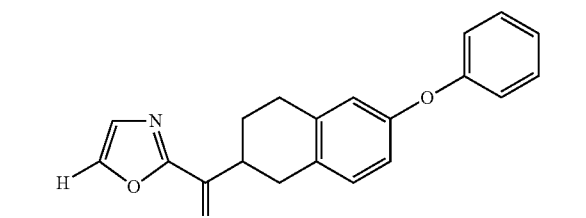
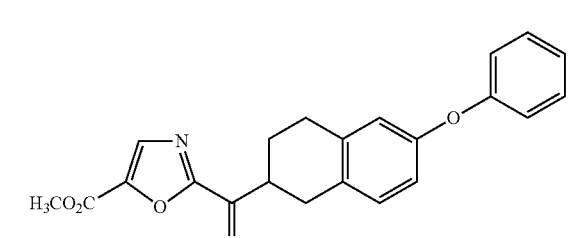
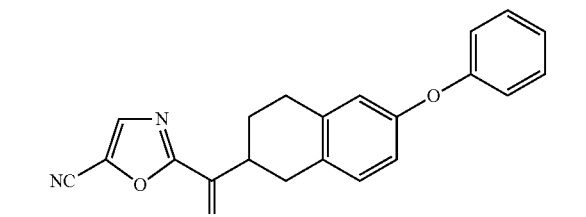
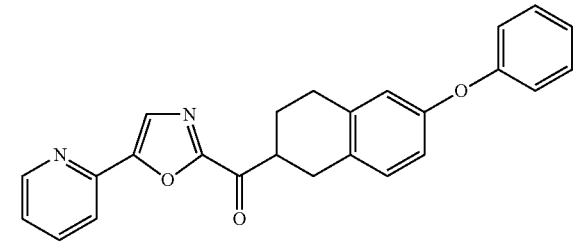
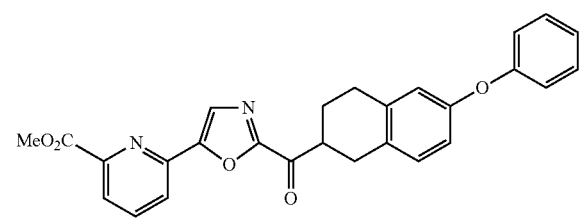
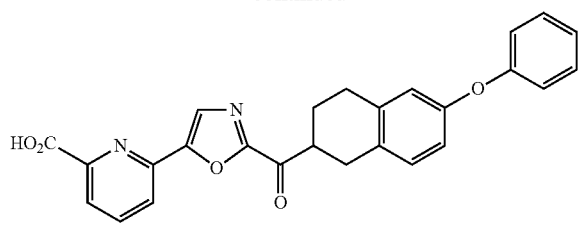
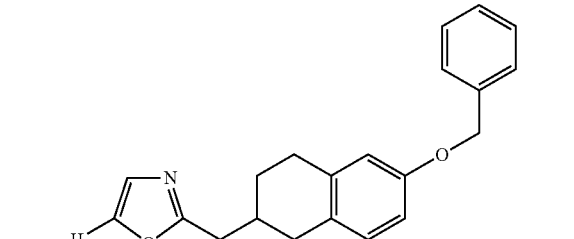
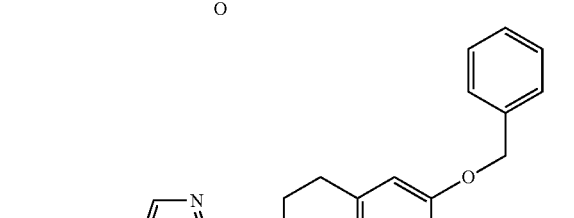
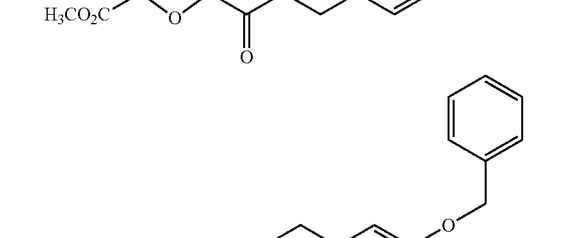
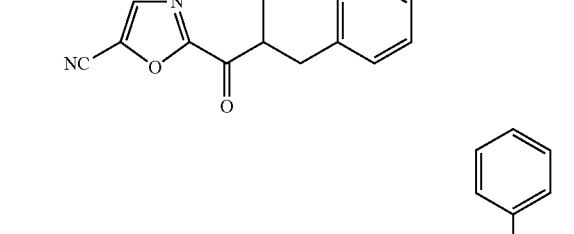
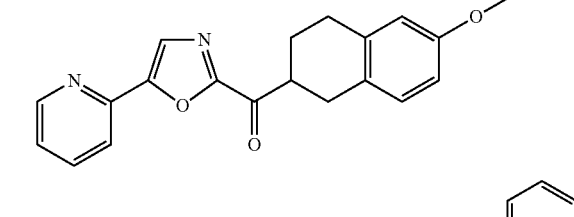
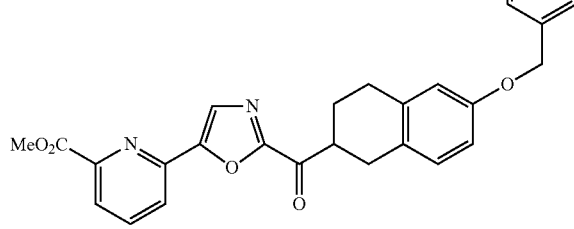

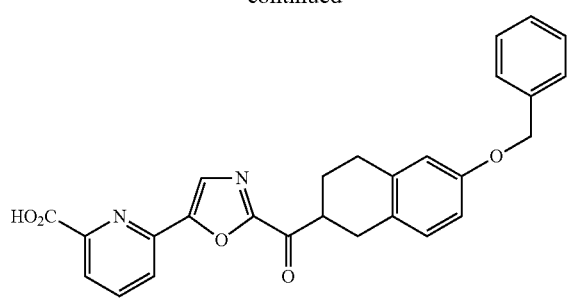
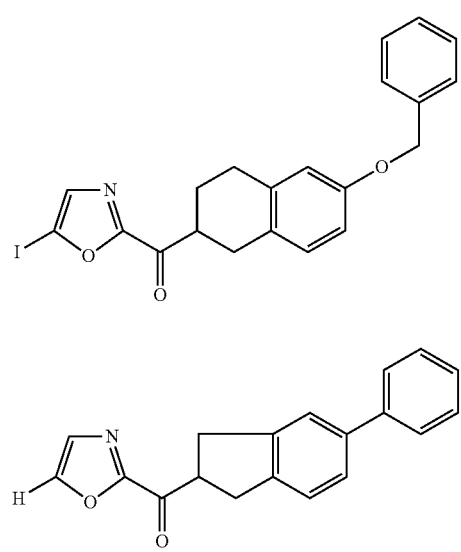
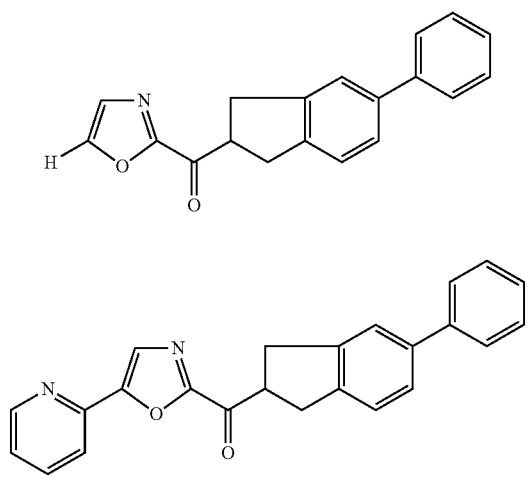
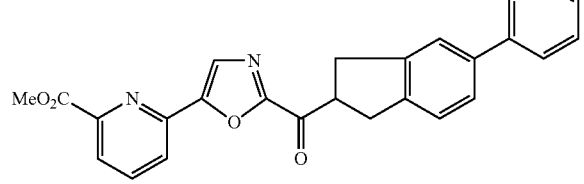
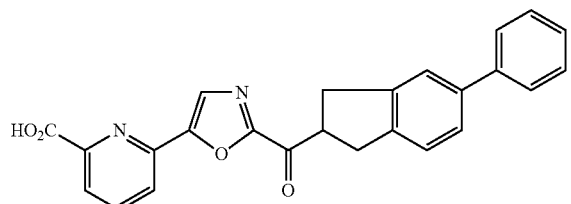
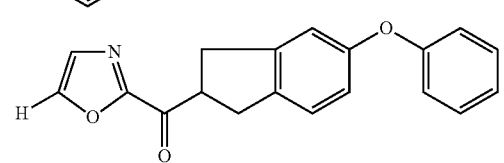
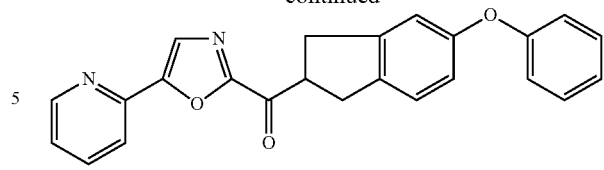
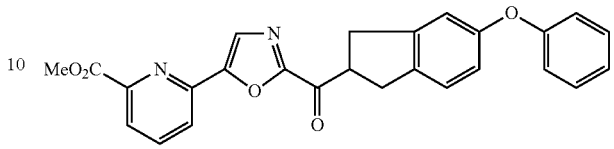
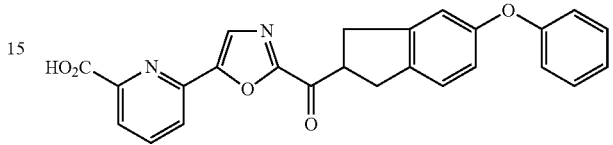
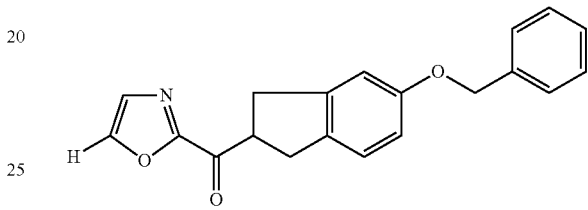
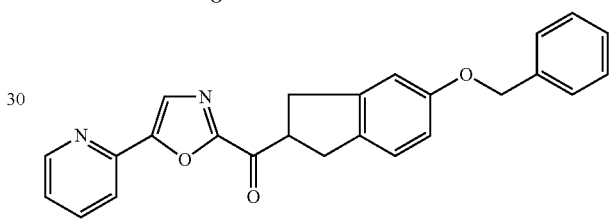
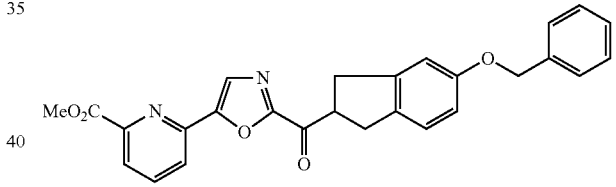
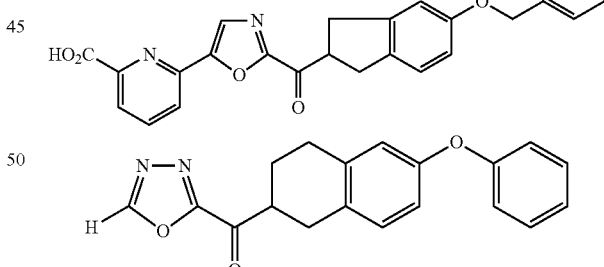
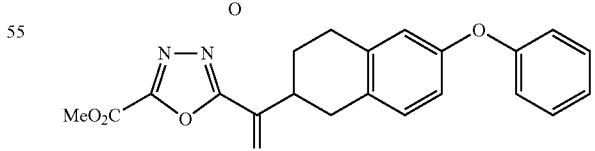
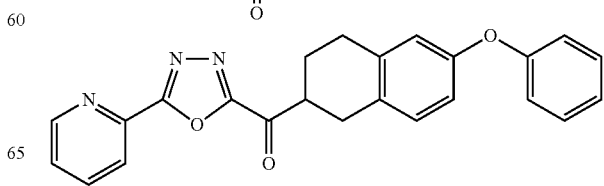

-continued

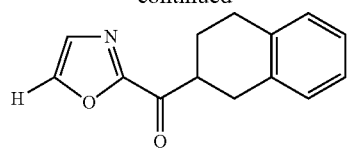

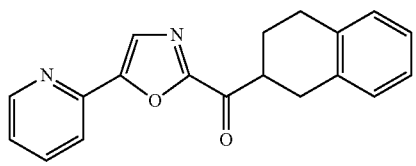

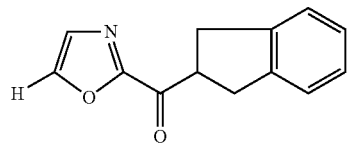

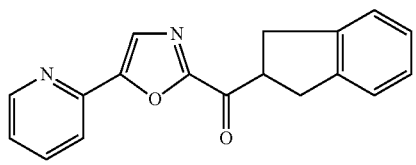

or a pharmaceutically acceptable salt thereof.

15. The compound of claim 14, wherein the compound is

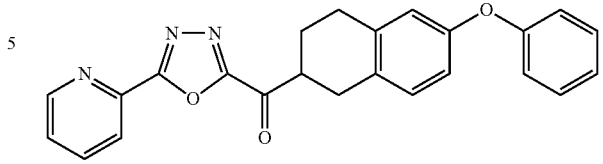

or a pharmaceutically acceptable salt thereof.

16. A pharmaceutical composition comprising the compound of claim 14 and a pharmaceutically acceptable excipient.

17. A method of inhibiting FAAH, comprising contacting the FAAH with an effective amount or concentration of a compound of claim 1.

18. The method of claim 17 wherein the contacting takes place in vitro or in vivo.

19. A method of treating pain or of treating a sleep disorder in a patient afflicted therewith, comprising administering to the patient an effective amount of a compound of claim 1 at a frequency and for a duration of time sufficient to provide a beneficial effect to the patient.

20. The method of claim 19 further comprising administration of a second medicament.

21. The method of claim 20 wherein the second medicament comprises an opiate analgesic, a non-opiate analgesic, a cannabinoid, an anti-inflammatory, a COX-2 inhibitor, a soporific, or a febricide.

22. The method of claim 19 wherein the compound is administered orally.

23. The method of claim 19 wherein the administration of a single dose of the compound results in a long-lasting amelioration of pain.

* * * * *

UNITED STATES PATENT AND TRADEMARK OFFICE
CERTIFICATE OF CORRECTION

PATENT NO. : 9,504,675 B2
APPLICATION NO. : 13/983369
DATED : November 29, 2016
INVENTOR(S) : Dale L. Boger It is certified that error appears in the above-identified patent and that said Letters Patent is hereby corrected as shown below:

On the Title Page

In Column 2, item (56) under "Other Publications", Line 15, delete "Searial" and insert --Serial-- therefor In the Specification In Column 8, Line 22, delete "2,4-2,5-" and insert --2,4-, 2,5- -- therefor In Column 18, Line 31, delete "(C1-C2)" and insert --($C_1$-$C_2$)-- therefor In Column 19, Line 22, delete "(C1-C2)" and insert --($C_1$-$C_2$)-- therefor In Column 19, Line 38, delete "$CF_3$." and insert --$CF_3$,-- therefor In Column 20, Line 7, delete "$C_{1-6}$-alkyl," and insert --$C_{1-6}$alkyl,-- therefor In Column 20, Line 26-34, delete " 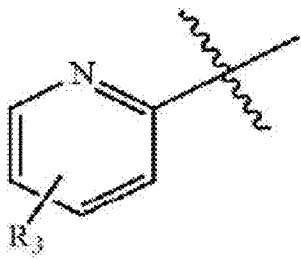 " and Signed and Sealed this
Fifteenth Day of May, 2018

Andrei Iancu
*Director of the United States Patent and Trademark Office* insert -- 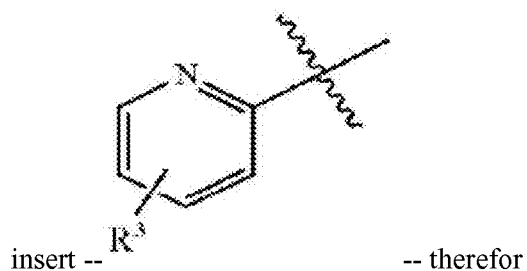 -- therefor

In Column 20, Line 56, delete "(C1-C2)" and insert --($C_1$-$C_2$)-- therefor

In Column 27, Line 16, delete "K$_i$(nM)" and insert --$K_i$(nM)-- therefor

In Column 29, Scheme 5, Line 61 (Approx.), delete "Bu$_3$.THF" and insert --$BH_3$.THF-- therefor In Column 32, Line 25, delete "C2-C4" and insert --$C_2$-$C_4$-- therefor In Column 39, Line 62, delete "IC50" and insert --$IC_{50}$-- therefor In Column 42, Line 49, delete "1.5H):" and insert --1.5H);-- therefor In Column 44, Line 67, delete "1H):" and insert --1H);-- therefor In Column 45, Line 17, delete "K;" and insert --$K_i$-- therefor In Column 46, Line 5, delete "ds-2-AG," and insert --$d_5$-2-AG,-- therefor In Column 46, Line 12, delete "rpm," and insert --μm,-- therefor In Column 48, Line 42, delete "of(S)-12" and insert --of (S)-12-- therefor In Column 62, Line 50, delete "δ6.93" and insert --δ 6.93-- therefor In Column 69, Line 25, delete "MeOH-(CH$_2$C2)" and insert --MeOH-($CH_2Cl_2$)-- therefor In Column 70, Line 32, delete "25.7," and insert --25.7;-- therefor In Column 70, Line 59, delete "(Sit," and insert --(S11,-- therefor In Column 71, Line 45-46, delete "(6-Phenyl-1,2,4-tetrahydronaphthalen-2-yl)(5-(pyridin-2-yl)oxazol-2-yl)methanone" and insert --(6-Phenyl-1,2,3,4-tetrahydronaphthalen-2-yl)(5-(pyridin-2-yl)oxazol-2-yl)methanone-- therefor In Column 73, Line 46, delete "$SiO_{2.30}$%" and insert --$SiO_2$, 30%-- therefor In Column 75, Line 44, delete "6203.4," and insert --δ 203.4,-- therefor In Column 78, Line 34, delete "1.5H):" and insert --1.5H);-- therefor In Column 84, Line 18, delete "M Hz)" and insert --MHz)-- therefor In Column 84, Line 32, delete "0.8." and insert --0.8,-- therefor In Column 85, Line 60, delete "δ7.53" and insert --δ 7.53-- therefor In Column 93, Line 11, delete "1.5H):" and insert --1.5H);-- therefor In Column 94, Line 10 (First Occurrence), delete "1H" and insert --1H,-- therefor In Column 94, Line 10 (Second Occurrence), delete "1H" and insert --1H,-- therefor In Column 94, Line 25, delete "0.3." and insert --0.3,-- therefor In Column 95, Line 28, delete "1H):" and insert --1H);-- therefor In Column 98, Line 13, delete "of(S)-21" and insert --of (S)-21-- therefor In Column 99, Line 34, delete "(acetone-d," and insert --(acetone-$d_6$,-- therefor In Column 102, Line 33, delete "35.3:" and insert --35.3;-- therefor In Column 102, Line 34, delete "$C_{19}H_5NO_2$" and insert --$C_{19}H_{15}NO_2$-- therefor In Column 102, Line 40-41, delete "2-((tert-Butyldimethylsllyloxy)(5-phenylindan-2-yl)methyl)oxazole" and insert --2-((tert-Butyldimethylsilyloxy)(5-phenylindan-2-yl)methyl)oxazole-- therefor In Column 103, Line 29, delete "$_0$-5%" and insert --0-5%-- therefor In Column 106, Line 58, delete "(THF-d," and insert --(THF-$d_8$,-- therefor In Column 107, Line 1, delete "5-Phenoxylindane-2-carboxylate" and insert --5-Phenoxyindane-2-carboxylate-- therefor In Column 107, Line 41-42, delete "5-phenoxyindan-2-carboxylate" and insert --5-phenoxyindane-2-carboxylate-- therefor In Column 109, Line 39-40, delete "2-(tert-Butyldimethylsilyloxy)(5-phenoxyindan-2-yl)methyl)-5-(tributylstannyl)oxazole" and insert --2-((tert-Butyldimethylsilyloxy)(5-phenoxyindan-2-yl)methyl)-5-(tributylstannyl)oxazole-- therefor In Column 109, Line 61, delete "$_0$-5%" and insert --0-5%-- therefor In Column 112, Line 34, delete "6-(2-(5-Phenoxyidane-2-carbonyl)picolinate" and insert --6-(2-(5-Phenoxyidane-2-carbonyl)oxazol-5-yl)picolinate-- therefor In Column 113, Line 65, delete "4H):" and insert --4H);-- therefor In Column 116, Line 51, delete "$_0$-5%" and insert --0-5%-- therefor In Column 117, Line 28, delete "3H):" and insert --3H);-- therefor In Column 119, Line 24, delete "δ8.04" and insert --δ 8.04-- therefor In Column 120, Line 31, before "200.1,", insert --δ--

In Column 120, Line 63, delete "1H):" and insert --1H);-- therefor

In Column 122, Line 52, delete "EDCl" and insert --EDCI-- therefor

In Column 123, Line 14-16, delete "{NV-[2-(tert-butyldimethylsilyloxy)-2-(6-phenoxy-1,2,3,4-tetrahydronaphthalen-2-yl)-acetyl]-hydrazino}-2-oxo-acetate" and insert --{N'-[2-(tert-butyldimethylsilyloxy)-2-(6-phenoxy-1,2,3,4-tetrahydronaphthalen-2-yl)-acetyl]-hydrazino}-2-oxo-acetate-- therefor In Column 124, Line 5-6, delete "(1,3,4-Oxadlazol-2-yl)(6-phenoxy-1,2,3,4-tetrahydronaphthalen-2-yl)methanone" and insert --(1,3,4-Oxadiazol-2-yl)(6-phenoxy-1,2,3,4-tetrahydronaphthalen-2-yl)methanone-- therefor In Column 125, Line 51, delete "EDCl" and insert --EDCI-- therefor In Column 126, Line 7-9, delete "2-((tert-Butyldimethylsilyloxy)(6-pheoxy-1,2,3,4-tetrahydrooaphthalen-2-yl)methyl)-5-(pyridin-2-yl)-1,3,4-oxadiazole" and insert --2-((tert-Butyldimethylsilyloxy)(6-pheoxy-1,2,3,4-tetrahydronaphthalen-2-yl)methyl)-5-(pyridin-2-yl)-1,3,4-oxadiazole-- therefor In Column 126, Line 20-22, delete "N-(2-(tert-butyldimethylsilyloxy)-2-(6-phenoxy-1,2,3,4-tetrahydronaphthalen-2-y l)acetyl)picolinohydrazide" and insert --N'-(2-(tert-butyldimethylsilyloxy)-2-(6-phenoxy-1,2,3,4-tetrahydronaphthalen-2-yl)acetyl)picolinohydrazide-- therefor In Column 126, Line 64, delete "1H" and insert --1H,-- therefor In Column 126, Line 66, delete "(," and insert --(m,-- therefor In Column 127, Line 36, delete "$C_{24}H_9N_3O_3$" and insert --$C_{24}H_{19}N_3O_3$-- therefor In Column 128, Line 38, delete "ml/228.1016" and insert --m/z 228.1016-- therefor In Column 129, Line 23-24, delete "2-((tert-butyldimetylsilyloxy)-1,2,3,4-tetrahydronaphthalen-2-yl)methyl)oxazole" and insert --2-((tert-butyldimethylsilyloxy)-1,2,3,4-tetrahydronaphthalen-2-yl)methyl)oxazole-- therefor In Column 130, Line 58, delete "1H):" and insert --1H);-- therefor In Column 131, Line 13, delete "0° C." and insert --0 °C.-- therefor In Column 131, Line 41, delete "δ9.78" and insert --δ 9.78-- therefor In Column 131, Line 58, delete "BH$_3$-THF" and insert --BH$_3$.THF-- therefor In Column 132, Line 64, delete "3H):" and insert --3H);-- therefor In the Claims In Column 136, Line 62, in Claim 1, delete "CH$_2$Ch$_2$;" and insert --CH$_2$CH$_2$;-- therefor In Column 137, Line 12, in Claim 1, delete "C(O)R',C(O)C(O)R'," and insert --C(O)R', C(O)C(O)R',-- therefor In Column 137, Line 54-61, in Claim 6, delete " 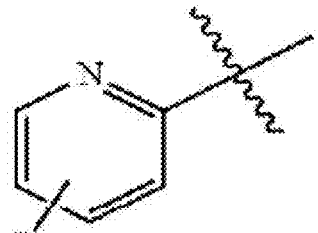 " and insert -- 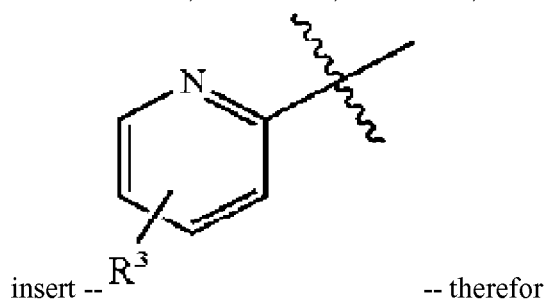 -- therefor